US012760017B2

(12) United States Patent
Zahler

(10) Patent No.: US 12,760,017 B2
(45) Date of Patent: Oct. 13, 2026

(54) T-TYPE CALCIUM CHANNEL ANTAGONISTS AND USES THEREOF

(71) Applicant: ACUREX BIOSCIENCES CORPORATION, San Carlos, CA (US)

(72) Inventor: Robert Zahler, San Carlos, CA (US)

(73) Assignee: ACUREX BIOSCIENCES CORPORATION, San Carlos, CA (US)

( * ) Notice: Subject to any disclaimer, the term of this patent is extended or adjusted under 35 U.S.C. 154(b) by 395 days.

(21) Appl. No.: 18/280,096

(22) PCT Filed: Mar. 3, 2022

(86) PCT No.: PCT/US2022/018682

§ 371 (c)(1),
(2) Date: Sep. 1, 2023

(87) PCT Pub. No.: WO2022/216386

PCT Pub. Date: Oct. 13, 2022

(65) Prior Publication Data

US 2024/0190865 A1 Jun. 13, 2024

Related U.S. Application Data

(60) Provisional application No. 63/228,505, filed on Aug. 2, 2021, provisional application No. 63/156,806, filed on Mar. 4, 2021.

(51) Int. Cl.

| | |
|---|---|
| ***C07D 471/04*** | (2006.01) |
| ***A61K 31/437*** | (2006.01) |
| ***A61K 31/5025*** | (2006.01) |
| ***A61P 25/28*** | (2006.01) |
| ***C07D 487/04*** | (2006.01) |
| ***C07D 498/04*** | (2006.01) |
| ***G01N 33/68*** | (2006.01) |

(52) U.S. Cl.

CPC .......... *C07D 471/04* (2013.01); *A61K 31/437* (2013.01); *A61K 31/5025* (2013.01); *A61P 25/28* (2018.01); *C07D 487/04* (2013.01); *C07D 498/04* (2013.01); *G01N 33/6896* (2013.01); *G01N 2333/914* (2013.01); *G01N 2800/50* (2013.01)

(58) Field of Classification Search

None

See application file for complete search history.

(56) References Cited

U.S. PATENT DOCUMENTS

| | | | |
|---|---|---|---|
| 7,875,636 | B2 | 1/2011 | Barrow et al. |
| 8,377,968 | B2 | 2/2013 | Pajouhesh et al. |
| 8,987,310 | B2 | 3/2015 | Barrow et al. |
| 9,403,798 | B2 | 8/2016 | Saito et al. |
| 10,562,857 | B2 | 2/2020 | Xie et al. |
| 2002/0193398 | A1 | 12/2002 | Barrow et al. |
| 2010/0249176 | A1 | 9/2010 | Barrow et al. |
| 2010/0261724 | A1 | 10/2010 | Barrow et al. |
| 2012/0264804 | A1 | 10/2012 | Gray et al. |
| 2015/0329533 | A1 | 11/2015 | Nam et al. |
| 2016/0340322 | A1 | 11/2016 | Adachi et al. |

FOREIGN PATENT DOCUMENTS

| | | | |
|---|---|---|---|
| EP | 3 572 403 | A1 | 7/2020 |
| WO | WO-2007/120729 | A2 | 10/2007 |
| WO | WO-2011/022315 | A1 | 2/2011 |
| WO | WO-2012/094615 | A2 | 7/2012 |
| WO | WO-2013/148640 | A1 | 10/2013 |
| WO | WO-2018/200850 | A1 | 11/2018 |
| WO | 2018237145 | A1 | 12/2018 |
| WO | WO-2019/175395 | A1 | 9/2019 |
| WO | WO-2020/072773 | A1 | 4/2020 |
| WO | WO-2021/007487 | A1 | 1/2021 |
| WO | WO-2021/046368 | A1 | 3/2021 |
| WO | 2022216386 | A2 | 10/2022 |
| WO | 2024081653 | A2 | 4/2024 |

OTHER PUBLICATIONS

CAS RN 1346959-96-3 (entered into STN on Dec. 1, 2011) (Year: 2011).*

Extended European Search Report for EP Application No. 22785131.8, mailed on Aug. 25, 2025, 9 pages.

Zhang et al. (Jan. 1, 2018) "Discovery of Novel PDE9A Inhibitors with Antioxidant Activities for Treatment of Alzheimer's Disease", Journal of Enzyme Inhibition and Medicinal Chemistry, 33(1):260-270.

Ashrafi, G et al. (Sep. 1, 2014, e-published Aug. 25, 2014). "Mitophagy of damaged mitochondria occurs locally in distal neuronal axons and requires PINK1 and Parkin," *The Journal of Cell Biology* 206(5):655-670.

Bell, D.C. et al. (Jun. 2018, e-published Jul. 18, 2017). "Using automated patch clamp electrophysiology platforms in pain-related ion channel research: insights from industry and academia," *Br. J. Pharmacology* 175(12):2312-2321.

(Continued)

*Primary Examiner* — Craig D Ricci

(74) *Attorney, Agent, or Firm* — Mintz, Levin, Cohn, Ferris, Glovsky and Popeo, P.C.

(57) ABSTRACT

Disclosed herein is a method of reducing Miro1 level in a cell, the method comprising contacting the cell with an effective amount of a T-type calcium channel antagonist.

19 Claims, 12 Drawing Sheets

(56) References Cited

OTHER PUBLICATIONS

Bezencon, O. et al. (Dec. 14, 2017). "Discovery of a Potent, Selective T-type Calcium Channel Blocker as a Drug Candidate for the Treatment of Generalized Epilepsies," *J. Med. Chem.* 60(23):9769-9789.

Brickley, K. et al. (May 20, 2011, e-published Mar. 30, 2011). "Trafficking kinesin protein (TRAK)-mediated transport of mitochondria in axons of hippocampal neurons," *Biol Chem* 286(20):18079-18092.

Glater, E.E. et al. (May 22, 2006). "Axonal transport of mitochondria requires milton to recruit kinesin heavy chain and is light chain independent," *The Journal of Cell Biology* 173(4):545-557.

Hsieh, C-H. et al. (Dec. 1, 2016, e-published Sep. 8, 2016). "Functional Impairment in Miro Degradation and Mitophagy Is a Shared Feature in Familial and Sporadic Parkinson's Disease," *Cell Stem Cell* 19(6):709-724.

Hsieh C-H et al. (Dec. 3, 2019, e-published Sep. 26, 2019). "Miro1 Marks Parkinson's Disease Subset and Miro1 Reducer Rescues Neuron Loss in Parkinson's Models," *Cell Metab.* 30(6):1131-1140.

International Search Report mailed on Nov. 18, 2022, for PCT Application No. PCT/US2022/018682, filed Mar. 3, 2022, 4 pages.

Koutsopoulos, O.S. et al. (May 2010). "Human Miltons associate with mitochondria and induce microtubule-dependent remodeling of mitochondrial networks," Biochim Biophys Acta 1803(5):564-574.

Leech, C.A. et al. (1994). "Application of patch clamp methods to the study of calcium currents and calcium channels," *Methods Cell Biol.* 40:135-151.

Liu, S. et al. (2012). "Parkinson's disease-associated kinase PINK1 regulates Miro protein level and axonal transport of mitochondria," PLoS Genetics 8(3)::e1002537.

Misko, A. et al. (Mar. 24, 2010). "Mitofusin 2 is necessary for transport of axonal mitochondria and interacts with the Miro/Milton complex," *J Neurosci* 30(12):4232-4240.

Russo, G.J. et al. (Apr. 29, 2009). "*Drosophila miro* is required for both anterograde and retrograde axonal mitochondrial transport," *J. Neurosci* 29(17):5443-5455.

Sheng, Z-H. et al. (Jan. 5, 2012). "Mitochondrial transport in neurons: impact on synaptic homeostasis and neurodegeneration," *Nat Rev Neurosci* 13(2):77-93.

Shi, Y. et al. (Feb. 2017, e-published Dec. 16, 2016). "Induced pluripotent stem cell technology: a decade of progress," *Nature Reviews Drug Discovery* 16(2):115-130.

Uebele, V.N. et al. (2009). "Positive allosteric interaction of structurally diverse T-type calcium channel antagonists," *Cell Biochem Biophys* 55(2):81-93.

Wang, X. et al. (Nov. 11, 2011). " PINK1 and Parkin target Miro for phosphorylation and degradation to arrest mitochondrial motility," *Cell* 147(4):893-906.

Written Opinion mailed on Nov. 18, 2022, for PCT Application No. PCT/US2022/018682, filed Mar. 3, 2022, 7 pages.

Xiang, Z. et al. (Dec. 21, 2011). "The Discovery and Characterization of ML218: A Novel, Centrally Active T-Type Calcium Channel Inhibitor with Robust Effects in STN Neurons and in a Rodent Model of Parkinson's Disease," *ACS Chemical Neuroscience* 2(12)730-742.

* cited by examiner

Climbing assay, day 10, 3 groups with n>15 flies, averaged 3 replicates per group

| Diagnosis | No. (Miro1 DMSO v.s. CCCP P<0.05) | No. (Miro1 DMSO v.s. CCCP P>0.05) | P (Fisher Exact) Compared to Healthy |
|---|---|---|---|
| HEALTHY | 9 (100 %) | 0 (0%) | |
| PD | 5 (16.7%) | 25 (83.3%) | <0.00001 |
| PD RISK (CARRIER) | 6 (14.3%) | 36 (85.7%) | <0.00001 |
| PD RISK (HYPOSMIA) | 3 (60%) | 2 (40%) | 0.1099 |
| LRRK2+, HYPOSMIA | 1 (16.7%) | 5 (83.3%) | 0.002 |

*FIG. 2C*

T-TYPE CALCIUM CHANNEL ANTAGONISTS AND USES THEREOF

CROSS REFERENCE TO RELATED APPLICATIONS

This application claims priority to U.S. Provisional Application Nos. 63/156,806, filed Mar. 4, 2021, and 63/228,505, filed Aug. 2, 2021, each of which is incorporated herein in its entirety for all purposes.

STATEMENT REGARDING FEDERALLY SPONSORED RESEARCH OR DEVELOPMENT

This invention was made with Government support under contract NS089583 awarded by the National Institutes of Health. The Government has certain rights in the invention.

BACKGROUND

Neurons are metabolically active cells with high energy demands at locations distant from the cell body. As a result, these cells are particularly dependent on mitochondrial function, as reflected by the observation that diseases of mitochondrial dysfunction often have a neurodegenerative component. Recent discoveries have highlighted that neurons are reliant particularly on the dynamic properties of mitochondria. Mitochondria are dynamic organelles by several criteria. They engage in repeated cycles of fusion and fission, which serve to intermix the lipids and contents of a population of mitochondria. In addition, mitochondria are actively recruited to subcellular sites, such as the axonal and dendritic processes of neurons. Finally, the quality of a mitochondrial population is maintained through mitophagy, a form of autophagy in which defective mitochondria are selectively degraded. Defects in the key features of mitochondrial dynamics, such as mitochondrial fusion, fission, transport and mitophagy are associated with neurodegenerative disorder. Several major neurodegenerative disorders—including Parkinson's, Alzheimer's and Huntington's disease—involve disruption of mitochondrial dynamics.

Mitochondrial movements are tightly controlled to maintain energy homeostasis and prevent oxidative stress. Mitochondrial motility ceases prior to the initiation of mitophagy, a crucial cellular mechanism by which depolarized mitochondria are degraded through autophagosomes and lysosomes. The arrest of motility may sequester damaged mitochondria, preventing them from moving and from reintroducing damage to other healthy mitochondria.

Miro is an outer mitochondrial membrane (OMM) protein that anchors the microtubule motors kinesin and dynein to mitochondria (Glater et al., "Axonal transport of mitochondria requires milton to recruit kinesin heavy chain and is light chain independent," *The Journal of cell biology,* 2006, 173:545-557; and Koutsopoulos et al., "Human Miltons associate with mitochondria and induce microtubule-dependent remodeling of mitochondrial networks," *Biochimica et biophysica acta,* 2010, 1803:564-574). This depolarization-triggered mitochondrial arrest is achieved by removal of Miro from the damaged mitochondrial surface (Wang et al., "PINK1 and Parkin target Miro for phosphorylation and degradation to arrest mitochondrial motility," *Cell,* 2011, 147:893-906). Miro is subsequently degraded by proteasomes (Wang et al., 2011). Evidence has shown that two PD-linked proteins, PINK1 (PTEN-induced putative kinase 1) and Parkin, act in concert to target Miro for degradation (Ashrafi et al., "Mitophagy of damaged mitochondria occurs locally in distal neuronal axons and requires PINK1 and Parkin," *The Journal of cell biology,* 2014, 206:655-670; Liu et al., "Parkinson's disease-associated kinase PINK1 regulates Miro protein level and axonal transport of mitochondria," *PLoS genetics,* 2012, 8:e1002537; and Wang et al., 2011). Mutations in PINK1 or Parkin are tied to rare forms of recessive early-onset PD.

Altered mitochondrial transport is one of the pathogenic changes in major adult-onset neurodegenerative diseases (Sheng Z H, Cai Q, "Mitochondrial transport in neurons: impact on synaptic homeostasis and neurodegeneration," *Nat Rev Neurosci,* 2012 Jan. 5; 13(2):77-93). In mutant LRRK2GS2019 cells, the mitochondrial outer membrane protein Miro is stabilized and remains on damaged mitochondria for longer than normal, prolonging active transport and inhibiting mitochondrial degradation (Hsieh et al., "Functional Impairment in Miro Degradation and Mitophagy Is a Shared Feature in Familial and Sporadic Parkinson's Disease," *Cell Stem Cell,* 2016 Dec. 1; 19(6): 709-724). Miro degradation and mitochondrial motility are also impaired in sporadic PD patients (Hsieh et al., 2016). Prolonged retention of Miro, and the downstream consequences that ensue, may constitute a central component of PD pathogenesis.

T-type voltage-dependent calcium channels or T-type calcium channels are low voltage activated calcium channels that become deinactivated during cell membrane hyperpolarization but then open to depolarization. There are three known T-type calcium channel subtypes: $Ca_v3.1$, $Ca_v3.2$, and $Ca_v3.3$. The entry of calcium into various cells has many different physiological responses associated with it. Within cardiac muscle cell and smooth muscle cells voltage-gated calcium channel activation initiates contraction directly by allowing the cytosolic concentration to increase. T-type calcium channels are present within cardiac and smooth muscle, as well as in many neuronal cells within the central nervous system.

There is a need for novel compounds and methods to reduce Miro1 level in a cell, for example, for treating neurodegenerative disease such as Parkinson's disease.

BRIEF SUMMARY

In an aspect, the present disclosure provides a compound of Formula (II):

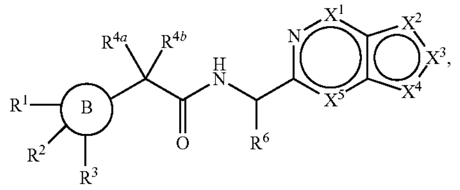

(II)

or a pharmaceutically acceptable salt thereof, wherein ring B is $C_6$-$C_{10}$ aryl or 5- to 10-membered heteroaryl;

$R^1$, $R^2$, and $R^3$ are each independently H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, $—(CH_2)_n—(C_3$-$C_7$ cycloalkyl), 4- to 7-membered heterocyclyl, or $—(CH_2)_n$-(4- to 7-membered heterocyclyl), wherein the phenyl, heteroaryl, cycloalkyl or heterocyclyl is optionally substituted by 1, 2, or 3 halogen, CN, $OR^{11}$, $NR^{12a}R^{12b}$, $C_1$-$C_6$ alkyl, $C_1$-$C_6$ alkoxy, $C_1$-$C_6$ alkylamino, or $C_1$-$C_6$ haloalkyl;

$R^{4a}$ and $R^{4b}$ are each independently H or $C_1$-$C_6$ alkyl, or $R^{4a}$ and $R^{4b}$ and the carbon atom to which they are attached form a $C_3$-$C_5$ cycloalkyl;

$R^6$ is H, $C_1$-$C_6$ alkyl, or $C_1$-$C_6$ haloalkyl; $X^1$ and $X^5$ are each independently N or $CR^8$, provided that at least one of $X^1$ and $X^5$ is $CR^8$; $X^2$, $X^3$, and $X^4$ are each independently N, $NR^9$, O, S, or $CR^9$, provided that at least one of $X^2$, $X^3$, and $X^4$ is N, $NR^9$, O, or S;

$R^8$ is H, halogen, CN, $OR^{11}$, $C_1$-$C_6$ alkyl, $C_2$-$C_6$ alkoxyalkyl, or $C_1$-$C_6$ haloalkyl;

$R^9$ is H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl;

each $R^{11}$, $R^{12a}$, and $R^{12b}$ is independently H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen or CN; and n is 1, 2, or 3;

provided that the compound does not have the structure:

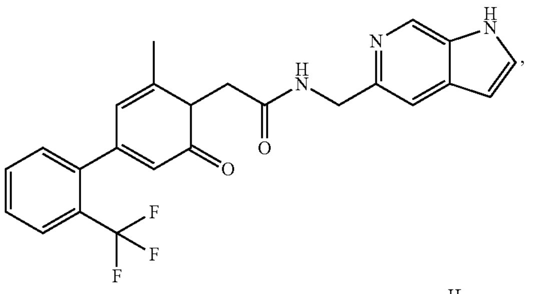

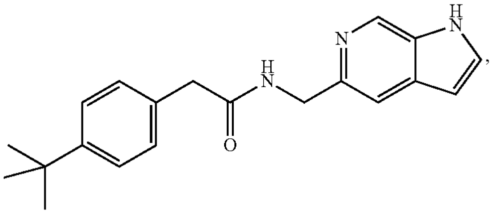

or

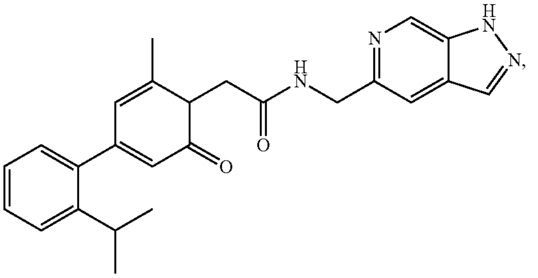

or a pharmaceutically acceptable salt thereof.

The compound of Formula (II) can have a structure wherein $X^1$ is $CR^8$. For example, $R^8$ can be H. The Formula (II) compound can comprise $X^2$, $X^3$, and $X^4$ that are each independently N, $NR^9$, or $CR^9$, provided that at least one of $X^2$, $X^3$, and $X^4$ is N or $NR^9$.

The disclosure also provides a compound of Formula (III):

(III)

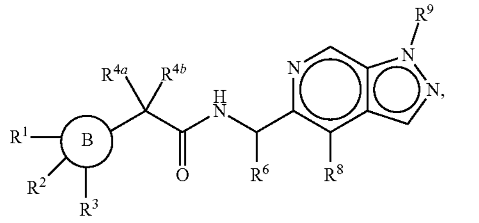

or a pharmaceutically acceptable salt thereof, wherein $R^1$, $R^2$, $R^3$, $R^{4a}$, $R^{4b}$, $R^6$, $R^8$, and $R^9$ are as defined anywhere herein.

The compound of Formula (II) or (III), or a pharmaceutical salt thereof, can have $R^1$, $R^2$, and $R^3$ that are each independently H, halogen, CN, OH, $NH_2$, $C_1$-$C_6$ alkyl, $C_1$-$C_6$ alkoxy, $C_1$-$C_6$ alkylamino, $C_2$-$C_6$ alkoxyalkyl, $C_1$-$C_6$ haloalkyl, or $C_3$-$C_7$ cycloalkyl, wherein the cycloalkyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl.

The compound of Formula (II) or (III), or a pharmaceutical salt thereof, can have $R^1$ and $R^2$ are each independently H, halogen, $C_1$-$C_6$ alkyl, $C_1$-$C_6$ alkoxy, $C_2$-$C_6$ alkoxyalkyl, $C_1$-$C_6$ haloalkyl, or $C_3$-$C_7$ cycloalkyl, wherein the cycloalkyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl. For example, $R^1$ and $R^2$ can be each independently H, halogen, $C_1$-$C_3$ alkyl, $C_1$-$C_3$ alkoxy, $C_2$-$C_3$ alkoxyalkyl, $C_1$-$C_3$ haloalkyl, or $C_3$-$C_5$ cycloalkyl, wherein the cycloalkyl is optionally substituted by 1, 2, or 3 halogen, CN, $C_1$-$C_3$ alkyl, $C_1$-$C_3$ alkoxy, $C_1$-$C_3$ alkylamino, or $C_1$-$C_3$ haloalkyl.

The compound of Formula (II) or (III), or a pharmaceutical salt thereof, can have $R^{4a}$ and $R^{4b}$ that are each independently H or $CH_3$.

The compound of Formula (II) or (III), or a pharmaceutical salt thereof, can have $R^6$ that is H or $C_1$-$C_3$ alkyl. For example, $R^6$ can be $CH_3$.

The disclosure also provides a compound of Formula (IV):

(IV)

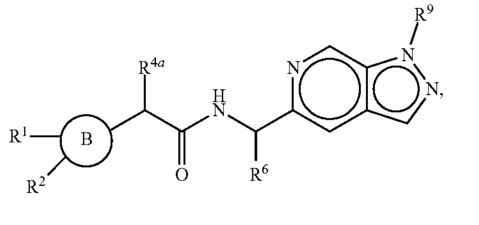

or a pharmaceutically acceptable salt thereof wherein $R^1$, $R^2$, $R^{4a}$, $R^6$, and $R^9$ are as defined anywhere herein.

The compound of Formula (II), (III), or (IV), or a pharmaceutical salt thereof, can have $R^9$ that is $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl. For example, $R^9$ can be $C_1$-$C_6$ alkyl, $C_2$-$C_6$ alkoxyalkyl, $C_1$-$C_6$ haloalkyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl.

The compound of Formula (II), (III), or (IV), or a pharmaceutical salt thereof, can have ring B that is phenyl or 5- to 6-membered heteroaryl. For example, ring B can be phenyl or pyridyl.

The disclosure also provides a compound of Formula (V):

(V)

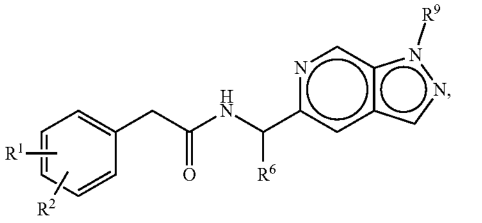

or a pharmaceutically acceptable salt thereof, wherein $R^1$, $R^2$, $R^6$, and $R^9$ are as defined anywhere herein.

Exemplary T-type calcium channel antagonists of the disclosure can have a structure of any one of the compounds in Table 1. Additional structures for compounds of the disclosure can be found in Table 2.

The present disclosure includes a pharmaceutical composition of a compound described herein, or a pharmaceutically acceptable salt thereof.

Further provided herein is a method of treating a neurodegenerative disorder in a subject comprising administering a compound described herein, or a pharmaceutically acceptable salt thereof.

In another aspect, described herein is a method of reducing Miro1 level in a cell, the method comprising contacting the cell with an effective amount of a T-type calcium channel antagonist. The T-type calcium channel antagonist can have a selectivity for a T-type calcium channel of at least about 1.2-fold or more over one or more of L-type, N-type, P-type, and/or R-type calcium channels. The method can comprise a T-type calcium channel antagonist having the structure of Formula (I):

(I)

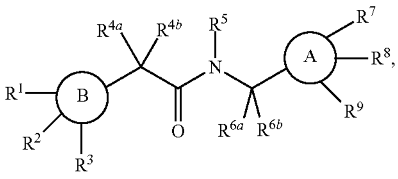

or a pharmaceutically acceptable salt thereof, wherein ring A and ring B are each independently $C_6$-$C_{10}$ aryl or 5- to 10-membered heteroaryl;

$R^1$, $R^2$, and $R^3$ are each independently H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, or 4- to 7-membered heterocyclyl, wherein the phenyl, heteroaryl, cycloalkyl or heterocyclyl is optionally substituted by 1, 2, or 3 halogen, CN, $OR^{11}$, $NR^{12a}R^{12b}$ $C_1$-$C_6$ alkyl, $C_1$-$C_6$ alkoxy, $C_1$-$C_6$ alkylamino, or $C_1$-$C_6$ haloalkyl;

$R^{4a}$ and $R^{4b}$ are each independently H or $C_1$-$C_6$ alkyl;

$R^5$ is H or $C_1$-$C_6$ alkyl;

$R^{6a}$ and $R^{6b}$ are each independently H or $C_1$-$C_6$ alkyl;

$R^7$ is H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, or 4- to 7-membered heterocyclyl, wherein the phenyl, heteroaryl, cycloalkyl or heterocyclyl is optionally substituted by 1, 2, or 3 halogen, CN, $OR^{11}$, $NR^{12a}R^{12b}$, $C_1$-$C_6$ alkyl, $C_1$-$C_6$ alkoxy, $C_1$-$C_6$ alkylamino, or $C_1$-$C_6$ haloalkyl;

$R^8$ is H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl;

$R^9$ is H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl; and each $R^{11}$, $R^{12a}$, and $R^{12b}$ is independently H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen or CN.

Ring A can be a 9- to 10-membered heteroaryl. Ring B can be phenyl or 5- to 6-membered heteroaryl. For example, the T-type calcium channel antagonist can have a structure of Formula (II), (III), (IV), or (V), or a pharmaceutically acceptable salt thereof.

The method of reducing Miro1 level described herein can be performed in any suitable cell. For example, the cell can be a muscle cell. In another example, the cell can be a neuronal cell. The reducing Miro1 level can be in vitro or ex vivo. Alternatively, the reducing Miro1 level can be in vivo.

In another aspect, provided herein is a method for identifying a subject at risk of developing a Miro1-related disorder, the method comprising: a) detecting whether a Miro1 level is similar or higher in a biological sample obtained from the subject and treated with a mitochondrial stressor, as compared to a control Miro1 level in a control biological sample obtained from the subject and is untreated; and b) identifying the subject at risk of developing a Miro1-related disorder if the Miro1 level is similar or higher in the biological sample compared to the control Miro1 level in the control biological sample, wherein the biological sample and the control biological sample comprise iPSCs or cells differentiated from iPSCs. The mitochondrial stressor can be carbonyl cyanide 3-chlorophenylhydrazone (CCCP). The method can further comprise treating the subject at risk of developing a Miro1-related disorder by administering a therapeutically effective amount of a compound described herein, or a pharmaceutically acceptable salt thereof.

In another aspect, provided is a method for identifying a subject at risk of developing a Miro1-related disorder, the method comprising: a) detecting whether a Miro1 level is similar or higher in a biological sample obtained from the subject and treated with a mitochondrial stressor, as compared to a control Miro1 level in a control biological sample obtained from the subject and is untreated; b) identifying the subject at risk of developing a Miro1-related disorder if the Miro1 level is similar or higher in the biological sample compared to the control Miro1 level in the control biological sample. The mitochondrial stressor can be carbonyl cyanide 3-chlorophenylhydrazone (CCCP); and c) treating the subject at risk of developing a Miro1-related disorder by administering a therapeutically effective amount of a compound described herein, or pharmaceutically acceptable salt thereof. The biological sample and the control biological sample can comprise fibroblasts.

The present disclosure further describes a method for treating a neurodegenerative disorder in a subject in need thereof, the method comprising: a) detecting whether a Miro1 level is similar or higher in a biological sample obtained from the subject and treated with a mitochondrial stressor, as compared to a control Miro1 level in a control biological sample obtained from the subject and is untreated; b) identifying the subject for treatment if the Miro1 level is similar or higher in the biological sample compared to the control Miro1 level in the control biological sample; and c) administering a therapeutically effective amount of a compound described herein, or pharmaceutically acceptable salt thereof, to the subject. The mitochondrial stressor can be carbonyl cyanide 3-chlorophenylhydrazone (CCCP). The biological sample and the control biological sample can comprise fibroblasts. Neurodegenerative disorders include Drug-induced Parkinsonism, Progressive supranuclear Palsy, Vascular Parkinsonism, Dementia with Lewy Bodies, diffuse Lewy body disease, Corticobasal degeneration, multisystem degeneration (Shy-drager syndrome), Parkinson's disease, Alzheimer's disease, Pick's disease, frontotemporal dementia, multiple systems atrophy, vascular dementia, and progressive supranuclear palsy (Steel-Richardson syndrome). The subject can be asymptomatic for the neurodegenerative disorder.

The Miro1 level as compared to a control Miro1 level can be determined by any method in the art, such as the methods described further herein. For example, the ratio of the Miro1 level to the control Miro1 level can be from about 0.5 to about 10. In another example, the ratio of the Miro1 level to the control Miro1 level can be from about 0.7 to about 4.

DETAILED DESCRIPTION

Figure 1:
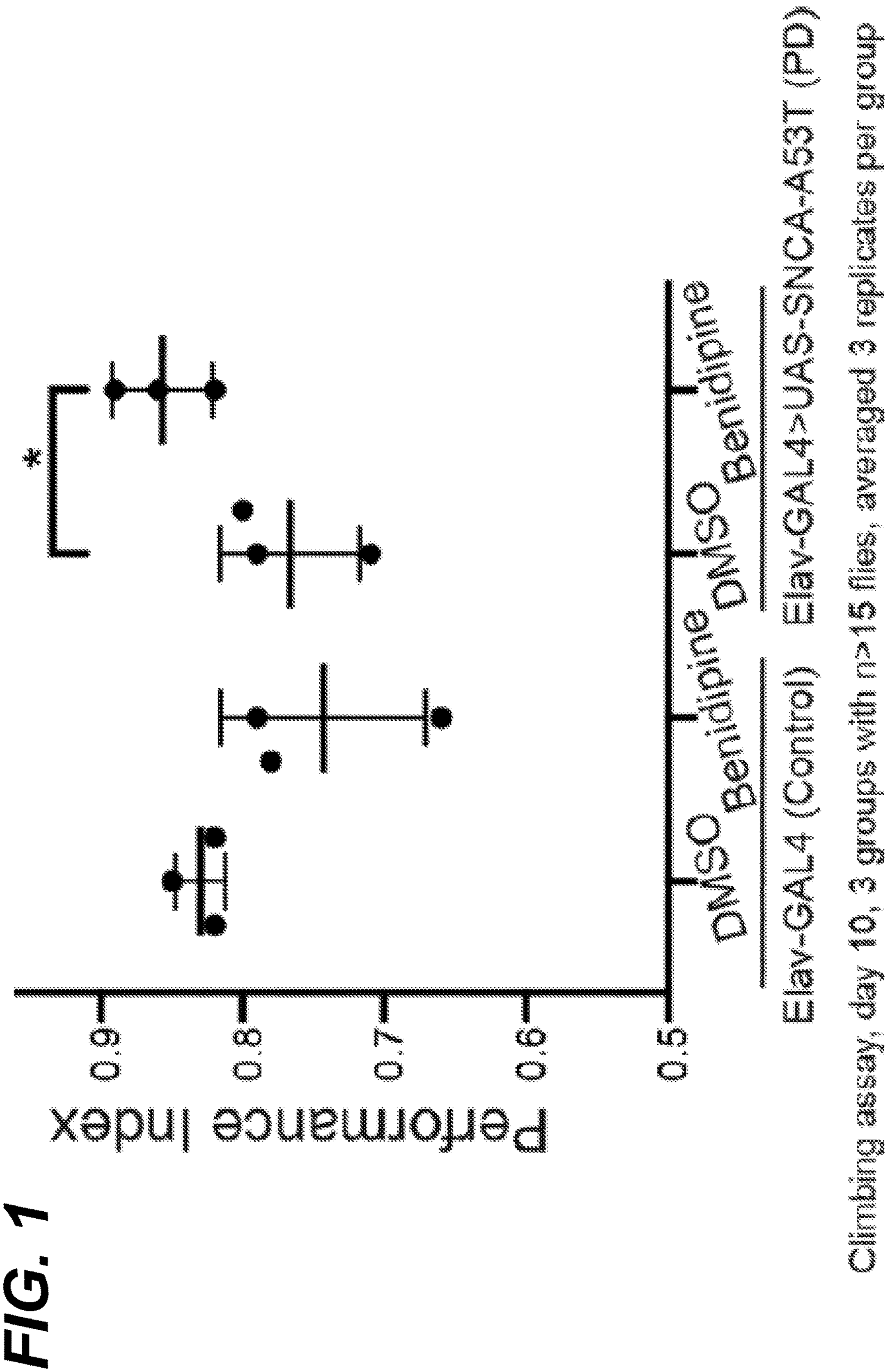
FIG. 1 shows the effect of benidipine in feed on locomotor decline in a Parkinson's disease fly model.

The present disclosure provides for, inter alia, methods and compositions of selective T-type calcium channel antagonists, and not selective L-type or N-type calcium channel antagonists, nor mixed L-/N-type or L-/N-/P-type calcium channel antagonists, are capable of reducing a Miro1 level in a cell. Accordingly, a selective T-type voltage-dependent calcium channel antagonist, or a mixed selectivity calcium channel antagonist that has T-type antagonist activity, may be useful in reducing a Miro1 level in diseases or conditions that would benefit from the reduction of a Miro1 level in a cell, for example, a neuronal cell. Such diseases or conditions include neurodegenerative diseases, such as Parkinson's disease.

Also disclosed herein is an amide compound of Formula (II). See, Examples 1-55. Such compounds have shown T-type calcium channel antagonist activity (Example 60). Therefore, a compound of Formula (II) is capable of reducing a Miro1 level in a cell, and may be useful in treating neurodegenerative diseases such as Parkinson's disease.

Further provided is a method of identifying a subject at risk of developing a Miro1-related disorder, by measuring a Miro1 level from the subject's biological sample, that had been treated with a mitochondrial stressor, in comparison with a control Miro1 level measured from a corresponding untreated biological sample. Miro1-related disorders include any of the neurodegenerative disorders described herein, for example, Parkinson's disease. As illustrated in Example 64, in normal subjects, the Miro1 level in cells from subject-derived biological samples, such as induced pluripotent stem cells (iPSCs) or skin fibroblasts, that have been treated with the mitochondrial stressor CCCP, was lower than the control Miro1 level in cells that were not treated. However, in Parkinson's disease patients and subjects at risk in developing Parkinson's, the Miro1 levels were similar or higher than the control Miro1 levels (FIGS. 2-4). Accordingly, Miro1 levels could be used for marking a subject at risk of developing a Miro1-related disorder, such as Parkinson's symptomatic and asymptomatic individuals. Further, the higher Miro1 levels correlated with cognitive decline as measured by MMSE scores (FIG. 5), suggesting that Miro1 could be utilized to monitor Parkinson's progression in combination with cognitive impairment. These results suggest that Miro1 levels could be used to identify subjects with presymptomatic Miro1-related disorders, including Parkinson's disease, and to treat the subjects with a compound capable of reducing a Miro1 level before symptoms appear.

I. DEFINITIONS

"Alkyl" is a linear or branched saturated monovalent hydrocarbon. For example, an alkyl group can have 1 to 18 carbon atoms (i.e., $C_{1-18}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), and 3,3-dimethyl-2-butyl ($—CH(CH_3)C(CH_3)_3$. Other alkyl groups include heptyl, octyl, nonyl, decyl, undecyl, dodecyl, pentadcyl, hexadecyl, heptadecyl and octadecyl.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers an alkoxy group linked to an alkyl group which is linked to the remainder of the compound such that the alkyl group is divalent. Alkoxyalkyl can have any suitable number of carbon, such as from 2 to 6 ($C_{2-6}$ alkoxyalkyl), 2 to 5 ($C_{2-5}$ alkoxyalkyl), 2 to 4 ($C_{2-4}$ alkoxyalkyl), or 2 to 3 ($C_{2-3}$ alkoxyalkyl). The number of carbons refers to the total number of carbons in the alkoxy and the alkyl group. For example, $C_6$ alkoxyalkyl refers to ethoxy ($C_2$ alkoxy) linked to a butyl ($C_4$ alkyl), and n-propoxy ($C_3$ alkoxy) linked to a isopropyl ($C_3$ alkyl). Alkoxy and alkyl are as defined above where the alkyl is divalent, and can include, but is not limited to, methoxymethyl ($CH_3OCH_2—$), methoxyethyl ($CH_3OCH_2CH_2—$) and others.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having 6 to 12 annular carbon atoms such as bicyclo[3.1.0]hexane and bicyclo[2.1.1]hexane), and polycyclic carbocycles (e.g., tricyclic and tetracyclic carbocycles with up to 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Heterocyclyl" or "heterocycle" or "heterocycloalkyl" as used herein refers to a single saturated or partially unsaturated non-aromatic ring or a multiple ring system having at least one heteroatom in the ring (i.e., at least one annular heteroatom selected from oxygen, nitrogen, and sulfur) wherein the multiple ring system includes at least non-aromatic ring containing at least one heteroatom. The multiple ring system can also include other aromatic rings and non-aromatic rings. Unless otherwise specified, a heterocyclyl group has from 3 to 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from 1 to 6 annular carbon atoms and from 1 to 3 annular heteroatoms selected from the group consisting of oxygen, nitrogen and sulfur in the ring. The heteroatoms can optionally be oxidized to form —N(—OH)—, =N(—$O^-$)—, —S(=O)— or —$S(=O)_2$—. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having 9 to 20 carbon atoms, e.g., 9 to 16 carbon atoms, in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from 1 to 6 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1-20 carbon atoms and 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl, thianaphthenyl, pyrrolo[2,3-b]pyridinyl, quinazolinyl-4(3H)-one, and triazolyl.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

A "compound of the disclosure" includes compounds described herein, for example a compound of the disclosure includes compounds of Formula (I), (II), (III), (IV), and (V), including the compounds of the Examples.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In some embodiments, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount can vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In some embodiments, the subject is a human.

"Disease" or "condition" refer to a state of being or health status of a patient or subject capable of being treated with a compound, pharmaceutical composition, or method provided herein.

II. COMPOUNDS

The present disclosure provides compounds useful as T-type voltage-dependent calcium channel antagonists.

In some embodiments, the compound has the structure of Formula (I):

(I)

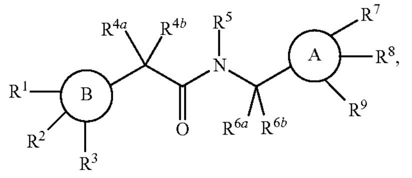

or a pharmaceutically acceptable salt thereof, wherein ring A and ring B are each independently $C_6$-$C_{10}$ aryl or 5- to 10-membered heteroaryl;

$R^1$, $R^2$, and $R^3$ are each independently H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, or 4- to 7-membered heterocyclyl, wherein the phenyl, heteroaryl, cycloalkyl or heterocyclyl is optionally substituted by 1, 2, or 3 halogen, CN, $OR^{11}$, $NR^{12a}R^{12b}$ $C_1$-$C_6$ alkyl, $C_1$-$C_6$ alkoxy, $C_1$-$C_6$ alkylamino, or $C_1$-$C_6$ haloalkyl;

$R^{4a}$ and $R^{4b}$ are each independently H or $C_1$-$C_6$ alkyl;

$R^5$ is H or $C_1$-$C_6$ alkyl;

$R^{6a}$ and $R^{6b}$ are each independently H or $C_1$-$C_6$ alkyl;

$R^7$ is H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, or 4- to 7-membered heterocyclyl, wherein the phenyl, heteroaryl, cycloalkyl or heterocyclyl is optionally substituted by 1, 2, or 3 halogen, CN, $OR^{11}$, $NR^{12a}R^{12b}$, $C_1$-$C_6$ alkyl, $C_1$-$C_6$ alkoxy, $C_1$-$C_6$ alkylamino, or $C_1$-$C_6$ haloalkyl;

$R^8$ is H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl;

$R^9$ is H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl; and each $R^{11}$, $R^{12a}$, and $R^{12b}$ is independently H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen or CN.

In some embodiments, ring A is a 9- to 10-membered heteroaryl.

In some embodiments, ring A is pyrrolopyridine, isoxazolopyridine, pyrazolopyridine, pyrazolopyridazine, or triazolopyridine. In some embodiments, ring A is pyrazolo[3,4-c]pyridin-5-yl, pyrazolo[4,3-c]pyridin-6-yl, isoxazolo[4,5-c]pyridin-6-yl, isoxazolo[5,4-c]pyridin-5-yl, pyrazolo[3,4-b]pyridin-5-yl, pyrazolo[3,4-c]pyridazin-5-yl, [1,2,3]triazolo[4,5-c]pyridin-6-yl, or pyrrolo[2,3-c]pyridin-5-yl. In some embodiments, ring A is pyrazolopyridine.

In some embodiments, the compound has the structure of Formula (II):

(II)

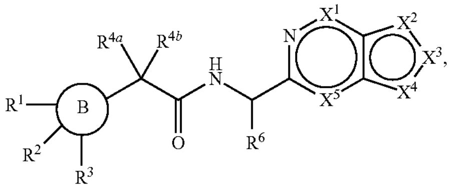

or a pharmaceutically acceptable salt thereof, wherein ring B is $C_6$-$C_{10}$ aryl or 5- to 10-membered heteroaryl;

$R^1$, $R^2$, and $R^3$ are each independently H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, $-(CH_2)_n-(C_3$-$C_7$ cycloalkyl), 4- to 7-membered heterocyclyl, or $-(CH_2)_n$-(4- to 7-membered heterocyclyl), wherein the phenyl, heteroaryl, cycloalkyl or heterocyclyl is optionally substituted by 1, 2, or 3 halogen, CN, $OR^{11}$, $NR^{12a}R^{12b}$ $C_1$-$C_6$ alkyl, $C_1$-$C_6$ alkoxy, $C_1$-$C_6$ alkylamino, or $C_1$-$C_6$ haloalkyl;

$R^{4a}$ and $R^{4b}$ are each independently H or $C_1$-$C_6$ alkyl, or $R^{4a}$ and $R^{4b}$ and the carbon atom to which they are attached form a $C_3$-$C_5$ cycloalkyl;

$R^6$ is H, $C_1$-$C_6$ alkyl, or $C_1$-$C_6$ haloalkyl;

$X^1$ and $X^5$ are each independently N or $CR^8$, provided that at least one of $X^1$ and $X^5$ is $CR^8$; $X^2$, $X^3$, and $X^4$ are each independently N, $NR^9$, O, S, or $CR^9$, provided that at least one of $X^2$, $X^3$, and $X^4$ is N, $NR^9$, O, or S;

$R^8$ is H, halogen, CN, $OR^{11}$, $C_1$-$C_6$ alkyl, $C_2$-$C_6$ alkoxyalkyl, or $C_1$-$C_6$ haloalkyl;

$R^9$ is H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl;

each $R^{11}$, $R^{12a}$, and $R^{12b}$ is independently H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen or CN; and n is 1, 2, or 3.

In some embodiments, $X^1$ is $CR^8$.

In some embodiments, $R^8$ is H.

In some embodiments, $X^2$, $X^3$, and $X^4$ are each independently N, $NR^9$, or $CR^9$, provided that at least one of $X^2$, $X^3$, and $X^4$ is N or $NR^9$.

In some embodiments, $X^1$ is N or $CR^8$, $X^2$ and $X^3$ are each independently N or $NR^9$, $X^4$ is N, $NR^9$, or $CR^9$, and $X^5$ is $CR^8$. For instance, $X^1$ can be $CR^8$, $X^2$ and $X^3$ can be each independently N or $NR^9$, $X^4$ can be N, $NR^9$, or $CR^9$, and $X^5$ can be $CR^8$. In some embodiments, $X^1$ is N or $CR^8$; $X^2$ is N or $NR^9$; $X^3$ is N, $NR^9$, or $CR^9$; $X^4$ is N or $CR^9$; and $X^5$ is $CR^9$. In some embodiments, $X^1$ is $CR^8$; $X^2$ is N or $NR^9$; $X^3$ is N, $NR^9$, or $CR^9$; $X^4$ is N or $CR^9$; and $X^5$ is $CR^9$.

In some embodiments of the compound of Formula (I) and/or (II), the compound does not have the structure:

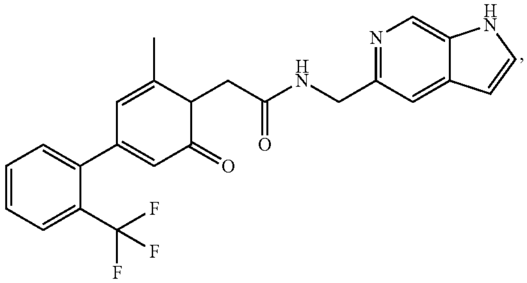 [SMILES: CC1=CC(c2ccccc2C(F)(F)F)=CC(=O)C1CC(=O)NCc1cc2cc[nH]c2cn1], or a pharmaceutically acceptable salt thereof.

In some embodiments of the compound of Formula (I) and/or (II), the compound does not have the structure:

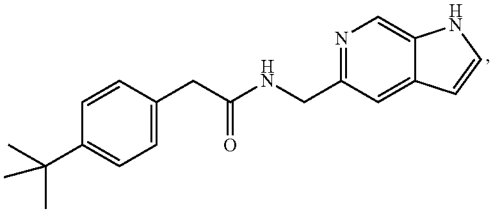 [SMILES: CC(C)(C)c1ccc(CC(=O)NCc2cc3cc[nH]c3cn2)cc1], or a pharmaceutically acceptable salt thereof.

In some embodiments of the compound of Formula (II), the compound has the structure:

(II)

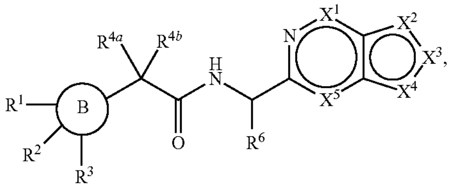

or a pharmaceutically acceptable salt thereof, wherein ring B is $C_6$-$C_{10}$ aryl or 5- to 10-membered heteroaryl;

$R^1$, $R^2$, and $R^3$ are each independently H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, $-(CH_2)_n-(C_3$-$C_7$ cycloalkyl), 4- to 7-membered heterocyclyl, or $-(CH_2)_n$-(4- to 7-membered heterocyclyl), wherein the phenyl, heteroaryl, cycloalkyl or heterocyclyl is optionally substituted by 1, 2, or 3 halogen, CN, $OR^{11}$, $NR^{12a}R^{12b}$ $C_1$-$C_6$ alkyl, $C_1$-$C_6$ alkoxy, $C_1$-$C_6$ alkylamino, or $C_1$-$C_6$ haloalkyl;

$R^{4a}$ and $R^{4b}$ are each independently H or $C_1$-$C_6$ alkyl, or $R^{4a}$ and $R^{4b}$ and the carbon atom to which they are attached form a $C_3$-$C_5$ cycloalkyl;

$R^6$ is H, $C_1$-$C_6$ alkyl, or $C_1$-$C_6$ haloalkyl; $X^1$ and $X^5$ are each independently N or $CR^8$, provided that at least one of $X^1$ and $X^5$ is $CR^8$; $X^2$, $X^3$, and $X^4$ are each independently N, $NR^9$, O, S, or $CR^9$, provided that at least one of $X^2$, $X^3$, and $X^4$ is N, $NR^9$, O, or S;

$R^8$ is H, halogen, CN, $OR^{11}$, $C_1$-$C_6$ alkyl, $C_2$-$C_6$ alkoxyalkyl, or $C_1$-$C_6$ haloalkyl;

$R^9$ is H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl;

each $R^{11}$, $R^{12a}$, and $R^{12b}$ is independently H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen or CN; and n is 1, 2, or 3;

provided that the compound does not have the structure:

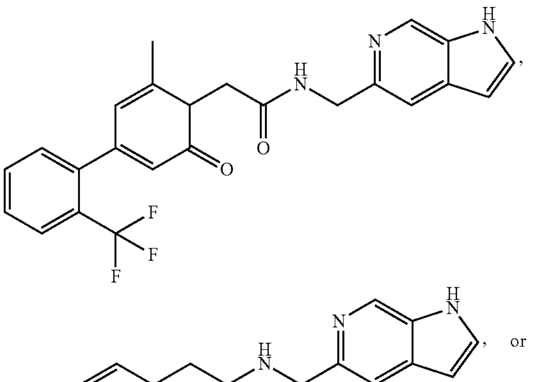

,

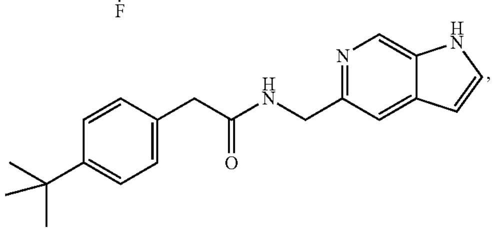

, or

-continued

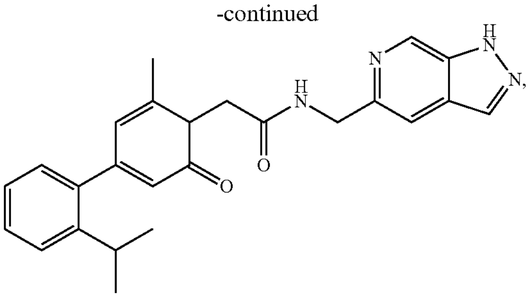

, or a pharmaceutically acceptable salt thereof.

In some embodiments, the compound has the structure of Formula (III):

(III)

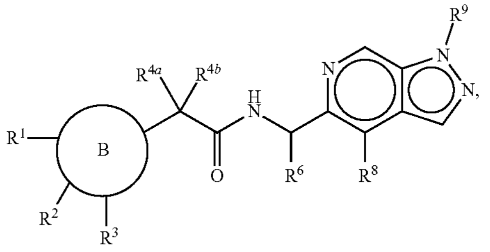

or a pharmaceutically acceptable salt thereof.

In some embodiments of the compound of Formula (I), (II), and/or (III), $R^1$, $R^2$, and $R^3$ are each independently H, halogen, CN, OH, $NH_2$, $C_1$-$C_6$ alkyl, $C_1$-$C_6$ alkoxy, $C_1$-$C_6$ alkylamino, $C_2$-$C_6$ alkoxyalkyl, $C_1$-$C_6$ haloalkyl, or $C_3$-$C_7$ cycloalkyl, wherein the cycloalkyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl.

In some embodiments of the compound of Formula (I), (II), and/or (III), $R^3$ is H, halogen, or CN. In some embodiments, $R^3$ is H or halogen. In some embodiments, $R^3$ is H.

In some embodiments of the compound of Formula (I), (II), and/or (III), $R^{4b}$ is H or $CH_3$.

In some embodiments of the compound of Formula (I), (II), and/or (III), $R^{4a}$ and $R^{4b}$ are each independently H or $CH_3$.

In some embodiments of the compound of Formula (I), (II), and/or (III), ring B is phenyl, 1H-benzo[d]imidazol-5-yl, 1H-indazol-5-yl, benzo[d][1,3]dioxol-5-yl, 2H-indazol-6-yl, thiophen-2-yl, pyridin-2-yl, or pyridin-3-yl; $R^1$ is F, Me, iPr, $CF_3$, $CF_2CH_3$, cyclopropyl, 1-fluorocyclopropyl, 1-cyanocyclopropyl, 2,2-difluorocyclopropyl, or 1-trifluoromethylcyclopropyl, 1,1-difluoromethylcyclopropyl; $R^2$ is H, F, Cl, CN, or $CH_3$; $R^3$ is H or $CH_3$.

In some embodiments, the compound has the structure of Formula (IV):

(IV)

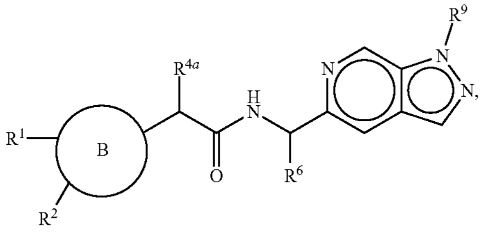

or a pharmaceutically acceptable salt thereof.

In some embodiments of the compound of Formula (I), (II), (III), and/or (IV), ring B is phenyl or 5- to 6-membered heteroaryl. In some embodiments, ring B is phenyl or pyridyl.

In some embodiments of the compound of Formula (I), (II), and/or (III), $R^{4a}$ is H or $CH_3$.

In some embodiments, the compound has the structure of Formula (V):

(V)

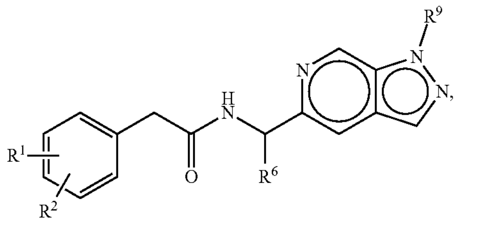

or a pharmaceutically acceptable salt thereof.

In some embodiments of the compound of Formula (I), (II), (III), (IV), and/or (V), $R^1$ is H, halogen, $C_1$-$C_6$ alkyl, $C_1$-$C_6$ alkoxy, or $C_2$-$C_6$ alkoxyalkyl. In some embodiments, $R^1$ is H, halogen, $C_1$-$C_3$ alkyl, or $C_1$-$C_3$ haloalkyl. In some embodiments, $R^1$ is H or halogen. In some embodiments, $R^1$ is $C_1$-$C_3$ haloalkyl. In some embodiments, $R^1$ is $CF_3$.

In some embodiments of the compound of Formula (I), (II), (III), (IV), and/or (V), $R^2$ is H, halogen, $C_1$-$C_6$ alkyl, $C_1$-$C_6$ alkoxy, or $C_2$-$C_6$ alkoxyalkyl. In some embodiments, $R^2$ is H, halogen, $C_1$-$C_3$ alkyl, or $C_1$-$C_3$ haloalkyl. In some embodiments, $R^2$ is H or halogen. In some embodiments, $R^2$ is H.

In some embodiments of the compound of Formula (I), (II), (III), (IV), and/or (V), $R^1$ and $R^2$ are each independently H, halogen, $C_1$-$C_6$ alkyl, $C_1$-$C_6$ alkoxy, $C_2$-$C_6$ alkoxyalkyl, $C_1$-$C_6$ haloalkyl, or $C_3$-$C_7$ cycloalkyl, wherein the cycloalkyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl. In some embodiments, $R^1$ and $R^2$ are each independently H, halogen, $C_1$-$C_3$ alkyl, $C_1$-$C_3$ alkoxy, $C_2$-$C_3$ alkoxyalkyl, $C_1$-$C_3$ haloalkyl, or $C_3$-$C_5$ cycloalkyl, wherein the cycloalkyl is optionally substituted by 1, 2, or 3 halogen, CN, $C_1$-$C_3$ alkyl, $C_1$-$C_3$ alkoxy, $C_1$-$C_3$ alkylamino, or $C_1$-$C_3$ haloalkyl. In some embodiments, $R^1$ and $R^2$ are each independently H, halogen, $C_1$-$C_3$ alkyl, or $C_1$-$C_3$ haloalkyl. In some embodiments, $R^1$ and $R^2$ are each independently H or halogen. In some embodiments, $R^1$ and $R^2$ are each independently H, $C_1$-$C_3$ alkyl, or $C_1$-$C_3$ haloalkyl. In some embodiments, $R^1$ and $R^2$ are each independently H or $C_1$-$C_3$ haloalkyl.

In some embodiments of the compound of Formula (I), (II), (III), (IV), and/or (V), $R^1$ is H or $C_1$-$C_3$ haloalkyl; and $R^2$ is H or halogen. In some embodiments, $R^1$ is $C_1$-$C_3$ haloalkyl; and $R^2$ is H. In some embodiments, $R^1$ is $CF_3$; and $R^2$ is H.

In some embodiments of the compound of Formula (I), (II), (III), (IV), and/or (V), $R^6$ is H or $C_1$-$C_3$ alkyl. In some embodiments, $R^6$ is $CH_3$.

In some embodiments of the compound of Formula (I), (II), (III), (IV), and/or (V), $R^9$ is $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl. In some embodiments, $R^9$ is $C_1$-$C_6$ alkyl, $C_2$-$C_6$ alkoxyalkyl, $C_1$-$C_6$ haloalkyl, $C_3$-$C_7$ cycloalkyl, or 4- to 7-membered heterocyclyl, wherein the cycloalkyl or heterocyclyl is substituted by 0, 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl. In some embodiments, $R^9$ is $C_1$-$C_3$ alkyl, $C_2$-$C_3$ alkoxyalkyl, $C_1$-$C_3$ haloalkyl, $C_3$-$C_7$ cycloalkyl, or 4- to 7-membered heterocyclyl, wherein the cycloalkyl or heterocyclyl is substituted by 0, 1, 2, or 3 F, Cl, CN, OH, $NH_2$, $C_1$-$C_3$ alkyl, $C_1$-$C_3$ alkoxy, $C_1$-$C_3$ alkylamino, or $C_1$-$C_3$ haloalkyl. In some embodiments, $R^9$ is $C_1$-$C_3$ alkyl, $C_2$-$C_3$ alkoxyalkyl, or $C_1$-$C_3$ haloalkyl. In some embodiments, $R^9$ is $C_1$-$C_3$ haloalkyl. In some embodiments, $R^9$ is $CH_2CF_3$.

In some embodiments of the compound of Formula (I), (II), (III), (IV), and/or (V), the compound does not have the structure:

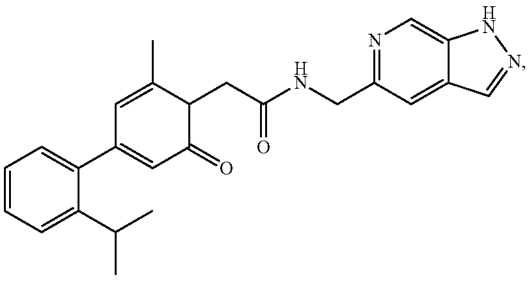 [SMILES: CC1=CC(c2ccccc2C(C)C)=CC(=O)C1CC(=O)NCc1cc2cn[nH]c2cn1]

or a pharmaceutically acceptable salt thereof.

Depending on the specific substitution pattern, the compound of Formula (I), (II), (III), (IV), and/or (V), or pharmaceutically acceptable salt thereof, can have one or more stereocenters. To facilitate compound evaluation, in certain instances, it may be advantageous to separate and to evaluate individual enantiomers and/or diastereomers. Methods to generate individual diastereomers and/or enantiomers are known in the art, including, but not limited to, chromatography, such as chiral chromatography, e.g., supercritical fluid chromatography on a chiral amylose column, and diastereoselective and/or enantioselective synthesis using a chiral auxiliary, for example, organometallic addition to a chiral sulfinimine. See, for instance, procedures described in Example 8. Accordingly, in some embodiments, the compound is enantiomerically enriched, and is present in from about 90% to about 99.999% enantiomeric excess (ee), such as from about 90% to about 99.99%, from about 93% to about 99.99%, from about 95% to about 99.99%, from about 95% to about 99.9%, from about 97% to about 99.9%, from about 98% to about 99.9%, or from about 99% to about 99.99% ee. Absent any other indication, the predominant isomer is the stereochemistry shown in the compound structure herein. In some embodiments, the compound is predominantly the R isomer. In some embodiments, the compound is predominantly the S isomer.

In some embodiments of the compound of Formula (I), (II), (III), (IV), and/or (V), the compound has a structure of any one of the compounds in Table 1 and Table 2, or a pharmaceutically acceptable salt thereof.

In some embodiments of the compound of Formula (I), (II), (III), (IV), and/or (V), the compound has a structure of any one of the compounds in Table 1, or a pharmaceutically acceptable salt thereof.

TABLE 1
| Example | Structure |
|---|---|
| 1 | 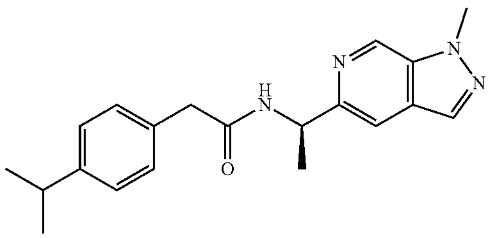 [SMILES: CC(C)c1ccc(CC(=O)N[C@H](C)c2cc3cnn(C)c3cn2)cc1] |
| 2 | 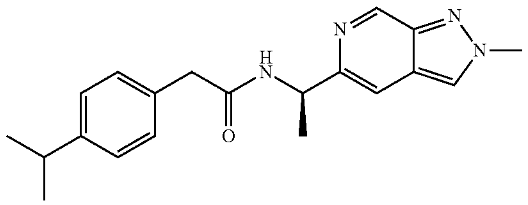 [SMILES: CC(C)c1ccc(CC(=O)N[C@H](C)c2cc3cn(C)nc3cn2)cc1] |
| 3 | 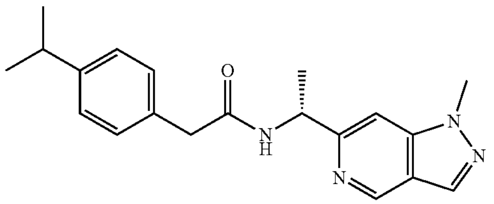 [SMILES: CC(C)c1ccc(CC(=O)N[C@H](C)c2cc3c(cn2)cnn3C)cc1] |
| 4 | 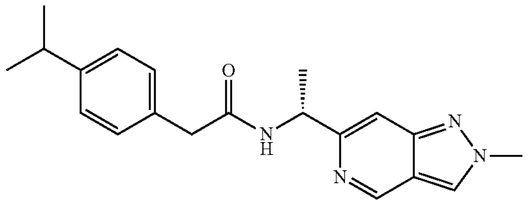 [SMILES: CC(C)c1ccc(CC(=O)N[C@H](C)c2cc3nn(C)cc3cn2)cc1] |
| 5 | 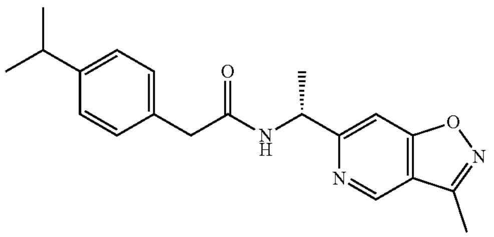 [SMILES: Cc1noc2cc([C@@H](C)NC(=O)Cc3ccc(C(C)C)cc3)ncc12] |
| 6 | 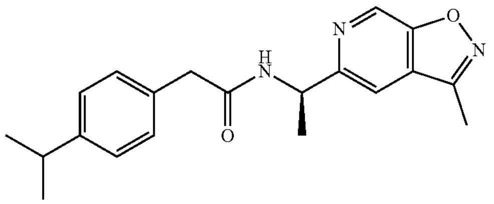 [SMILES: Cc1noc2cnc([C@@H](C)NC(=O)Cc3ccc(C(C)C)cc3)cc12] |

TABLE 1-continued
| Example | Structure |
| --- | --- |
| 7 | 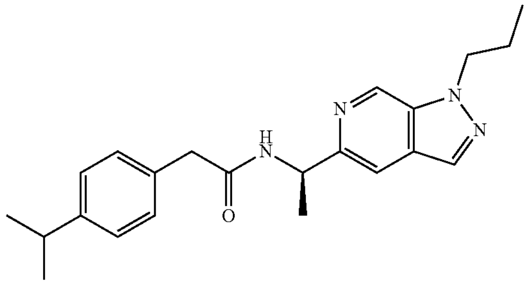 [SMILES: CCCn1ncc2cc([C@@H](C)NC(=O)Cc3ccc(C(C)C)cc3)ncc21] |
| 8 | 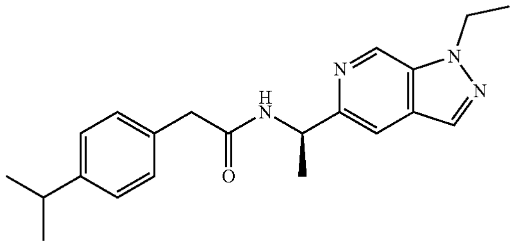 [SMILES: CCn1ncc2cc([C@@H](C)NC(=O)Cc3ccc(C(C)C)cc3)ncc21] |
| 9 | 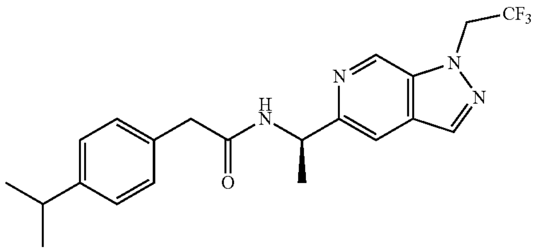 [SMILES: CC(C)c1ccc(CC(=O)N[C@H](C)c2cc3cnn(CC(F)(F)F)c3cn2)cc1] |
| 10 | 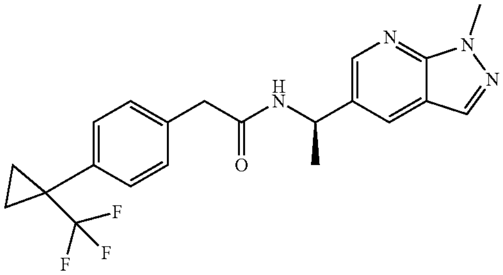 [SMILES: C[C@@H](NC(=O)Cc1ccc(C2(C(F)(F)F)CC2)cc1)c1cnc2c(cnn2C)c1] |
| 11 | 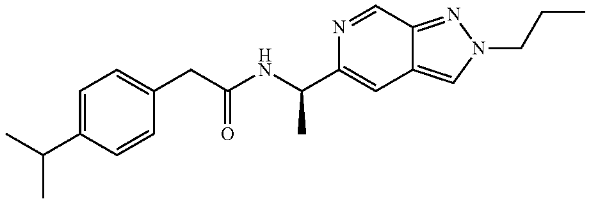 [SMILES: CCCn1cc2cc([C@@H](C)NC(=O)Cc3ccc(C(C)C)cc3)ncc2n1] |
| 12 | 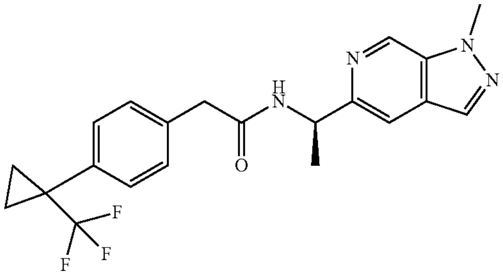 [SMILES: C[C@@H](NC(=O)Cc1ccc(C2(C(F)(F)F)CC2)cc1)c1cc2cnn(C)c2cn1] |

TABLE 1-continued
| Example | Structure |
| --- | --- |
| 13 | 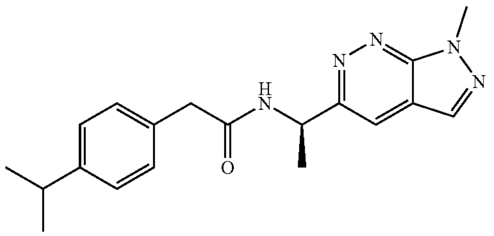 [SMILES: CC(C)c1ccc(CC(=O)N[C@H](C)c2cc3cnn(C)c3nn2)cc1] |
| 14 | 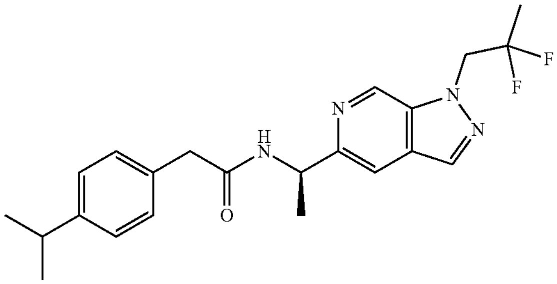 [SMILES: CC(C)c1ccc(CC(=O)N[C@H](C)c2cc3cnn(CC(C)(F)F)c3cn2)cc1] |
| 15 | 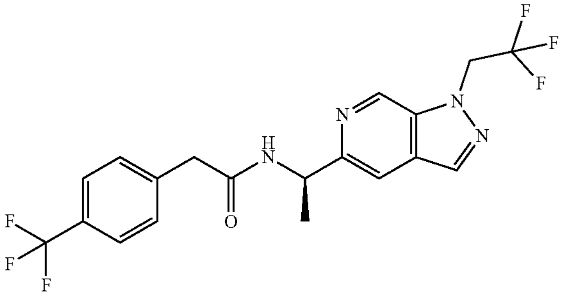 [SMILES: C[C@@H](NC(=O)Cc1ccc(C(F)(F)F)cc1)c1cc2cnn(CC(F)(F)F)c2cn1] |
| 16 | 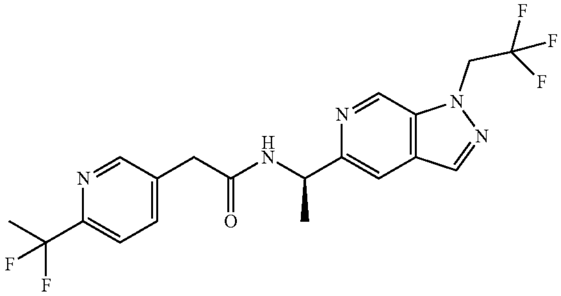 [SMILES: C[C@@H](NC(=O)Cc1ccc(C(C)(F)F)nc1)c1cc2cnn(CC(F)(F)F)c2cn1] |
| 17 | 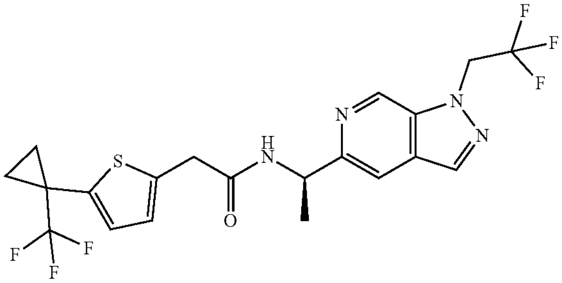 [SMILES: C[C@@H](NC(=O)Cc1ccc(C2(C(F)(F)F)CC2)s1)c1cc2cnn(CC(F)(F)F)c2cn1] |

TABLE 1-continued
| Example | Structure |
| --- | --- |
| 18 | 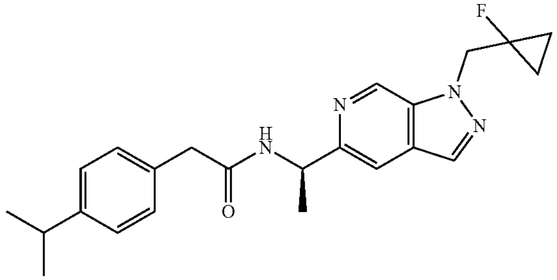 [SMILES: CC(C)c1ccc(CC(=O)N[C@H](C)c2cc3cnn(CC4(F)CC4)c3cn2)cc1] |
| 19 | 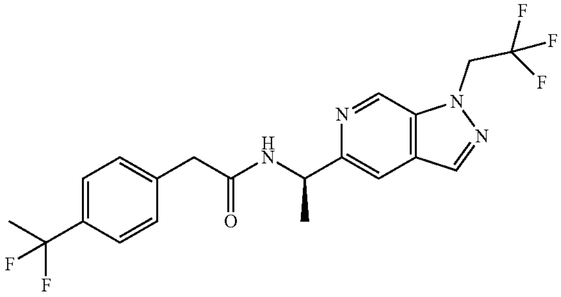 [SMILES: C[C@@H](NC(=O)Cc1ccc(C(C)(F)F)cc1)c1cc2cnn(CC(F)(F)F)c2cn1] |
| 20 | 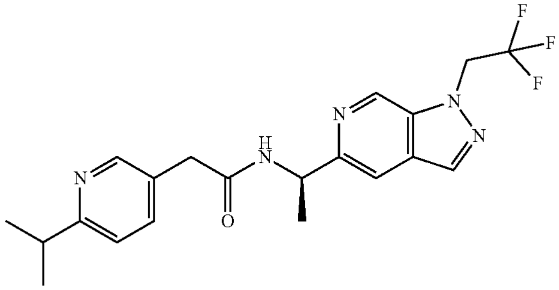 |
| 21 | 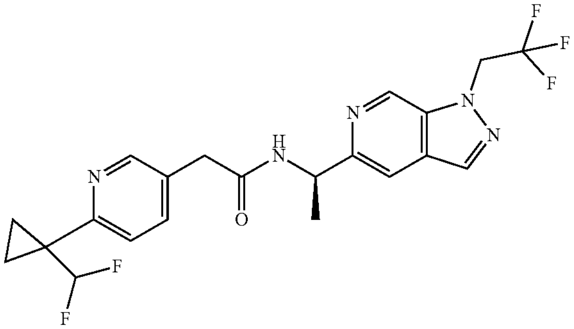 |
| 22 | 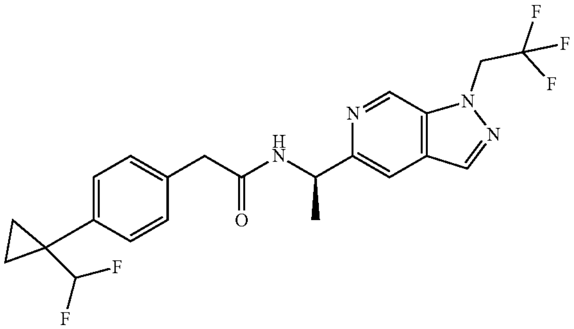 |

TABLE 1-continued
| Example | Structure |
| --- | --- |
| 23 | 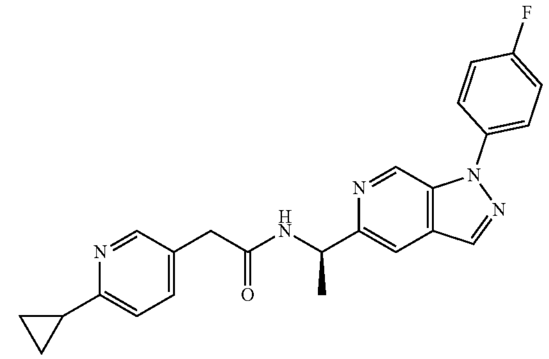 [SMILES: C[C@@H](NC(=O)Cc1ccc(C2CC2)nc1)c1cc2cnn(-c3ccc(F)cc3)c2cn1] |
| 24 | 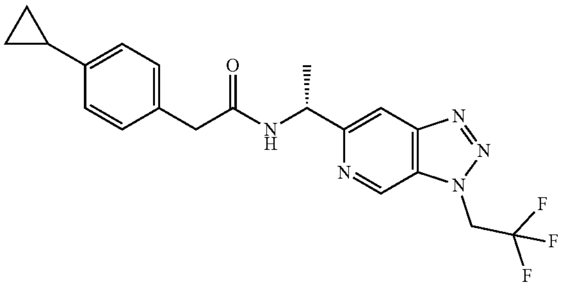 [SMILES: C[C@@H](NC(=O)Cc1ccc(C2CC2)cc1)c1cc2nnn(CC(F)(F)F)c2cn1] |
| 25 | 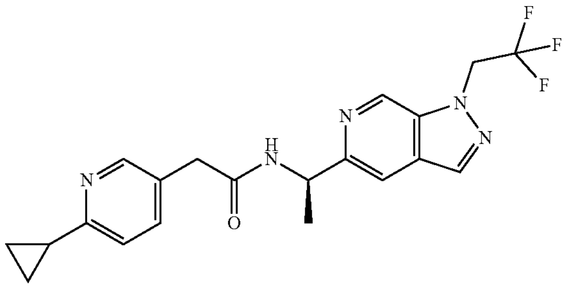 [SMILES: C[C@@H](NC(=O)Cc1ccc(C2CC2)nc1)c1cc2cnn(CC(F)(F)F)c2cn1] |
| 26 | 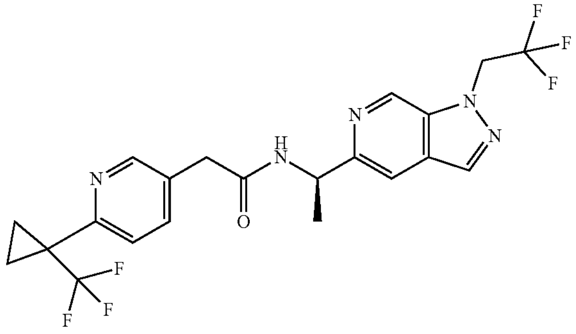 [SMILES: C[C@@H](NC(=O)Cc1ccc(C2(C(F)(F)F)CC2)nc1)c1cc2cnn(CC(F)(F)F)c2cn1] |

TABLE 1-continued
| Example | Structure |
| --- | --- |
| 27 | 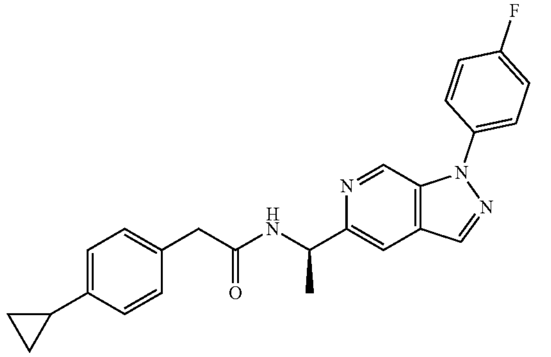 [SMILES: C[C@@H](NC(=O)Cc1ccc(C2CC2)cc1)c1cc2cnn(-c3ccc(F)cc3)c2cn1] |
| 28 | 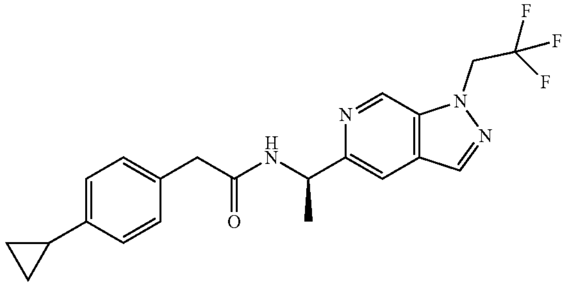 |
| 29 | 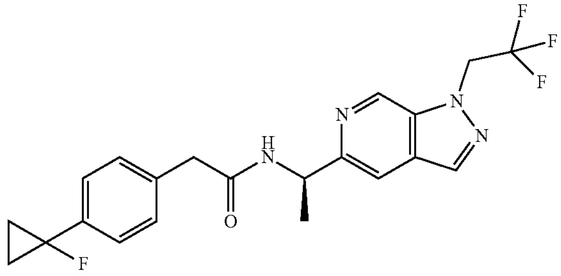 [SMILES: C[C@@H](NC(=O)Cc1ccc(C2(F)CC2)cc1)c1cc2cnn(CC(F)(F)F)c2cn1] |
| 30 | 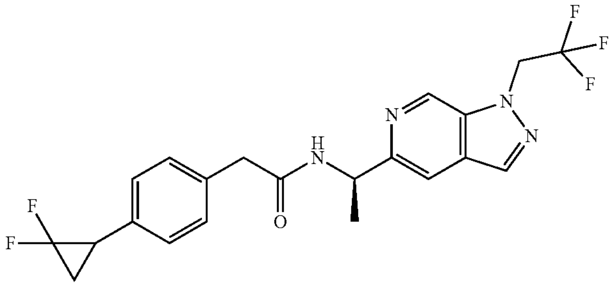 [SMILES: C[C@@H](NC(=O)Cc1ccc(C2CC2(F)F)cc1)c1cc2cnn(CC(F)(F)F)c2cn1]<br>Diastereomer A |
| 31 | 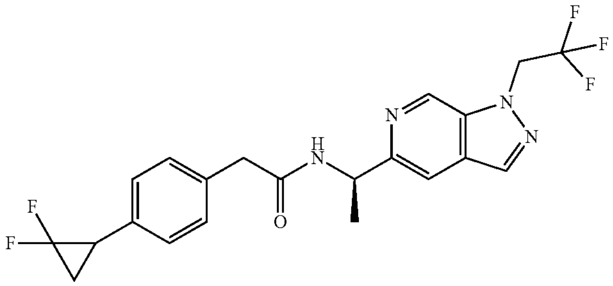 [SMILES: C[C@@H](NC(=O)Cc1ccc(C2CC2(F)F)cc1)c1cc2cnn(CC(F)(F)F)c2cn1]<br>Diastereomer B |

TABLE 1-continued
| Example | Structure |
| --- | --- |
| 32 | 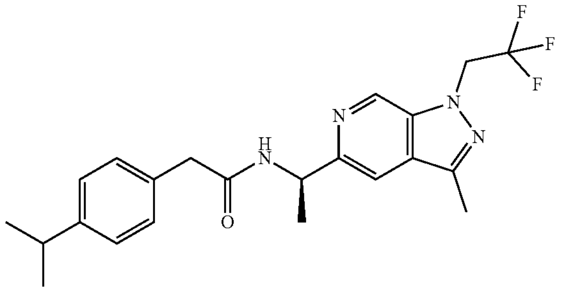 [SMILES: Cc1nn(CC(F)(F)F)c2cnc([C@@H](C)NC(=O)Cc3ccc(C(C)C)cc3)cc12] |
| 33 | 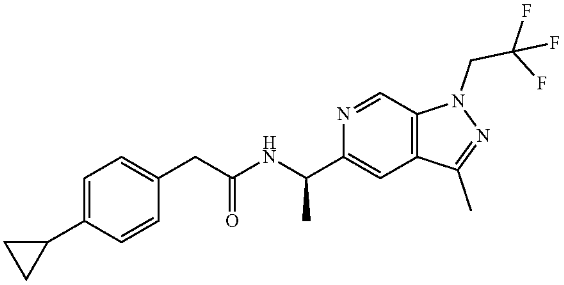 [SMILES: Cc1nn(CC(F)(F)F)c2cnc([C@@H](C)NC(=O)Cc3ccc(C4CC4)cc3)cc12] |
| 34 | 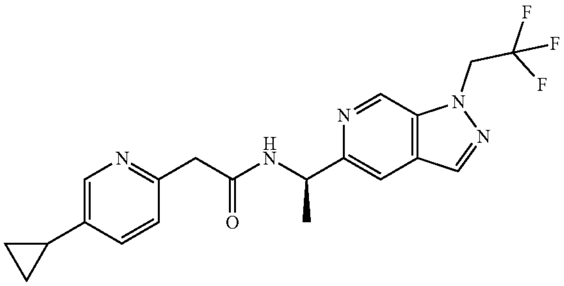 [SMILES: C[C@@H](NC(=O)Cc1ccc(C2CC2)cn1)c1cc2cnn(CC(F)(F)F)c2cn1] |
| 35 | 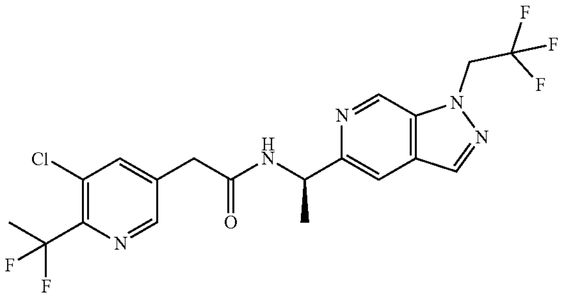 [SMILES: C[C@@H](NC(=O)Cc1cnc(C(C)(F)F)c(Cl)c1)c1cc2cnn(CC(F)(F)F)c2cn1] |

For example, in some embodiments, the compound of the disclosure has the structure:
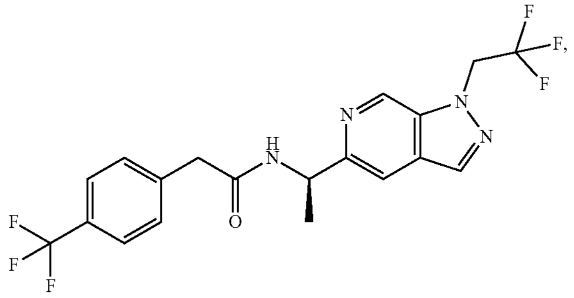 [SMILES: C[C@@H](NC(=O)Cc1ccc(C(F)(F)F)cc1)c1cc2cnn(CC(F)(F)F)c2cn1]
or a pharmaceutically acceptable salt thereof.
In some embodiments of the compound of Formula (I), (II), (III), (IV), and/or (V), the compound has a structure of any one of the compounds in Table 2, or a pharmaceutically acceptable salt thereof.
TABLE 2
| Example | Structure |
|---|---|
| 36 | 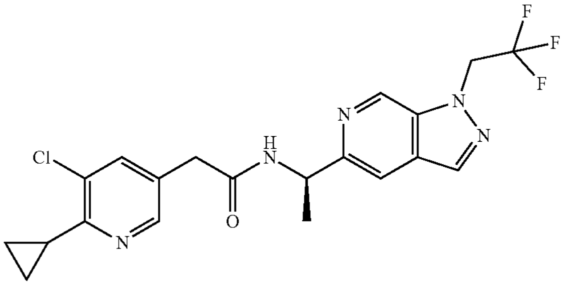 [SMILES: C[C@@H](NC(=O)Cc1cnc(C2CC2)c(Cl)c1)c1cc2cnn(CC(F)(F)F)c2cn1] |
| 37 | 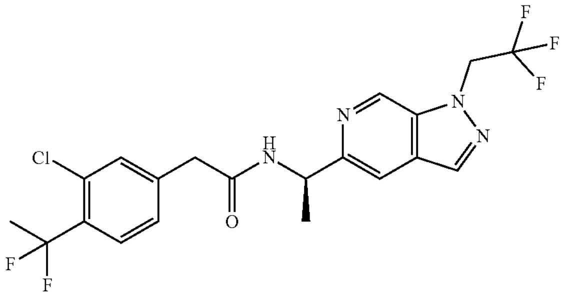 [SMILES: C[C@@H](NC(=O)Cc1ccc(C(C)(F)F)c(Cl)c1)c1cc2cnn(CC(F)(F)F)c2cn1] |
| 38 | 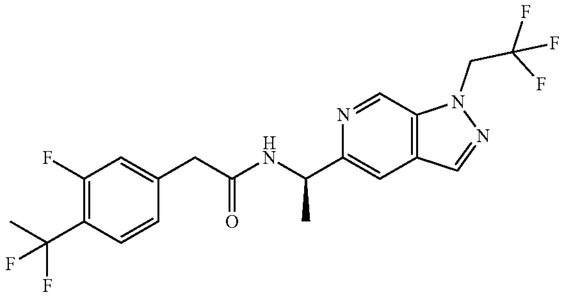 [SMILES: C[C@@H](NC(=O)Cc1ccc(C(C)(F)F)c(F)c1)c1cc2cnn(CC(F)(F)F)c2cn1] |

TABLE 2-continued
| Example | Structure |
|---|---|
| 39 | 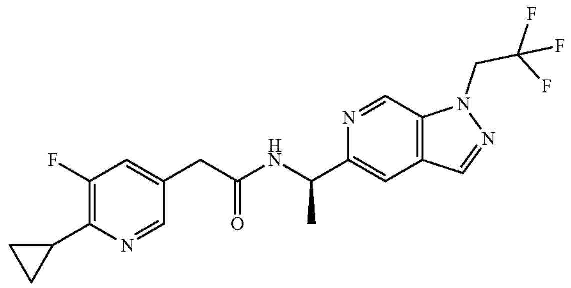 [SMILES: C[C@@H](NC(=O)Cc1cnc(C2CC2)c(F)c1)c1cc2cnn(CC(F)(F)F)c2cn1] |
| 40 | 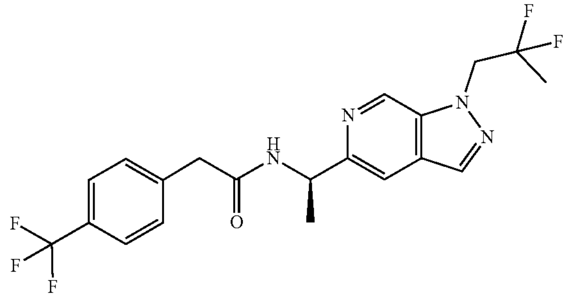 [SMILES: C[C@@H](NC(=O)Cc1ccc(C(F)(F)F)cc1)c1cc2cnn(CC(C)(F)F)c2cn1] |
| 41 | 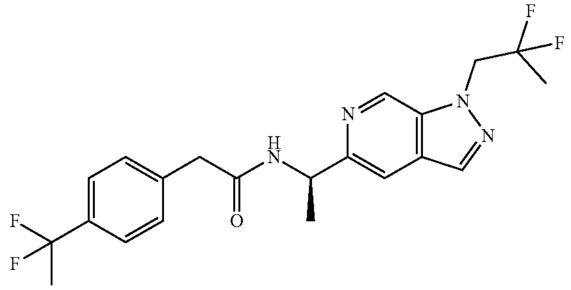 [SMILES: C[C@@H](NC(=O)Cc1ccc(C(C)(F)F)cc1)c1cc2cnn(CC(C)(F)F)c2cn1] |
| 42 | 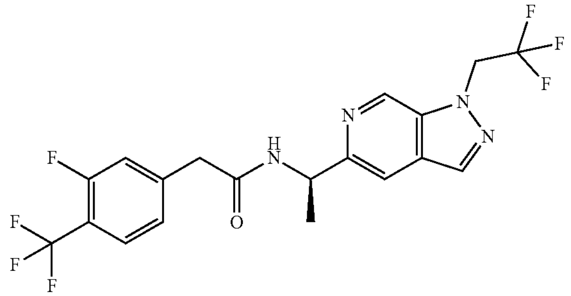 |
| 43 | 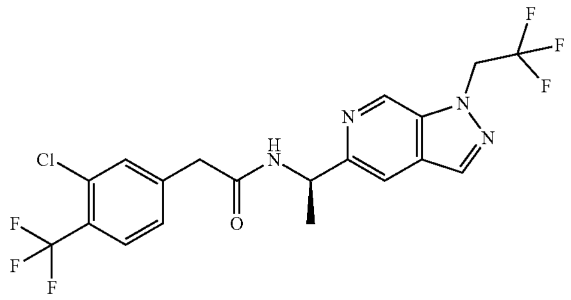 [SMILES: C[C@@H](NC(=O)Cc1ccc(C(F)(F)F)c(Cl)c1)c1cc2cnn(CC(F)(F)F)c2cn1] |

TABLE 2-continued
| Example | Structure |
| --- | --- |
| 44 | 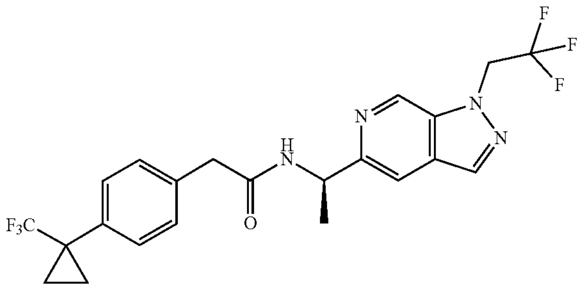 [SMILES: C[C@@H](NC(=O)Cc1ccc(C2(C(F)(F)F)CC2)cc1)c1cc2cnn(CC(F)(F)F)c2cn1] |
| 45 | 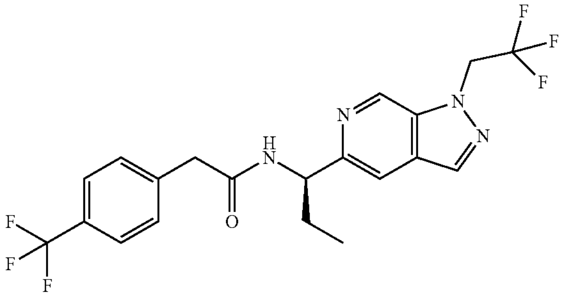 [SMILES: CC[C@@H](NC(=O)Cc1ccc(C(F)(F)F)cc1)c1cc2cnn(CC(F)(F)F)c2cn1] |
| 46 | 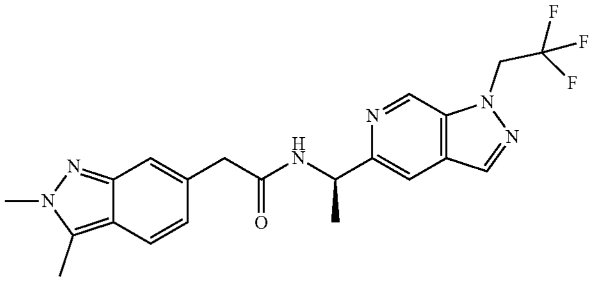 [SMILES: Cc1c2ccc(CC(=O)N[C@H](C)c3cc4cnn(CC(F)(F)F)c4cn3)cc2nn1C] |
| 47 | 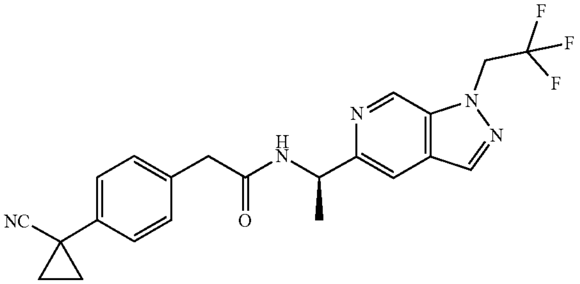 [SMILES: C[C@@H](NC(=O)Cc1ccc(C2(C#N)CC2)cc1)c1cc2cnn(CC(F)(F)F)c2cn1] |
| 48 | 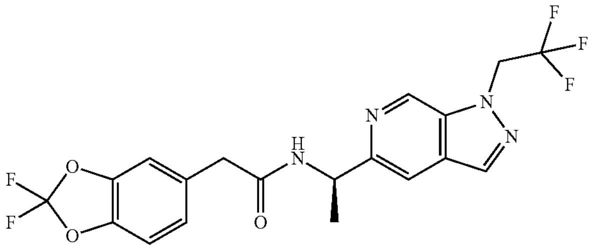 [SMILES: C[C@@H](NC(=O)Cc1ccc2c(c1)OC(F)(F)O2)c1cc2cnn(CC(F)(F)F)c2cn1] |

TABLE 2-continued
| Example | Structure |
|---|---|
| 49 | 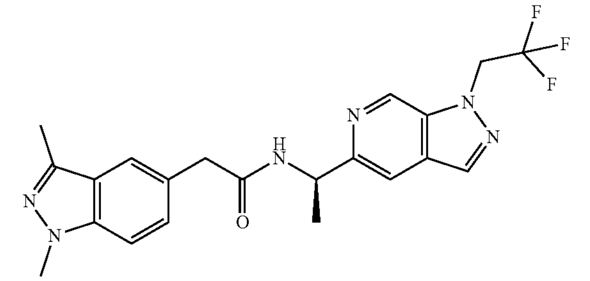 [SMILES: Cc1nn(C)c2ccc(CC(=O)N[C@H](C)c3cc4cnn(CC(F)(F)F)c4cn3)cc12] |
| 50 | 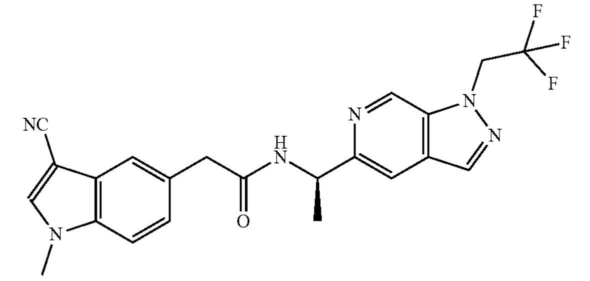 [SMILES: C[C@@H](NC(=O)Cc1ccc2c(c1)c(C#N)cn2C)c1cc2cnn(CC(F)(F)F)c2cn1] |
| 51 | 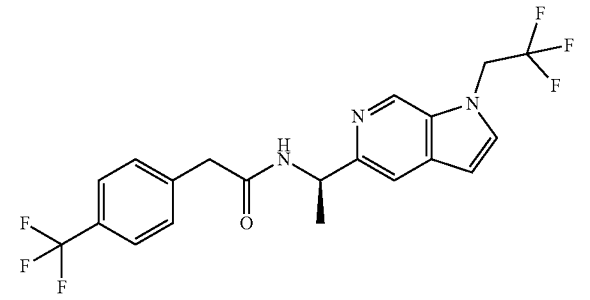 [SMILES: C[C@@H](NC(=O)Cc1ccc(C(F)(F)F)cc1)c1cc2ccn(CC(F)(F)F)c2cn1] |
| 52 | 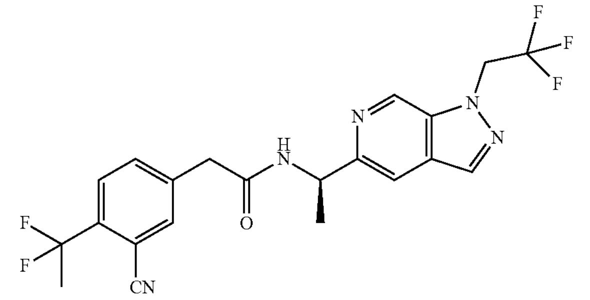 [SMILES: C[C@@H](NC(=O)Cc1ccc(C(C)(F)F)c(C#N)c1)c1cc2cnn(CC(F)(F)F)c2cn1] |
| 53 | 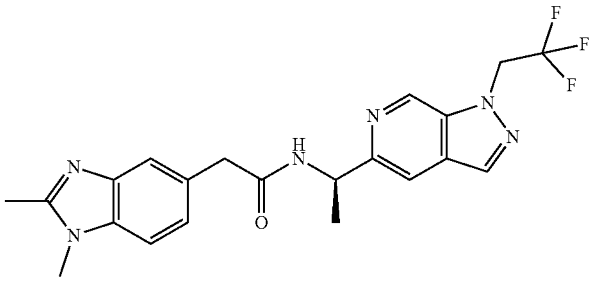 [SMILES: Cc1nc2cc(CC(=O)N[C@H](C)c3cc4cnn(CC(F)(F)F)c4cn3)ccc2n1C] |

TABLE 2-continued
| Example | Structure |
|---|---|
| 54 | 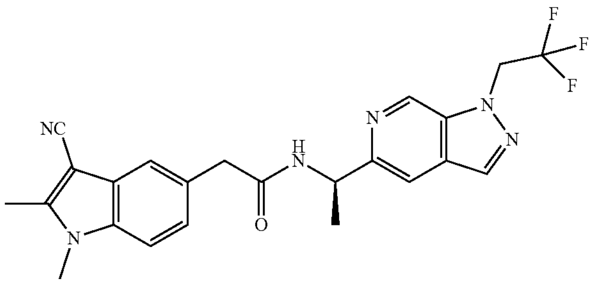 [SMILES: Cc1c(C#N)c2cc(CC(=O)N[C@H](C)c3cc4cnn(CC(F)(F)F)c4cn3)ccc2n1C] |
| 55 | 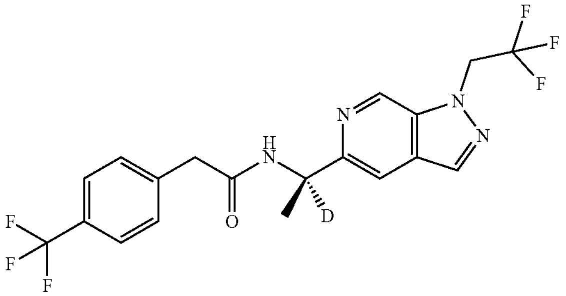 [SMILES: [2H][C@](C)(NC(=O)Cc1ccc(C(F)(F)F)cc1)c1cc2cnn(CC(F)(F)F)c2cn1] |
In some embodiments of the compound of Formula (I), the compound has a structure of any one of the compounds in Table 3, or a pharmaceutically acceptable salt thereof.
TABLE 3
| Example | Structure |
|---|---|
| 56 | 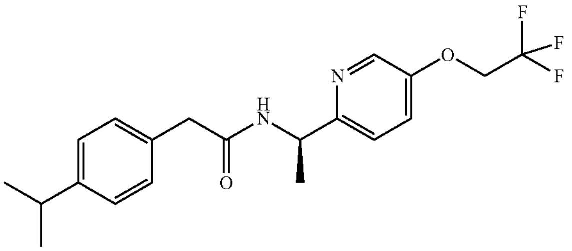 [SMILES: CC(C)c1ccc(CC(=O)N[C@H](C)c2ccc(OCC(F)(F)F)cn2)cc1] |
| 57 | 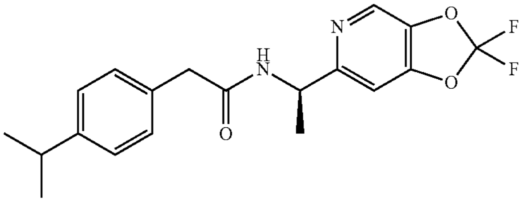 [SMILES: CC(C)c1ccc(CC(=O)N[C@H](C)c2cc3c(cn2)OC(F)(F)O3)cc1] |
| 58 | 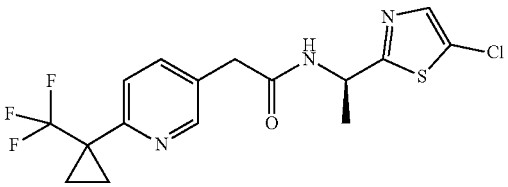 [SMILES: C[C@@H](NC(=O)Cc1ccc(C2(C(F)(F)F)CC2)nc1)c1ncc(Cl)s1] |

TABLE 3-continued

| Example | Structure |
| --- | --- |
| 59 | 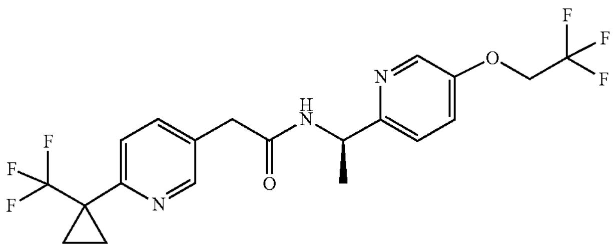 [SMILES: C[C@@H](NC(=O)Cc1ccc(C2(C(F)(F)F)CC2)nc1)c1ccc(OCC(F)(F)F)cn1] |

The compounds described herein are T-type calcium channel antagonists or T-type voltage-dependent calcium channel antagonists. Accordingly, a compound of the disclosure can show T-type calcium channel antagonist activity in one or more assays known in the art or described herein.

Compound Activity

The compounds of the disclosure generally have activity in one or more T-type calcium channel antagonist assays described herein or known in the art. In some embodiments, the compound of the disclosure has T-type calcium channel antagonist activity in a patch clamp assay. In some embodiments, the compound has $IC_{50}$<20 μM in a patch clamp assay. In some embodiments, the compound has $IC_{50}$<10 μM in a patch clamp assay. In some embodiments, the compound has $IC_{50}$<1 μM in a patch clamp assay. In some embodiments, the compound has $IC_{50}$<100 nM in a patch clamp assay. In some embodiments, the compound has $IC_{50}$<10 nM in a patch clamp assay. In some embodiments, the compound has $IC_{50}$<1 nM in a patch clamp assay. In some embodiments, the compound has $IC_{50}$<0.1 nM in a patch clamp assay. In some embodiments, the compound has $IC_{50}$<0.01 nM in a patch clamp assay.

In some embodiments, the compound has an $IC_{50}$ in the range of about 0.01 nM to about 20 μM in a patch clamp assay. In some embodiments, the compound has an $IC_{50}$ in the range of about 0.01 nM to about 10 μM in a patch clamp assay. In some embodiments, the compound has an $IC_{50}$ in the range of about 0.01 nM to about 1 μM in a patch clamp assay. In some embodiments, the compound has an $IC_{50}$ in the range of about 0.01 nM to about 100 nM in a patch clamp assay. In some embodiments, the compound has an $IC_{50}$ in the range of about 0.01 nM to about 10 nM in a patch clamp assay. In some embodiments, the compound has an $IC_{50}$ in the range of about 0.1 nM to about 100 nM in a patch clamp assay. In some embodiments, the compound has an $IC_{50}$ in the range of about 0.1 nM to about 10 nM in a patch clamp assay.

Compound Selectivity Over Other Ion Channels

Compound selectivity is generally preferred in order to effect the desired pharmacological effect while reducing the potential of undesired off-target effects. Accordingly, in some embodiments, the compound of the disclosure is selective for T-type calcium channels over other types, including L-type, N-type, P-type, and/or R-type calcium channels. In some embodiments, the compound of the disclosure is selective for T-type calcium channels over L-type calcium channels. In some embodiments, the compound of the disclosure is selective for T-type calcium channels over N-type calcium channels. In some embodiments, the compound of the disclosure is selective for T-type calcium channels over P-type calcium channels. In some embodiments, the compound of the disclosure is selective for T-type calcium channels over R-type calcium channels.

Comparator ion channels for selectivity determinations include $Ca_v1.2$ (L-type), $Ca_v1.3$ (L-type), $Ca_v2.1$ (P-type), $Ca_v2.2$ (N-type), $Ca_v2.3$ (L-type), $K_v1.5$, $K_v4.3$, KChIP2, $K_v7.1$, KCNE1 (minK), $K_v7.2$, $K_v7.3$, $K_v11.1$ (hERG), HCN4, Kir2.1, Kir3.1, Kir3.4, $Na_v1.1$, $Na_v1.2$, $Na_v1.5$, and $Na_v1.6$.

Selectivity can be determined by comparing the antagonist activity of a given compound on at least two different ion channel types on a comparable assay format. Any suitable assay that can measure calcium channel antagonist activity can be used in determining selectivity. In some embodiments, selectivity can be determined by comparing $IC_{50}$ or % inhibition values. Illustrative assays that can be used to determine activity and selectivity are described further below. For example, a compound selectivity of T-type calcium channel $Ca_v3.1$ can be measured over the R-type calcium channel $Ca_v2.3$ by comparing the compound's antagonist $IC_{50}$ values obtained for each calcium channel by patch clamp assay. A given compound having $Ca_v3.1$ $IC_{50}$=100 nM and $Ca_v2.3$ $IC_{50}$=1000 nM is ten-fold more active against $Ca_v3.1$ than $Ca_v2.3$ and, accordingly, has a ten-fold selectivity for the T-type calcium channel over the R-type calcium channel.

In some embodiments, a compound of the present disclosure has selectivity for T-type calcium channel of at least about 1.2, 1.5, 2, 3, 4, 5, 6, 7, 8, 9, 10, 15, 20, 30, 40, 50, 60, 70, 80, 90, 100, 200, 300, 400, 500, 1000, 2000, 3000, 4000, 5000, 10000, 100000-fold or more over one or more, e.g., 2, 3, or more, other calcium channel types including L-type, N-type, P-type, and/or R-type calcium channels. The selectivity for T-type calcium channels over other calcium channel types including L-type, N-type, P-type, and/or R-type calcium channels may be determined by any assay known in the art, for example, by patch clamp assay. In some embodiments, a compound of the present disclosure has selectivity for T-type calcium channel of at least about 1.2-fold or more over one or more, e.g., 2, 3, or more, other calcium channel types including L-type, N-type, P-type, and/or R-type calcium channels. In some embodiments, a compound of the present disclosure has selectivity for T-type calcium channel of at least about 1.5-fold or more over one or more, e.g., 2, 3, or more, other calcium channel types including L-type, N-type, P-type, and/or R-type calcium channels. In some embodiments, a compound of the present disclosure has selectivity for T-type calcium channel of at least about 10-fold or more over one or more, e.g., 2, 3, or more, other calcium channel types including L-type, N-type, P-type, and/or R-type calcium channels. In some embodiments, a compound of the present disclosure has selectivity for T-type calcium channel of at least about 100-fold or more over one or more, e.g., 2, 3, or more, other calcium channel types including L-type, N-type, P-type, and/or R-type calcium channels. In some embodiments, a compound of the present disclosure has selectivity for T-type calcium channel of at least about 1000-fold or more over one or more, e.g., 2, 3, or more, other calcium channel types including L-type, N-type, P-type, and/or R-type calcium channels. In some embodiments, a compound of the present disclosure has selectivity for T-type calcium channel of at least about 10000-fold or more over one or more, e.g., 2, 3, or more, other calcium channel types including L-type, N-type, P-type, and/or R-type calcium channels. In some embodiments, a compound of the present disclosure has selectivity for T-type calcium channel of at least about 100000-fold or more over one or more, e.g., 2, 3, or more, other calcium channel types including L-type, N-type, P-type, and/or R-type calcium channels.

In some embodiments, a compound of the present disclosure has selectivity for T-type calcium channel in the range of from about 1.2-fold to about 100000-fold over one or more, e.g., 2, 3, or more, other calcium channel types including L-type, N-type, P-type, and/or R-type calcium channels. The selectivity for T-type calcium channels over other calcium channel types including L-type, N-type, P-type, and/or R-type calcium channels may be determined by any assay known in the art, for example, by patch clamp assay. In some embodiments, a compound of the present disclosure has selectivity for T-type calcium channel in the range of from about 1.2-fold to about 10000-fold over one or more, e.g., 2, 3, or more, other calcium channel types including L-type, N-type, P-type, and/or R-type calcium channels. In some embodiments, a compound of the present disclosure has selectivity for T-type calcium channel in the range of from about 1.2-fold to about 1000-fold over one or more, e.g., 2, 3, or more, other calcium channel types including L-type, N-type, P-type, and/or R-type calcium channels. In some embodiments, a compound of the present disclosure has selectivity for T-type calcium channel in the range of from about 1.2-fold to about 100-fold over one or more, e.g., 2, 3, or more, other calcium channel types including L-type, N-type, P-type, and/or R-type calcium channels. In some embodiments, a compound of the present disclosure has selectivity for T-type calcium channel in the range of from about 10-fold to about 100000-fold over one or more, e.g., 2, 3, or more, other calcium channel types including L-type, N-type, P-type, and/or R-type calcium channels. In some embodiments, a compound of the present disclosure has selectivity for T-type calcium channel in the range of from about 100-fold to about 100000-fold over one or more, e.g., 2, 3, or more, other calcium channel types including L-type, N-type, P-type, and/or R-type calcium channels.

III. COMPOSITIONS

The disclosure provides for, inter alia, compositions of one or more compounds that are T-type calcium channel antagonists as disclosed herein. The compositions of the one or more compounds can decrease the level of Miro1 in a cell by acting through T-type calcium channels.

In some embodiments, the composition comprises a compound of the present disclosure, or a salt thereof. In some embodiments, the composition further comprises a carrier or excipient.

In some embodiments, the present disclosure provides a pharmaceutical composition, or pharmaceutical formulation, comprising a pharmaceutically effective amount of a compound of the present disclosure, or a pharmaceutically acceptable salt thereof, and a pharmaceutically acceptable carrier or excipient. The pharmaceutical composition is capable of delivering an amount of a compound of the disclosure sufficient to produce a therapeutically effective treatment as described further below. Also provided herein is a pharmaceutical formulation comprising a pharmaceutically effective amount of a compound of Formula (I), (II), (III), (IV), and/or (V), or a pharmaceutically acceptable salt thereof, and a pharmaceutically acceptable carrier or excipient.

The compounds herein are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations suitable for topical administration to the eye also include eye drops wherein the active ingredient is dissolved or suspended in a suitable carrier, especially an aqueous solvent for the active ingredient. The active ingredient can be present in such formulations in a concentration of about 0.5 to about 20%, such as about 0.5 to about 10%, for example about 1.5% w/w.

IV. METHODS

A. Assays

Calcium channel antagonist activity, including T-type calcium channel antagonist activity, can be assessed using patch clamp assays or fluorescence imaging plate reader (FLIPR) assays known in the art. See, for example, Leech, C. A. and Holz, G. G., IV. Methods Cell Biol. 1994; 40: 135-151; Bell, D. C. and Dallas, M. L. Br. J. Pharmacology 2018, 175, 2312-2321; Bezengon et al., J. Med. Chem. 2017, 60, 9769; Uebele et al., Cell Biochem Biophys 2009. 55, 81; Xiang et al, ACS Chemical Neuroscience 2011, 2, 730; and U.S. Pat. No. 10,562,857.

A T-type calcium channel antagonist capable of reducing Miro1 level and/or activity may be validated as such by any convenient method in the art for detecting the level and/or activity of Miro1 in the presence versus absence of the T-type calcium channel antagonist. For example, the level and/or the phosphorylation state of a Miro protein (Ser156, Thr298 or Thr299 of Miro1 and Miro2, see, e.g., Wang et al. Cell 2011, 147(4): 893-906) may be detected, for example by immunoprecipitation with a mitochondrial transport protein-specific antibody followed by Western blotting with a phospho-specific or a general antibody, where an increase in phosphorylation of Miro proteins and/or a decrease of total Miro protein levels, or a decrease in phosphorylation of Khc following contact with the agent may indicate that the agent will treat Parkinson's Disease. As another example, the level and/or the ubiquitination of a Miro protein may be detected, for example by immunoprecipitation with a mitochondrial transport protein-specific antibody followed by Western blotting with a ubiquitin-specific antibody, where an increase in ubiquitination following contact with the candidate agent indicates that the agent will treat Parkinson's Disease. As another example, the ability of the target mitochondrial protein to transport mitochondria within a cell may be assessed by, for example, treating cultured cells (e.g., neurons) with the T-type calcium channel antagonist and observing the transport of mitochondria in the cells as compared to cells not treating with the T-type calcium channel antagonist, e.g., using live cell imaging techniques (see, e.g., Brickley and Stephenson J. Biol Chem 286(20): 18079-92 (2011); Misko et al. J Neurosci 30(19): 4232-40 (2010); Russo G J et al. J. Neurosci 29(17):5443-55 (2009)). As another example, because the formation of a complex between Miro (e.g., Miro 1 and 2), TRAK (e.g., TRAK1 and 2), and Khc is essential for mitochondrial transport in neurons (see e.g., Brickley and Stephenson J. Biol Chem 286(20): 18079-92 (2011)), the effect of T-type calcium channel antagonist on Miro function may be assessed by assessing the ability of Miro, TRAK and Khc to form a complex in the presence of the T-type calcium channel antagonist. Such an assessment can be performed using any technique to determine protein-protein interaction including, but not limited to, co-immunoprecipitation and affinity purification techniques. In specific embodiments, the ability is assessed in a cell having a familial PD mutation, e.g. a PINK1 or LRRK2 mutation.

Affinity assays, which are often immunoassays, are an assay or analytic procedure that relies on the binding of the target molecule, i.e. Miro1, to receptors, antibodies or other macromolecules. A detection method is used to determine the presence and extent of the binding complexes that are formed. Many formats for such assays are known and used in the art, and are suitable for detection of Miro1 degradation following mitochondrial uncoupling or depolarization. In some embodiments, the assay format is suitable for high-throughput analysis.

Included in suitable assay formats are immunoassays that utilize antibodies specific for Miro1. Suitable antibodies for this purpose are known and commercially available as polyclonal or monoclonal compositions, e.g. from Invitrogen, including monoclonals CL1095, CL1083; from Sigma Aldrich including clone 4H4, Santa Cruz Biotechnology Anti-Rho T1 Antibody (A-8); and the like.

Assays of interest include, for example, Western blots; immunohistochemistry; immunoprecipitation; etc., and particularly include immunoassays such as enzyme-linked immunosorbent assay (ELISA), radioimmunoassay (RIA); enzyme immunoassay (EIA).

Enzyme-linked immunosorbent assays (ELISAs) are used to qualitatively and quantitatively analyze the presence or concentration of a particular soluble antigen such as Miro1, in liquid samples, such as cell lysates. These assays generally make use of the ability of multiwell plates or others to bind antibodies which trap the cognate antigen. Usually a colorimetric endpoint that can be detected via absorbance wavelength and quantitated from a known standard curve of antigen or antibody dilutions is used. The detection antibody is often labelled with an enzyme such as horseradish peroxidase or alkaline phosphatase, or a fluorescent tag, or an electrochemiluminescent label or through an intermediary label such as biotin.

Common ELISA formats include the sandwich ELISA, so named because the analyte is "sandwiched" between two different antibodies. The capture substrate in this format is a capture antibody, often a monoclonal antibody, to increase the specificity of the assay and reduce background noise. The analyte is bound to the capture antibody, then detected by binding to a detection antibody. A variation of sandwich ELISA assay, called Single-Molecule Assay (Simoa), uses beads are coated with a capture antibody; each bead is bound to either one or zero target molecule, and individual beads are detected with another antibody (detection antibody) and a labeling enzyme.

Other ELISA formats include indirect ELISA, where the capture substrate is the specific antigen that is being tested and the detection step is mediated by a primary antibody and an enzyme-conjugated secondary antibody which is reactive against the primary antibody. Thus, the primary antibody that recognizes the antigen is not labeled. In a direct ELISA the capture substrate is the specific antigen that is being tested, and the enzyme that catalyzes the color-change reaction is conjugated to the antigen detector antibody.

Immuno-PCR (I-PCR) is a technique that combines the sensitivity of the nucleic acid amplification by PCR with the specificity of the antibody-based assays resulting in an increase of the detection sensitivity.

An exemplary method for measuring Miro1 reduction after compound administration is described in Hsieh C-H, Li L, Vanhauwaert R, Nguyen K T, Davis M D, Bu G, et al. Miro1 Marks Parkinson's Disease Subset and Miro1 Reducer Rescues Neuron Loss in Parkinson's Models. Cell Metab. 2019; 1131-1140.

B. Methods of Reducing Miro1

Provided herein is a method of reducing Miro1 level in a cell, the method comprising contacting the cell with an effective amount of a T-type calcium channel antagonist. In some embodiments, the T-type calcium channel antagonist has the structure of one or more of the compounds of Formula (I), (II), (III), (IV), and/or (V) described herein. For instance, the method of reducing Miro1 level in a cell can be performed with any one of the compounds of Table 1, Table 2, and Table 3, or a pharmaceutically acceptable salt thereof. The present disclosure further shows that calcium channel antagonists having at least some activity against T-type calcium channels could effect dose-dependent reduction of Miro1 level in Western blot and fibroblast assays (Examples 61 and 62). Compounds having T-type calcium channel antagonist activity and exhibiting Miro1 reducing capability include benidipine (1,4-dihydro-2,6-dimethyl-4-(3-nitrophenyl)-3,5-pyridine-dicarboxylic acid methyl 1-(phenylmethyl)-3-piperidinyl ester); MK-8998 ((R)-2-(4-Isopropylphenyl)-N-(1-(5-(2,2,2-trifluoroethoxy)pyridin-2-yl)ethyl) acetamide); ABT-639 (5-[(8aR)-3,4,6,7,8,8a-hexahydro-1H-pyrrolo[1,2-a]pyrazine-2-carbonyl]-4-chloro-2-fluoro-N-(2-fluorophenyl)benzenesulfonamide); ACT-709478 (N-(1-((5-cyanopyridin-2-yl)methyl)-1H-pyrazol-3-yl)-2-(4-(1-(trifluoromethyl)cyclopropyl)phenyl)acetamide), and zonisamide (1,2-benzisoxazole-3-methanesulfonamide). One illustrative compound, benidipine, exhibited in vivo activity rescuing locomotor deficits in a Parkinson's disease fly model (Example 63).

T-type calcium channel antagonists have been described in U.S. Pat. Nos. 8,377,968; 9,403,798; 10,562,857; US application publication nos. 20120264804; 20150329533; 20160340322; EP 3572403; and PCT publication nos. WO2011022315; WO2012094615; WO2013148640; WO2018200850; WO2019175395; WO2020072773; and WO2021007487; each of which are incorporated in its entirety by reference thereto. Any one of the T-type calcium channel antagonists in the aforementioned publications can be used in a method as described herein.

A reduction of a Miro1 level in a method as described herein is a reduction in the amount of a Miro1 protein and/or a reduction in the activity of a Miro1 protein. In some embodiments, the reduction of a Miro1 level is a reduction in the amount of a Miro1 protein as determined by any assay method, including assays known in the art and the assays described in the present disclosure, that results in a reduction in the Miro1 activity. In Examples 37-39 described herein, the T-type calcium channel antagonist did not induce a Miro1 level in a disease-derived fibroblast or an iPSC DA neuronal cell above that observed in a naïve healthy fibroblast or control iPSC DA neuronal cell. Further, the T-type calcium channel antagonist did not reduce a Miro1 level in a disease-derived fibroblast or an iPSC DA neuronal cell below the control level observed in a naïve healthy fibroblast or control iPSC DA neuronal cell.

Any suitable cell can be used in a method of reducing, or downregulating, Miro1 level described herein. Cultured cells may be derived from patient or control samples; and may be modified to generate genetically-modified cells, in vitro differentiated cells, cells exposed to a candidate therapeutic agent; and the like. In some embodiments, the cell is a muscle cell. For example, the muscle cell can be a cardiac cell, that is, a cardiomyocyte. In some embodiments, the cell is a renal cell. In some embodiments, the cell is a liver cell. In some embodiments, the cell is a neuronal cell. The method can be performed in a cell in vitro, ex vivo, or in vivo. In some embodiments, the reducing Miro1 level is in vitro or ex vivo. In some embodiments, the reducing Miro1 level is in vivo.

Any suitable biological sample comprising cells can be used in the methods described herein. The methods can be performed with a biological sample obtained from a subject, including without limitation biological samples such as fibroblasts, such as skin fibroblasts, peripheral blood lymphocytes, iPSCs, and the like.

A Miro1 level measured in a method described herein can be compared to a control Miro1 level by any method known in the art. See, for example, the ELISA assay described in Hsieh C-H, et al. Cell Metab. 2019; 1131-1140.

In some embodiments, a T-type calcium channel antagonist reduces the level of Miro1 to a normal range. For example, in some embodiments, a Miro1 normal range can be the range observed between untreated or naïve healthy fibroblast or iPSC DA neuron cells (top of the range) and mitochondrial stressor-challenged healthy fibroblast or iPSC DA neuron cells (bottom of the range).

In some embodiments, a T-type calcium channel antagonist reduces, or downregulates, the level of Miro1 to within about 50%, about 40%, about 30%, or about 20% relative to a control level of Miro1. In some embodiments, the control level of Miro1 is measured in a control cell from a control subject that does not have or is not suspected of having a disease or disorder mediated by an aberrant Miro1 level. For example, a T-type calcium channel antagonist can downregulate the Miro1 level in a neuronal cell from a Parkinson's disease patient to within about 50% relative to a control level of Miro1 in a control neuronal cell from an age-matched patient that does not have or is not suspected of having Parkinson's disease.

The level of Miro1 in a cell after contacting with the T-type calcium channel antagonist can be higher or lower than the control level of Miro1 in the control cell. In some embodiments, the level of Miro1 in a cell after contacting with the T-type calcium channel antagonist is about 20%, about 30%, about 40%, or about 50% higher than the control level of Miro1 in the control cell. In some embodiments, the level of Miro1 in a cell after contacting with the T-type calcium channel antagonist is from about 20% to about 50% higher than the control level of Miro1 in the control cell. In some embodiments, the level of Miro1 in a cell after contacting with the T-type calcium channel antagonist is about 20%, about 30%, about 40%, or about 50% lower than the control level of Miro1 in the control cell. In some embodiments, the level of Miro1 in a cell after contacting with the T-type calcium channel antagonist is from about 20% to about 50% lower than the control level of Miro1 in the control cell.

Any suitable concentration of a T-type calcium channel antagonist in a cell can be used to effect reducing the Miro1 level in the cell to a desired level. In some embodiments, the concentration of T-type calcium channel antagonist in the cell can be from about 1 nM to about 100 μM, such as from about 1 nM to about 10 μM, from about 1 nM to about 1 μM, from about 10 nM to about 100 μM, from about 10 nM to about 10 μM, from about 10 nM to about 1 μM, from about 100 nM to about 100 μM, from about 100 nM to about 10 μM, from about 100 nM to about 1 μM, from about 1 μM to about 100 μM, or from about 1 μM to about 10 μM.

In some embodiments, a T-type calcium channel antagonist reduces the level or biological activity of Miro1 by about 20% or more, for example, about 30% or more, about 40% or more, or about 50% or more, about 60% or more, about 70% or more, or about 80% or more, e.g. about 90%, about 95%, or about 100%, relative to an untreated control not contacted with the T-type calcium channel antagonist. In some embodiments, a T-type calcium channel antagonist reduces the level or biological activity of Miro1 by about 20% relative to an untreated control not contacted with the T-type calcium channel antagonist. In some embodiments, a T-type calcium channel antagonist reduces the level or biological activity of Miro1 by about 25% relative to an untreated control not contacted with the T-type calcium channel antagonist. In some embodiments, a T-type calcium channel antagonist reduces the level or biological activity of Miro1 by about 30% relative to an untreated control not contacted with the T-type calcium channel antagonist. In some embodiments, a T-type calcium channel antagonist reduces the level or biological activity of Miro1 by about 35% relative to an untreated control not contacted with the T-type calcium channel antagonist. In some embodiments, a T-type calcium channel antagonist reduces the level or biological activity of Miro1 by about 40% relative to an untreated control not contacted with the T-type calcium channel antagonist. In some embodiments, a T-type calcium channel antagonist reduces the level or biological activity of Miro1 by about 45% relative to an untreated control not contacted with the T-type calcium channel antagonist. In some embodiments, a T-type calcium channel antagonist reduces the level or biological activity of Miro1 by about 50% relative to an untreated control not contacted with the T-type calcium channel antagonist. In some embodiments, a T-type calcium channel antagonist reduces the level or biological activity of Miro1 by about 55% relative to an untreated control not contacted with the T-type calcium channel antagonist. In some embodiments, a T-type calcium channel antagonist reduces the level or biological activity of Miro1 by about 60% relative to an untreated control not contacted with the T-type calcium channel antagonist. In some embodiments, a T-type calcium channel antagonist reduces the level or biological activity of Miro1 by about 65% relative to an untreated control not contacted with the T-type calcium channel antagonist. In some embodiments, a T-type calcium channel antagonist reduces the level or biological activity of Miro1 by about 70% relative to an untreated control not contacted with the T-type calcium channel antagonist. In some embodiments, a T-type calcium channel antagonist reduces the level or biological activity of Miro1 by about 75% relative to an untreated control not contacted with the T-type calcium channel antagonist. In some embodiments, a T-type calcium channel antagonist reduces the level or biological activity of Miro1 by about 80% relative to an untreated control not contacted with the T-type calcium channel antagonist. In some embodiments, a T-type calcium channel antagonist reduces the level or biological activity of Miro1 by about 85% relative to an untreated control not contacted with the T-type calcium channel antagonist. In some embodiments, a T-type calcium channel antagonist reduces the level or biological activity of Miro1 by about 90% relative to an untreated control not contacted with the T-type calcium channel antagonist. In some embodiments, a T-type calcium channel antagonist reduces the level or biological activity of Miro1 by about 95% relative to an untreated control not contacted with the T-type calcium channel antagonist.

In some embodiments, a T-type calcium channel antagonist reduces the level or biological activity of Miro1 by about 20% to about 100% relative to an untreated control not contacted with the T-type calcium channel antagonist. In embodiments, a T-type calcium channel antagonist reduces the level or biological activity of Miro1 by about 20% to about 90% relative to an untreated control not contacted with the T-type calcium channel antagonist. In embodiments, a T-type calcium channel antagonist reduces the level or biological activity of Miro1 by about 20% to about 80% relative to an untreated control not contacted with the T-type calcium channel antagonist. In embodiments, a T-type calcium channel antagonist reduces the level or biological activity of Miro1 by about 20% to about 70% relative to an untreated control not contacted with the T-type calcium channel antagonist. In embodiments, a T-type calcium channel antagonist reduces the level or biological activity of Miro1 by about 20% to about 60% relative to an untreated control not contacted with the T-type calcium channel antagonist. In embodiments, a T-type calcium channel antagonist reduces the level or biological activity of Miro1 by about 20% to about 50% relative to an untreated control not contacted with the T-type calcium channel antagonist. In embodiments, a T-type calcium channel antagonist reduces the level or biological activity of Miro1 by about 20% to about 40% relative to an untreated control not contacted with the T-type calcium channel antagonist. In embodiments, a T-type calcium channel antagonist reduces the level or biological activity of Miro1 by about 30% to about 50% relative to an untreated control not contacted with the T-type calcium channel antagonist. In embodiments, a T-type calcium channel antagonist reduces the level or biological activity of Miro1 by about 40% to about 60% relative to an untreated control not contacted with the T-type calcium channel antagonist. C. Methods of Identifying a Subject at Risk of Developing a Miro1-Related Disorder A deficiency in the ability to degrade or clear Miro1 from cells is believed to correlate with the development of a Miro1-related disorder, for example, a neurodegenerative disorder, such as Parkinson's disease, before a subject displays an overt symptom of the neurodegenerative disorder, such as one or more of the symptoms described herein. Accordingly, in some embodiments, the subject is asymptomatic for a neurodegenerative disorder. Example 64 shows experimental data that supports correlation of a deficiency to remove Miro1 from cells derived from Parkinson's disease patients or those at risk of developing Parkinson's disease. See also, FIGS. 2-5, showing high Miro1 ratio correlation to Parkinson's disease in patient-derived skin fibroblast and iPSC cells. Hence, Miro1 may be used as a predictive biomarker for a neurodegenerative disorder in a subject at risk of developing such disorder, for example, as an initial step in treating the neurodegenerative disorder before symptoms appear. The subject at risk can have familial history of developing a neurodegenerative disorder, can present a genetic marker associated with increased risk of developing a neurodegenerative disorder, for example, LRRK2 G2019S mutation for Parkinson's disease, or can have no known risk of developing a neurodegenerative disorder.

As previously described in Hsieh C-H, et al. Cell Metab. 2019; 1131-1140, and PCT publication WO 2021/046368, a Miro1 level in cells treated with a mitochondrial stressor is expected to be lower than a control Miro1 level in untreated control cells due to mitophagy processes induced by the mitochondrial stressor. With biological sample cells derived from a subject, a Miro1 level that is similar or higher in cells treated with a mitochondrial stressor compared to a control Miro1 level in untreated control cells may indicate a neurodegenerative disorder that correlates with defective mitophagy processes.

In some embodiments, provided is a method for identifying a subject at risk of developing a Miro1-related disorder, the method comprising: a) detecting whether a Miro1 level is similar or higher in a biological sample obtained from the subject and treated with a mitochondrial stressor, as compared to a control Miro1 level in a control biological sample obtained from the subject and is untreated; and b) identifying the subject at risk of developing a Miro1-related disorder if the Miro1 level is similar or higher in the biological sample compared to the control Miro1 level in the control biological sample, wherein the biological sample and the control biological sample comprise iPSCs or cells differentiated from iPSCs. In some embodiments, the method further comprises treating the subject at risk of developing a Miro1-related disorder by administering a therapeutically effective amount of a compound described herein, or pharmaceutically acceptable salt thereof. In certain embodiments, the compound is a compound as described in Table 1, or a pharmaceutically acceptable salt thereof.

In some embodiments, provided is a method for identifying a subject at risk of developing a Miro1-related disorder, the method comprising: a) detecting whether a Miro1 level is similar or higher in a biological sample obtained from the subject and treated with a mitochondrial stressor, as compared to a control Miro1 level in a control biological sample obtained from the subject and is untreated; b) identifying the subject at risk of developing a Miro1-related disorder if the Miro1 level is similar or higher in the biological sample compared to the control Miro1 level in the control biological sample; and c) treating the subject at risk of developing a Miro1-related disorder by administering a therapeutically effective amount of a compound described herein, or pharmaceutically acceptable salt thereof. In some embodiments, the compound is a compound of Formula (I), (II), (III), (IV), and/or (V), or pharmaceutically acceptable salt thereof. In certain embodiments, the compound is a compound as described in Table 1, or a pharmaceutically acceptable salt thereof.

A Miro-1 related disorder is any disease or disorder that correlates with abnormal degradation and/or clearance of a Miro1 protein, and includes any one of the neurodegenerative disorders described herein. In some embodiments, the Miro-1 related disorder is Drug-induced Parkinsonism, Progressive supranuclear Palsy, Vascular Parkinsonism, Dementia with Lewy Bodies, diffuse Lewy body disease, Corticobasal degeneration, multisystem degeneration (Shy-drager syndrome), Parkinson's disease, Alzheimer's disease, Pick's disease, frontotemporal dementia, multiple systems atrophy, vascular dementia, or progressive supranuclear palsy (Steel-Richardson syndrome). In some embodiments, the Miro1-related disorder is Parkinson's disease. In some embodiments, the Miro1-related disorder is Alzheimer's disease. In some embodiments, the Miro1-related disorder is Pick's disease. In some embodiments, the Miro1-related disorder is frontotemporal dementia. In some embodiments, the Miro1-related disorder is multiple systems atrophy.

Further provided herein is a method for treating a neurodegenerative disorder in a subject in need thereof, the method comprising: a) detecting whether a Miro1 level is similar or higher in a biological sample obtained from the subject and treated with a mitochondrial stressor, as compared to a control Miro1 level in a control biological sample obtained from the subject and is untreated; b) identifying the subject for treatment if the Miro1 level is similar or higher in the biological sample compared to the control Miro1 level in the control biological sample; and c) administering a therapeutically effective amount of a compound as described herein, or pharmaceutically acceptable salt thereof, to the subject. In some embodiments, the neurodegenerative disorder is Drug-induced Parkinsonism, Progressive supranuclear Palsy, Vascular Parkinsonism, Dementia with Lewy Bodies, diffuse Lewy body disease, Corticobasal degeneration, multisystem degeneration (Shy-drager syndrome), Parkinson's disease, Alzheimer's disease, Pick's disease, frontotemporal dementia, multiple systems atrophy, vascular dementia, or progressive supranuclear palsy (Steel-Richardson syndrome). In some embodiments, the compound is a compound of Formula (I), (II), (III), (IV), and/or (V), or pharmaceutically acceptable salt thereof. In certain embodiments, the compound is a compound as described in Table 1, or a pharmaceutically acceptable salt thereof. Example 65 illustrates one compound of the disclosure, Example 15, showing a dose-dependent rescue of Miro1 deficit in fibroblasts of a P301L tau donor at risk for developing frontotemporal dementia (FTD).

Any suitable biological sample described herein can be used in the methods. In some embodiments, the biological sample and the control biological sample comprise fibroblasts. For example, skin fibroblasts can be directly obtained from the subject. In some embodiments, the biological sample and the control biological sample comprise iPSCs or cells differentiated from iPSCs.

iPSCs can be directly obtained from a subject or be cultured from other cell types obtained from a subject according to any method known in the art. See, Shi, Y. et al. Nature Reviews Drug Discovery vol. 16, pages 115-130 (2017), and references cited therein. For example, iPSCs can be dedifferentiated from fibroblast cells that were directly obtained from a subject. Additionally, iPSCs can be redifferentiated into a variety of different cell types, including neuronal cells, skin cells, blood cells, and liver cells.

Such cells differentiated from iPSCs of a subject can be used to determine a personalized therapy in a convenient manner without directly obtaining a target cell type directly from a subject. In an illustrative example, a skin fibroblast can be obtained from a subject at risk for developing Parkinson's disease. The skin fibroblast can be dedifferentiated into iPSCs, which can then be redifferentiated into motor neurons. The motor neurons differentiated from iPSCs can be tested in an assay described herein for Miro1 deficit with and without treatment of a mitochondrial stressor in order to identify whether the subject may be responsive to a Miro1 reducing therapy, such as one containing a compound of the disclosure.

Methods for comparing a Miro1 level to a control Miro1 level are known in the art. When detecting whether a Miro1 level is similar or higher in a biological sample obtained from the subject and treated with a mitochondrial stressor, as compared to a control Miro1 level in a control biological sample obtained from the subject and is untreated, the ratio of the Miro1 level to the control Miro1 level can be compared. In some embodiments, the ratio of the Miro1 level to the control Miro1 level is from about 0.5 to about 10, such as from about 0.5 to about 5, from about 0.6 to about 6, from about 0.7 to about 4, from about 0.7 to about 3, from about 0.8 to about 3, or from about 0.9 to about 2. For example, the ratio of the Miro1 level to the control Miro1 level can be from about 0.5 to about 10. In another example, the ratio of the Miro1 level to the control Miro1 level can be from about 0.7 to about 4.

Any mitochondrial stressor known in the art may be used in the methods described herein. Suitable mitochondrial stressors include mitochondrial depolarizing agents, such as carbonyl cyanide 4-(trifluoromethoxy)phenylhydrazone (FCCP) and carbonyl cyanide 3-chlorophenylhydrazone (CCCP); mitochondrial electron transport chain inhibitors, including Complex I inhibitors, such as rotenone, piericidin A, 1-methyl-4-phenyl-1,2,3,6-tetrahydropyridine (MPTP), and paraquat, Complex III inhibitors, such as antimycin A, Complex V inhibitors, such as oligomycin A, and mitochondrial membrane potassium ionophores, such as valinomycin; metabolic modulators, including modulators of insulin signaling, such as metformin, and inhibitors of mTOR master signaling pathway required for cell growth and metabolism, such as rapamycin. In some embodiments, the mitochondrial stressor is carbonyl cyanide 3-chlorophenylhydrazone (CCCP). In some embodiments, the mitochondrial stressor is carbonyl cyanide 4-(trifluoromethoxy)phenylhydrazone (FCCP).

D. Methods of Treatment

Provided herein is a method of treating a neurodegenerative disorder, the method comprising administering to the subject a therapeutically effective amount of a T-type calcium channel antagonist, or a pharmaceutical composition thereof, described herein. In some embodiments, the T-type calcium channel antagonist is a compound of Formula (I), (II), (III), (IV), and/or (V), or a pharmaceutically acceptable salt thereof. In some embodiments, the method delivers a therapeutically effective amount of a compound of the disclosure, or a pharmaceutical composition thereof, sufficient to treat one or more symptoms of a condition described further below.

Neurodegenerative disorders included within the methods of the present disclosure include, but are not limited to neurological disorders that share symptoms similar to those seen in Parkinson's disease related disorders. In some cases, the neurological disorders may show symptoms similar to Parkinson's disease, atypical Parkinson's disease or Parkinson's plus disease. Examples include but are not limited to Drug-induced Parkinsonism, Progressive supranuclear Palsy, Vascular Parkinsonism, Dementia with Lewy Bodies, diffuse Lewy body disease, Corticobasal degeneration, multisystem degeneration (Shy-drager syndrome), Alzheimer's disease, Pick's disease, frontotemporal dementia, multiple systems atrophy, vascular dementia, and progressive supranuclear palsy (Steel-Richardson syndrome). Other conditions also included within the methods of the present invention include age-related dementia and other dementias and conditions with memory loss including vascular dementia, diffuse white matter disease (Binswanger's disease), dementia of endocrine or metabolic origin, dementia of head trauma and diffuse brain damage, dementia pugilistica and frontal lobe dementia. In some cases, the neurological disorder may not respond well to dopaminergic treatments and may be caused as a result of various vascular, drug-related, infectious, toxic, structural and other known secondary causes. Drug-induced Parkinsonism may be caused by agents that block post-synaptic dopamine D2 receptors with high affinity, such as anti-psychotic and anti-emetic medications and sodium valproate, anti-depressants, reserpine, tetrabenazine etc.

A variety of subjects are suitable for treatment with a T-type calcium channel antagonist of the present disclosure. Suitable subjects include any subject who displays symptoms of Parkinson's disease such as bradykinesia, repetitive movements, tremors, limb rigidity, gait and balance problems, inability to aim the eyes due to weakness of eye muscles, weakness, sensory loss, non-motor manifestations such as REM sleep behavior disorder, neuropsychiatric symptoms including mood disturbances and cognitive changes, anxiety, apathy, changes in thinking ability, level of attention or alertness and visual hallucinations, intellectual and functional deterioration, forgetfulness, personality changes, autonomic dysfunction affecting cardiovascular, respiratory, urogenital, gastrointestinal and sudomotor function, difficulties in breathing and swallowing, inability to sweat, orthostatic hypotension, pain, constipation, and loss of olfaction, e.g., hyposmia. In some embodiments, the subjects may experience predominant speech or language disorder, predominant frontal presentation and gait freezing.

In some embodiments, the subject may not display any overt symptoms of Parkinson's disease. In some cases, the subject in need may show increased susceptibility to infections, hypothermia, weaker bones, joint stiffness, arthritis, stooped posture, slowed movements, decrease in overall energy, constipation, urinary incontinence, memory loss, slower thinking, slower reflexes, difficulty with balance, decrease in visual acuity, diminished peripheral vision, hearing loss, wrinkling skin, greying hair, weight loss, loss of muscle tissue.

In some embodiments, the subject is selected from those that have been diagnosed as having Alzheimer's disease; subjects who have suffered one or more strokes; subjects who have suffered traumatic head injury; individuals who have high serum cholesterol levels; subjects who have proteinopathies including deposits in brain tissue; subjects who have had one or more cardiac events; subjects undergoing cardiac surgery; and subjects with multiple sclerosis.

In some embodiments, the subject displays symptoms associated with neurological diseases that include motor neuron diseases such as amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Also other neurodegenerative disorders resulting from cerebral ischemia or infaction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

V. EXAMPLES

Abbreviations. Certain abbreviations and acronyms are used in describing the experimental details. Although most of these would be understood by one skilled in the art, listed below are many of these abbreviations and acronyms.

| Abbreviation | Meaning |
|---|---|
| ACN | acetonitrile |
| Bn | benzyl |
| Boc | tert-butoxycarbonyl |
| Bu | butyl |
| nBuLi | n-butyllithium |
| cBu | cyclobutyl |
| $CDCl_3$ | Chloroform-d |
| cHex | Cyclohexyl |
| cPr | cyclopropyl |
| DCM | dichloromethane |
| DMAP | 4-dimethylaminopyridine |
| DMSO | dimethylsulfoxide |
| DMF | dimethylformamide |
| EA | Ethyl acetate |
| EDCI | N-(3-dimethylaminopropyl)-N'-ethylcarbodiimide hydrochloride |
| Et | ethyl |
| iBu | isobutyl |
| iPr | isopropyl |
| LC | liquid chromatography |
| Me | methyl |
| m/z | mass to charge ratio |
| MS or ms | mass spectrum |
| NMP | N-methyl-2-pyrrolidone |
| Ph | phenyl |
| $Ph_3P$ | triphenylphosphine |
| prep. HPLC | preparative high performance liquid chromatography (also prep-HPLC) |
| RT | room temperature |
| tBu | tert -butyl |
| TEA | triethylamine |
| TFA | trifluoroacetic acid |
| THF | tetrahydrofuran |
| TLC | thin layer chromatography |
| TMS | trimethylsilyl |
| TMSCl | trimethylsilyl chloride |
| δ | parts per million referenced to residual non-deuterated solvent peak |

Example 1. (R)-2-(4-isopropylphenyl)-N-(1-(1-methyl-1H-pyrazolo[3,4-c]pyridin-5-yl)ethyl)acetamide

Step 1. Synthesis of 5-bromo-1H-pyrazolo[3,4-c]pyridine

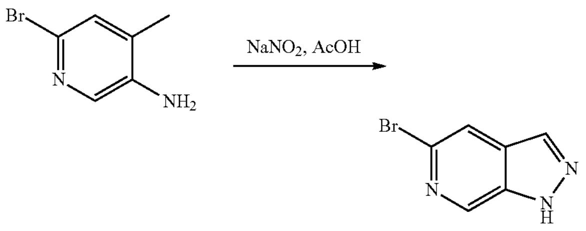

To a solution of 6-bromo-4-methylpyridin-3-amine (1.0 g) in acetic acid (60 mL) were added sodium nitrite (0.37 mL) while cooling in an ice bath. The reaction was stirred at RT overnight. Then the reaction was concentrated and then treated with saturated aqueous $NaHCO_3$. The aqueous mixture was extracted with EA. The organic layer was separated, washed with brine, dried over with $Na_2SO_4$, filtered and concentrated in vacuo. Then the residue was purified by silica gel column chromatography, to give 5-bromo-1H-pyrazolo[3,4-c]pyridine (442 mg). LC/MS ESI (m/z): 198 $[M+H]^+$.

Step 2. Synthesis of 1H-pyrazolo[3,4-c]pyridine-5-carbaldehyde

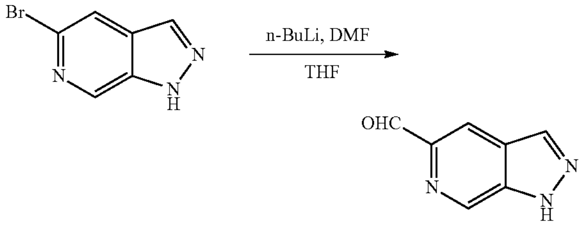

To a solution of 5-bromo-1H-pyrazolo[3,4-c]pyridine (3.3 g) in anhydrous THE (100 mL) was added n-BuLi (20.0 mL, 2 N in THF) at −78° C. The mixture was stirred at −78° C. for 1 hr. DMF (3.87 mL) was then added to the mixture at −78° C., and the mixture was stirred at −78° C. for 1 hr. The reaction was warmed to rt and quenched with an $NH_4Cl$ solution. The two phases were separated, and the aqueous phase was extracted with DCM (10 mL×3). The combined organic layers were dried over $Na_2SO_4$, filtered and concentrated to give a residue, which was purified by column chromatography on silica gel (DCM:MeOH=1:0 to 20:1) to give 1H-pyrazolo[3,4-c]pyridine-5-carbaldehyde (1.0 g) as a white solid. LC/MS ESI (m/z): 148 $[M+H]^+$.

Step 3. Synthesis of 1-methyl-1H-pyrazolo[3,4-c]pyridine-5-carbaldehyde

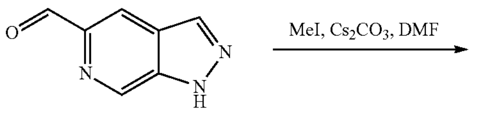

-continued

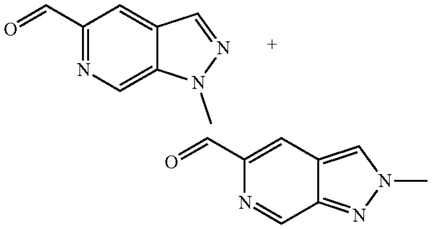

To a solution of 1H-pyrazolo[3,4-c]pyridine-5-carbaldehyde (1 g) in DMF (15 mL) was added $Cs_2CO_3$ (4.4 g) and iodomethane (1.1 g). The mixture was stirred at 25° C. for 12 hr. The mixture was then diluted with water and extracted with EtOAc. The combined extracts were dried, filtered and concentrated to give 1-methyl-1H-pyrazolo[3,4-c]pyridine-5-carbaldehyde (400 mg) [$^1$H NMR (400 MHz, DMSO-d6) δ 10.12 (s, 1H), 9.35 (s, 1H), 8.43 (s, 2H), 4.25 (s, 3H).] and 2-methyl-2H-pyrazolo[3,4-c]pyridine-5-carbaldehyde (200 mg) [$^1$H NMR (400 MHz, DMSO-d6) δ 10.05 (s, 1H), 9.27 (s, 1H), 8.80 (s, 1H), 8.43 (d, J=1.2 Hz, 1H), 4.31 (s, 3H).] as a yellow solid. LC/MS ESI (m/z): 162 $[M+H]^+$.

Step 4. Synthesis of (R,E)-2-methyl-N-((1-methyl-1H-pyrazolo[3,4-c]pyridin-5-yl)methylene)propane-2-sulfinamide

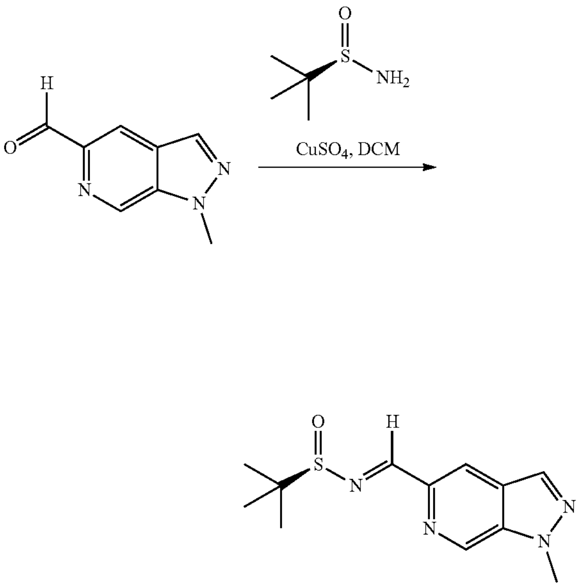

To a solution of 1-methyl-1H-pyrazolo[3,4-c]pyridine-5-carbaldehyde (235 mg) in DCM (15 mL) were added (R)-2-methylpropane-2-sulfinamide (230 mg) and $CuSO_4$ (349 mg). The reaction was stirred at rt overnight. The solution was filtered through a pad of Celite and the filtrate was concentrated. The residue was purified by silica gel column to give (R,E)-2-methyl-N-((1-methyl-1H-pyrazolo[3,4-c]pyridin-5-yl)methylene)propane-2-sulfinamide (340 mg). $^1$H NMR (400 MHz, $CDCl_3$) δ 9.06 (s, 1H), 8.83 (s, 1H), 8.34 (s, 1H), 8.17 (s, 1H), 4.25 (s, 3H), 1.31 (s, 9H) ppm. LC/MS ESI (m/z): 265 $[M+H]^+$.

Step 5. Synthesis of (R)-2-methyl-N—((R)-1-(1-methyl-1H-pyrazolo[3,4-c]pyridin-5-yl)ethyl)propane-2-sulfinamide

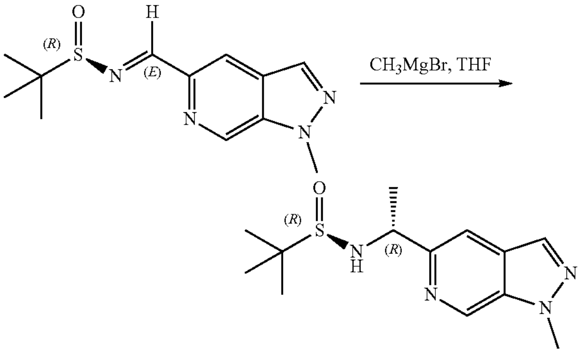

To a solution of (R,E)-2-methyl-N-((1-methyl-1H-pyrazolo[3,4-c]pyridin-5-yl)methylene)propane-2-sulfinamide (347 mg) in anhydrous THF (20 mL) were added $CH_3MgBr$ (3.0M in ether, 2.2 mL) dropwise. The reaction was stirred at −60° C. for 2 hr. Then the reaction was quenched with saturated $NH_4Cl$ and extracted with EtOAc. The organic layer was separated, washed with additional saturated NaCl, dried over with $Na_2SO_4$, filtered and concentrated in vacuo. Then the residue was purified by silica gel column chromatography to give (R)-2-methyl-N—((R)-1-(1-methyl-1H-pyrazolo[3,4-c]pyridin-5-yl)ethyl)propane-2-sulfinamide (314 mg) as pale yellow oil. LC/MS ESI (m/z): 281 $[M+H]^+$.

Step 6. Synthesis of (R)-1-(1-methyl-1H-pyrazolo[3,4-c]pyridin-5-yl)ethan-1-amine hydrochloride

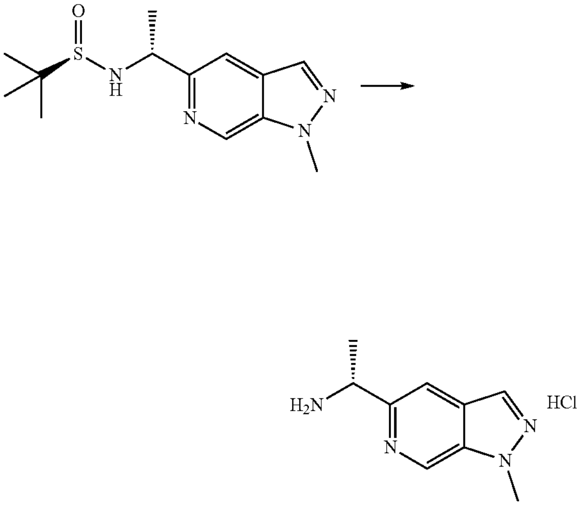

To a solution of (R)-2-methyl-N—((R)-1-(1-methyl-1H-pyrazolo[3,4-c]pyridin-5-yl)ethyl)propane-2-sulfinamide (57 mg) in dioxane (2.0 mL) were added HCl-Dioxane (4M in dioxane, 1.0 mL), and the reaction was stirred at rt for 30 min. Then the mixture was concentrated to provide crude (R)-1-(1-methyl-1H-pyrazolo[3,4-c]pyridin-5-yl)ethan-1-amine hydrochloride, which was used for next step. LC/MS ESI (m/z): 177 $[M+H]^+$.

Step 7. Synthesis of (R)-2-(4-isopropylphenyl)-N-(1-(1-methyl-1H-pyrazolo[3,4-c]pyridin-5-yl)ethyl) acetamide

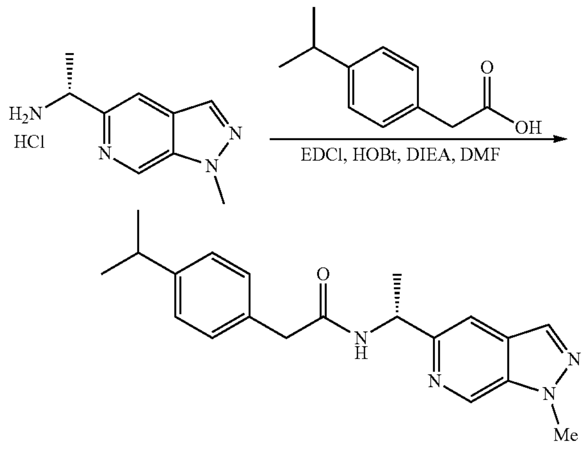

A solution of crude (R)-1-(1-methyl-1H-pyrazolo[3,4-c]pyridin-5-yl)ethan-1-amine hydrochloride (70 mg), 2-[4-(propan-2-yl)phenyl]acetic acid (77.88 mg), EDCI (91.38 mg), HOBt (64.41 mg) and DIEA (0.08 mL) in DMF (5 mL) was stirred at 25° C. for 3 hr. The mixture was diluted with water and extracted with EtOAc. The combined extracts were dried, filtered and concentrated to provide a residue. The residue was purified by prep-HPLC [Column: YMC-Actus Triart C18 250*21 mm; Mobile phase: from 20% to 95% MeCN with $H_2O$ (0.1% $NH_3H_2O$); flow rate: 15 mL/min; wavelength: 220 nm/254 nm] and SFC (Column: ChiralPak IA, 250×21.3 mm I.D., 5 μm; Mobile phase: A for $CO_2$ and B for MEOH+0.1% $NH_3H_2O$; Gradient: B 35%; wavelength: 220 nm) to give (R)-2-(4-isopropylphenyl)-N-(1-(1-methyl-1H-pyrazolo[3,4-c]pyridin-5-yl)ethyl)acetamide (17.1 mg) as a white solid. LC/MS ESI (m/z): 337 (M+H)+; $^1$H NMR (400 MHz, $CDCl_3$) δ 8.83 (s, 1H), 7.98 (s, 1H), 7.50 (s, 1H), 7.20 (s, 4H), 6.62 (d, J=7.6 Hz, 1H), 5.30-5.23 (m, 1H), 4.18 (s, 3H), 3.60-3.52 (m, 2H), 2.95-2.88 (m, 1H), 1.46 (d, J=6.8 Hz, 3H), 1.26 (d, J=8.0 Hz, 6H) ppm.

Example 2. (R)-2-(4-isopropylphenyl)-N-(1-(2-methyl-2H-pyrazolo[3,4-c]pyridin-5-yl)ethyl)acetamide Step 1. Synthesis of (R,E)-2-methyl-N-((2-methyl-2H-pyrazolo[3,4-c]pyridin-5-yl)methylene)propane-2-sulfinamide

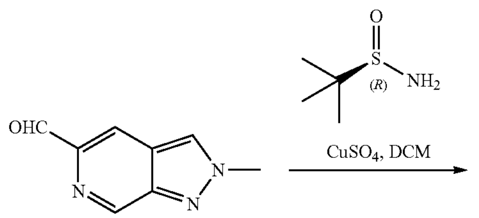

-continued

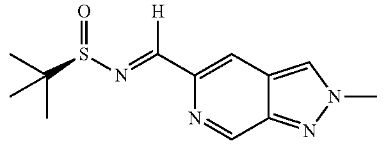

To a solution of 2-methyl-2H-pyrazolo[3,4-c]pyridine-5-carbaldehyde (210 mg) in anhydrous dichloromethane (10 mL) were added (R)-2-methylpropane-2-sulfinamide (190 mg) and $CuSO_4$ (520 mg), and the reaction was stirred at rt for overnight. Then, the mixture was filtered, and the filtrate was concentrated in vacuo. The residue was purified by silica gel column to give (R,E)-2-methyl-N-((2-methyl-2H-pyrazolo[3,4-c]pyridin-5-yl)methylene)propane-2-sulfinamide (421 mg, crude) as a white solid. LC/MS ESI: 265 $(M+H)^+$. $^1$H NMR (400 MHz, DMSO) δ 9.25 (s, 1H), 8.71 (s, 1H), 8.59 (s, 1H), 8.49 (s, 1H), 4.31 (s, 3H), 1.21 (s, 9H).

Step 2. Synthesis of (R)-2-methyl-N—((R)-1-(2-methyl-2H-pyrazolo[3,4-c]pyridin-5-yl)ethyl)propane-2-sulfinamide

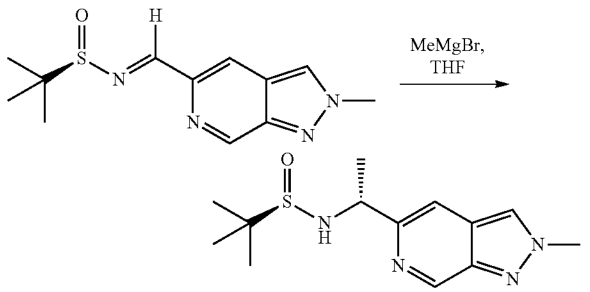

To a solution of (R,E)-2-methyl-N-((2-methyl-2H-pyrazolo[3,4-c]pyridin-5-yl)methylene)propane-2-sulfinamide (274 mg) in THF (8.0 mL) was added methylmagnesium bromide (1.38 mL, 3M in ether) at −78° C., and the mixture was stirred at −78° C. for 4 hr. The mixture was then quenched with $NH_4Cl$ solution and extracted with EtOAc. The combined extracts were dried, filtered and concentrated to give (R)-2-methyl-N—((R)-1-(2-methyl-2H-pyrazolo[3,4-c]pyridin-5-yl)ethyl)propane-2-sulfinamide (285 mg). LC/MS ESI: 281 (M+H)+. $^1$H NMR (400 MHz, $CDCl_3$) δ 9.20 (s, 1H), 7.90 (s, 1H), 7.49 (d, J=0.8 Hz, 1H), 4.65-4.62 (m, 1H), 4.43 (d, J=6.0 Hz, 1H), 4.28 (d, J=3.0 Hz, 3H), 1.57 (d, J=6.7 Hz, 3H), 1.25 (s, 9H).

Step 3. Synthesis of (R)-1-(2-methyl-2H-pyrazolo[3,4-c]pyridin-5-yl)ethan-1-amine hydrochloride

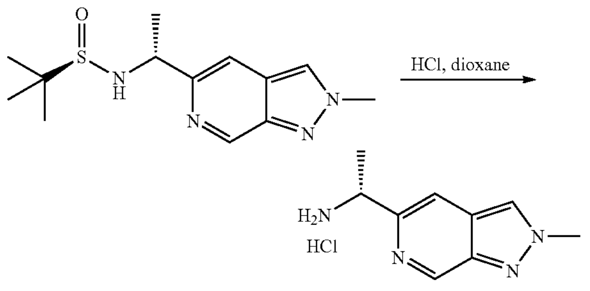

To a solution of (R)-2-methyl-N—((R)-1-(2-methyl-2H-pyrazolo[3,4-c]pyridin-5-yl)ethyl)propane-2-sulfinamide (215 mg) in dioxane (6 mL) were added 4N HCl-dioxane (2 mL), and the reaction was stirred at rt for 1 hr. The reaction was then concentrated and used directly in the next step. LC/MS ESI: 177 (M+H)+.

Step 4. Synthesis of (R)-2-(4-isopropylphenyl)-N-(1-(2-methyl-2H-pyrazolo[3,4-c]pyridin-5-yl)ethyl) acetamide

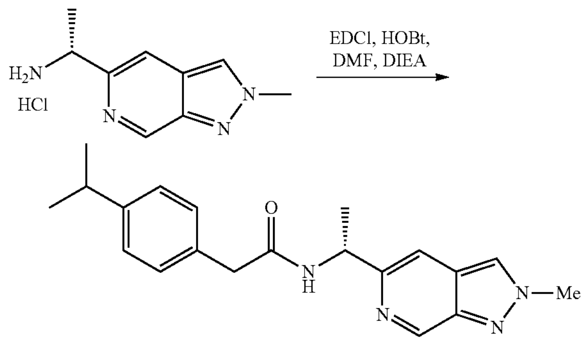

(R)-1-(2-methyl-2H-pyrazolo[3,4-c]pyridin-5-yl)ethan-1-amine hydrochloride (135 mg), EDCI (177 mg), HOBt (125 mg) and 2-(4-isopropylphenyl)acetic acid (151 mg) were dissolved in anhydrous N,N-dimethylformamide (5.0 mL), and DIEA (0.51 mL, 3.064) was then added to the solution. The reaction was stirred at rt for 1 h and extracted from water with ethyl acetate. The organic layer was separated, washed with saturated aqueous NaCl, and concentrated in vacuo. The residue was purified by prep-HPLC [Column: YMC-Actus Triart C180250*21 mm; Mobile phase: from 20% to 95% MeCN with H2O (0.1% $NH_3H_2O$); flow rate: 15 mL/min; wavelength: 220 nm/254 nm] and SFC (Column:ChiralPak IA, 250×21.3 mm I.D., 5 μm; Mobile phase: A for $CO_2$ and B for MEOH+0.1% $NH_3H_2O$; Gradient: B 40%; Flow rate: 50 mL/min; Back pressure: 100 bar; Column temperature: 35° C.; Wavelength:220 nm), to give (R)-2-(4-isopropylphenyl)-N-(1-(2-methyl-2H-pyrazolo[3,4-c]pyridin-5-yl)ethyl)acetamide (46.5 mg). LC/MS ESI: 337 $(M+H)^+$. $^1H$ NMR (400 MHz, $CDCl_3$) δ 9.11 (s, 1H), 7.89 (s, 1H), 7.38 (s, 1H), 7.18 (s, 4H), 6.64 (d, J=6.8 Hz, 1H), 5.24-5.16 (m, 1H), 4.27 (s, 3H), 3.54-3.52 (m, 2H), 2.93-2.86 (m, 1H), 1.45 (d, J=6.8 Hz, 3H), 1.24 (d, J=6.9 Hz, 6H).

Example 3. (R)-2-(4-isopropylphenyl)-N-(1-(1-methyl-1H-pyrazolo[4,3-c]pyridin-6-yl)ethyl)acetamide Step 1. Synthesis of methyl 1-methyl-1H-pyrazolo[4,3-c]pyridine-6-carboxylate and methyl 2-methyl-2H-pyrazolo[4,3-c]pyridine-6-carboxylate

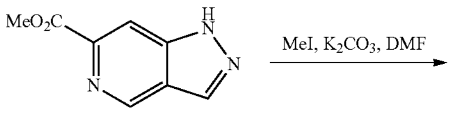

-continued

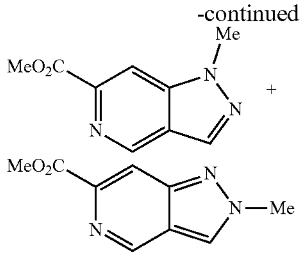

To a solution of methyl 1H-pyrazolo[4,3-c]pyridine-6-carboxylate (2.0 g) in anhydrous DMF (20 mL) were added $Cs_2CO_3$ (5.5 g) and iodomethane (1.8 g), and the reaction was stirred at RT for 18 hr. Water and EtOAc were then added to the reaction mixture. The two phases were separated, and the aqueous phase was extracted with DCM (10 mL×3). The combined organic layers were dried over $Na_2SO_4$, filtered and concentrated to give a residue which was purified by silica gel column chromatography to give methyl 1-methyl-1H-pyrazolo[4,3-c]pyridine-6-carboxylate (1.2 g) and methyl 2-methyl-2H-pyrazolo[4,3-c]pyridine-6-carboxylate (0.54 g).

Methyl 1-methyl-1H-pyrazolo[4,3-c]pyridine-6-carboxylate: LC/MS ESI (m/z):192 $[M+H]^+$; $^1H$ NMR (400 MHz, DMSO-d6) δ 9.17 (d, J=1.2 Hz, 1H), 8.44 (t, J=1.0 Hz, 1H), 8.41 (d, J=0.9 Hz, 1H), 4.17 (s, 3H), 3.92 (s, 3H).

Methyl 2-methyl-2H-pyrazolo[4,3-c]pyridine-6-carboxylate: LC/MS ESI (m/z):192 $[M+H]^+$; $^1H$ NMR (400 MHz, DMSO-d6) δ 9.23 (d, J=1.2 Hz, 1H), 8.78 (s, 1H), 8.28 (t, J=1.0 Hz, 1H), 4.28 (s, 3H), 3.89 (s, 3H).

Step 2. Synthesis of (1-methyl-1H-pyrazolo[4,3-c] pyridin-6-yl)methanol

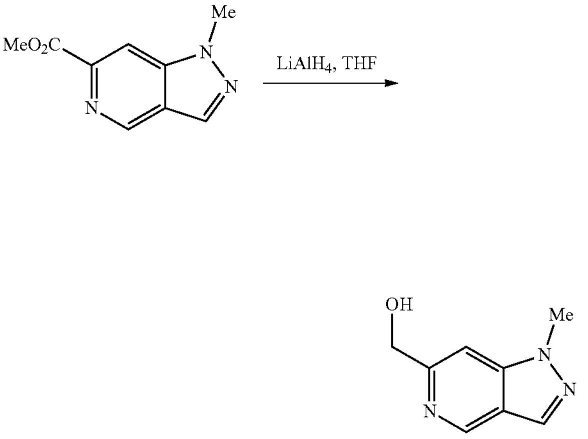

To a solution of methyl 1-methyl-1H-pyrazolo[4,3-c]pyridine-6-carboxylate (350 mg) in THF (5 mL) was added lithium aluminum hydride (208.42 mg) at 0° C., and the mixture was stirred at 25° C. for 2 hr. The mixture was then quenched with an aqueous NaOH solution (2M) and extracted with DCM. The combined extracts were dried, filtered and concentrated to give (1-methyl-1H-pyrazolo[4,3-c]pyridin-6-yl)methanol (160 mg) as a yellow oil, which was directly used for next step. LC/MS ESI (m/z): 164 [M+H]+

Step 3. Synthesis of 1-methyl-1H-pyrazolo[4,3-c]pyridine-6-carbaldehyde

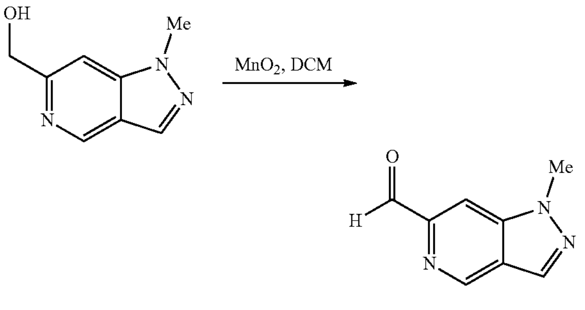

To a solution of (1-methyl-1H-pyrazolo[4,3-c]pyridin-6-yl)methanol (160 mg) in DCM (5 mL) was added manganese dioxide (426.3 mg). The mixture was stirred at 25° C. for 3 hr. The mixture was then filtered, and the filtrate was concentrated in vacuo to provide a residue, which was directly used for next reaction. LC/MS ESI (m/z): 265 [M+H]+

Step 4. Synthesis of methyl (R,E)-2-methyl-N-((1-methyl-1H-pyrazolo[4,3-c]pyridin-6-yl)methylene)propane-2-sulfinamide

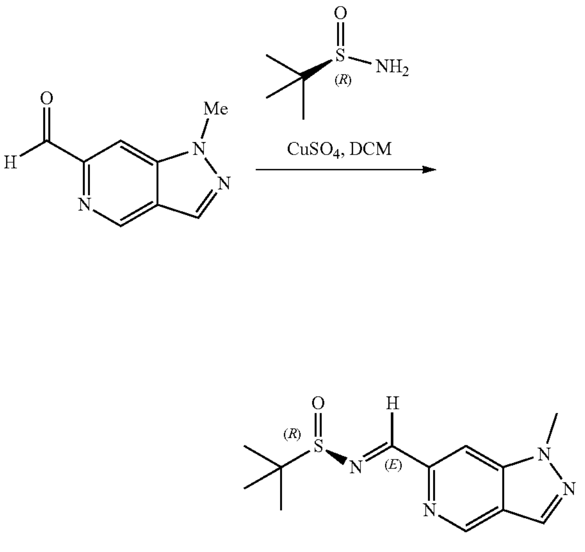

To the solution of (1-methyl-1H-pyrazolo[4,3-c]pyridin-6-yl)methanol (140 mg) in $CH_2Cl_2$ (10 mL) was added (R)-2-methylpropane-2-sulfinamide (105.3 mg) and copper (II) sulfate (693.3 mg) at rt, and the mixture was stirred at rt overnight. LC/MS showed the reaction was complete. The reaction mixture was quenched by ice-water and then extracted twice with EtOAc. The combined extracts were concentrated, and the residue was purified by column chromatography on silica gel (PE:EA=2:1) to give (R,E)-2-methyl-N-((1-methyl-1H-pyrazolo[4,3-c]pyridin-6-yl)methylene)propane-2-sulfinamide (110 mg) as a yellow solid. LC/MS ESI (m/z): 265 $[M+H]^+$.

Step 5. Synthesis of (R)-2-methyl-N—((R)-1-(1-methyl-1H-pyrazolo[4,3-c]pyridin-6-yl)ethyl)propane-2-sulfinamide

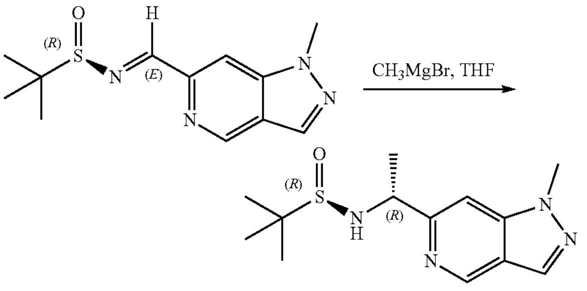

To a solution of (R,E)-2-methyl-N-((1-methyl-1H-pyrazolo[4,3-c]pyridin-6-yl)methylene)propane-2-sulfinamide (110 mg) in THF (5 mL) was added $CH_3MgBr$ (0.41 mL, 3M in ether) under $N_2$ at −78° C., and the mixture was stirred at −78° C. for 1 h. LC/MS showed the reaction was complete. The reaction mixture was then quenched with ice-water and extracted with twice EtOAc. The combined extracts were dried over $Na_2SO_4$, filtered and concentrated. The residue was purified by column chromatography on silica gel (DCM/MeOH=10:1) to give (R)-2-methyl-N—((R)-1-(1-methyl-1H-pyrazolo[4,3-c]pyridin-6-yl)ethyl)propane-2-sulfinamide (80 mg) as a light yellow oil. LC/MS ESI (m/z): 281 $[M+H]^+$.

Step 6. Synthesis of (R)-1-(1-methyl-1H-pyrazolo[4,3-c]pyridin-6-yl)ethan-1-amine hydrochloride

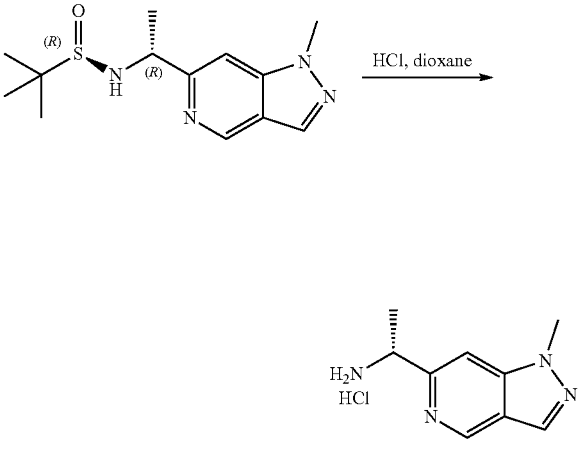

To a solution of (R)-2-methyl-N—((R)-1-(1-methyl-1H-pyrazolo[4,3-c]pyridin-6-yl)ethyl)propane-2-sulfinamide (85 mg) in dioxane (3.0 mL) was added 4N HCl in dioxane (253.9 mg) at room temperature, and the mixture was stirred at room temperature for 2 hrs. LC/MS showed the reaction was completed. The solvent was removed to give (R)-1-(1-methyl-1H-pyrazolo[4,3-c]pyridin-6-yl)ethan-1-amine hydrochloride (85 mg). LC/MS ESI (m/z): 177 $[M+H]^+$.

Step 7. Synthesis of (R)-2-(4-isopropylphenyl)-N-(1-(1-methyl-1H-pyrazolo[4,3-c]pyridin-6-yl)ethyl)acetamide

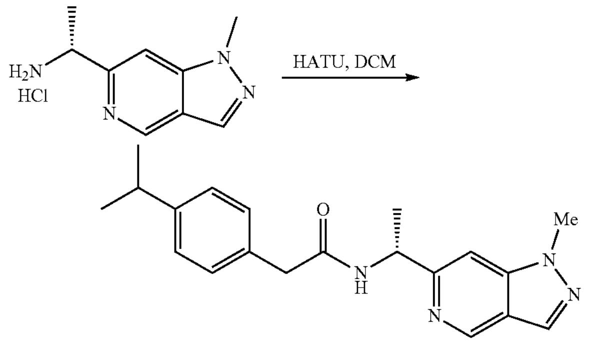

To a solution of (R)-1-(1-methyl-1H-pyrazolo[4,3-c]pyridin-6-yl)ethan-1-amine hydrochloride (91 mg) in $CH_2Cl_2$ (5 mL) was added 2-(4-isopropylphenyl)acetic acid (92 mg), HATU (392 mg) and triethylamine (156 mg), and the mixture was stirred at room temperature for 2 hrs. LC/MS showed the reaction was complete. The reaction mixture was then quenched by ice-water and extracted with twice EtOAc. The combined extracts were concentrated, and the residue was purified by column chromatography on silica gel (PE:EA=3:1) and then prep-HPLC [Column: YMC-Actus Triart C18 250*21 mm; Mobile phase: from 20% to 95% MeCN with $H_2O$ (0.1% FA); flow rate: 15 mL/min; wavelength: 220 nm/254 nm] and SFC (Mobile phase: A for $CO_2$ and B for MEOH+0.1% $NH_3H2O$; Gradient: B 40%) to give (R)-2-(4-isopropylphenyl)-N-(1-(1-methyl-1H-pyrazolo[4,3-c]pyridin-6-yl)ethyl)acetamide (28 mg) as a white solid. LC/MS ESI (m/z): 337 $[M+H]^+$; $^1H$ NMR (400 MHz, $CDCl_3$) δ 8.82 (s, 1H), 8.14 (s, 1H), 7.36 (s, 1H), 7.20-7.11 (m, 4H), 6.87 (d, J=7.5 Hz, 1H), 5.28-5.24 (m, 1H), 4.06 (s, 3H), 3.57 (s, 2H), 2.89-2.85 (m, 1H), 1.50 (t, J=8.0 Hz, 3H), 1.23 (t, J=8.0 Hz, 6H).

Example 4. (R)-2-(4-isopropylphenyl)-N-(1-(2-methyl-2H-pyrazolo[4,3-c]pyridin-6-yl)ethyl)acetamide

Step 1. (2-methyl-2H-pyrazolo[4,3-c]pyridin-6-yl) methanol

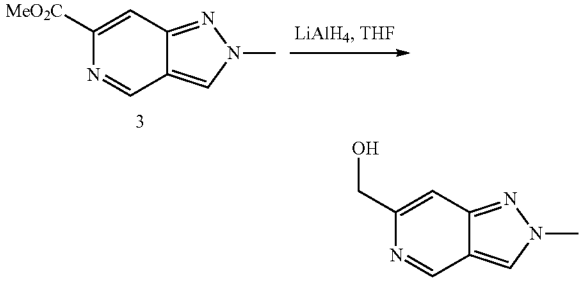

3

10

To a solution of methyl 2-methyl-2H-pyrazolo[4,3-c]pyridine-6-carboxylate (530 mg) in THF (10 mL) was added lithium aluminum hydride (315.6 mg) at 0° C., and the mixture was stirred at 25° C. for 3 hr. The mixture was then quenched with aqueous NaOH (2M) and extracted with DCM. The combined extracts were dried, filtered and concentrated to give (2-methyl-2H-pyrazolo[4,3-c]pyridin-6-yl) methanol (280 mg, colorless oil), which was used for next step directly. LC/MS ESI (m/z): 164 $[M+H]^+$.

Step 2. 2-methyl-2H-pyrazolo[4,3-c]pyridine-6-carbaldehyde

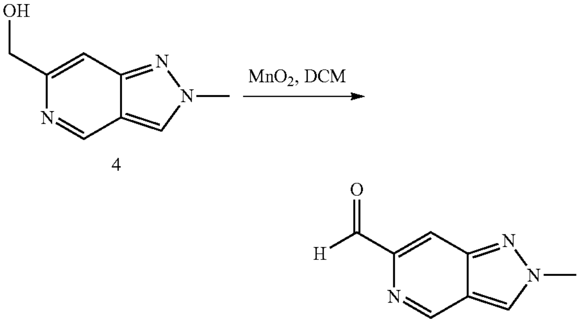

4

5

To a solution of (2-methyl-2H-pyrazolo[4,3-c]pyridin-6-yl)methanol (280 mg) in DCM (5 mL) was added manganese dioxide (0.12 mL), and the mixture was stirred at 25° C. for 3 hr. The mixture was then filtered, and the filtrate was concentrated in vacuo to provide crude 2-methyl-2H-pyrazolo[4,3-c]pyridine-6-carbaldehyde, which was directly used for next step. LC/MS ESI (m/z): 162 $[M+H]^+$.

Step 3. (R,E)-2-methyl-N-((2-methyl-2H-pyrazolo[4,3-c]pyridin-6-yl)methylene)propane-2-sulfinamide

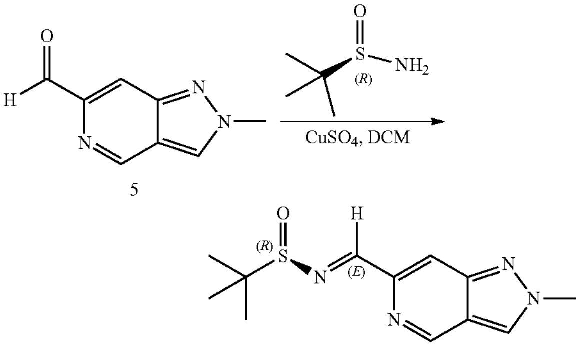

5

6

A solution of 2-methyl-2H-pyrazolo[4,3-c]pyridine-6-carbaldehyde (280 mg), (R)-2-methylpropane-2-sulfinamide (316 mg) and copper sulfate pentahydrate (465 mg) in DCM (5.0 mL) was stirred at 25° C. for 3 hr. The mixture was then filtered and concentrated to give a yellow oil, which was purified by column chromatography on silica gel (DCM:MeOH=50:1 to 20:1) to give (R,E)-2-methyl-N-((2-methyl-2H-pyrazolo[4,3-c]pyridin-6-yl)methylene)propane-2-sulfinamide (400 mg) as a yellow solid. LC/MS ESI (m/z): 265 $[M+H]^+$ Step 4. (R)-2-methyl-N—((R)-1-(2-methyl-2H-pyrazolo[4,3-c]pyridin-6-yl)ethyl)propane-2-sulfinamide

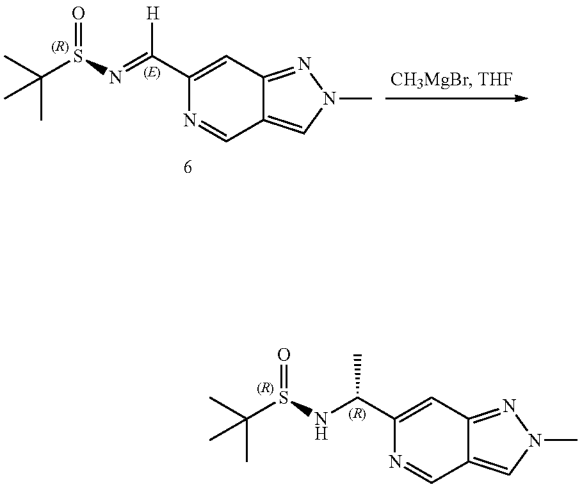

6

7

To a solution of (R,E)-2-methyl-N-((2-methyl-2H-pyrazolo[4,3-c]pyridin-6-yl)methylene)propane-2-sulfinamide (180 mg) in THE (5 mL) was added $CH_3MgBr$ (3M in ether, 2.0 mL) at −70° C., and the mixture was stirred at −70° C. for 2 hr. The reaction mixture was then quenched with saturated aqueous ammonium chloride (5 mL) and extracted with EtOAc (10 mL). The organic layer was dried, filtered and concentrated to give a yellow oil, which was purified by column chromatography on silica gel (DCM:MeOH=50:1 to 20:1) to give (R)-2-methyl-N—((R)-1-(2-methyl-2H-pyrazolo[4,3-c]pyridin-6-yl)ethyl)propane-2-sulfinamide (40 mg) as a white solid. LC/MS ESI (m/z): 281 $[M+H]^+$ Step 5. (R)-1-(2-methyl-2H-pyrazolo[4,3-c]pyridin-6-yl)ethan-1-amine hydrochloride

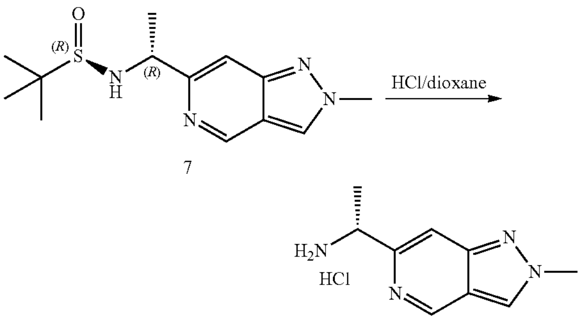

7

8

To a solution of 2-methyl-N-[(1R)-1-{2-methyl-2H-pyrazolo[4,3-c]pyridin-6-yl}ethyl]propane-2-sulfinamide (40 mg) in dioxane (2 mL) was added HCl/dioxane (4 N in dioxane, 1 mL), and the mixture was stirred at 25° C. for 30 min. The mixture was then concentrated to get (R)-1-(2-methyl-2H-pyrazolo[4,3-c]pyridin-6-yl)ethan-1-amine hydrochloride (30 mg, crude) as a white solid. LC/MS ESI (m/z): 177 $[M+H]^+$ Step 6. (R)-2-(4-isopropylphenyl)-N-(1-(2-methyl-2H-pyrazolo[4,3-c]pyridin-6-yl)ethyl)acetamide

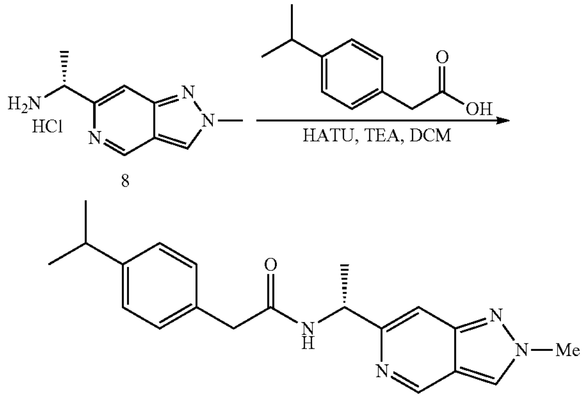

8

A solution of (R)-1-(2-methyl-2H-pyrazolo[4,3-c]pyridin-6-yl)ethan-1-amine hydrochloride (30 mg), 2-[4-(propan-2-yl)phenyl]acetic acid (33.4 mg), HATU (97 mg) and TEA (0.07 mL) in DCM (2.0 mL) was stirred at 25° C. for 12 hr. The mixture was diluted with water and extracted with EtOAc. The combined extracts were dried, filtered and concentrated to give a residue product, which was purified by prep-HPLC [Column: Shim-pack GIST C18 250*21 mm; Mobile phase: from 10% to 85% MeCN with $H_2O$ (0.1% $NH_3H_2O$); flow rate: 15 mL/min; wavelength: 220 nm/254 nm] to give (R)-2-(4-isopropylphenyl)-N-(1-(2-methyl-2H-pyrazolo[4,3-c]pyridin-6-yl)ethyl)acetamide (14 mg) as a colorless oil. LC/MS ESI (m/z): 337 $(M+H)^+$;

$^1H$ NMR (400 MHz, $CDCl_3$) δ 9.02 (s, 1H), 8.06 (s, 1H), 7.40 (s, 1H), 7.20 (s, 4H), 6.67 (d, J=7.6 Hz, 1H), 5.26-6.19 (m, 1H), 4.25 (s, 3H), 3.57-3.56 (m, 2H), 2.94-2.87 (m, 1H), 1.46 (d, J=6.8 Hz, 3H), 1.25 (d, J=8.0 Hz, 6H).

Example 5. (R)-2-(4-isopropylphenyl)-N-(1-(3-methylisoxazolo[4,5-c]pyridin-6-yl)ethyl)acetamide Synthesis of 4,6-dichloro-N-methoxy-N-methylnicotinamide

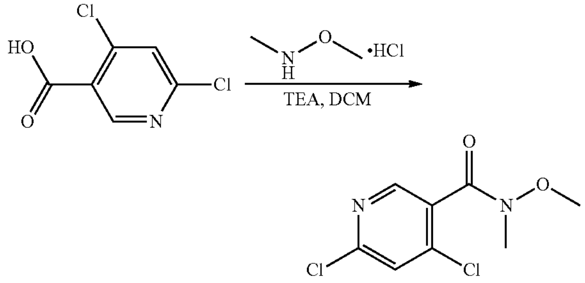

To a solution of 4,6-dichloronicotinic acid (5.0 g) in DCM (70 mL) was added HATU (10.9 g, 28.6) at rt, and the reaction was stirred for 10 min. Then N-methoxymethanamine, HCl (3.0 g) and TEA (10.8 mL) were added at rt, and the mixture was stirred at rt for 2 h. The mixture was then quenched with water and extracted with EA. The combined extracts were washed with brine, dried over with $Na_2SO_4$ and concentrated in vacuo to give 4,6-dichloro-N-methoxy-N-methylnicotinamide (6.0 g) as a yellow oil. LC/MS ESI: 234 $(M+H)^+$. $^1H$ NMR (400 MHz, DMSO-d6) δ 8.58 (s, 1H), 7.96 (s, 1H), 3.49 (s, 3H), 3.32 (s, 3H).

Synthesis of 1-(4,6-dichloropyridin-3-yl)ethan-1-one

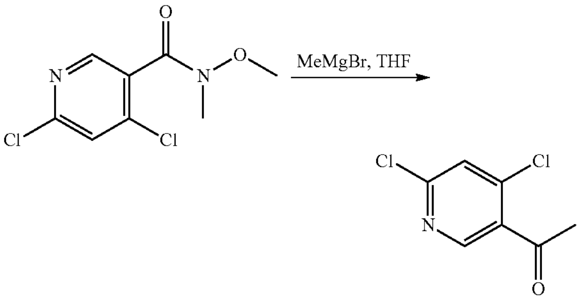

4,6-Dichloro-N-methoxy-N-methylnicotinamide (6.0 g) was dissolved in anhydrous THE (86 mL) and stirred at 0-5° C. for 10 min. MeMgBr (14 mL, 3 M in ether) was then added slowly to the solution. After 2 h at 0-5° C., the starting material was consumed, and the reaction was quenched with saturated aqueous ammonium chloride and extracted with ethyl acetate. The combined extracts were washed with brine, dried over with $Na_2SO_4$, and evaporated to give an oil. The oil was purified by silica gel column chromatography affording 1-(4,6-dichloropyridin-3-yl)ethan-1-one (4.3 g). LC/MS ESI: 190 $(M+H)^+$. $^1H$ NMR (400 MHz, $CDCl_3$) δ 8.62 (s, 1H), 7.46 (s, 1H), 2.68 (s, 3H).

Step 3. Synthesis of (E)-1-(4-chloro-6-styrylpyridin-3-yl)ethan-1-one and (E)-1-(6-chloro-4-styrylpyridin-3-yl)ethan-1-one

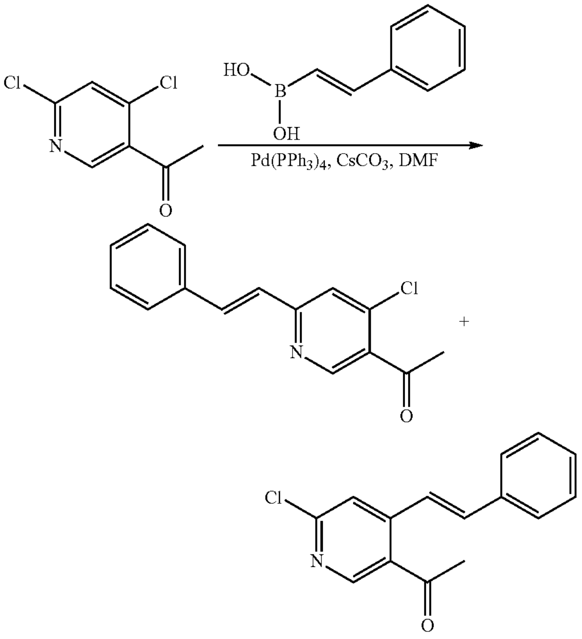

To a mixture of 1-(4,6-dichloropyridin-3-yl)ethan-1-one (228 mg) and (E)-styrylboronic acid (266 mg) in DMF (6.0 mL) was added $Pd(PPh_3)_4$ (100 mg) and 2 N $Cs_2CO_3$ (1.8 mL). The reaction was charged with $N_2$ for three time and stirred at 80° C. for 6 h, 50 mL of EA was added to the reaction. The organic phase was washed with brine, dried over $Na_2SO_4$, filtered. The filtrate was concentrated under vacuo, and the residue was purified by silica gel column chromatography (10% EA in PE) to give (E)-1-(4-chloro-6-styrylpyridin-3-yl)ethan-1-one and (E)-1-(6-chloro-4-styrylpyridin-3-yl)ethan-1-one as a mixture of isomers. LC/MS ESI (m/z): 258 $(M+H)^+$.

Synthesis of 1-(4-chloro-6-((E)-styryl)pyridin-3-yl)ethan-1-one oxime (N201201-118)

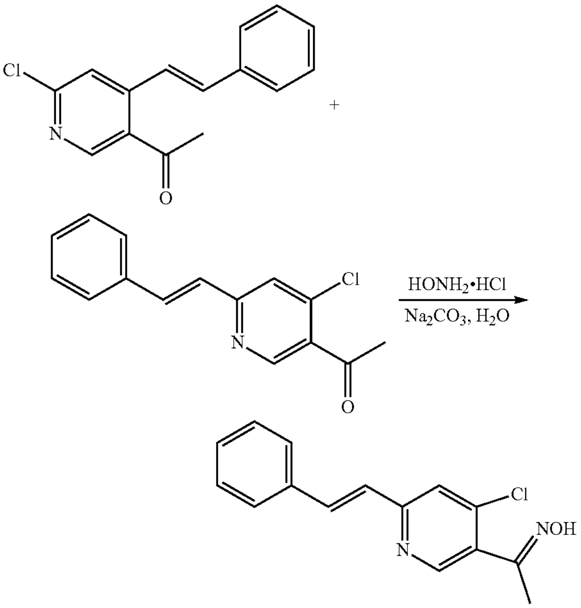

To a solution of (E)-1-(4-chloro-6-styrylpyridin-3-yl)ethan-1-one and (E)-1-(6-chloro-4-styrylpyridin-3-yl)ethan-1-one (1.5 g, mixture of isomers) in EtOH (25 mL) and $H_2O$ (5 mL) were added hydroxylamine hydrochloride (0.80 g) and $Na_2CO_3$ (1.2 g). The reaction was stirred at 65° C. overnight. The reaction was diluted with EA and water. The two phases were separated, and the aqueous phase was extracted with DCM (10 mL×3). The combined organic layers were dried over $Na_2SO_4$, filtered and concentrated to give a residue, which was purified by silica gel column chromatography to give 1-(4-chloro-6-((E)-styryl)pyridin-3-yl)ethan-1-one oxime (307 mg). LC/MS ESI: 273 $(M+H)^+$.

Synthesis of (E)-3-methyl-6-styrylisoxazolo[4,5-c]pyridine (N201201-122)

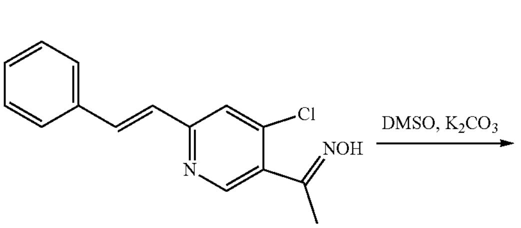

-continued

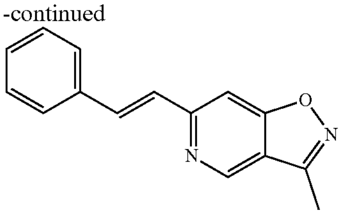

To a solution of 1-(4-chloro-6-((E)-styryl)pyridin-3-yl) ethan-1-one oxime (307 mg) in DMSO (15 mL) were added $K_2CO_3$ (466.741 mg), and the reaction was stirred at 100° C. for 2 hr. After cooling to rt, water and EtOAc were added. The two phases were separated, and the aqueous phase was extracted with DCM (10 mL×3). The combined organic layers were dried over $Na_2SO_4$, filtered and concentrated to give a residue, which was purified by silica gel column chromatography to give (E)-3-methyl-6-styrylisoxazolo[4,5-c]pyridine (235 mg). LC/MS ESI: 237 M+H)$^+$; $^1$H NMR (400 MHz, DMSO-d6) δ 9.15 (d, J=0.7 Hz, 1H), 7.87-7.83 (m, 2H), 7.70 (d, J=7.3 Hz, 2H), 7.46-7.42 (m, 3H), 7.36 (d, J=7.3 Hz, 1H), 2.64 (s, 3H).

Synthesis of 3-methylisoxazolo[4,5-c]pyridine-6-carbaldehyde

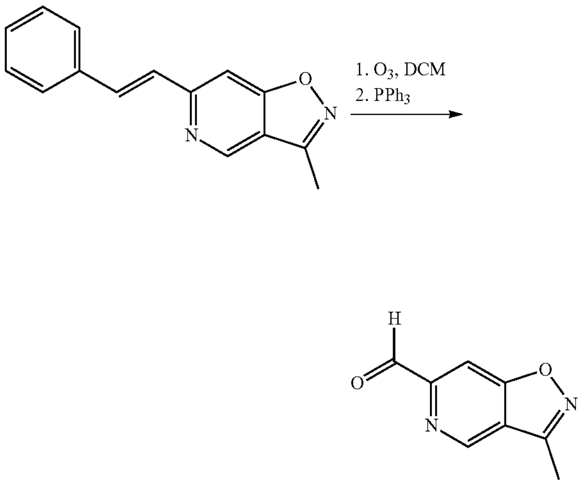

Ozone was bubbled through a solution of (E)-3-methyl-6-styrylisoxazolo[4,5-c]pyridine (486 mg) in anhydrous DCM (20 mL) at −78° C. for 10 mins. The ozone gas was then purged with nitrogen for ten minutes, and $PPh_3$ (644 mg) was added at room temperature. The reaction was stirred for another 40 minutes. The solvent was filtered, and the filtrate was concentrated in vacuum to get a residue, which was purified by silica gel column chromatography to give 3-methylisoxazolo[4,5-c]pyridine-6-carbaldehyde (150 mg). LC/MS ESI: 163 (M+H)$^+$; $^1$H NMR (400 MHz, $CDCl_3$) δ 10.27 (s, 1H), 9.15 (d, J=0.4 Hz, 1H), 8.14 (d, J=0.8 Hz, 1H), 2.74 (s, 3H).

Synthesis of (R,E)-2-methyl-N-((3-methylisoxazolo[4,5-c]pyridin-6-yl)methylene)propane-2-sulfinamide

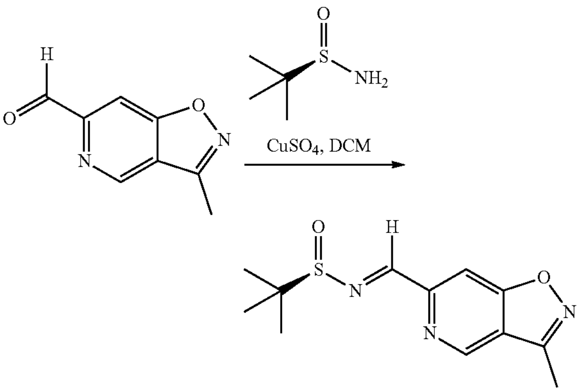

To a solution of 3-methylisoxazolo[4,5-c]pyridine-6-carbaldehyde (150 mg) in anhydrous DCM (15 mL) was added (R)-2-methylpropane-2-sulfinamide (145.8 mg) and $CuSO_4$ (738 mg), and the reaction mixture was stirred at rt overnight. The reaction was then filtered and the filtrate was concentrated in vacuum. The residue was purified by silica gel column chromatography, to give (R,E)-2-methyl-N-((3-methylisoxazolo[4,5-c]pyridin-6-yl)methylene)propane-2-sulfinamide (197 mg) as a white solid. LC/MS ESI: 266 (M+H)$^+$; $^1$H NMR (400 MHz, $CDCl_3$) δ 9.10 (d, J=0.9 Hz, 1H), 8.86 (s, 1H), 8.19 (d, J=0.9 Hz, 1H), 2.72 (s, 3H), 1.32 (s, 9H) ppm.

Synthesis of (R)-2-methyl-N—((R)-1-(3-methylisoxazolo[4,5-c]pyridin-6-yl)ethyl)propane-2-sulfinamide (N201201-131)

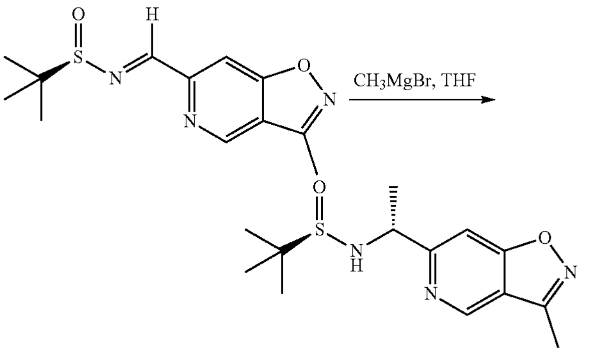

To a solution of (R,E)-2-methyl-N-((3-methylisoxazolo[4,5-c]pyridin-6-yl)methylene)propane-2-sulfinamide (197 mg) in anhydrous THF (10 mL) was added $CH_3MgBr$ (1.2 mL, 3.0M in ether) dropwise at −78° C. under $N_2$. The Grignard regent was added at such a rate that the internal reaction temperature was never warmer than −60° C. After addition, the reaction mixture was stirred for 2 h at −78° C. then warmed to room temperature and quenched with saturated aqueous ammonium chloride. The organic layer was separated, and the aqueous layer was extracted once with ethyl acetate. The combined organic layers were dried over with $Na_2SO_4$, filtered and concentrated to provide a residue which was purified by silica gel column chromatography (R)-2-methyl-N—((R)-1-(3-methylisoxazolo[4,5-c]pyridin-6-yl)ethyl)propane-2-sulfinamide (187 mg). LC/MS ESI: 282 $(M+H)^+$; 1H NMR (400 MHz, $CDCl_3$) δ 8.93 (d, J=1.0 Hz, 1H), 7.47 (d, J=1.2 Hz, 1H), 4.72-4.63 (m, 2H), 2.64 (s, 3H), 1.57 (d, J=6.5 Hz, 3H), 1.26 (s, 9H).

Synthesis of (R)-1-(3-methylisoxazolo[4,5-c]pyridin-6-yl)ethan-1-amine, hydrochloride

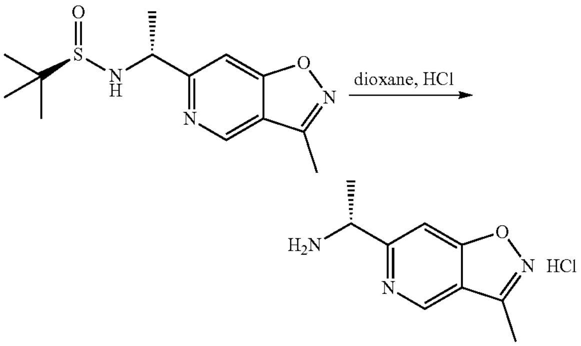

To a solution of (R)-2-methyl-N—((R)-1-(3-methylisoxazolo[4,5-c]pyridin-6-yl)ethyl)propane-2-sulfinamide (172 mg) in dioxane (6.0 mL) were added 4N HCl-Dioxane (2.0 mL). The reaction was stirred at rt for 20 min, and the mixture was concentrated to provide (R)-1-(3-methylisoxazolo[4,5-c]pyridin-6-yl)ethan-1-amine, hydrochloride, as a residue, which was directly used in the next step. LC/MS ESI: 178 $(M+H)^+$.

Synthesis of (R)-2-(4-isopropylphenyl)-N-(1-(3-methylisoxazolo[4,5-c]pyridin-6-yl)ethyl)acetamide

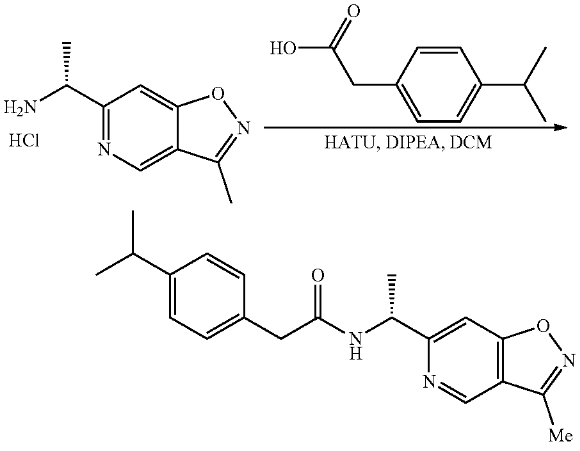

(R)-1-(3-methylisoxazolo[4,5-c]pyridin-6-yl)ethan-1-amine hydrochloride (108 mg) was dissolved in anhydrous DCM (10 mL) and then 2-(4-isopropylphenyl)acetic acid (119.5 mg), HATU (347.6 mg) and DIPEA (0.2 mL) were added. The reaction was stirred at rt for 1 h, and the mixture was diluted with water. The two phases were separated, and the aqueous phase was extracted with DCM (10 mL×3). The combined organic layers were dried over $Na_2SO_4$, filtered and concentrated to give a residue, which was purified by prep-HPLC [Column: Shim-pack GIST C18 250*21 mm; Mobile phase: from 10% to 95% MeCN with $H_2O$ (0.1% $NH_3H_2O$); flow rate: 15 mL/min; wavelength: 220 nm/254 nm] to give (R)-2-(4-isopropylphenyl)-N-(1-(3-methylisoxazolo[4,5-c]pyridin-6-yl)ethyl)acetamide (93.7 mg) as a white solid. LC/MS ESI: 338 $(M+H)^+$; $^1$H NMR (400 MHz, $CDCl_3$) δ 8.83 (s, 1H), 7.34 (s, 1H), 7.23-7.18 (m, 4H), 6.60 (d, J=7.3 Hz, 1H), 5.29-5.22 (m, 1H), 3.57 (s, 2H), 2.95-2.90 (m, 1H), 2.63 (s, 3H), 1.46 (d, J=6.9 Hz, 3H), 1.26 (d, J=6.9 Hz, 6H).

Example 6. (R)-2-(4-isopropylphenyl)-N-(1-(3-methylisoxazolo[5,4-c]pyridin-5-yl)ethyl)acetamide

Synthesis of 2,5-dichloro-N-methoxy-N-methylisonicotinamide

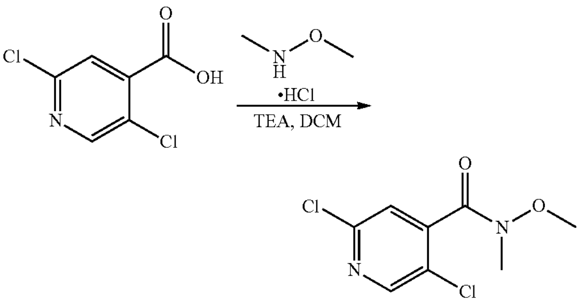

To a solution of 2,5-dichloroisonicotinic acid (5.0 g) in DCM (70 mL) were added HATU (10.9 g) at rt, and the reaction was stirred at rt for 10 min. Hydrochloride N-methoxymethanamine (3.0 g) and TEA (10.8 mL) was then added to the reaction mixture, and the mixture solution was stirred at rt for 2 h. The reaction was quenched with water and extracted with EA. The organic layer was separated, washed with brine, dried over with $Na_2SO_4$ and concentrated in vacuo. The residue was purified by silica gel column chromatography to give 2,5-dichloro-N-methoxy-N-methylisonicotinamide (6.0 g) as a white solid.

Synthesis of 1-(2,5-dichloropyridin-4-yl)ethan-1-one. (N201201-101)

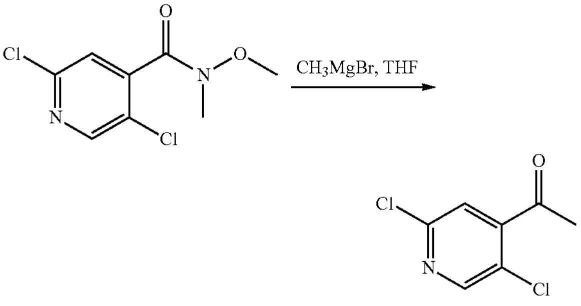

2,5-dichloro-N-methoxy-N-methylisonicotinamide (5.0 g) was dissolved in anhydrous tetrahydrofuran (71 mL) and stirred at 0-5° C. under $N_2$ for 10 mins. Then, $CH_3MgBr$ (11 mL, 3.0M in ether) was slowly added to the solution, and the reaction was stirred at 0-5° C. for 2 h. The reaction was quenched with saturated aqueous ammonium chloride and extracted with ethyl acetate. The combined extracts were washed with brine, dried over $Na_2SO_4$, filtered and evaporated to give an oil which was purified by silica gel column chromatography to give 1-(2,5-dichloropyridin-4-yl)ethan-1-one (3.4 g). LC/MS ESI (m/z): 189.9 $[M+H]^+$ Synthesis of (E)-1-(5-chloro-2-styrylpyridin-4-yl)ethan-1-one

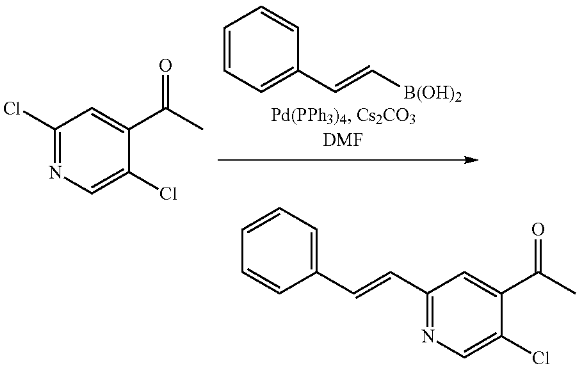

To a solution of 1-(2,5-dichloropyridin-4-yl)ethan-1-one (1.1 g), (E)-styrylboronic acid (1.3 g) in DMF was added 2.0 N $Cs_2CO_3$ (6.0 mL) and $Pd(PPh_3)_4$ (420 mg). The reaction mixture was stirred at 80° C. for 5 hours. EA (50 mL) and $H_2O$ (40 mL) were added. The two phases were separated, and the aqueous phase was extracted with DCM (10 mL×3). The combined organic layers were dried over $Na_2SO_4$, filtered and concentrated to give a residue, which was purified by silica gel column chromatography (eluting with 10% EA in PE) to give (E)-1-(5-chloro-2-styrylpyridin-4-yl)ethan-1-one as yellow solid (900 mg).

Synthesis of 1-(5-chloro-2-((E)-styryl)pyridin-4-yl)ethan-1-one oxime

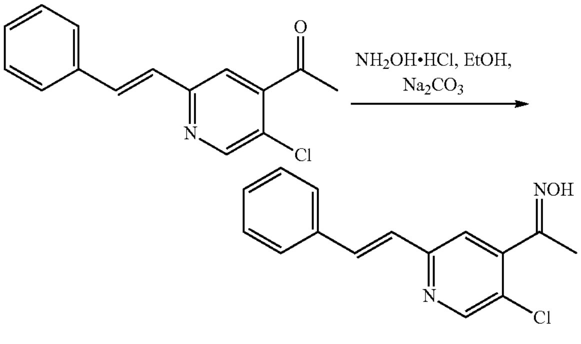

To a solution of 1-(5-chloro-2-styrylpyridin-4-yl)ethan-1-one (1.48 g) in EtOH (25 mL) and $H_2O$ (5 mL) were added $NH_2OH$ HCl (0.8 g) and $Na_2CO_3$ (1.21 g). The reaction was stirred at 65° C. overnight. Then the reaction was then diluted with EA and water. The two phases were separated, and the aqueous phase was extracted with DCM (10 mL×3). The combined organic layers were dried over $Na_2SO_4$, filtered and concentrated to give a residue, which was purified by silica gel column chromatography to give 1-(5-chloro-2-((E)-styryl)pyridin-4-yl)ethan-1-one oxime (294 mg). LC/MS ESI (m/z): 273 $[M+H]^+$. $^1H$ NMR (400 MHz, DMSO-d6) δ 11.02 (s, 1H), 8.71 (s, 1H), 7.76-7.70 (m, 3H), 7.57 (s, 1H), 7.49 (t, J=7.4 Hz, 2H), 7.40 (t, J=11.7 Hz, 2H), 2.18 (s, 3H) ppm.

Synthesis of (E)-3-methyl-5-styrylisoxazolo[5,4-c]pyridine

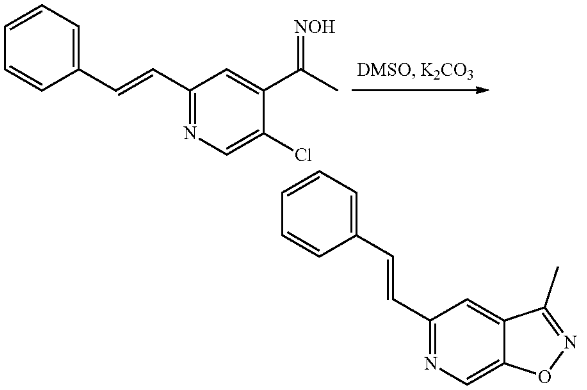

To a solution of 1-(5-chloro-2-((E)-styryl)pyridin-4-yl)ethan-1-one oxime (294 mg) in DMSO (10 mL) were added $K_2CO_3$ (448.2 mg). The reaction was stirred at 100° C. for 2 hr. After cooling to RT, water and EtOAc were added to the reaction mixture. The two phases were separated, and the aqueous phase was extracted with DCM (10 mL×3). The combined organic layers were dried over $Na_2SO_4$, filtered and concentrated to give a residue, which was purified by silica gel column chromatography to give (E)-3-methyl-5-styrylisoxazolo[5,4-c]pyridine (231 mg) as a yellow solid. LC/MS ESI (m/z): 237 $[M+H]^+$. $^1H$ NMR (400 MHz, DMSO-d6) δ 9.17 (s, 1H), 8.06 (s, 1H), 7.69 (t, J=11.2 Hz, 3H), 7.50-7.39 (m, 3H), 7.33 (t, J=7.3 Hz, 1H), 2.63 (s, 3H).

Synthesis of 3-methylisoxazolo[5,4-c]pyridine-5-carbaldehyde (N201201-109/115)

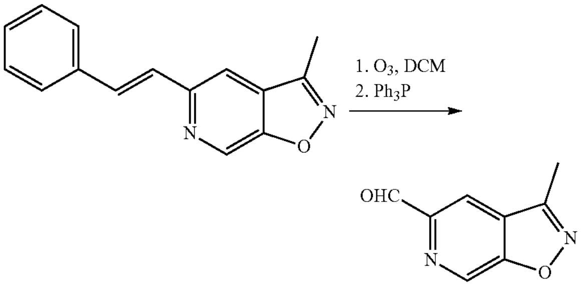

Ozone was bubbled through a solution of (E)-3-methyl-5-styrylisoxazolo[5,4-c]pyridine (483 mg) in anhydrous DCM (10 mL) at −78° C. for 10 min. Excess ozone gas was then purged with nitrogen, followed by the addition of triphenylphosphine (644 mg). The mixture was stirred for another 40 min and then concentrated in vacuum to get a residue, which was purified by silica gel column chromatography to give 3-methylisoxazolo[5,4-c]pyridine-5-carbaldehyde (200 mg). LC/MS ESI (m/z):163 $[M+H]^+$.

$^1H$ NMR (400 MHz, $CDCl_3$) δ 10.23 (s, 1H), 9.16 (s, 1H), 8.35 (d, J=0.9 Hz, 1H), 2.70 (s, 3H).

Synthesis of (R,E)-2-methyl-N-((3-methylisoxazolo[5,4-c]pyridin-5-yl)methylene)propane-2-sulfinamide

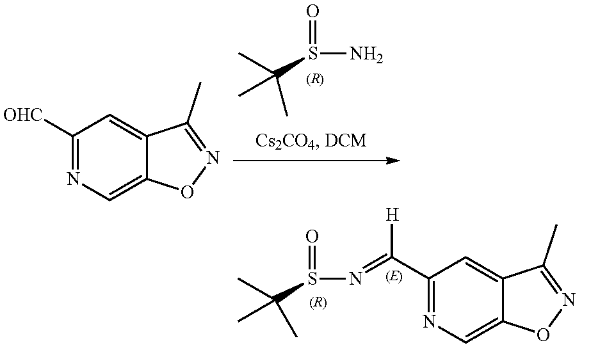

To a solution of 3-methylisoxazolo[5,4-c]pyridine-5-carbaldehyde (0.23 g) in anhydrous dichloromethane (10 mL) were added (R)-2-methylpropane-2-sulfinamide (0.26 g) and $CuSO_4$ (1.15 g), and the reaction was stirred at rt overnight. The reaction solution was then filtered and concentrated in vacuum. The residue was purified by silica gel column chromatography to give (R,E)-2-methyl-N-((3-methylisoxazolo[5,4-c]pyridin-5-yl)methylene)propane-2-sulfinamide (309 mg) as a white solid. LC/MS ESI (m/z): 266 $[M+H]^+$. $^1H$ NMR (400 MHz, DMSO-d6) δ 9.33 (d, J=1.1 Hz, 1H), 8.69-8.62 (m, 2H), 2.69 (s, 3H), 1.24 (s, 9H) ppm.

Synthesis of (R)-2-methyl-N—((R)-1-(3-methylisoxazolo[5,4-c]pyridin-5-yl)ethyl)propane-2-sulfinamide

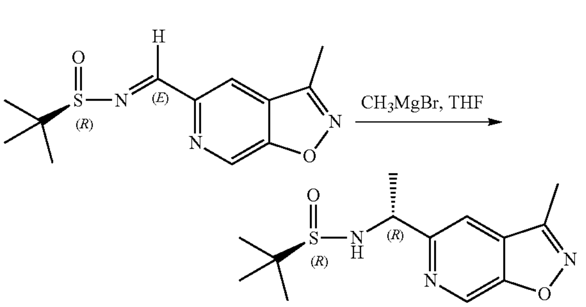

To a solution of (R,E)-2-methyl-N-((3-methylisoxazolo[5,4-c]pyridin-5-yl)methylene)propane-2-sulfinamide (337 mg) in Anhydrous tetrahydrofuran (5.0 mL) was added $CH_3MgBr$ (1.7 mL, 3.0M in $Et_2O$) dropwise at −78° C. The Grignard regent was added at a rate such that the internal reaction temperature was never higher than −60° C. After addition, the mixture was stirred for 3 h at −78, then warmed to room temperature. The reaction was quenched with saturated aqueous ammonium chloride. The two phases were separated, and the aqueous phase was extracted with DCM (10 mL×3). The combined organic layers were dried over $Na_2SO_4$, filtered and concentrated to give a residue, which was purified by silica gel column chromatography to give (R)-2-methyl-N—((R)-1-(3-methylisoxazolo[5,4-c]pyridin-5-yl)ethyl)propane-2-sulfinamide (226 mg). LC/MS ESI (m/z):282 $[M+H]^+$.

Synthesis of (R)-1-(3-methylisoxazolo[5,4-c]pyridin-5-yl)ethan-1-amine, hydrochloride

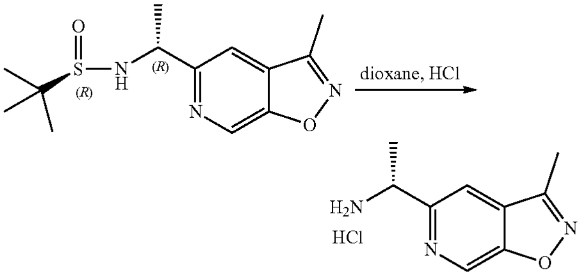

To a solution of (R)-2-methyl-N—((R)-1-(3-methylisoxazolo[5,4-c]pyridin-5-yl)ethyl)propane-2-sulfinamide (219 mg) in dioxane (3 mL) were added 4N HCl-Dioxane (1 mL), and the reaction was stirred at rt for 30 min. Then the mixture was concentrated in vacuo to get a crude product of (R)-1-(3-methylisoxazolo[5,4-c]pyridin-5-yl)ethan-1-amine, hydrochloride, which was used as is in next step. LC/MS ESI (m/z):178 $[M+H]^+$.

Synthesis of (R)-2-(4-isopropylphenyl)-N-(1-(3-methylisoxazolo[5,4-c]pyridin-5-yl)ethyl)acetamide

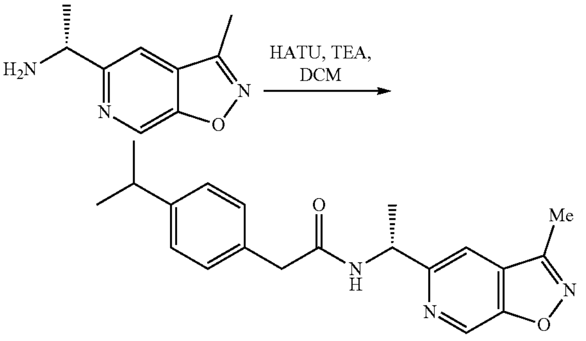

(R)-1-(3-methylisoxazolo[5,4-c]pyridin-5-yl)ethan-1-amine, hydrochloride (137 mg) was dissolved in anhydrous DCM (15 mL) and then 2-[4-(propan-2-yl)phenyl]acetic acid (151.6 mg), HATU (587.9 mg) and TEA (0.32 mL) were added to the solution. The reaction was stirred at rt for 1 h and then diluted with water. The two phases were separated, and the aqueous phase was extracted with DCM (10 mL×3). The combined organic layers were dried over $Na_2SO_4$, filtered and concentrated to give a residue, which was purified by Prep-HPLC [Column: YMC-Actus Triart C18 250*21 mm; Mobile phase: from 20% to 95% MeCN with $H_2O$ (0.1% $NH_3H_2O$); flow rate: 15 mL/min; wavelength: 220 nm/254 nm] to give (R)-2-(4-isopropylphenyl)-N-(1-(3-methylisoxazolo[5,4-c]pyridin-5-yl)ethyl)acetamide (146.8 mg) as a colorless oil. LC/MS ESI (m/z):338

[M+H]$^+$; $^1$H NMR (400 MHz, $CDCl_3$) δ 8.88 (s, 1H), 7.48 (s, 1H), 7.20-7.16 (m, 4H), 6.55 (d, J=7.6 Hz, 1H), 5.32-5.25 (m, 1H), 3.55 (s, 2H), 2.92-2.89 (m, 1H), 2.60 (s, 3H), 1.47 (d, J=6.8 Hz, 3H), 1.25 (d, J=6.9 Hz, 6H).

Example 7. (R)-2-(4-isopropylphenyl)-N-(1-(1-propyl-1H-pyrazolo[3,4-c]pyridin-5-yl)ethyl)acetamide

Synthesis of methyl 1-propyl-1H-pyrazolo[3,4-c]pyridine-5-carbaldehyde

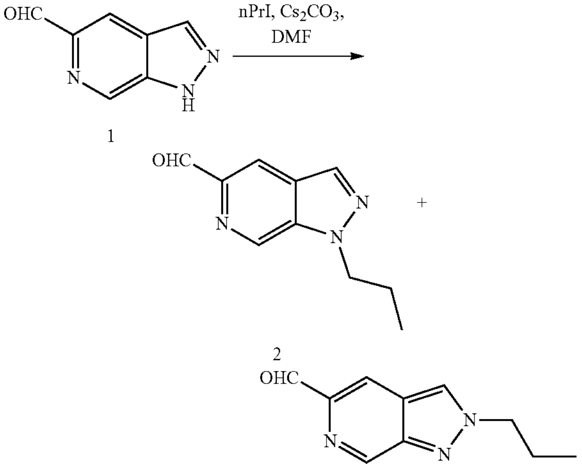

1

2

2A

A solution of 1H-pyrazolo[3,4-c]pyridine-5-carbaldehyde (480 mg), 1-iodopropane (0.35 mL) and $Cs_2CO_3$ (1.6 g) in DMF (1.0 mL) was stirred at 25° C. for 12 hr. The mixture was diluted with water and extracted with EtOAc. The combined extracts were dried, filtered and concentrated to give a residue which was purified by column chromatography on silica gel (DCM:MeOH=1:0 to 20:1) to give 1-propyl-1H-pyrazolo[3,4-c]pyridine-5-carbaldehyde (185 mg) as a white solid. $^1$H NMR (400 MHz, $CDCl_3$) δ 10.22 (s, 1H), 9.06 (s, 1H), 8.39 (d, J=1.2 Hz, 1H), 8.24 (s, 1H), 4.51 (t, J=7.2 Hz, 2H), 2.06-2.04 (m, 2H), 0.96 (t, J=7.2 Hz, 3H). and 2-propyl-2H-pyrazolo[3,4-c]pyridine-5-carbaldehyde (125 mg) as a white solid. $^1$H NMR (400 MHz, $CDCl_3$): δ 10.18 (s, 1H), 9.32 (s, 1H), 8.32 (d, J=1.2 Hz, 1H), 8.20 (s, 1H), 4.49 (t, J=7.2 Hz, 2H), 2.12-2.08 (m, 2H), 0.98 (t, J=7.2 Hz, 3H).

Synthesis of (R,E)-2-methyl-N-((1-propyl-1H-pyrazolo[3,4-c]pyridin-5-yl)methylene)propane-2-sulfinamide (N201201-161)

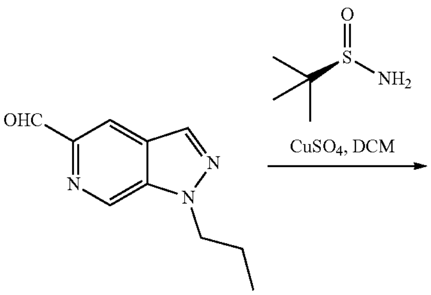

-continued

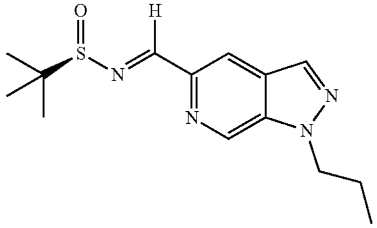

To a solution of 1-propyl-1H-pyrazolo[3,4-c]pyridine-5-carbaldehyde (185 mg) in anhydrous DCM (11 mL) were added (R)-2-methylpropane-2-sulfinamide (154.0 mg) and $CuSO_4$ (234.1 mg). The reaction was stirred at RT for overnight. The solid was filtered with Celite. Then, the filtrate was concentrated to provide a residue, which was purified by silica gel column chromatography to give (R,E)-2-methyl-N-((1-propyl-1H-pyrazolo[3,4-c]pyridin-5-yl)methylene)propane-2-sulfinamide (233 mg). LC/MS ESI (m/z): 293 [M+H]$^+$; $^1$H NMR (400 MHz, DMSO-d6) δ 9.36 (s, 1H), 8.64 (s, 1H), 8.54 (s, 1H), 8.40 (s, 1H), 4.57 (t, J=6.9 Hz, 2H), 1.94-1.89 (m, 2H), 1.22 (s, 9H), 0.84 (t, J=7.4 Hz, 3H).

Synthesis of (R)-2-methyl-N—((R)-1-(1-propyl-1H-pyrazolo[3,4-c]pyridin-5-yl)ethyl)propane-2-sulfinamide (N201201-166)

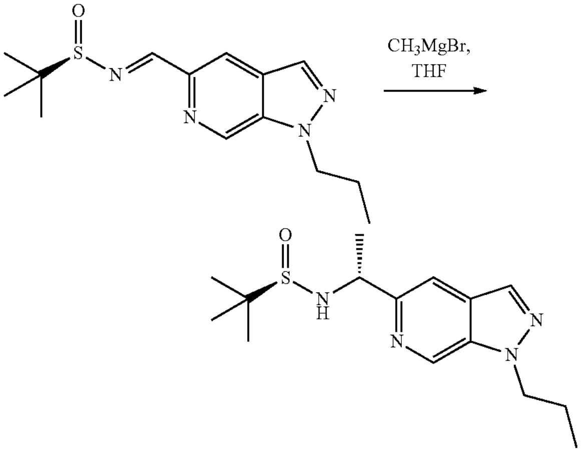

To a solution of (R,E)-2-methyl-N-((1-propyl-1H-pyrazolo[3,4-c]pyridin-5-yl)methylene)propane-2-sulfinamide (233 mg) in anhydrous THF (10 mL) was added 3M $CH_3MgBr$ (1.328 mL, 3M in ether) dropwise under $N_2$, and the reaction was stirred at −60° C. for 2 hr. The reaction was quenched with aq. $NH_4Cl$ and extracted with EA. The combined extracts were washed with saturated NaCl, dried over with $Na_2SO_4$, filtered and concentrated in vacuo. The residue was then purified by silica gel column chromatography to give (R)-2-methyl-N—((R)-1-(1-propyl-1H-pyrazolo[3,4-c]pyridin-5-yl)ethyl)propane-2-sulfinamide (146 mg). LC/MS ESI (m/z): 309 [M+H]$^+$; $^1$H NMR (400 MHz, DMSO-d6) δ 9.14 (s, 1H), 8.19 (d, J=0.6 Hz, 1H), 7.80 (d, J=0.6 Hz, 1H), 5.63 (d, J=7.5 Hz, 1H), 4.62-4.44 (m, 2H), 1.93-1.84 (m, 2H), 1.48 (d, J=6.8 Hz, 3H), 1.14 (s, 9H), 0.83 (t, J=7.4 Hz, 3H) ppm.

Synthesis of (R)-1-(1-propyl-1H-pyrazolo[3,4-c]pyridin-5-yl)ethanamine, hydrochloride

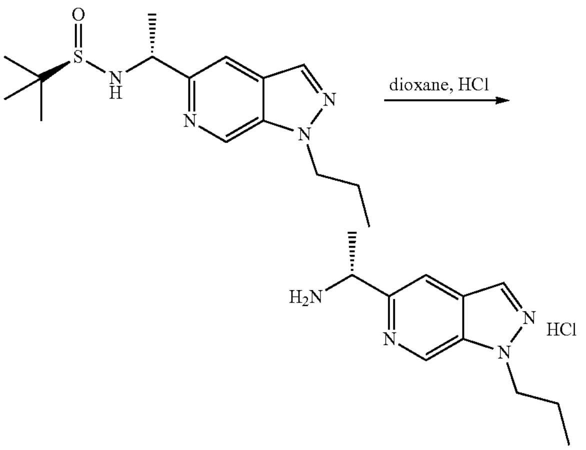

To a solution of (R)-2-methyl-N—((R)-1-(1-propyl-1H-pyrazolo[3,4-c]pyridin-5-yl)ethyl)propane-2-sulfinamide (95 mg) in dioxane (3 mL) was added 4N HCl-dioxane (1.0 mL). The reaction was stirred at rt for 30 min. Then the mixture was concentrated to provide (R)-1-(1-propyl-1H-pyrazolo[3,4-c]pyridin-5-yl)ethanamine hydrochloride, which was used directly in the next step. LC/MS ESI (m/z): 205 $[M+H]^+$.

Synthesis of (R)-2-(4-isopropylphenyl)-N-(1-(1-propyl-1H-pyrazolo[3,4-c]pyridin-5-yl)ethyl)acetamide

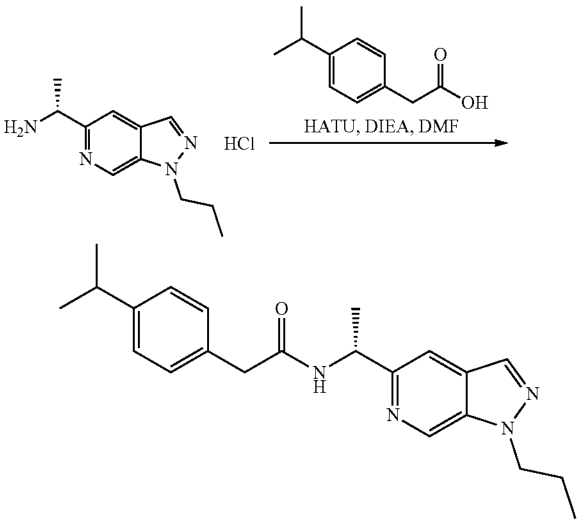

To a solution of (R)-1-(1-propyl-1H-pyrazolo[3,4-c]pyridin-5-yl)ethanamine hydrochloride (82 mg) in anhydrous DMF were added DIEA (0.12 mL, Solution A). To a solution of 2-(4-isopropylphenyl)acetic acid (78.7 mg) in anhydrous DMF were added HATU (167.9 mg) and stirred 3 min at RT (Solution B). Solution A was added to the solution B and stirred at RT for 1 h. The mixture was diluted with water, and the aqueous phase was extracted with DCM (10 mL×3). The combined extracts were dried over $Na_2SO_4$, filtered and concentrated to give a residue, which was purified by Prep-HPLC [Column: YMC Triart C18 250*20 mm I.D, 5 um; Mobile phase: from 10% to 95% MeCN with $H_2O$ (0.1% FA); flow rate: 14 mL/min; wavelength: 220 nm/254 nm] to give (R)-2-(4-isopropylphenyl)-N-(1-(1-propyl-1H-pyrazolo[3,4-c]pyridin-5-yl)ethyl)acetamide. LC/MS ESI (m/z): 365 $[M+H]^+$; $^1H$ NMR (400 MHz, $CDCl_3$) δ 8.82 (s, 1H), 7.98 (s, 1H), 7.49 (s, 1H), 7.19 (s, 4H), 6.62 (d, J=7.8 Hz, 1H), 5.28-5.21 (m, 1H), 4.42 (t, J=7.0 Hz, 2H), 3.56-3.55 (m, 2H), 2.92-2.88 (m, 1H), 2.00-1.96 (m, 2H), 1.46 (d, J=6.8 Hz, 3H), 1.25 (d, J=6.9 Hz, 6H), 0.93 (t, J=7.4 Hz, 3H).

Example 8. (R)—N-(1-(1-ethyl-1H-pyrazolo[3,4-c]pyridin-5-yl)ethyl)-2-(4-isopropylphenyl)acetamide Synthesis of 5-bromo-1H-pyrazolo[3,4-c]pyridine

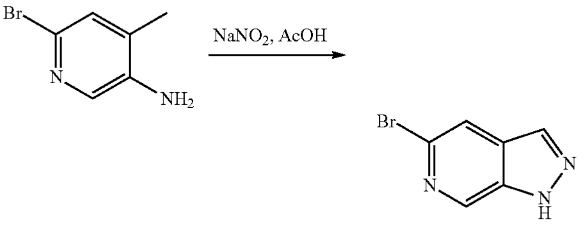

To a solution of 6-bromo-4-methylpyridin-3-amine (1.0 g) in acetic acid (60 mL) were added sodium nitrite (0.37 mL) in an ice bath. The reaction was stirred at RT overnight. Then the reaction was concentrated and then treated with saturated aqueous $NaHCO_3$. The aqueous mixture was extracted with EA. The combined extracts were washed with brine, dried over with $Na_2SO_4$, filtered and concentrated in vacuo. Then the residue was purified by silica gel column chromatography, to give 5-bromo-1H-pyrazolo[3,4-c]pyridine (442 mg). LC/MS ESI (m/z): 198 $[M+H]^+$.

Synthesis of 1H-pyrazolo[3,4-c]pyridine-5-carbaldehyde

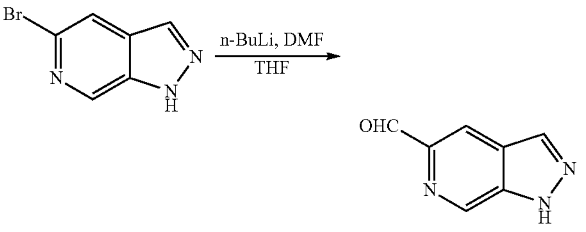

To a solution of 5-bromo-1H-pyrazolo[3,4-c]pyridine (3.3 g) in anhydrous THE (100 mL) was added n-BuLi (20.0 mL, 2 N in THF) at −78° C. The mixture was stirred at −78° C. for 1 hr. DMF (3.87 mL) was then added to the mixture at −78° C., and the mixture was stirred at −78° C. for 1 hr. The reaction was warmed to rt and quenched with an $NH_4Cl$ solution. The two phases were separated, and the aqueous phase was extracted with DCM (10 mL×3). The combined organic layers were dried over $Na_2SO_4$, filtered and concentrated to give a residue, which was purified by column chromatography on silica gel (DCM:MeOH=1:0 to 20:1) to give 1H-pyrazolo[3,4-c]pyridine-5-carbaldehyde (1.0 g) as a white solid. LC/MS ESI (m/z): 148 [M+H]+

Synthesis of 1-ethyl-1H-pyrazolo[3,4-c]pyridine-5-carbaldehyde

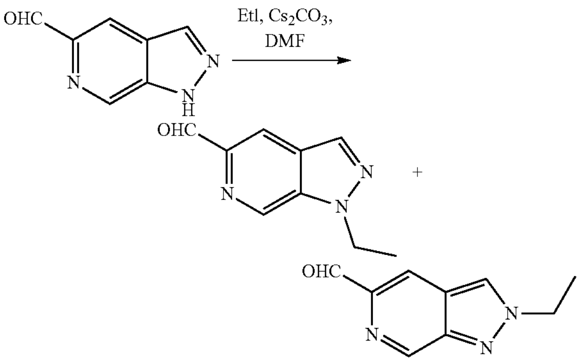

A solution of 1H-pyrazolo[3,4-c]pyridine-5-carbaldehyde (480 mg), ethyl iodide (0.35 mL) and $Cs_2CO_3$ (1.6 g) in DMF (1.0 mL) was stirred at 25° C. for 12 hr. The mixture was then diluted with water and extracted with EtOAc. The combined extracts were dried, filtered and concentrated to give a residue, which was purified by column chromatography on silica gel (DCM:MeOH=1:0 to 20:1) to give 1-ethyl-1H-pyrazolo[3,4-c]pyridine-5-carbaldehyde (185 mg) as a white solid. $^1$H NMR (400 MHz, DMSO-d6) δ10.11 (s, 1H), 9.39 (s, 1H), 8.53-8.39 (m, 2H), 4.65 (q, J=7.2 Hz, 2H), 1.47 (t, J=7.2 Hz, 3H). and 2-propyl-2H-pyrazolo[3,4-c]pyridine-5-carbaldehyde (125 mg) as a white solid. $^1$H NMR (400 MHz, DMSO): 10.05 (s, 1H), 9.36-9.23 (m, 1H), 8.85 (s, 1H), 8.43 (d, J=1.2 Hz, 1H), 4.60 (q, J=7.2 Hz, 2H), 1.55 (t, J=7.2 Hz, 3H).

Synthesis of (R,E)-N-((1-ethyl-1H-pyrazolo[3,4-c]pyridin-5-yl)methylene)-2-methylpropane-2-sulfinamide

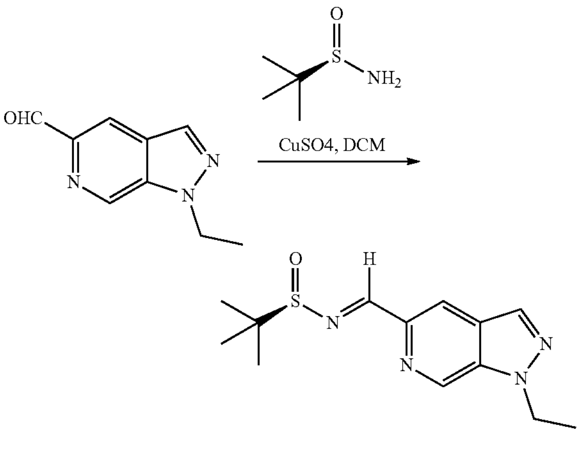

To a solution of 1-ethyl-1H-pyrazolo[3,4-c]pyridine-5-carbaldehyde (186 mg) in anhydrous DCM (10 mL) were added 2-methylpropane-2-sulfinamide (157.6 mg) and $CuSO_4$ (239.4 mg). The reaction was stirred at rt overnight. The mixture was then filtered, and the filtrate was concentrated in vacuum to get a residue, which was purified by silica to give (R,E)-N-((1-ethyl-1H-pyrazolo[3,4-c]pyridin-5-yl)methylene)-2-methylpropane-2-sulfinamide (207 mg) as a white solid. LC/MS ESI (m/z): 279 [M+H]+; $^1$H NMR (400 MHz, DMSO-d6) δ 9.35 (s, 1H), 8.64 (s, 1H), 8.54 (d, J=1.2 Hz, 1H), 8.39 (d, J=0.6 Hz, 1H), 4.66-4.61 (m, 2H), 1.47 (t, J=7.2 Hz, 3H), 1.22 (s, 9H) ppm.

Synthesis of (R)—N—((R)-1-(1-ethyl-1H-pyrazolo[3,4-c]pyridin-5-yl)ethyl)-2-methylpropane-2-sulfinamide

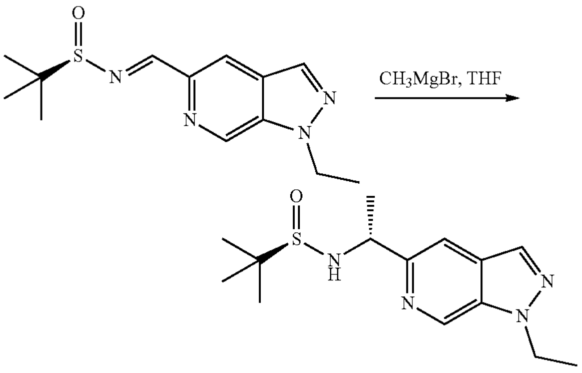

To a solution of (R,E)-N-((1-ethyl-1H-pyrazolo[3,4-c]pyridin-5-yl)methylene)-2-methylpropane-2-sulfinamide (207 mg) in anhydrous THE (15 mL) were added $CH_3MgBr$ (1.24 mL, 3.0M in ether) dropwise. The reaction was stirred at −60° C. for 2 hr. The reaction was then quenched with saturated $NH_4Cl$ solution. The two phases were separated, and the aqueous phase was extracted with DCM (10 mL×3). The combined organic layers were dried over $Na_2SO_4$, filtered and concentrated to give a residue, which was purified by silica gel column chromatography, to give (R)—N—((R)-1-(1-ethyl-1H-pyrazolo[3,4-c]pyridin-5-yl)ethyl)-2-methylpropane-2-sulfinamide (103 mg) as a yellow oil: LC/MS ESI (m/z): 295 [M+H]+.

Synthesis of (R)-1-(1-ethyl-1H-pyrazolo[3,4-c]pyridin-5-yl)ethan-1-amine, hydrochloride

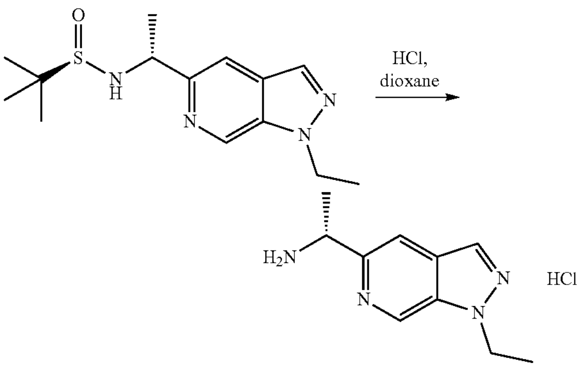

To a solution of (R)—N—((R)-1-(1-ethyl-1H-pyrazolo[3,4-c]pyridin-5-yl)ethyl)-2-methylpropane-2-sulfinamide (142 mg) in dioxane (3 mL) was added 4N HCl-dioxane (1 mL), and the reaction was stirred at rt for 30 min. The mixture was then concentrated to provide the (R)-1-(1-ethyl-1H-pyrazolo[3,4-c]pyridin-5-yl)ethan-1-amine, hydrochloride, which was used directly for next step. LC/MS ESI (m/z): 191 $[M+H]^+$.

Synthesis of (R)—N-(1-(1-ethyl-1H-pyrazolo[3,4-c]pyridin-5-yl)ethyl)-2-(4-isopropylphenyl)acetamide

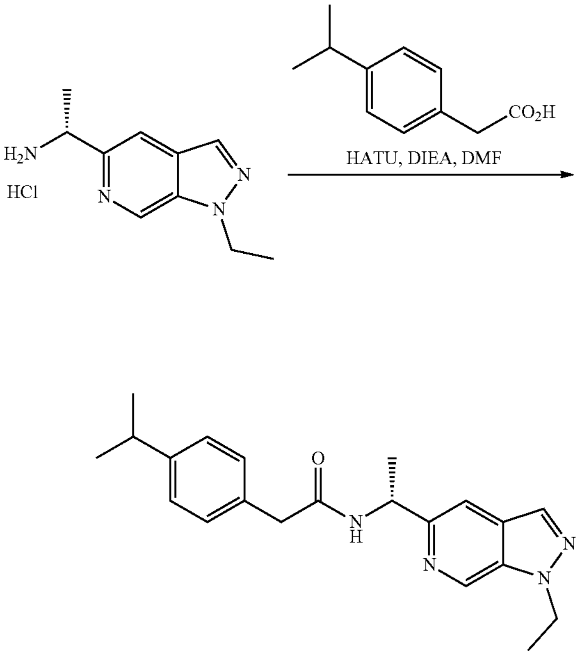 [SMILES: Cl ; CCn1ncc2cc([C@@H](C)N)ncc21 ; CC(C)c1ccc(CC(=O)O)cc1 ; CCn1ncc2cc([C@@H](C)NC(=O)Cc3ccc(C(C)C)cc3)ncc21]

To a solution of (R)-1-(1-ethyl-1H-pyrazolo[3,4-c]pyridin-5-yl)ethanamine hydrochloride (134 mg) in anhydrous DMF were added DIEA (0.5 mL) to provide Solution A. To a solution of 2-(4-isopropylphenyl)acetic acid (95.9 mg) in anhydrous DMF was added HATU (225 mg) and stirred at RT for 3 min to provide Solution B. Solution A was added to the Solution B and stirred at RT for 1 h. The reaction was diluted with EA and water. The two phases were separated, and the aqueous phase was extracted with DCM (10 mL×3). The combined organic layers were dried over $Na_2SO_4$, filtered and concentrated to give a residue, which was purified by prep-HPLC [Column: Xbudge prep C18 250*19 mm Sum OBD; Mobile phase: from 10% to 95% MeCN with $H_2O$ (0.1 FA); flow rate: 20 mL/min; wavelength: 205 nm/254 nm] and SFC (Column:ChiralPak IA, 250×21.3 mm I.D., 5 μm; Mobile phase: A for $CO_2$ and B for MEOH+0.1% NH3H2O; Gradient: B 40%; wavelength: 220 nm) to give (R)—N-(1-(1-ethyl-1H-pyrazolo[3,4-c]pyridin-5-yl)ethyl)-2-(4-isopropylphenyl)acetamide (44.8 mg) as a white solid. LC/MS ESI (m/z): 351 $[M+H]^+$; $^1H$ NMR (400 MHz, $CDCl_3$) δ 8.83 (s, 1H), 7.97 (s, 1H), 7.49 (s, 1H), 7.19 (s, 4H), 6.62 (d, J=7.2 Hz, 1H), 5.28-5.21 (m, 1H), 4.52 (q, J=7.3 Hz, 2H), 3.55 (s, 2H), 2.92-2.87 (m, 1H), 1.56 (t, J=7.3 Hz, 3H), 1.46 (d, J=6.8 Hz, 3H), 1.25 (d, J=6.9 Hz, 6H).

Example 9. (R)—N-(1-(1-ethyl-1H-pyrazolo[3,4-c]pyridin-5-yl)ethyl)-2-(4-isopropylphenyl)acetamide Step 1. Synthesis of 1-(2,2,2-trifluoroethyl)-1H-pyrazolo[3,4-c]pyridine-5-carbaldehyde

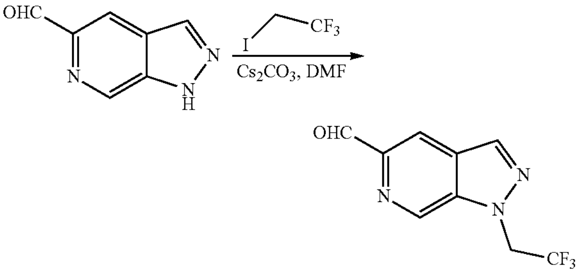

A solution of 1H-pyrazolo[3,4-c]pyridine-5-carbaldehyde (760 mg), 1,1,1-trifluoro-2-iodoethane (0.51 mL) and $Cs_2CO_3$ (2.5 g) in DMF (10 mL) was stirred at 100° C. for 12 hr. The mixture was diluted with water and extracted with EtOAc. The combined extracts were dried, filtered and concentrated to give a residue. The residue was purified by column chromatography on silica gel (DCM:MeOH=1:0 to 20:1) to give 1-(2,2,2-trifluoroethyl)-1H-pyrazolo[3,4-c]pyridine-5-carbaldehyde (500 mg) as a yellow solid. LC/MS ESI (m/z): 230 $[M+H]^+$.

Step 2. Synthesis of (R,E)-2-methyl-N-((1-(2,2,2-trifluoroethyl)-1H-pyrazolo[3,4-c]pyridin-5-yl)methylene)propane-2-sulfinamide

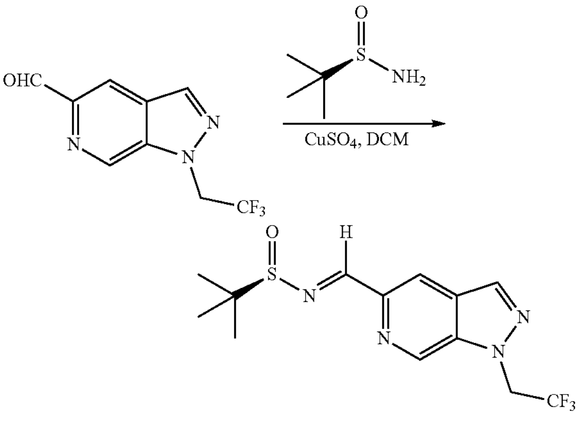

A solution of 1-(2,2,2-trifluoroethyl)-1H-pyrazolo[3,4-c]pyridine-5-carbaldehyde (500 mg), (R)-2-methylpropane-2-sulfinamide (396.7 mg) and copper sulfate pentahydrate (1.0 g) in DCM (15 mL) was stirred at 25° C. for 12 hr. The mixture was filtered and concentrated to give a residue. The residue was purified by column chromatography on silica gel (DCM:MeOH=1:0 to 20:1) to give (R,E)-2-methyl-N-((1-(2,2,2-trifluoroethyl)-1H-pyrazolo[3,4-c]pyridin-5-yl)methylene)propane-2-sulfinamide (450 mg) as a yellow solid. LC/MS ESI (m/z): 333 $[M+H]^+$.

Step 3. Synthesis of (R)-2-methyl-N—((R)-1-(1-(2,2,2-trifluoroethyl)-1H-pyrazolo[3,4-c]pyridin-5-yl)ethyl)propane-2-sulfinamide

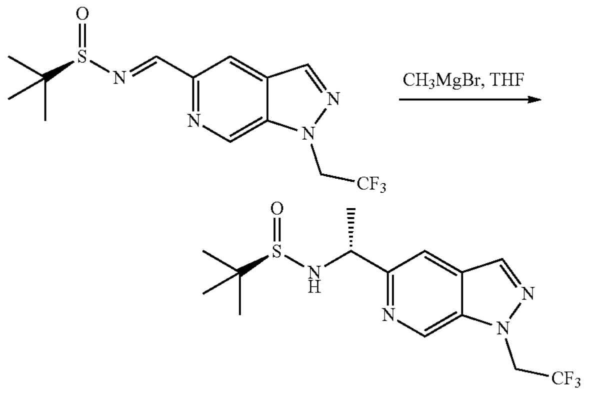

To a solution of (R,E)-2-methyl-N-((1-(2,2,2-trifluoroethyl)-1H-pyrazolo[3,4-c]pyridin-5-yl)methylene)propane-2-sulfinamide (450 mg) in THE (5 mL) was added $CH_3MgBr$ (3.0M in ether, 1.35 mL) at −78° C. The mixture was stirred at −78° C. for 2 hr. The mixture was quenched with $NH_4Cl$ solution and extracted with EtOAc. The combined extracts were dried, filtered and concentrated to give a residue. The residue was purified by column chromatography on silica gel (DCM:MeOH=1:0 to 20:1) to give (R)-2-methyl-N—((R)-1-(1-(2,2,2-trifluoroethyl)-1H-pyrazolo[3,4-c]pyridin-5-yl)ethyl)propane-2-sulfinamide (350 mg) as a yellow solid. LC/MS ESI (m/z): 349 $[M+H]^+$.

Step 4. Synthesis of (R)-1-(1-(2,2,2-trifluoroethyl)-1H-pyrazolo[3,4-c]pyridin-5-yl)ethan-1-amine hydrochloride

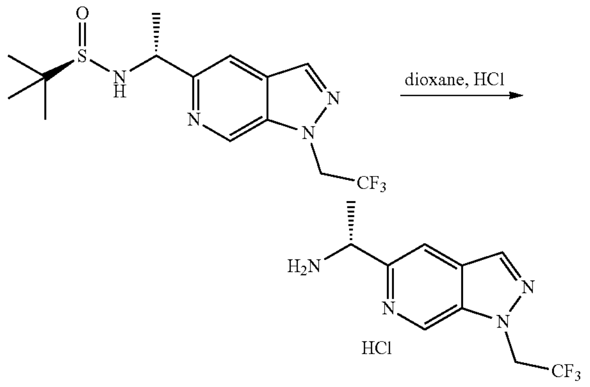

To a solution of (R)-2-methyl-N—((R)-1-(1-(2,2,2-trifluoroethyl)-1H-pyrazolo[3,4-c]pyridin-5-yl)ethyl)propane-2-sulfinamide (300 mg) in dioxane (2.0 mL) was added HCl/dioxane (4N in dioxane, 2.0 mL). The mixture was stirred at 25° C. for 30 min. The mixture was concentrated to give (R)-1-(1-(2,2,2-trifluoroethyl)-1H-pyrazolo[3,4-c]pyridin-5-yl)ethan-1-amine hydrochloride (300 mg, crude) as a white solid. LC/MS ESI (m/z): 245 $[M+H]^+$.

Step 5. Synthesis of (R)-2-(4-isopropylphenyl)-N-(1-(1-(2,2,2-trifluoroethyl)-1H-pyrazolo[3,4-c]pyridin-5-yl)ethyl)acetamide

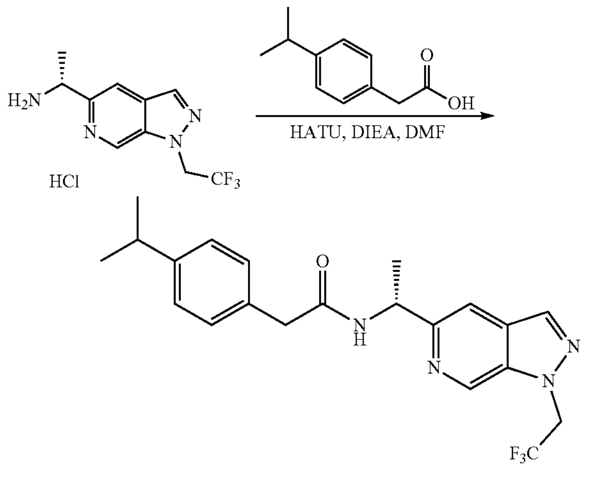

A solution of (R)-1-(1-(2,2,2-trifluoroethyl)-1H-pyrazolo[3,4-c]pyridin-5-yl)ethan-1-amine hydrochloride (300 mg), 2-[4-(propan-2-yl)phenyl]acetic acid (240.8 mg), HATU (560.49 mg) and DIEA (0.41 mL) in DCM (10 mL) was stirred at 25° C. for 12 hr. The mixture was washed with water. The organic layer was dried, filtered and concentrated to give a residue. The residue was purified by prep-HPLC [Column: YMC-Actus Triart C18 250*21 mm; Mobile phase: from 50% to 95% MeCN with H2O (0.1% FA); flow rate: 20 mL/min; wavelength: 220 nm/254 nm] and SFC (Column:ChiralPak IA, 250×21.3 mm I.D., 5 μm; Mobile phase: A for $CO_2$ and B for MEOH+0.1% $NH_3H_2O$; Gradient: B 40%; wavelength: 220 nm) to give (R)-2-(4-isopropylphenyl)-N-(1-(1-(2,2,2-trifluoroethyl)-1H-pyrazolo[3,4-c]pyridin-5-yl)ethyl)acetamide (128.6 mg) as a white solid. LC/MS ESI (m/z): 405 $(M+H)^+$; $^1H$ NMR (400 MHz, $CDCl_3$) δ 8.85 (s, 1H), 8.08 (s, 1H), 7.54 (s, 1H), 7.24-7.12 (m, 4H), 6.58 (d, J=7.6 Hz, 1H), 5.27-5.24 (m, 1H), 5.03 (q, J=8.4 Hz, 2H), 3.59-3.51 (m, 2H), 2.95-2.85 (m, 1H), 1.46 (d, J=6.8 Hz, 3H), 1.25 (d, J=6.6 Hz, 3H); $^{19}F$ NMR (377 MHz, $CDCl_3$) δ −70.8 ppm.

Example 10. (R)—N-(1-(1-methyl-1H-pyrazolo[3,4-b]pyridin-5-yl)ethyl)-2-(4-(1-(trifluoromethyl)cyclopropyl)phenyl)acetamide Synthesis of 1-methyl-1H-pyrazolo[3,4-b]pyridine-5-carbaldehyde

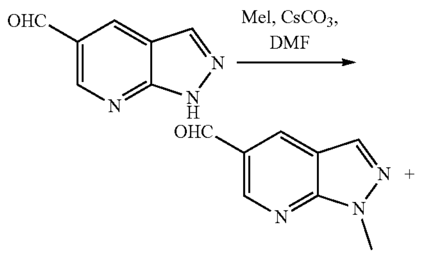

-continued

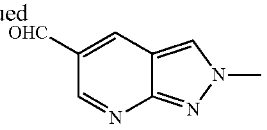

To a solution of 1H-pyrazolo[3,4-b]pyridine-5-carbaldehyde (594 mg) in anhydrous DMF (10 mL) were added $Cs_2CO_3$ (1.97 g) and iodomethane (630.3 mg), and the reaction was stirred at rt overnight. The reaction was diluted with EA and water. The organic layer was separated, washed with saturated NaCl solution, and concentrated in vacuo. The residue was purified by silica gel column chromatography to give 1-methyl-1H-pyrazolo[3,4-b]pyridine-5-carbaldehyde (285 mg). 1-methyl-1H-pyrazolo[3,4-b]pyridine-5-carbaldehyde: LC/MS ESI (m/z): 162 $[M+H]^+$; $^1H$ NMR (400 MHz, DMSO-d6) δ 10.15 (d, J=1.3 Hz, 1H), 9.06 (s, 1H), 8.81 (s, 1H), 8.41 (d, J=2.1 Hz, 1H), 4.12 (d, J=1.2 Hz, 3H).

2-methyl-2H-pyrazolo[3,4-b]pyridine-5-carbaldehyde: LC/MS ESI (m/z): 162 $[M+H]^+$; $^1H$ NMR (400 MHz, DMSO) δ 10.07 (s, 1H), 9.01 (d, J=2.1 Hz, 1H), 8.86 (d, J=2.1 Hz, 1H), 8.75 (s, 1H), 4.25 (s, 3H).

Synthesis of (R,E)-2-methyl-N-((1-methyl-1H-pyrazolo[3,4-b]pyridin-5-yl) methylene)propane-2-sulfinamide

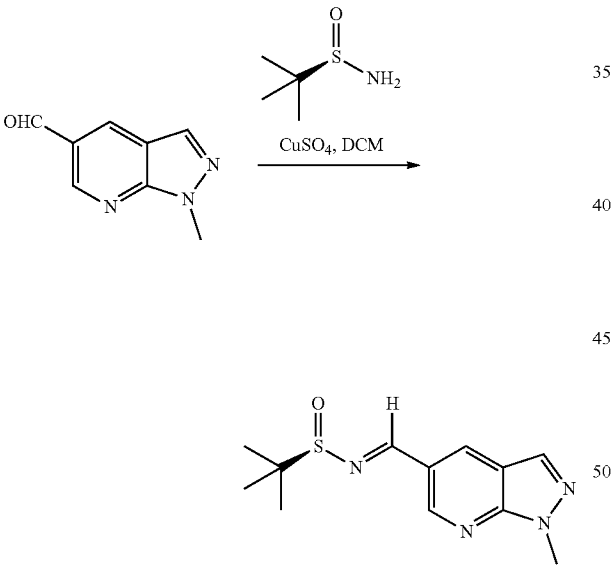

To a solution of 1-methyl-1H-pyrazolo[3,4-b]pyridine-5-carbaldehyde (285 mg) in anhydrous DCM (15 mL) were added (R)-2-methylpropane-2-sulfinamide (278.6 mg) and $CuSO_4$ (423.4 mg), and the reaction was stirred at RT overnight. The solution was filtered through a pad of Celite and the filtrate was concentrated. The residue was purified by silica gel column to give (R,E)-2-methyl-N-((1-methyl-1H-pyrazolo[3,4-b]pyridin-5-yl)methylene)propane-2-sulfinamide (158 mg). LC/MS ESI (m/z): 265 $[M+H]^+$; $^1H$ NMR (400 MHz, $CDCl_3$) δ 9.06 (d, J=1.9 Hz, 1H), 8.74 (s, 1H), 8.51 (d, J=1.9 Hz, 1H), 8.13 (s, 1H), 4.20 (s, 3H), 1.29 (s, 9H) ppm.

Step 3. Synthesis of (R)-2-methyl-N—((R)-1-(1-methyl-1H-pyrazolo[3,4-b]pyridin-5-yl)ethyl)propane-2-sulfinamide

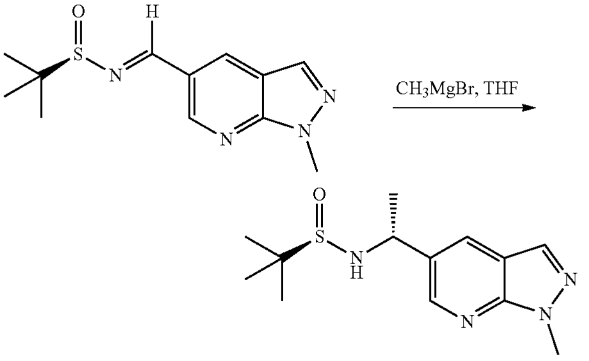

To a solution of (R,E)-2-methyl-N-((1-methyl-1H-pyrazolo[3,4-b]pyridin-5-yl)methylene)propane-2-sulfinamide (407 mg) in anhydrous THF (30 mL) was dropwise added $CH_3MgBr$ (9.0 mL, 3.0M in ether) and the reaction was stirred at −78° C. for 6 hr. The reaction was quenched with saturated aqueous $NH_4Cl$ and extracted with EtOAc. The combined extracts were separated, washed with saturated NaCl solution, dried over $Na_2SO_4$, filtered, and concentrated in vacuo. The residue was purified by silica gel column chromatography to give (R)-2-methyl-N—((R)-1-(1-methyl-1H-pyrazolo[3,4-b]pyridin-5-yl)ethyl)propane-2-sulfinamide (236 mg). LC/MS ESI (m/z): 281 $[M+H]^+$; $^1H$ NMR (400 MHz, $CDCl_3$) δ 8.56 (d, J=2.0 Hz, 1H), 8.04-7.95 (m, 2H), 4.79-4.73 (m, 1H), 4.16 (s, 3H), 3.43 (d, J=2.7 Hz, 1H), 1.63 (d, J=6.7 Hz, 3H), 1.21 (s, 9H).

Step 4. Synthesis of (R)-1-(1-methyl-1H-pyrazolo[3,4-b]pyridin-5-yl)ethan-1-amine hydrochloride

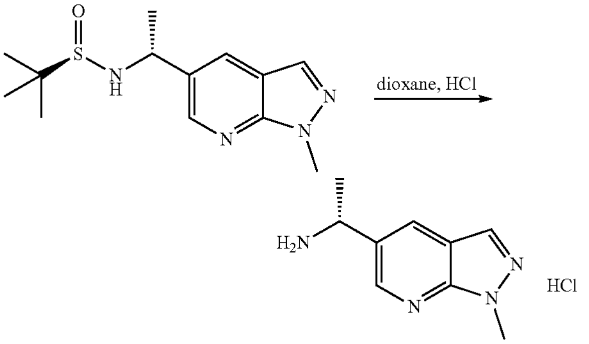

To a solution of (R)-2-methyl-N—((R)-1-(1-methyl-1H-pyrazolo[3,4-b]pyridin-5-yl)ethyl)propane-2-sulfinamide (77 mg) in dioxane (3 mL) was added 4N HCl-Dioxane (1.0 mL), and the reaction was stirred at rt for 30 min. Then the mixture was concentrated to provide (R)-1-(1-methyl-1H-pyrazolo[3,4-b]pyridin-5-yl)ethan-1-amine hydrochloride and used directly for next step. LC/MS ESI (m/z): 177 $[M+H]^+$.

Step 5. Synthesis of (R)—N-(1-(1-methyl-1H-pyrazolo[3,4-b]pyridin-5-yl)ethyl)-2-(4-(1-(trifluoromethyl)cyclopropyl)phenyl)acetamide

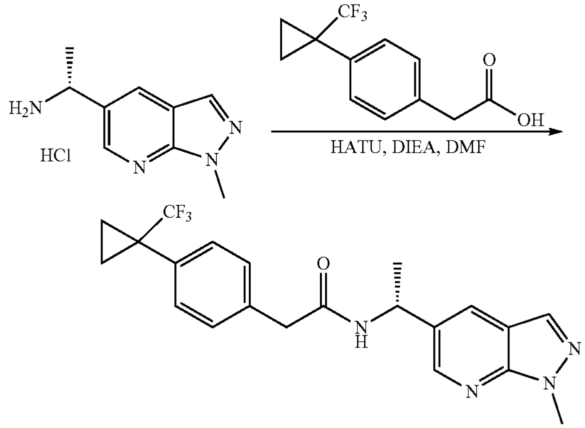

To a solution of (R)-1-(1-methyl-1H-pyrazolo[3,4-b]pyridin-5-yl)ethan-1-amine hydrochloride (107 mg) in anhydrous DMF (4.0 mL) were added DIEA (0.5 mL) to provide Solution A. To a solution of 2-(4-(1-(trifluoromethyl)cyclopropyl)phenyl)acetic acid (134.8 mg) in anhydrous DMF (4.0 mL) was added HATU (230.9 mg) and stirred at RT for 10 min to provide Solution B. Then Solution B was added to solution A and stirred at rt for 1 h. The reaction was then diluted with EA and water. The organic layer was separated, washed with saturated NaCl solution, dried over with $Na_2SO_4$ and concentrated in vacuo. The residue was then purified by prep-HPLC (Column: YMC Triart C18 250*20 mm I.D, 5 um; Mobile phase: from 20% to 95% MeCN with $H_2O$ (0.1% FA); flow rate: 15 mL/min; wavelength: 220 nm/254 nm) to give (R)—N-(1-(1-methyl-1H-pyrazolo[3,4-b]pyridin-5-yl)ethyl)-2-(4-(1-(trifluoromethyl)cyclopropyl)phenyl)acetamide (67.3 mg). LC/MS ESI (m/z): 403 $[M+H]^+$; $^1H$ NMR (400 MHz, $CDCl_3$) δ 8.48 (s, 1H), 7.94 (s, 1H), 7.88 (s, 1H), 7.43 (d, J=8.0 Hz, 2H), 7.22 (d, J=8.2 Hz, 2H), 5.71 (d, J=7.4 Hz, 1H), 5.30-5.23 (m, 1H), 4.14 (s, 3H), 3.56 (s, 2H), 1.52 (d, J=7.0 Hz, 3H), 1.37-1.34 (m, 2H), 1.02-1.01 (m, 2H); $^{19}F$ NMR (377 MHz, $CDCl_3$) δ −70.08 (s).

Example 11. (R)-2-(4-isopropylphenyl)-N-(1-(2-propyl-2H-pyrazolo[3,4-c]pyridin-5-yl)ethyl)acetamide Synthesis of (R,E)-2-methyl-N-((2-propyl-2H-pyrazolo[3,4-c]pyridin-5-yl)methylene)propane-2-sulfinamide

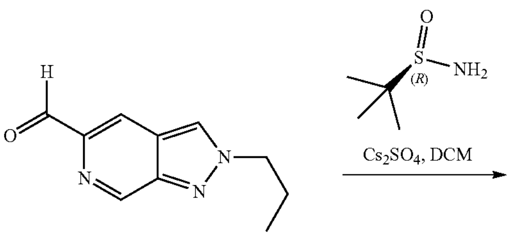

-continued

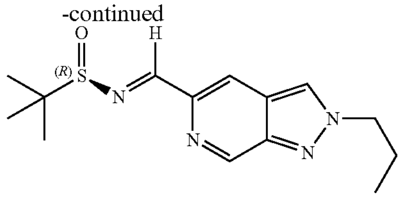

To a solution of 2-propyl-2H-pyrazolo[3,4-c]pyridine-5-carbaldehyde (34 mg) in $CH_2Cl_2$ (2 mL) was added (R)-2-methylpropane-2-sulfinamide (28.3 mg) and copper sulfate pentahydrate (129.5 mg) at rt. The reaction was stirred at room temperature overnight, and LC/MS showed the reaction was complete. The reaction mixture was quenched with ice-water and then extracted with EtOAc. The combined extracts were concentrated, and the residue was purified by column chromatography on silica gel (PE:EA=3:1) to give (R,E)-2-methyl-N-((2-propyl-2H-pyrazolo[3,4-c]pyridin-5-yl)methylene)propane-2-sulfinamide (25 mg, yellow solid). LC/MS ESI (m/z): 293 $[M+H]^+$.

Synthesis of (R)-2-methyl-N—((R)-1-(2-propyl-2H-pyrazolo[3,4-c]pyridin-5-yl)ethyl)propane-2-sulfinamide

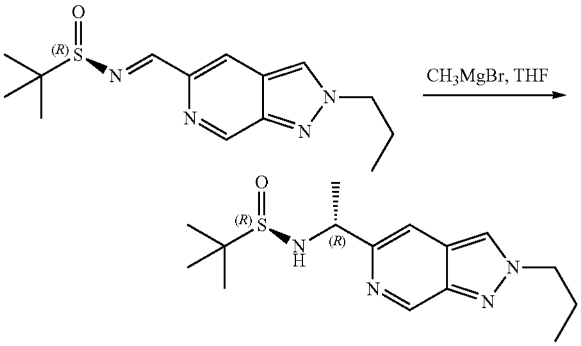

To a solution of (R,E)-2-methyl-N-((2-propyl-2H-pyrazolo[3,4-c]pyridin-5-yl)methylene)propane-2-sulfinamide (100 mg) in THF (3.0 mL) was added $CH_3MgBr$ (0.45 mL; 3M in ether) at −78° C. under nitrogen. The mixture was stirred at −78° C. for 2 hrs, and LC/MS showed the reaction was complete. The reaction mixture was quenched with ice-water and then extracted with EtOAc twice. The combined extracts were concentrated, and the residue was purified by column chromatography on silica gel (PE:EA=3:1) to give (R)-2-methyl-N—((R)-1-(2-propyl-2H-pyrazolo[3,4-c]pyridin-5-yl)ethyl)propane-2-sulfinamide (80 mg) as yellow solid. LC/MS ESI (m/z): 309 $[M+H]^+$.

Synthesis of (R)-1-(2-propyl-2H-pyrazolo[3,4-c]pyridin-5-yl)ethan-1-amine hydrochlorid

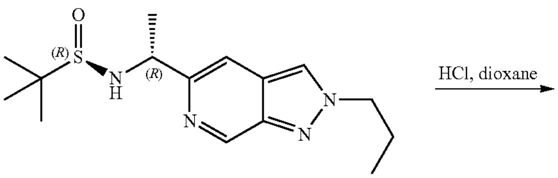

-continued

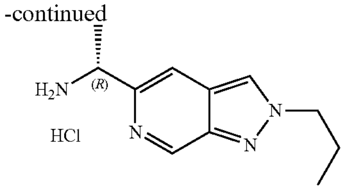

To a solution of (R)-2-methyl-N—((R)-1-(2-propyl-2H-pyrazolo[3,4-c]pyridin-5-yl)ethyl)propane-2-sulfinamide (80 mg) in dioxane (3 mL) was added HCl-dioxane (0.18 mL, 4N in dioxane) at room temperature. The mixture was stirred at room temperature for 2 hrs, and LC/MS showed the reaction was complete. The solvent was concentrated to give the (R)-1-(2-propyl-2H-pyrazolo[3,4-c]pyridin-5-yl)ethan-1-amine hydrochloride (120 mg, yellow solid), which was used directly for next step. LC/MS ESI (m/z): 204 $[M+H]^+$.

Step 4. Synthesis of (R)-2-(4-isopropylphenyl)-N-(1-(2-propyl-2H-pyrazolo[3,4-c]pyridin-5-yl)ethyl)acetamide

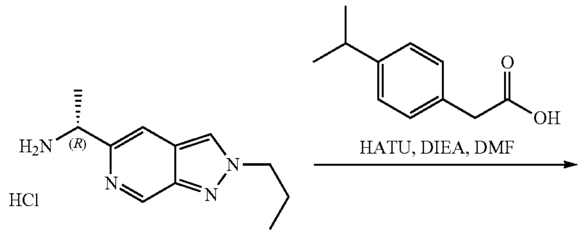

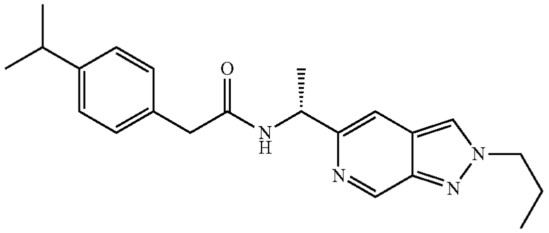

To a solution of 2-(4-isopropylphenyl)acetic acid (50 mg) in DMF (3.0 mL) were added (R)-1-(2-propyl-2H-pyrazolo[3,4-c]pyridin-5-yl)ethan-1-amine hydrochloride (57.0 mg), HATU (160 mg) and DIEA (108.6 mg). The mixture was stirred at room temperature for 2 hrs, and LC/MS showed the reaction was complete. The reaction mixture was quenched by ice-water and then extracted with EtOAc twice. The combined extracts were concentrated, and the residue was purified by column chromatography on silica gel (PE: EA=1:1) and further purified by prep-HPLC [Column: YMC-Triart C18 250*20.0 mm; Mobile phase: from 80% to 5% $H_2O$ (0.1% FA), from 20% to 95% MeCN; flow rate: 20 mL/min; wavelength: 220 nm/254 nm] and SFC (Column: ChiralPak IA, 250×21.3 mm I.D., 5 μm; Mobile phase: A for $CO_2$ and B for MEOH+0.1% $NH_3H_2O$; Gradient: B 40%; wavelength: 220 nm) to give (R)-2-(4-isopropylphenyl)-N-(1-(2-propyl-2H-pyrazolo[3,4-c]pyridin-5-yl)ethyl) acetamide (6.7 mg) as a colorless oil. LC/MS ESI (m/z): 365 $[M+H]^+$.

$^1H$ NMR (400 MHz, $CDCl_3$) δ 9.12 (s, 1H), 7.89 (s, 1H), 7.39 (s, 1H), 7.17 (s, 4H), 6.66 (d, J=7.7 Hz, 1H), 5.23-5.15 (m, 1H), 4.42 (t, J=7.1 Hz, 2H), 3.53-3.52 (m, 2H), 2.90-2.85 (m, 1H), 2.08-2.02 (m, 2H), 1.44 (t, J=6.9 Hz, 3H), 1.24 (d, J=6.9 Hz, 6H), 0.95 (t, J=7.4 Hz, 3H).

Example 12. (R)—N-(1-(1-methyl-1H-pyrazolo[3,4-c]pyridin-5-yl)ethyl)-2-(4-(1-(trifluoromethyl)cyclopropyl)phenyl)acetamide Synthesis of (R)—N-(1-(1-methyl-1H-pyrazolo[3,4-c]pyridin-5-yl)ethyl)-2-(4-(1-(trifluoromethyl)cyclopropyl)phenyl)acetamide

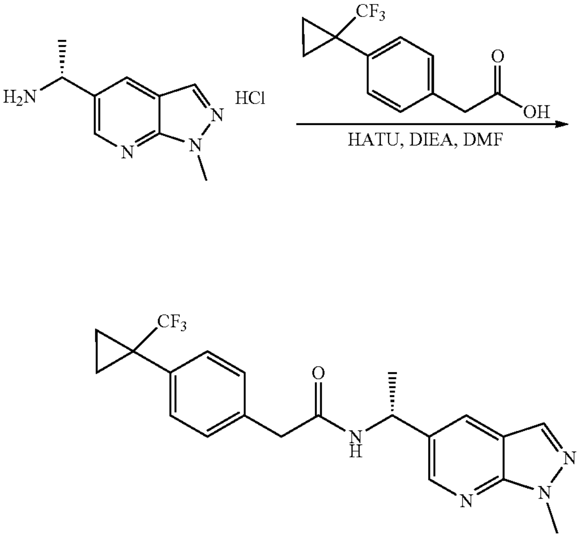

To a solution of (R)-1-(1-methyl-1H-pyrazolo[3,4-c]pyridin-5-yl)ethan-1-amine hydrochloride (41.2 mg) in anhydrous DMF (5.0 mL) was added DIEA (0.21 mL) to provide Solution A. To a solution of 2-(4-(1-(trifluoromethyl)cyclopropyl)phenyl)acetic acid (51.9 mg) in anhydrous DMF (5.0 mL) was added HATU (88.9 mg) and stirred at rt for 5 min to provide Solution B. Solution A was added to the solution B and stirred at RT for 1 h. The reaction was then diluted with EA and water. The organic layer was separated, washed with saturated NaCl, dried over $Na_2SO_4$ and concentrated in vacuo to get a residue, which was purified by (Column: YMC-Actus Triart C18 250*21 mm; Mobile phase: from 20% to 95% MeCN with $H_2O$ (0.1% FA); flow rate: 14 mL/min; wavelength: 220 nm/254 nm) and SFC (Column: ChiralPak IA, 250×21.3 mm I.D., 5 μm; Mobile phase: A for $CO_2$ and B for MEOH+0.1% $NH_3H_2O$; Gradient: B 40%; Wavelength: 220 nm) to give (R)—N-(1-(1-methyl-1H-pyrazolo[3,4-c]pyridin-5-yl)ethyl)-2-(4-(1-(trifluoromethyl)cyclopropyl)phenyl)acetamide (28.5 mg). LC/MS ESI (m/z): 403 $[M+H]^+$; $^1H$ NMR (400 MHz, $CDCl_3$) δ 8.80 (s, 1H), 7.97 (s, 1H), 7.49 (s, 1H), 7.42 (d, J=8.0 Hz, 2H), 7.24 (d, J=8.1 Hz, 2H), 6.74 (d, J=7.6 Hz, 1H), 5.27-5.20 (m, 1H), 4.17 (s, 3H), 3.57 (s, 2H), 1.47 (d, J=6.8 Hz, 3H), 1.36-1.34 (m, 2H), 1.04-1.00 (m, 2H). $^{19}F$ NMR (377 MHz, $CDCl_3$) δ −70.07 (s).

Example 13. (R)-2-(4-isopropylphenyl)-N-(1-(1-methyl-1H-pyrazolo[3,4-c]pyridazin-5-yl)ethyl)acetamide Synthesis of 5-chloro-1-methyl-1H-pyrazolo[3,4-c]pyridazin-3-ol

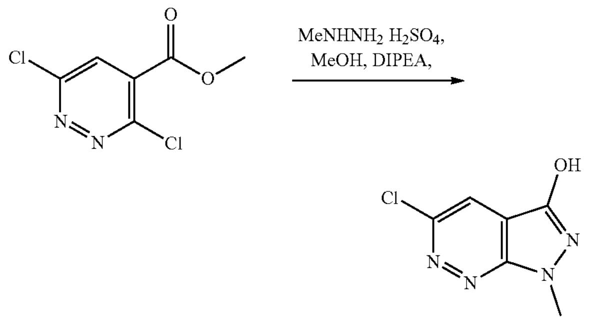

A solution of methyl 3,6-dichloropyridazine-4-carboxylate (500 mg), methylhydrazine sulfate (417 g) and DIEA (1.1 g) in MeOH (20 mL) was stirred at 70° C. for 12 hr. The mixture was concentrated to give a residue, which was purified by column chromatography on silica gel (DCM: MeOH=50:1 to 10:1) to provide 5-chloro-1-methyl-1H-pyrazolo[3,4-c]pyridazin-3-ol (400 mg) as an orange solid. LC/MS ESI (m/z): 185 $(M+H)^+$; $^1H$ NMR (400 MHz, $CDCl_3$) δ 11.90 (s, 1H), 8.23 (s, 1H), 3.96 (s, 3H).

Synthesis of 5-chloro-1-methyl-1H-pyrazolo[3,4-c]pyridazin-3-yl trifluoromethanesulfonate

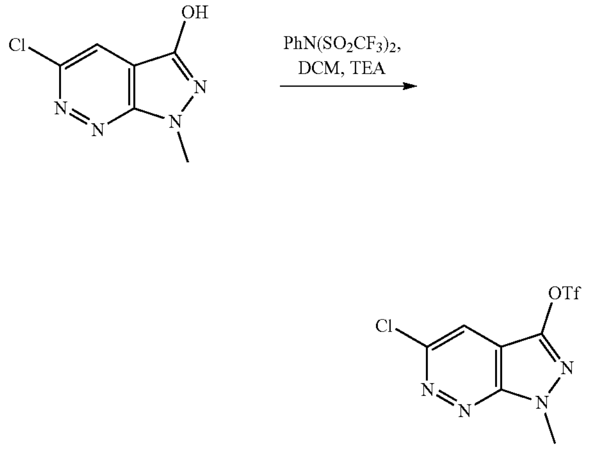

To a solution of 5-chloro-1-methyl-1H-pyrazolo[3,4-c]pyridazin-3-ol (2.0 g) in DCM (30 mL) were added N-bis(trifluoromethanesulfonyl)aniline (7.7 g), TEA (4.5 mL) and DMAP (264.7 mg). The mixture was stirred at 25° C. for 12 hr and was then washed with water. The organic layer was dried, filtered and concentrated to give a residue, which was purified by chromatography on silica gel (PE:DCM=50:1 to 0:1) to give 5-chloro-1-methyl-1H-pyrazolo[3,4-c]pyridazin-3-yl trifluoromethanesulfonate (600 mg) as a white solid. LC/MS ESI (m/z): 317 $[M+H]^+$.

Synthesis of 5-chloro-1-methyl-1H-pyrazolo[3,4-c]pyridazine

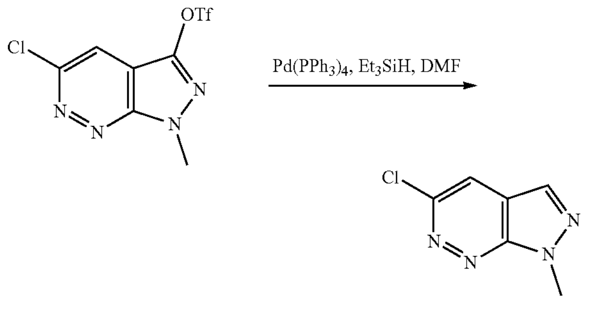

A solution of 5-chloro-1-methyl-1H-pyrazolo[3,4-c]pyridazin-3-yl trifluoromethanesulfonate (1.1 g), $Pd(PPh_3)_4$ (0.20 g) and triethylsilane (1.12 mL) in DMF (2 mL) was stirred at 60° C. for 12 hr. The mixture was diluted with water and DCM, the two phases were separated, and the aqueous phase was extracted with DCM (10 mL×3). The combined organic layers were dried over $Na_2SO_4$, filtered and concentrated to give a residue, which was purified by silica gel chromatography (PE:DCM=50:1 to 0:1) to give 5-chloro-1-methyl-1H-pyrazolo[3,4-c]pyridazine (400 mg) as a white solid. LC/MS ESI (m/z): 169 $[M+H]^+$; $^1H$ NMR (400 MHz, $CDCl_3$) δ 8.00 (s, 1H), 7.79 (s, 1H), 4.28 (s, 3H).

Synthesis of 1-methyl-5-vinyl-1H-pyrazolo[3,4-c]pyridazine

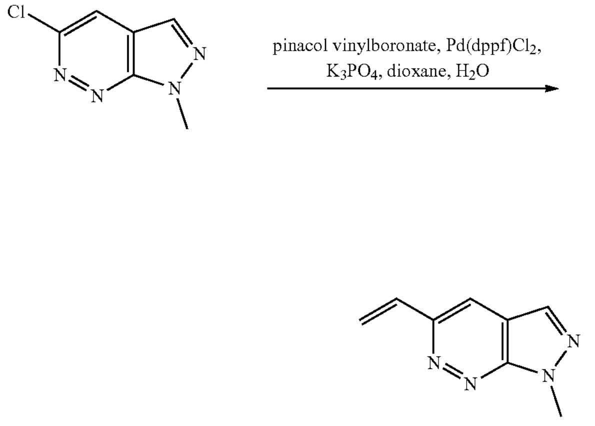

A solution of 5-chloro-1-methyl-1H-pyrazolo[3,4-c]pyridazine (400 mg), pinacol vinylboronate (0.80 mL), $K_3PO_4$ (1.2 g) and dichloro[1,1'-bis(dicyclohexylphosphino)ferrocene]palladium(II) (179.3 mg) in dioxane (20 mL) and $H_2O$ (4 mL) was charged with $N_2$ and stirred at 100° C. for 12 hr under $N_2$. The mixture was diluted with water and extracted with EtOAc. The combined extracts were dried, filtered and concentrated to give a residue, which was purified by chromatography (PE:DCM=50:1 to 0:1) to give 1-methyl-5-vinyl-1H-pyrazolo[3,4-c]pyridazine (400 mg, crude) as a yellow solid, which was used for next step. LC/MS ESI (m/z): 161 $[M+H]^+$.

Synthesis of 1-methyl-1H-pyrazolo[3,4-c]pyridazine-5-carbaldehyde

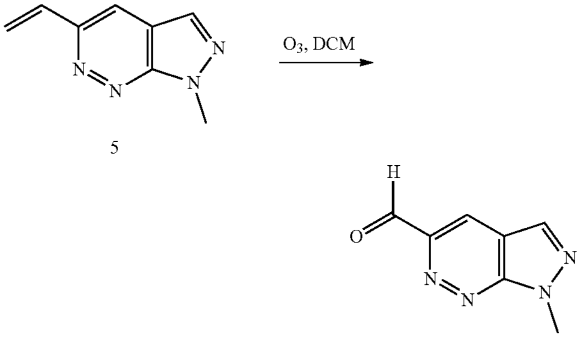

5

6

Ozone was bubbled through a solution of 1-methyl-5-vinyl-1H-pyrazolo[3,4-c]pyridazine (382 mg) in anhydrous DCM (10 mL) at −78° C. for 10 mins. Excess ozone was purged with nitrogen for 10 mins, and then $PPh_3$ (751 mg) was added and stirred at rt for 40 min. The reaction mixture was concentrated in vacuo to afford the crude product, which was used for next step. LC/MS ESI (m/z): 163 $[M+H]^+$.

Synthesis of (R,E)-2-methyl-N-((1-methyl-1H-pyrazolo[3,4-c]pyridazin-5-yl)methylene)propane-2-sulfinamide

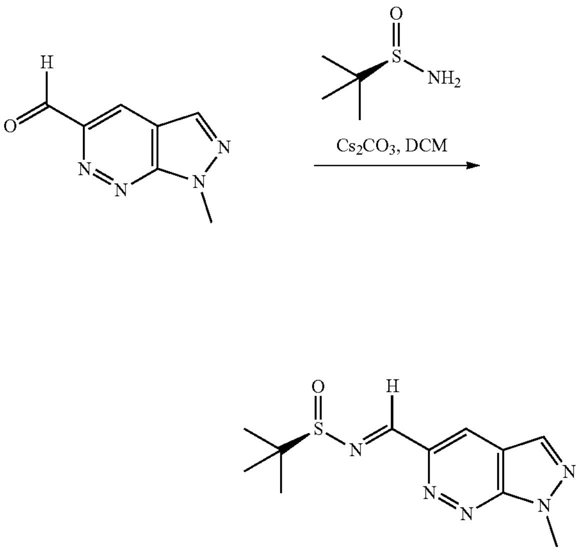

To a solution of 1-methyl-1H-pyrazolo[3,4-c]pyridazine-5-carbaldehyde (400 mg) in anhydrous DCM (10 mL) were added $CuSO_4$ (1.18 g) and (R)-2-methylpropane-2-sulfinamide (358.8 mg), and the reaction was stirred at rt overnight. The solution was filtered through a pad of Celite and the filtrate was concentrated. The residue was purified by silica gel column to give (R,E)-2-methyl-N-((1-methyl-1H-pyrazolo[3,4-c]pyridazin-5-yl)methylene)propane-2-sulfinamide (255 mg). LC/MS ESI (m/z): 266 $[M+H]^+$; $^1H$ NMR (400 MHz, $CDCl_3$) δ 9.26 (s, 1H), 8.59 (s, 1H), 8.24 (s, 1H), 4.42 (s, 3H), 1.32 (s, 9H).

Synthesis of (R)-2-methyl-N—((R)-1-(1-methyl-1H-pyrazolo[3,4-c]pyridazin-5-yl)ethyl)propane-2-sulfinamide

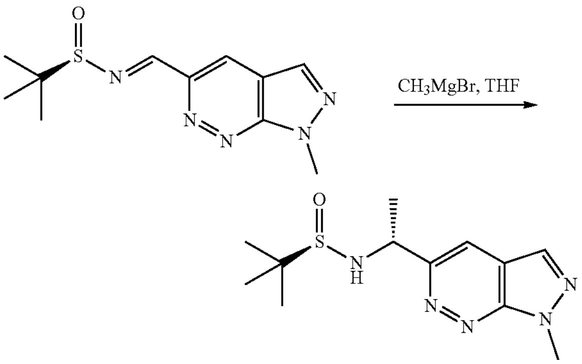

To a solution of (R,E)-2-methyl-N-((1-methyl-1H-pyrazolo[3,4-c]pyridazin-5-yl)methylene)propane-2-sulfinamide (205 mg) in anhydrous THF (15 mL) was added 3M $CH_3MgBr$ (1.29 mL, 3.0M in ether) dropwise at −78° C. under nitrogen. The reaction was stirred at −78° C. for 2 hr. Then the reaction was quenched with saturated $NH_4Cl$ solution and extracted with EA. The combined extracts were washed with brine, dried over $Na_2SO_4$ and concentrated in vacuo. The residue was purified by silica gel column chromatography to give (R)-2-methyl-N—((R)-1-(1-methyl-1H-pyrazolo[3,4-c]pyridazin-5-yl)ethyl)propane-2-sulfinamide (50 mg). LC/MS ESI (m/z): 282 $[M+H]^+$; $^1H$ NMR (400 MHz, $CDCl_3$) δ 8.08 (s, 1H), 7.87 (s, 1H), 4.95 (t, J=6.8 Hz, 1H), 4.35 (s, 3H), 1.71 (d, J=6.8 Hz, 3H), 1.26 (s, 9H) ppm.

Synthesis of (R)-1-(1-methyl-1H-pyrazolo[3,4-c]pyridazin-5-yl)ethan-1-amine hydrochloride

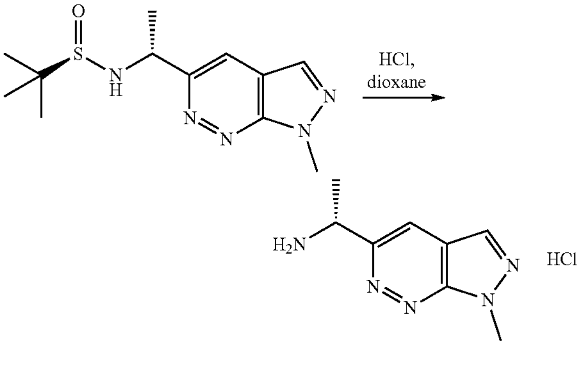

To a solution of (R)-2-methyl-N—((R)-1-(1-methyl-1H-pyrazolo[3,4-c]pyridazin-5-yl)ethyl)propane-2-sulfinamide (55 mg) in dioxane (1.5 mL) were added 4M HCl-dioxane (1 mL), and the reaction was stirred at rt for 30 min. The mixture was then concentrated to provide (R)-1-(1-methyl-1H-pyrazolo[3,4-c]pyridazin-5-yl)ethan-1-amine hydrochloride as a residue, which was then used for next step. LC/MS ESI (m/z): 178 $[M+H]^+$.

Synthesis of (R)-2-(4-isopropylphenyl)-N-(1-(1-methyl-1H-pyrazolo[3,4-c]pyridazin-5-yl)ethyl)acetamide (N201201-266)

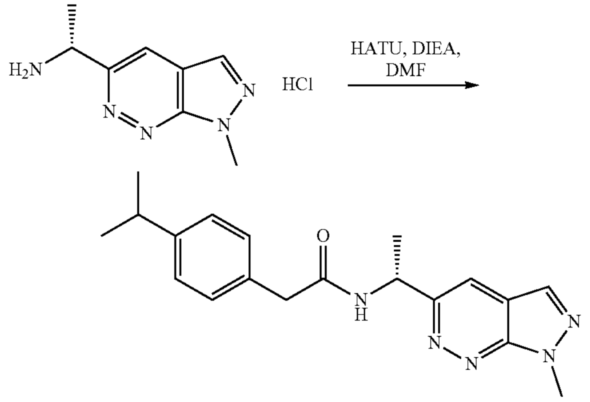

To a solution of (R)-1-(1-methyl-1H-pyrazolo[3,4-c]pyridazin-5-yl)ethan-1-amine hydrochloride (61 mg) in DMF (1 mL) was added DIEA (242.6 mg, 0.31 mL) to provide Solution A. To a solution of 2-(4-isopropylphenyl)acetic acid (55.8 mg) in DMF (1 mL) were added HATU (131 mg) and stirred for 5 min at rt to provide Solution B. Solution B was added to Solution A and stirred at rt for 1 h. The reaction was then diluted with EA and water. The two phases were separated, and the aqueous phase was extracted with DCM (10 mL×3). The combined organic layers were dried over $Na_2SO_4$, filtered and concentrated to give a residue, which was purified by prep-HPLC (Column: YMC-Actus Triart C18 250*21 mm; Mobile phase: from 20% to 95% MeCN with $H_2O$ (0.1% TFA); flow rate: 15 mL/min; wavelength: 220 nm/254 nm) to give (R)-2-(4-isopropylphenyl)-N-(1-(1-methyl-1H-pyrazolo[3,4-c]pyridazin-5-yl)ethyl)acetamide (14.6 mg). LC/MS ESI (m/z): 338 $[M+H]^+$; $^1H$ NMR (400 MHz, $CDCl_3$) δ 8.06 (s, 1H), 7.75 (s, 1H), 7.19 (s, 4H), 6.68 (d, J=7.6 Hz, 1H), 5.48-5.41 (m, 1H), 4.34 (s, 3H), 3.55-3.54 (m, 2H), 2.93-2.86 (m, 1H), 1.60 (d, J=6.9 Hz, 3H), 1.24 (d, J=6.9 Hz, 6H) ppm.

Example 14. (R)—N-(1-(1-(2,2-difluoropropyl)-1H-pyrazolo[3,4-c]pyridin-5-yl)ethyl)-2-(4-isopropylphenyl)acetamide Synthesis of 2,2-difluoropropyl 4-methylbenzenesulfonate

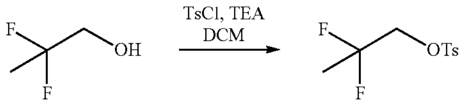

To a solution of 2,2-difluoropropan-1-ol (2.0 g) in anhydrous DCM (40 mL) was added TEA (8.7 mL). TsCl (11.9 g) was added to the reaction solution at 0° C., and the reaction was stirred at RT overnight. The reaction was then diluted with water, the two phases were separated, and the aqueous phase was extracted with DCM (10 mL×3). The combined organic layers were dried over $Na_2SO_4$, filtered, and concentrated to give a residue, which was purified by silica gel column chromatography to give 2,2-difluoropropyl 4-methylbenzenesulfonate (5 g). LC/MS ESI (m/z): 251 $[M+H]^+$; $^1H$ NMR (400 MHz, $CDCl_3$) δ 7.81 (d, J=8.3 Hz, 2H), 7.37 (d, J=8.1 Hz, 2H), 4.09 (t, J=11.1 Hz, 2H), 2.47 (s, 3H), 1.64 (t, J=18.7 Hz, 3H) ppm; $^{19}F$ NMR (377 MHz, $CDCl_3$) δ −98.43 (s).

Synthesis of 1-(2,2-difluoropropyl)-1H-pyrazolo[3,4-c]pyridine-5-carbaldehyde

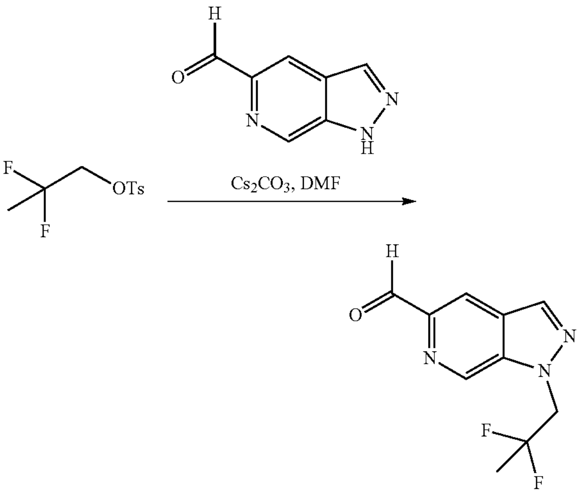

To a solution of 1H-pyrazolo[3,4-c]pyridine-5-carbaldehyde (498 mg) in anhydrous DMF (30 mL) were added $Cs_2CO_3$ (1.3 g) and 2,2-difluoropropyl 4-methylbenzenesulfonate (1.0 g). The reaction was stirred at 100° C. overnight, and the reaction was then diluted with EA and water. The two phases were separated, and the aqueous phase was extracted with DCM (10 mL×3). The combined organic layers were dried over $Na_2SO_4$, filtered, and concentrated to give a residue, which was purified by silica gel column chromatography to give 1-(2,2-difluoropropyl)-1H-pyrazolo[3,4-c]pyridine-5-carbaldehyde (181 mg). LC/MS ESI (m/z): 226 $[M+H]^+$; $^1H$ NMR (400 MHz, $CDCl_3$) δ 10.23 (s, 1H), 9.13 (s, 1H), 8.41 (d, J=1.2 Hz, 1H), 8.29 (s, 1H), 4.88 (t, J=12.1 Hz, 2H), 1.67 (t, J=18.7 Hz, 3H) ppm. 19F NMR (377 MHz, $CDCl_3$) δ −93.83 (s).

Synthesis of (R,E)-N-((1-(2,2-difluoropropyl)-1H-pyrazolo[3,4-c]pyridin-5-yl)methylene)-2-methylpropane-2-sulfinamide

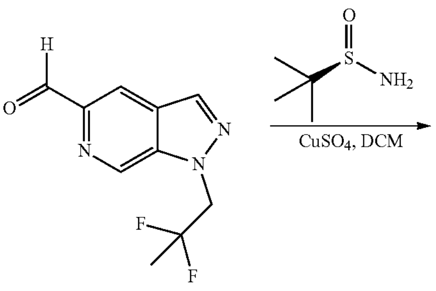

-continued

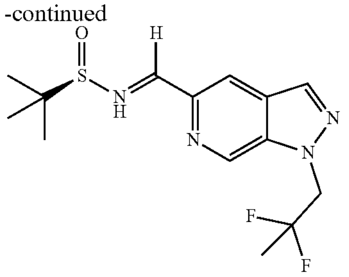

To a solution of 1-(2,2-difluoropropyl)-1H-pyrazolo[3,4-c]pyridine-5-carbaldehyde (209 mg) in anhydrous DCM (14 mL) were added $CuSO_4$ (444.4 mg) and (R)-2-methylpropane-2-sulfinamide (146.2 mg). The reaction was stirred at rt overnight, the solution was then filtered through a pad of Celite, and the filtrate was concentrated. The residue was purified by silica gel column to give (R,E)-N-((1-(2,2-difluoropropyl)-1H-pyrazolo[3,4-c]pyridin-5-yl)methylene)-2-methylpropane-2-sulfinamide (229 mg). LC/MS ESI (m/z): 329 $[M+H]^+$; $^1H$ NMR (400 MHz, CDCl3) δ 9.12 (s, 1H), 8.84 (s, 1H), 8.36 (d, J=1.1 Hz, 1H), 8.23 (d, J=0.6 Hz, 1H), 4.86 (t, J=12.1 Hz, 2H), 1.66 (t, J=18.4 Hz 3H), 1.31 (s, 9H). ppm. $^{19}F$ NMR (377 MHz, $CDCl_3$) δ −93.83 (s).

Synthesis of (R)—N—((R)-1-(1-(2,2-difluoropropyl)-1H-pyrazolo[3,4-c]pyridin-5-yl)ethyl)-2-methylpropane-2-sulfinamide

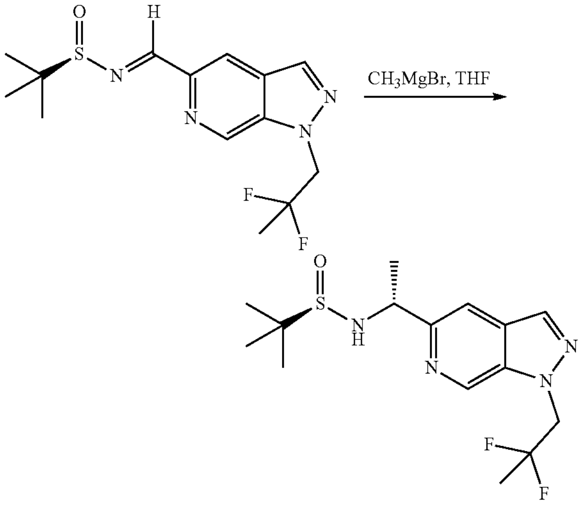

To a solution of (R,E)-N-((1-(2,2-difluoropropyl)-1H-pyrazolo[3,4-c]pyridin-5-yl)methylene)-2-methylpropane-2-sulfinamide (229 mg) in anhydrous THE (9.0 mL) was added $CH_3MgBr$ (1.2 mL, 3.0 M in ether) dropwise at −78° C. under nitrogen. The reaction was stirred at −78° C. for 2 hr. The reaction solution was then quenched with aqueous $NH_4Cl$ and extracted with EA. The organic layer was separated, washed with brine, dried, and concentrated in vacuo. The residue was then purified by silica gel column chromatography, to give (R)—N—((R)-1-(1-(2,2-difluoropropyl)-1H-pyrazolo[3,4-c]pyridin-5-yl)ethyl)-2-methylpropane-2-sulfinamide (193 mg) as a yellow oil. LC/MS ESI (m/z): 345 $[M+H]^+$; $^1H$ NMR (400 MHz, $CDCl_3$) δ 8.97 (s, 1H), 8.06 (d, J=0.5 Hz, 1H), 7.62 (d, J=0.9 Hz, 1H), 4.79 (t, J=12.0 Hz, 2H), 4.73-4.66 (m, 1H), 4.49 (d, J=6.2 Hz, 1H), 1.68-1.56 (m, 6H), 1.25 (s, 9H). ppm. $^{19}F$ NMR (377 MHz, $CDCl_3$) δ −93.56 (d, J=5.5 Hz).

Synthesis of (R)-1-(1-(2,2-difluoropropyl)-1H-pyrazolo[3,4-c]pyridin-5-yl)ethan-1-amine hydrochloride

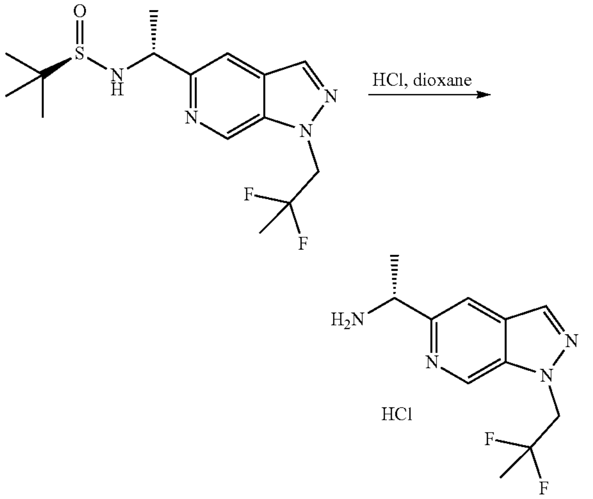

To a solution of (R)—N—((R)-1-(1-(2,2-difluoropropyl)-1H-pyrazolo[3,4-c]pyridin-5-yl)ethyl)-2-methylpropane-2-sulfinamide (153 mg) in dioxane (3.0 mL) were added 4N HCl-dioxane (1.5 mL). The reaction was stirred at rt for 30 min, and the mixture was then concentrated to provide crude (R)-1-(1-(2,2-difluoropropyl)-1H-pyrazolo[3,4-c]pyridin-5-yl)ethan-1-amine hydrochloride, which was directly used for next step. LC/MS ESI (m/z): 241 $[M+H]^+$ Synthesis of (R)—N-(1-(1-(2,2-difluoropropyl)-1H-pyrazolo[3,4-c]pyridin-5-yl)ethyl)-2-(4-isopropylphenyl)acetamide

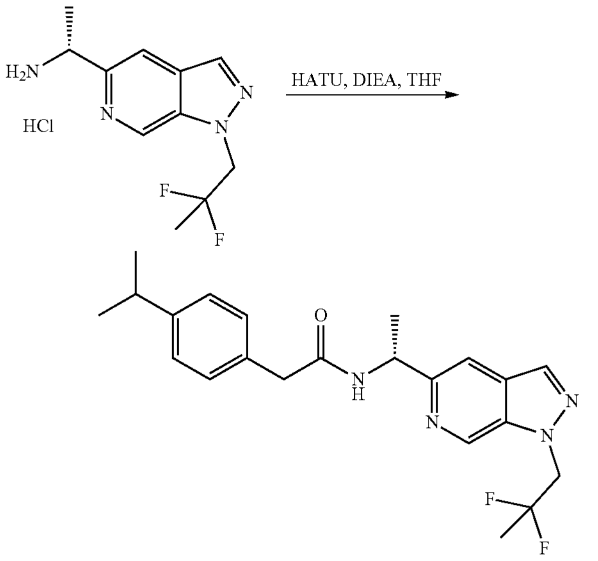

To a solution of (R)-1-(1-(2,2-difluoropropyl)-1H-pyrazolo[3,4-c]pyridin-5-yl)ethan-1-amine hydrochloride (123 mg) in anhydrous DMF (3 mL) was added DIEA to provide Solution A. To a solution of 2-(4-isopropylphenyl)acetic acid (80.75 mg) in anhydrous DMF were added HATU (156 mg) and stirred 15 min at rt to provide Solution B. Solution B was added to the solution A and stirred at rt for 1 h. The reaction was then diluted with EA and water. The two phases were separated, and the aqueous phase was extracted with DCM (10 mL×3). The combined organic layers were dried over $Na_2SO_4$, filtered, and concentrated to give a residue, which was purified by [Column: YMC-Actus Triart C18 250*21 mm; Mobile phase: from 20% to 95% MeCN with $H_2O$ (0.1% FA); flow rate: 15 mL/min; wavelength: 220 nm/254 nm] and SFC (Column:ChiralPak IA, 250×21.3 mm I.D., 5 μm; Mobile phase: A for $CO_2$ and B for MEOH+0.1% $NH_3H_2O$; Gradient: B 40%; Wavelength:220 nm) to give (R)—N-(1-(1-(2,2-difluoropropyl)-1H-pyrazolo[3,4-c]pyridin-5-yl)ethyl)-2-(4-isopropylphenyl)acetamide (98.6 mg). LC/MS ESI (m/z): 401 $[M+H]^+$; $^1$H NMR (400 MHz, $CDCl_3$) δ 8.88 (s, 1H), 8.04 (s, 1H), 7.51 (s, 1H), 7.19 (s, 4H), 6.61 (d, J=7.4 Hz, 1H), 5.29-5.22 (m, 1H), 4.78 (t, J=12.0 Hz, 2H), 3.55-3.54 (m, 2H), 2.94-2.87 (m, 1H), 1.66-1.56 (m, 3H), 1.46 (d, J=6.8 Hz, 3H), 1.25 (d, J=6.9 Hz, 6H); $^{19}$F NMR (377 MHz, $CDCl_3$) δ −93.56 (s).

Example 15. (R)—N-(1-(1-(2,2,2-trifluoroethyl)-1H-pyrazolo[3,4-c]pyridin-5-yl)ethyl)-2-(4-(trifluoromethyl)phenyl)acetamide

Synthesis of (R)—N-(1-(1-(2,2,2-trifluoroethyl)-1H-pyrazolo[3,4-c]pyridin-5-yl)ethyl)-2-(4-(trifluoromethyl)phenyl)acetamide

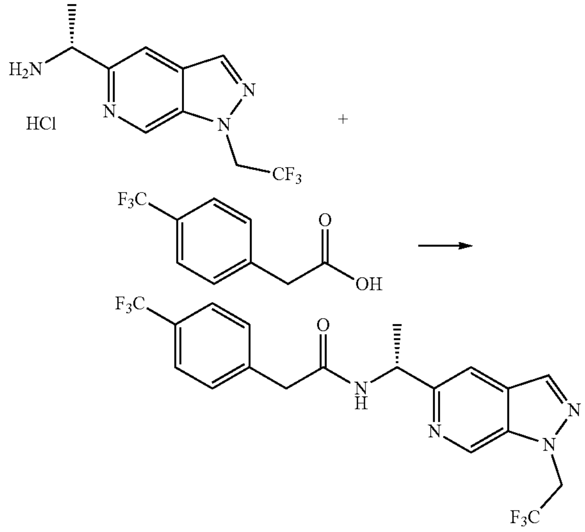

A solution of 2-(4-(trifluoromethyl)phenyl)acetic acid (96.4 mg) and HATU (269.5 mg) in 3 mL DMF was stirred at room temperature for 15 min (Solution A). DIEA (0.48 mL) was added to (R)-1-[1-(2,2,2-trifluoroethyl)-1H-pyrazolo[3,4-c]pyridin-5-yl]ethan-1-amine hydrochloride (see Example 9, 150 mg) in 2 mL DMF until the pH of the solution higher than 7 by wet pH paper (Solution B). Solution B was added to Solution A, and the reaction was stirred for 1 hour, at which time LCMS showed the reaction was complete. The reaction was diluted with EA and water. The two phases were separated, the aqueous phase was extracted with DCM (10 mL×2). The combined organic layers were dried over $Na_2SO_4$, filtered, and concentrated in vacuo. The residue was purified by silica gel column chromatography, eluting with methanol in DCM (0-7%) to afford a crude product, which was purified by prep-HPLC (Column: YMC-Actus Triart C18 250*20 mm; Mobile phase: from 28% to 95% MeCN with H2O (0.1% FA); flow rate: 15 mL/min; wavelength: 220 nm/254 nm) and SFC (Column: ChiralPak IA, 250×21.2 mm I.D., 5 μm; Mobile phase: A for CO2 and B for MEOH+0.1% NH3H2O; Gradient: B 40%; Flow rate: 50 mL/min; Wavelength: 210 nm) to give N-[(1R)-1-[1-(2,2,2-trifluoroethyl)-1H-pyrazolo[3,4-c]pyridin-5-yl]ethyl]-2-[4-(trifluoromethyl)phenyl]acetamide (92.1 mg) as white solid. LC/MS ESI (m/z): 431 $[M+H]^+$. $^1$H-NMR (400 MHz, $CDCl_3$): δ 8.87 (s, 1H), 8.10 (s, 1H), 7.63-7.51 (m, 3H), 7.40 (d, J=8.0 Hz, 2H), 6.72 (d, J=6.9 Hz, 1H), 5.26-5.24 (m, 1H), 5.04 (q, J=8.3 Hz, 2H), 3.63 (s, 2H), 1.48 (d, J=6.8 Hz, 3H). $^{19}$F-NMR (377 MHz, $CDCl_3$): δ −62.54, −70.81.

Example 16. (R)-2-(6-(1,1-difluoroethyl)pyridin-3-yl)-N-(1-(1-(2,2,2-trifluoroethyl)-1H-pyrazolo[3,4-c]pyridin-5-yl)ethyl)acetamide

Synthesis of 2-(1,1-difluoroethyl)-5-methylpyridine

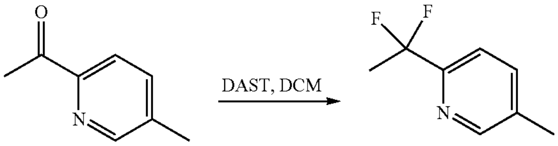

To a solution of 1-(5-methylpyridin-2-yl)ethan-1-one (2.0 g) in DCM (30 mL) was added DAST (19.6 mL) at 0° C. The mixture was stirred at 25° C. for 48 hr. The mixture was quenched with $NaHCO_3$ solution. The two phases were separated, and the aqueous phase was extracted with DCM (10 mL×3). The combined organic layers were dried over $Na_2SO_4$, filtered, and concentrated to give a residue, which was purified by chromatography on silica gel (PE:EA=1:0 to 20:1) to give 2-(1,1-difluoroethyl)-5-methylpyridine (1.1 g) as colorless oil. LC/MS ESI (m/z): 158 $[M+H]^+$.

Synthesis of 5-(bromomethyl)-2-(1,1-difluoroethyl)pyridine

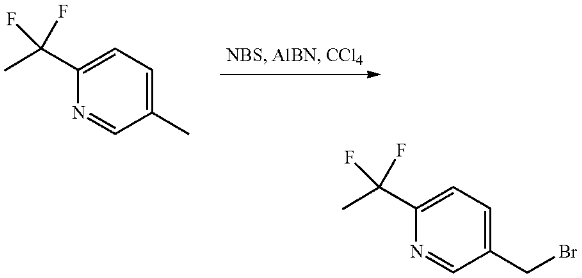

To a solution of 2-(1,1-difluoroethyl)-5-methylpyridine (1.02 g) in $CCl_4$ (30 mL) were added NBS (1.28 g) and AIBN (0.048 mL). The reaction was stirred at 80° C. overnight. The reaction was filtered, and the filtrate was concentrated in vacuo to provide a residue, which was purified by silica gel column chromatography (PE:EA=1:0 to 10:1) to afford 5-(bromomethyl)-2-(1,1-difluoroethyl) pyridine (780 mg). $^1$H NMR (400 MHz, $CDCl_3$) δ 8.65 (d, J=1.6 Hz, 1H), 7.85-7.83 (m, 1H), 7.66-7.64 (m, 1H), 4.49 (s, 2H), 2.07-1.97 (m, 3H); LC/MS ESI (m/z): 237 $[M+H]^+$.

Synthesis of 2-(6-(1,1-difluoroethyl)pyridin-3-yl)acetonitrile

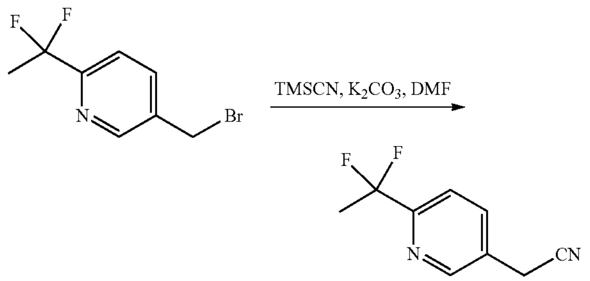

To a solution of 5-(bromomethyl)-2-(1,1-difluoroethyl) pyridine (780 mg) in DMF (15 mL) were added TMSCN (1.6 mL) and $K_2CO_3$ (685 mg). The reaction was stirred at 50° C. overnight. The reaction was diluted with DCM and water. The two phases were separated, and the aqueous phase was extracted with DCM (10 mL×3). The combined organic layers were dried over $Na_2SO_4$, filtered, and concentrated to give a residue, which was purified by silica gel column chromatography (PE:EA=10:1) to give 2-[6-(1,1-difluoroethyl)pyridin-3-yl]acetonitrile (194 mg). LC/MS ESI (m/z): 183 $[M+H]^+$.

Synthesis of 2-(6-(1,1-difluoroethyl)pyridin-3-yl)acetic acid

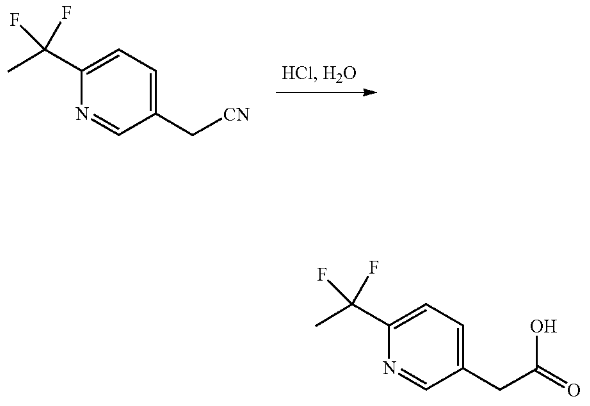

A solution of 2-[6-(1,1-difluoroethyl)pyridin-3-yl]acetonitrile (194 mg) in concentrated aqueous HCl (3.0 mL) was stirred at 100° C. for 2 hr. The mixture was added to water and extracted with EA. The combined extracts were dried, filtered and concentrated to provide 2-(6-(1,1-difluoroethyl)pyridin-3-yl)acetic acid (110 mg, crude) as a white solid. LC/MS ESI (m/z): 200 [M−H].

Synthesis of (R)-2-(6-(1,1-difluoroethyl)pyridin-3-yl)-N-(1-(1-(2,2,2-trifluoroethyl)-1H-pyrazolo[3,4-c] pyridin-5-yl)ethyl)acetamide

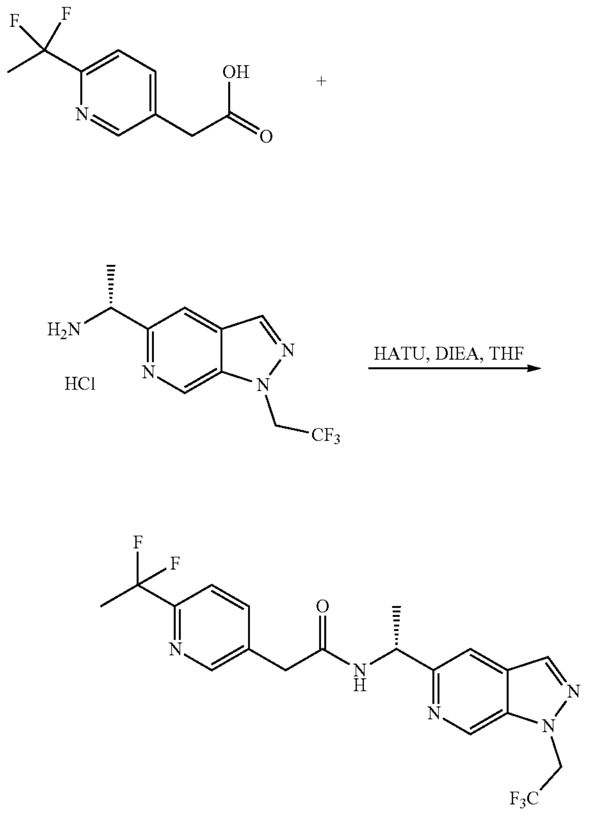

A solution of 2-[6-(1,1-difluoroethyl)pyridin-3-yl]acetic acid (110 mg) and HATU (312 mg) in DMF (2.0 mL) was stirred at room temperature for 15 min. Then (R)-1-(1-(2,2,2-trifluoroethyl)-1H-pyrazolo[3,4-c]pyridin-5-yl)ethan-1-amine hydrochloride (173.6 mg) and DIEA (0.542 mL, 3.281) were added. The mixture was stirred at rt for 1 hour, and LC/MS showed the reaction was complete. The reaction was diluted with EA and water, the two phases were separated, and the aqueous phase was extracted with DCM (10 mL×3). The combined organic layers were dried over $Na_2SO_4$, filtered, and concentrated to give a residue, which was purified by prep-HPLC [Column: YMC-Actus Triart C18 250*20 mm Mobile phase: from 15% to 95% MeCN with $H_2O$ (10% FA); flow rate: 15 mL/min; wavelength: 220 nm/254 nm] and SFC (Column:ChiralPak IA, 250×21.3 mm I.D., 5 μm; Mobile phase: A for $CO_2$ and B for IPA+0.1% NH3H2O; Gradient: B 40%; flow rate: 50 mL/min; wavelength: 210 nm) to afford (R)-2-(6-(1,1-difluoroethyl)pyridin-3-yl)-N-(1-(1-(2,2,2-trifluoroethyl)-1H-pyrazolo[3,4-c] pyridin-5-yl)ethyl)acetamide (121 mg) as a white solid. LC/MS ESI (m/z): 428 $[M+H]^+$; $^1$H-NMR (400 MHz, $CDCl_3$) δ 8.93 (s, 1H), 8.54 (s, 1H), 8.13 (s, 1H), 7.78 (dd, J=8.1, 2.1 Hz, 1H), 7.60 (dd, J=4.2, 3.2 Hz, 2H), 6.96 (t, J=14.2 Hz, 1H), 5.28-5.24 (m, 1H), 5.07 (q, J=8.3 Hz, 2H), 3.62 (s, 2H), 2.05-1.95 (m, 3H), 1.52 (t, J=6.3 Hz, 3H). $^{19}$F-NMR (377 MHz, $CDCl_3$) δ −70.76, −90.68.

Example 17. (R)—N-(1-(1-(2,2,2-trifluoroethyl)-1H-pyrazolo[3,4-c]pyridin-5-yl)ethyl)-2-(5-(1-(trifluoromethyl)cyclopropyl)thiophen-2-yl)acetamide Step 1. Synthesis of (1-(5-bromothiophen-2-yl)-2,2,2-trifluoroethoxy)trimethylsilane

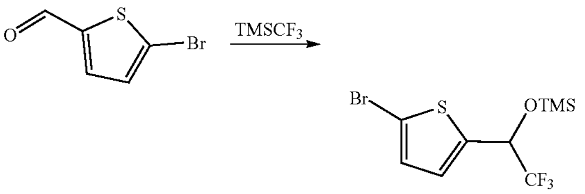

To a solution of 5-bromothiophene-2-carbaldehyde (8.4 mL, 70.7 mmol) in 1,2-dimethoxyethane (30 mL) were added (trifluoromethyl)trimethylsilane (13.7 mL, 91.9 mmol) and cesium fluoride (0.26 mL, 7.01 mmol) at 0° C. The mixture was stirred at room temperature for 3 hrs, and TLC showed the reaction was complete. The reaction mixture was quenched with ice-water and then extracted twice with EtOAc. The combined extracts were concentrated, and the residue was purified by column chromatography on silica gel (PE:EA=3:1) to give (1-(5-bromothiophen-2-yl)-2,2,2-trifluoroethoxy)trimethylsilane (19.6 g) as colorless oil.

Step 2. Synthesis of 1-(5-bromothiophen-2-yl)-2,2,2-trifluoroethan-1-ol

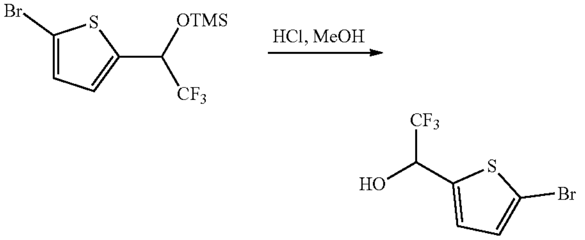

To a solution of (1-(5-bromothiophen-2-yl)-2,2,2-trifluoroethoxy)trimethylsilane (19.4 g, 58.2 mmol) in MeOH (20 mL) was added HCl (9.7 mL, 116.4 mmol, 12 mol/L) at 0° C. The mixture was stirred at room temperature for 3 hrs, and TLC showed the reaction was complete. The reaction mixture was quenched by ice-water and then extracted twice with EtOAc. The combined extracts were concentrated, and the residue was purified by column chromatography on silica gel (PE:EA=5:1) to give 1-(5-bromothiophen-2-yl)-2,2,2-trifluoroethan-1-ol (14.8 g) as colorless oil.

Step 3. Synthesis of 1-(5-bromothiophen-2-yl)-2,2,2-trifluoroethan-1-one

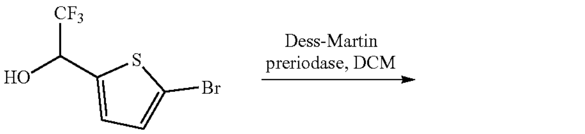

-continued

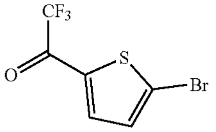

To the solution of 1-(5-bromothiophen-2-yl)-2,2,2-trifluoroethan-1-ol (17.3 g, 66.3 mmol) in $CH_2Cl_2$ (30 mL) was added Dess-Martin periodinane (30.9 mL, 99.4 mmol) at 0° C. The mixture was warmed to room temperature and stirred for 3 hrs. TLC showed the reaction was complete. The reaction mixture was quenched with ice-water and then extracted twice with EtOAc. The combined extracts were concentrated, and the residue was purified by column chromatography on silica gel (100% PE) to give 1-(5-bromothiophen-2-yl)-2,2,2-trifluoroethan-1-one (10.4 g) as a light yellow oil. $^1H$ NMR (400 MHz, $CDCl_3$): δ 7.64 (dd, J=2.5, 1.3 Hz, 1H), 7.17-7.12 (m, 1H); $^{19}F$ NMR (377 MHz, $CDCl_3$): δ −72.2.

Step 4. Synthesis of 2-bromo-5-(3,3,3-trifluoroprop-1-en-2-yl)thiophene

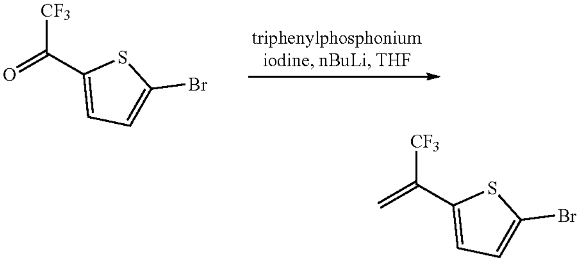

Methyl triphenylphosphonium iodine (1.8 g, 4.6 mmol) was dissolved in THE (25 mL) under argon atmosphere. The suspension was cooled 0° C., followed by dropwise addition of n-BuLi (2.5 mL, 2.5 N). The mixture was stirred at 0° C. for 10 minutes, and the reaction was then cooled to −78° C. 1-(5-bromothiophen-2-yl)-2,2,2-trifluoroethanone (1.0 g, 3.9 mmol) in THE (1.0 mL) was added. The mixture was stirred at −78° C. for 30 min and then stirred at rt overnight. The reaction was quenched with sat. $NH_4Cl$ and extracted with petroleum ether (10 mL). The organic layer was washed with saturated NaCl, dried with anhydrous $Na_2SO_4$, and filtered. The filtrate was concentrated, and the residue was purified by column chromatography on silica gel (PE:EA=10:1) to give 2-bromo-5-(3,3,3-trifluoroprop-1-en-2-yl)thiophene as a colorless oil (435 mg). $^1H$ NMR (400 MHz, $CDCl_3$): δ 7.00-6.98 (m, 1H), 6.96-6.93 (m, 1H), 5.82 (s, 1H), 5.75 (s, 1H). $^{19}F$ NMR (377 MHz, $CDCl_3$): δ −65.9.

Step 5. Synthesis of 2-bromo-5-(1-(trifluoromethyl)cyclopropyl)thiophene

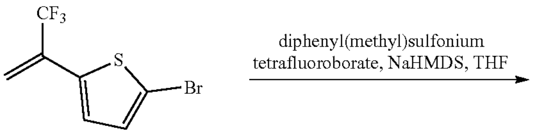

-continued

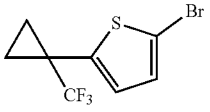

To an oven dried 20 mL vial containing 2-bromo-5-(3,3,3-trifluoroprop-1-en-2-yl)thiophene (200 mg, 0.78 mmol) and methyldiphenylsulfonium tetrafluoroborate (291 mg, 1.0 mmol) in anhydrous tetrahydrofuran (5 mL) was added sodium bis(trimethylsilyl)amide (1 M in THF, 1.2 mL) at 0° C. under nitrogen. The reaction mixture was stirred at 0° C. for 10 min and then at room temperature for 1 h. The reaction was quenched with 250 μL of methanol and the crude mixture was concentrated in vacuo to get a residue, which was purified by automated flash column chromatography (eluant:100 PE % to 50% PE in EA) to provide 2-bromo-5-(1-(trifluoromethyl)cyclopropyl)thiophene as colorless oil (70 mg). $^1H$ NMR (400 MHz, $CDCl_3$): δ 6.90 (d, J=3.6 Hz, 1H), 6.86 (d, J=4.0 Hz, 1H), 1.42-1.39 (m, 2H), 1.15-1.11 (m, 2H); $^{19}F$ NMR (377 MHz, $CDCl_3$): δ −70.4.

Step 6. Synthesis of ethyl 2-(5-(1-(trifluoromethyl)cyclopropyl)thiophen-2-yl)acetate

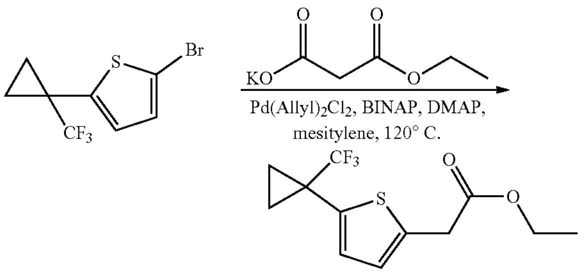

A Schlenk tube equipped with a stir bar was evacuated and backfilled with nitrogen. $Pd_2(allyl)_2Cl_2$ (3.65 mg, 0.01 mmol), BINAP (18.7 mg, 0.03 mmol), DMAP (6.1 mg, 0.05 mmol) and ethyl potassium malonate (128 mg, 0.75 mmol) were added. Then 2-bromo-5-(1-(trifluoromethyl)cyclopropyl)thiophene (136 mg, 0.5 mmol) and mesitylene (2 mL) were added. The reaction mixture was stirred under $N_2$ in the sealed the tube for 10 min at rt, then heated at 120° C. overnight. Upon completion, the reaction was cooled to rt and diluted with EA (30 mL). The resulting mixture was washed with saturated NaCl and concentrated. The residue was purified by flash column chromatography (eluting with 5%-10% PE in EA) to give ethyl 2-(5-(1-(trifluoromethyl)cyclopropyl)thiophen-2-yl)acetate as yellow liquid (50 mg). $^1$HNMR (400 MHz, $CDCl_3$): δ 6.95 (d, J=3.6 Hz, 1H), 6.78 (d, J=4.0 Hz, 1H), 4.21-4.16 (m, 2H), 3.76 (s, 2H), 1.40-1.37 (m, 2H), 1.28 (t, J=6.8 Hz, 3H), 1.16-1.12 (m, 2H) ppm; $^{19}$FNMR (377 MHz, $CDCl_3$): δ −70.34 ppm.

Step 7. Synthesis of 2-(5-(1-(trifluoromethyl)cyclopropyl)thiophen-2-yl)acetic acid

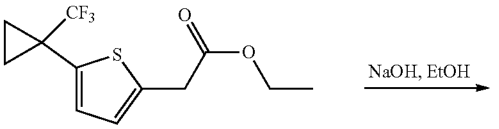

-continued

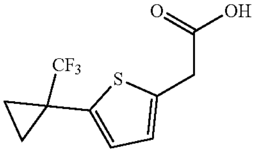

To a mixture of ethyl 2-(5-(1-(trifluoromethyl)cyclopropyl)thiophen-2-yl)acetate (50 mg, 0.18 mmol) in ethanol (10 mL) was added NaOH (7.2 mg, 0.18 mmol), and the mixture was stirred under reflux for 16 h. After cooling to rt, the pH of the reaction was adjusted to 2 by adding 1 N hydrogen chloride. The reaction mixture was then extracted with ethyl acetate (2×20 mL), and the combined extracts were washed with sat. NaCl. The organic phase was concentrated to give 2-(5-(1-(trifluoromethyl)cyclopropyl)thiophen-2-yl)acetic acid as a brown solid (40 mg). $^1$HNMR (400 MHz, $CDCl_3$): 6.96 (d, J=3.6 Hz, 1H), 6.80 (d, J=3.6 Hz, 1H), 3.82 (s, 2H), 1.41-1.38 (m, 2H), 1.16-1.14 (m, 2H); $^{19}$FNMR (377 MHz, $CDCl_3$): δ −70.4.

Step 8. Synthesis of (R)—N-(1-(1-(2,2,2-trifluoroethyl)-1H-pyrazolo[3,4-c]pyridin-5-yl)ethyl)-2-(5-(1-(trifluoromethyl)cyclopropyl)thiophen-2-yl)acetamide

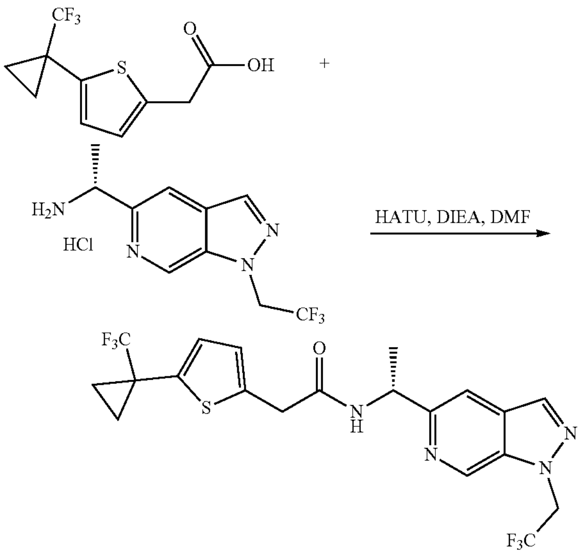

A solution 2-(5-(1-(trifluoromethyl)cyclopropyl)thiophen-2-yl)acetic acid (158 mg) and HATU (360 mg) in DMF (2.5 mL) was stirred at rt for 15 min. Then (R)-1-[1-(2,2,2-trifluoroethyl)-1H-pyrazolo[3,4-c]pyridin-5-yl]ethan-1-amine hydrochloride (200 mg) and DIEA (0.63 mL) were added, and the mixture was stirred for 1 hour. LC/MS showed the reaction was complete. The reaction was diluted with EA and water. The organic layer was separated, washed with brine, dried over $Na_2SO_4$, filtered, and concentrated in vacuo. The residue was purified by prep-HPLC [Column: YMC-Actus Triart C18 250*21 mm; Mobile phase: from 30% to 95% MeCN with $H_2O$ (0.1% FA); flow rate: 15 mL/min; wavelength: 220 nm/254 nm] and SFC (Column: ChiralPak IA, 250×21.3 mm I.D., 5 μm; Mobile phase: A for $CO_2$ and B for MEOH+0.1% $NH_3H2O$; Gradient: B 40%;

flow rate: 50 mL/min; wavelength: 210 nm) to afford (R)—N-(1-(1-(2,2,2-trifluoroethyl)-1H-pyrazolo[3,4-c]pyridin-5-yl)ethyl)-2-(5-(1-(trifluoromethyl)cyclopropyl)thiophen-2-yl)acetamide (80.9 mg) as a white solid. LC/MS ESI (m/z): 477 $[M+H]^+$; $^1$H-NMR (400 MHz, $CDCl_3$) δ 8.90 (s, 1H), 8.12 (s, 1H), 7.60 (s, 1H), 6.97 (d, J=3.5 Hz, 2H), 6.79 (d, J=3.5 Hz, 1H), 5.28-5.24 (m, 1H), 5.05 (q, J=8.3 Hz, 2H), 3.78-3.68 (m, 2H), 1.51 (d, J=6.8 Hz, 3H), 1.39-1.35 (m, 2H), 1.13-1.11 (m, 2H); $^{19}$F-NMR (377 MHz, $CDCl_3$) δ −70.32, −70.81.

Example 18. (R)—N-(1-(1-((1-fluorocyclopropyl)methyl)-1H-pyrazolo[3,4-c]pyridin-5-yl)ethyl)-2-(4-isopropylphenyl)acetamide Synthesis of 1-((1-fluorocyclopropyl)methyl)-1H-pyrazolo[3,4-c]pyridine-5-carbaldehyde

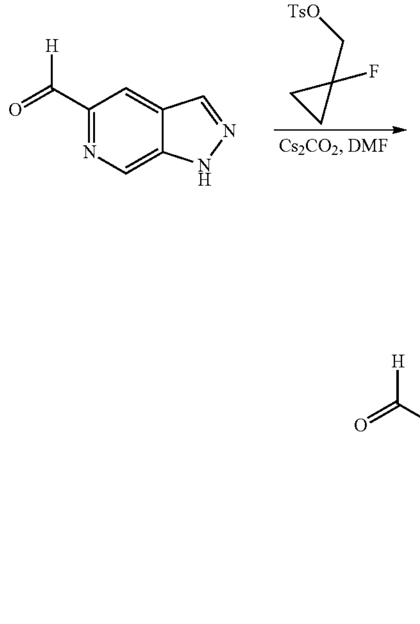

To a solution of 1H-pyrazolo[3,4-c]pyridine-5-carbaldehyde (546 mg) in anhydrous DMF (1.5 mL) were added $Cs_2CO_3$ (1.45 g) and (1-fluorocyclopropyl)methyl 4-methylbenzenesulfonate (1.09 g) and the reaction was stirred at rt for 4 hr. The reaction was diluted with EA and water. The two phases were separated, and the aqueous phase was extracted with DCM (10 mL×3). The combined organic layers were dried over $Na_2SO_4$, filtered, and concentrated to provide a residue, which was purified by silica gel column to give 1-((1-fluorocyclopropyl)methyl)-1H-pyrazolo[3,4-c]pyridine-5-carbaldehyde (192 mg). LC/MS ESI (m/z): 230 $[M+H]^+$; $^1$H NMR (400 MHz, $CDCl_3$) δ 10.23 (s, 1H), 9.18 (d, J=0.7 Hz, 1H), 8.41 (d, J=1.1 Hz, 1H), 8.27 (s, 1H), 4.88 (d, J=21.2 Hz, 2H), 1.29-1.10 (m, 2H), 1.05-0.91 (m, 2H).

Synthesis of (R,E)-N-((1-((1-fluorocyclopropyl)methyl)-1H-pyrazolo[3,4-c]pyridin-5-yl)methylene)-2-methylpropane-2-sulfinamide

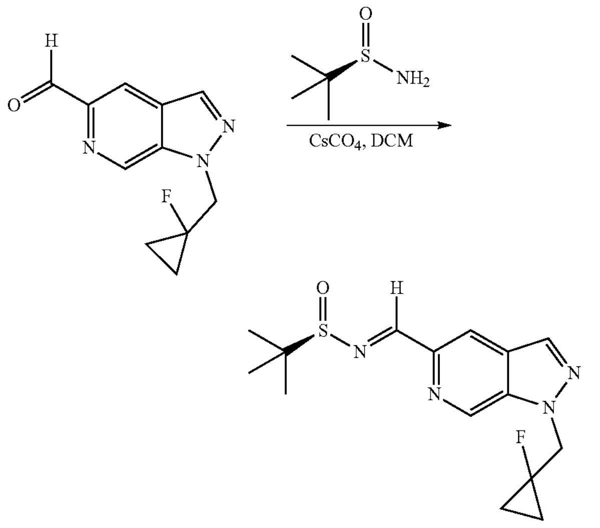

To a solution of 1-((1-fluorocyclopropyl)methyl)-1H-pyrazolo[3,4-c]pyridine-5-carbaldehyde (192 mg) in anhydrous DCM (8.0 mL) were added $CuSO_4$ (419.4 mg) and (R)-2-methylpropane-2-sulfinamide (138.0 mg). The reaction was stirred at rt overnight. The solution was then filtered through a pad of Celite, and the filtrate was concentrated. The residue was purified by silica gel column to give (R,E)-N-((1-((1-fluorocyclopropyl)methyl)-1H-pyrazolo[3,4-c]pyridin-5-yl)methylene)-2-methylpropane-2-sulfinamide (294 mg). LC/MS ESI (m/z): 323 $[M+H]^+$; $^1$H NMR (400 MHz, $CDCl_3$) δ 9.17 (d, J=0.8 Hz, 1H), 8.83 (s, 1H), 8.35 (d, J=1.1 Hz, 1H), 8.20 (d, J=0.5 Hz, 1H), 4.86 (d, J=21.0 Hz, 2H), 1.31 (s, 9H), 1.22-1.13 (m, 2H), 1.01-0.93 (m, 2H) ppm.

Synthesis of (R)—N—((R)-1-(1-((1-fluorocyclopropyl)methyl)-1H-pyrazolo[3,4-c]pyridin-5-yl)ethyl)-2-methylpropane-2-sulfinamide

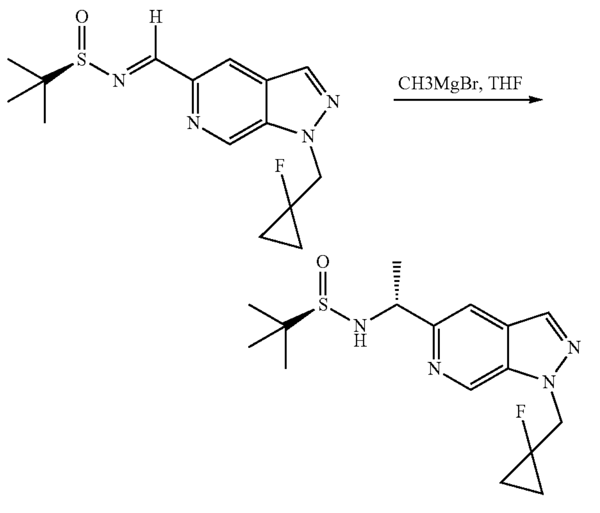

To a solution of (R,E)-N-((1-((1-fluorocyclopropyl)methyl)-1H-pyrazolo[3,4-c]pyridin-5-yl)methylene)-2-methylpropane-2-sulfinamide (290 mg) in anhydrous THE (12 mL) was added $CH_3MgBr$ (1.499 mL, 3.0M in ether) dropwise at −78° C. under nitrogen, and the reaction was stirred at −78° C. for 2 hr. The reaction solution was then quenched with aqueous $NH_4Cl$. The two phases separated, and the aqueous phase was extracted with EA. The combined organic layer was dried over $Na_2SO_4$, filtered and concentrated in vacuo to provide a residue, which was purified by silica gel column chromatography to give (R)—N—((R)-1-(1-((1-fluorocyclopropyl)methyl)-1H-pyrazolo[3,4-c]pyridin-5-yl)ethyl)-2-methylpropane-2-sulfinamide (228 mg). LC/MS ESI (m/z): 339 $[M+H]^+$.

Synthesis of (R)-1-(1-((1-fluorocyclopropyl)methyl)-1H-pyrazolo[3,4-c]pyridin-5-yl)ethan-1-amine hydrochloride

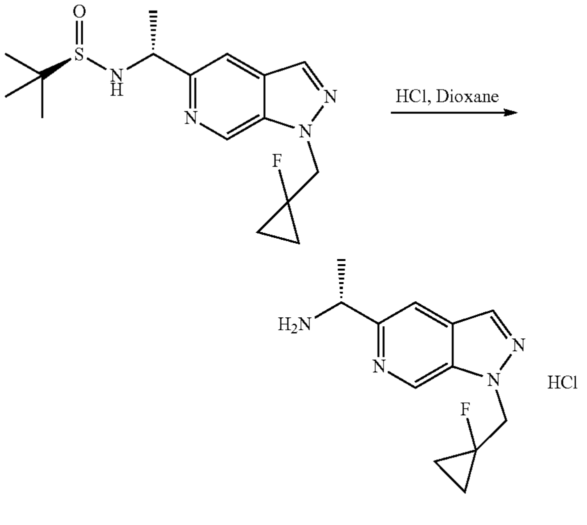

To a solution of (R)—N—((R)-1-(1-((1-fluorocyclopropyl)methyl)-1H-pyrazolo[3,4-c]pyridin-5-yl)ethyl)-2-methylpropane-2-sulfinamide (212 mg) in dioxane (5 mL) was added 4N HCl-dioxane (2.5 mL). The reaction was stirred at rt for 30 min. The mixture was concentrated and used for next step directly. LC/MS ESI (m/z): 235 $[M+H]^+$ Synthesis of (R)—N-(1-(1-((1-fluorocyclopropyl)methyl)-1H-pyrazolo[3,4-c]pyridin-5-yl)ethyl)-2-(4-isopropylphenyl)acetamide

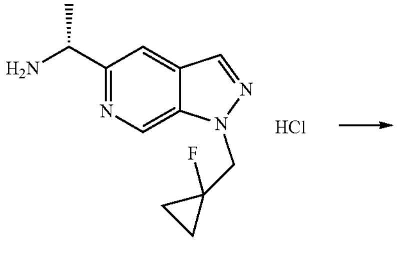

-continued

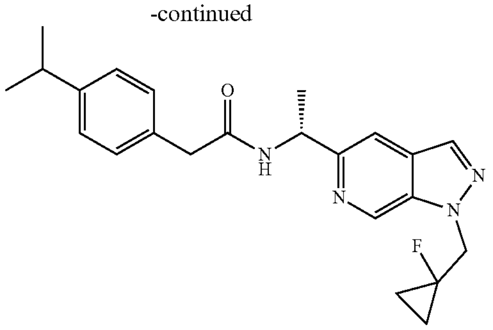

To a solution of (R)-1-(1-((1-fluorocyclopropyl)methyl)-1H-pyrazolo[3,4-c]pyridin-5-yl)ethan-1-amine hydrochloride (170 mg) in anhydrous DMF was added DIEA (487 mg) to provide Solution A. To a solution of 2-(4-isopropylphenyl)acetic acid (107.8 mg) in anhydrous DMF was added HATU (252.9 mg) and stirred 15 min at RT to provide Solution B. Solution B was added to the solution A, and the resulting mixture was stirred at rt for 1 h. The reaction was then diluted with EA and water. The two phases were separated, and the aqueous phase was extracted with DCM (10 mL×3). The combined organic layers were dried over $Na_2SO_4$, filtered, and concentrated to give a residue, which was purified by prep-HPLC (Column: YMC-Actus Triart C18 250*21 mm; Mobile phase: from 20% to 95% MeCN with $H_2O$ (1% $NH_3H_2O$); flow rate: 15 mL/min; wavelength: 220 nm/254 nm) to give (R)—N-(1-(1-((1-fluorocyclopropyl)methyl)-1H-pyrazolo[3,4-c]pyridin-5-yl)ethyl)-2-(4-isopropylphenyl)acetamide (162.2 mg). LC/MS ESI (m/z): 395 $[M+H]^+$; $^1H$ NMR (400 MHz, $CDCl_3$) δ 8.95 (s, 1H), 8.03 (s, 1H), 7.54 (s, 1H), 7.19 (s, 4H), 6.74 (d, J=6.9 Hz, 1H), 5.30-5.23 (m, 1H), 4.80 (d, J=21.1 Hz, 2H), 3.55 (s, 2H), 2.93-2.86 (m, 1H), 1.49 (d, J=6.8 Hz, 3H), 1.24 (d, J=6.9 Hz, 6H), 1.18-1.13 (m, 2H), 0.95-0.93 (m, 2H) ppm; $^{19}F$ NMR (377 MHz, $CDCl_3$) δ −183.10 (s).

Example 19. (R)-2-(4-(1,1-difluoroethyl)phenyl)-N-(1-(1-(2,2,2-trifluoroethyl)-1H-Pyrazolo[3,4-c]pyridin-5-yl)ethyl)acetamide Step 1. ethyl 2-(4-(1,1-difluoroethyl)phenyl)acetate

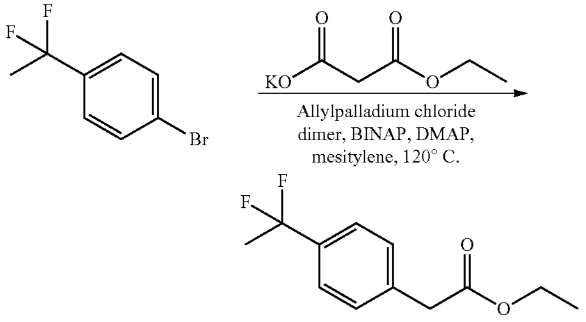

A solution of 1-bromo-4-(1,1-difluoroethyl)benzene (0.54 mL), ethyl potassium malonate (924.0 mg), allylpalladium chloride dimer (26.5 mg), BINAP (135.2 mg) and DMAP (442.2 mg) in 1,3,5-trimethylbenzene (10 mL) was charged with $N_2$ and stirred at 140° C. for 1 hr. The mixture was then stirred at 120° C. for an additional 12 hr. The reaction was diluted with water and extracted with EtOAc. The combined extracts were dried, filtered and concentrated to give a residue, which was purified by column chromatography on silica gel (PE:EA=20:1) to give ethyl 2-[4-(1,1-difluoroethyl)phenyl]acetate (180 mg) as colorless oil. $^1$H NMR (400 MHz, $CDCl_3$) δ 7.47 (d, J=8.4 Hz, 2H), 7.34 (d, J=8.0 Hz, 2H), 4.20-4.12 (m, 2H), 3.64 (s, 2H), 1.91 (t, J=18.4 Hz, 3H), 1.26 (t, J=7.2 Hz, 3H).

Step 2. 2-(4-(1,1-difluoroethyl)phenyl)acetic acid

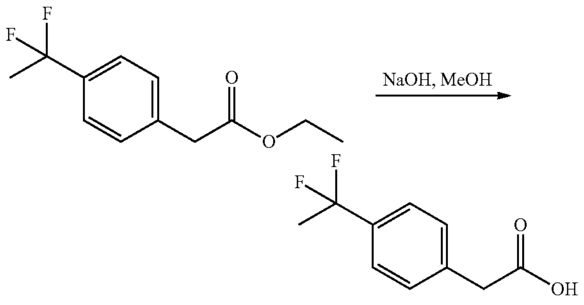

To a solution of ethyl 2-[4-(1,1-difluoroethyl)phenyl]acetate (150 mg) in MeOH (0.5 mL) was added NaOH (2M in $H_2O$, 2.0 mL), and the mixture was stirred at 25° C. for 12 hr. The mixture was adjusted pH=3 and extracted with EtOAc. The combined extracts were dried, filtered, and concentrated to give 2-[4-(1,1-difluoroethyl)phenyl]acetic acid (110 mg) as a white solid. LC/MS ESI (m/z): 199 [M−H].

Step 3. (R)-2-(4-(1,1-difluoroethyl)phenyl)-N-(1-(1-(2,2,2-trifluoroethyl)-1H-pyrazolo[3,4-c]pyridin-5-yl)ethyl)acetamide

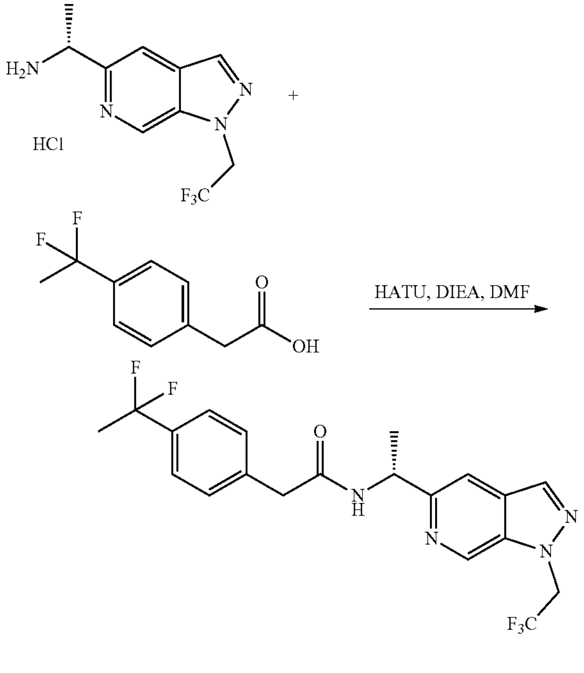

A solution of (1R)-1-[1-(2,2,2-trifluoroethyl)-1H-pyrazolo[3,4-c]pyridin-5-yl]ethan-1-amine hydrochloride (140 mg), 2-[4-(1,1-difluoroethyl)phenyl]acetic acid (114.8 mg), HATU (239.8 mg) and DIEA (0.28 mL) in DMF (5.0 mL) was stirred at 25° C. for 1 hr. The mixture was diluted with water and extracted with DCM. The combined extracts were dried, filtered, and concentrated to give a residue. The residue was purified by prep-HPLC [Column: YMC-Actus Triart C18 250*20 mm; Mobile phase: from 25% to 95% MeCN with $H_2O$ (0.1% FA); flow rate: 15 mL/min; wavelength: 220 nm/254 nm] to give (R)-2-(4-(1,1-difluoroethyl)phenyl)-N-(1-(1-(2,2,2-trifluoroethyl)-1H-pyrazolo[3,4-c]pyridin-5-yl)ethyl)acetamide (109.9 mg) as a white solid. LC/MS ESI (m/z): 427 $(M+H)^+$; $^1$H NMR (400 MHz, $CDCl_3$) δ 8.91 (s, 1H), 8.12 (s, 1H), 7.59 (s, 1H), 7.46 (d, J=8.0 Hz, 2H), 7.33 (d, J=8.0 Hz, 2H), 6.77 (s, 1H), 5.28-5.24 (m, 1H), 5.05 (q, J=8.4 Hz, 2H), 3.61 (s, 2H), 1.91 (t, J=18.0 Hz, 3H), 1.50 (d, J=6.8 Hz, 3H) ppm; $^{19}$F NMR (377 MHz, $CDCl_3$) δ −70.78, −87.35 ppm.

Example 20. (R)-2-(6-isopropylpyridin-3-yl)-N-(1-(1-(2,2,2-trifluoroethyl)-1H-pyrazolo[3,4-c]pyridin-5-yl)ethyl)acetamide Synthesis of methyl 6-(prop-1-en-2-yl)nicotinate

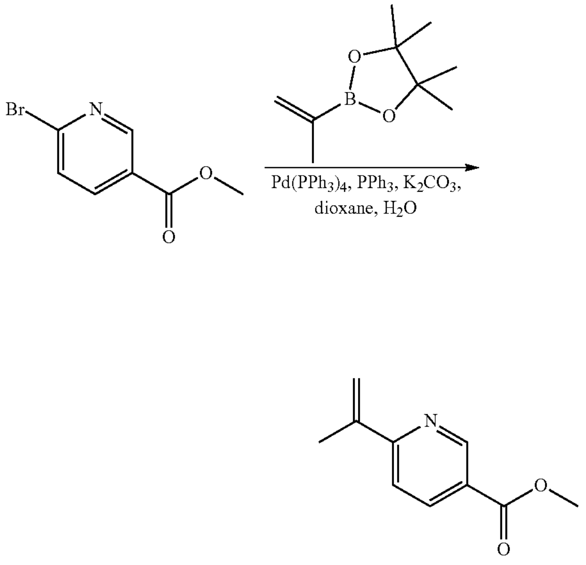

To a solution of methyl 6-bromonicotinate (7.0 g) in dioxane/water (20 mL, 9:1) were added 4,4,5,5-tetramethyl-2-(prop-1-en-2-yl)-1,3,2-dioxaborolane (6.1 mL), $Pd(PPh_3)_4$ (0.75 g), $PPh_3$ (1.70 g) and $K_2CO_3$ (13.44 g). The mixture was charged with $N_2$ and stirred at 80° C. overnight under nitrogen, at which point LC/MS showed the reaction was complete. The reaction mixture was quenched by ice-water and then extracted with EtOAc twice. The combined extracts were concentrated, and the residue was purified by column chromatography on silica gel (PE:EA=10:1) to give methyl 6-(prop-1-en-2-yl)nicotinate (4.9 g) as a white solid. $^1$H NMR (400 MHz, $CDCl_3$) δ 9.36-8.82 (m, 1H), 8.24 (dd, J=8.3, 2.2 Hz, 1H), 7.54 (d, J=8.3 Hz, 1H), 6.00 (d, J=0.5 Hz, 1H), 5.53-5.02 (m, 1H), 3.94 (s, 3H), 2.23 (d, J=0.5 Hz, 3H) ppm.

Synthesis of methyl 6-isopropylnicotinate

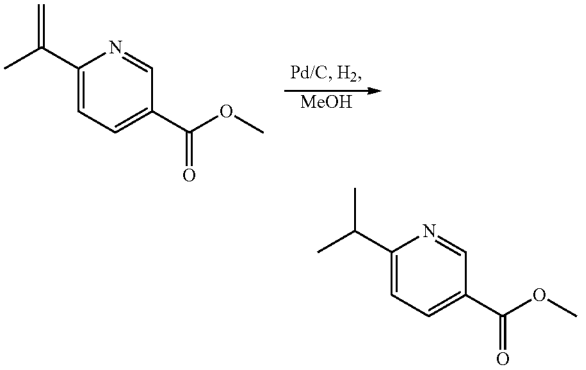

To a solution of methyl 6-(prop-1-en-2-yl)nicotinate (2.5 g) in MeOH (20 mL) was added 10% Pd/C (1.46 mL). The mixture was stirred at room temperature under hydrogen for 2 hrs, and LC/MS showed the reaction was complete. The reaction was filtered, and the solvent was concentrated to provide a residue, which was purified by column chromatography on silica gel (PE:EA=5:1) to give methyl 6-isopropylnicotinate (2.0 g) as a colorless oil. $^1H$ NMR (400 MHz, $CD_3OD$) δ 9.01 (d, J=2.1 Hz, 1H), 8.29 (dd, J=8.2, 2.1 Hz, 1H), 7.44 (d, J=8.2 Hz, 1H), 3.93 (s, 3H), 3.13 (m, 1H), 1.32 (d, J=6.9 Hz, 6H) ppm.

Synthesis of (6-isopropylpyridin-3-yl)methanol

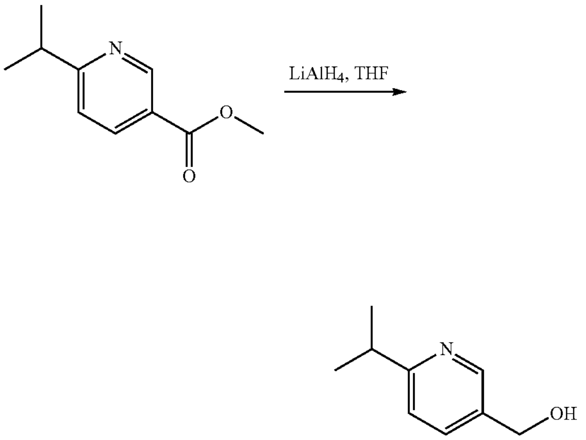

To a solution of methyl 6-isopropylnicotinate (1.5 g) in THF (10 mL) was added $LiAlH_4$ (0.95 g) and the mixture was stirred at room temperature for 4 hrs. LC/MS showed the reaction was complete. The reaction mixture was then quenched by ice-water and extracted with EtOAc twice. The combined extracts were concentrated, and the residue was purified by column chromatography on silica gel (PE:EA=1:1) to give (6-isopropylpyridin-3-yl)methanol (1.0 g) as a colorless oil. $^1H$ NMR (400 MHz, DMSO-d6) δ 8.41 (d, J=1.7 Hz, 1H), 7.63 (dd, J=8.0, 2.3 Hz, 1H), 7.23 (d, J=8.0 Hz, 1H), 5.24 (t, J=5.7 Hz, 1H), 4.48 (d, J=5.6 Hz, 2H), 3.05-2.95 (m, 1H), 1.22 (d, J=6.9 Hz, 6H); LC/MS ESI (m/z): 152 $[M+H]^+$.

Step 4. Synthesis of 5-(bromomethyl)-2-isopropylpyridine

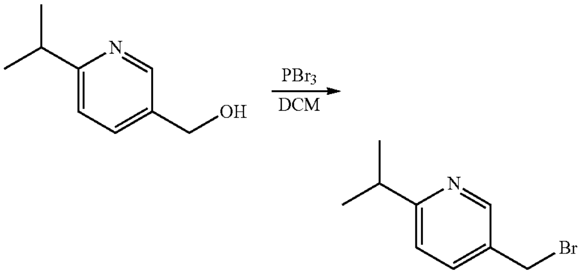

To a solution of (6-isopropylpyridin-3-yl)methanol (1.0 g) in $CH_2Cl_2$ (10 mL) was added phosphorus tribromide (1.24 mL). The mixture was stirred at room temperature overnight, at which point LC/MS showed the reaction was complete. The reaction mixture was quenched with ice-water and then extracted with EtOAc twice. The combined extracts were concentrated, and the residue was purified by column chromatography on silica gel (PE:EA=5:1) to give 5-(bromomethyl)-2-isopropylpyridine (1.1 g) as a colorless oil. $^1H$ NMR (400 MHz, DMSO-d6) δ 8.61-8.47 (m, 1H), 7.86-7.69 (m, 1H), 7.30 (t, J=11.2 Hz, 1H), 4.72 (s, 2H), 3.12-2.90 (m, 1H), 1.22 (d, J=6.9 Hz, 6H); LC/MS ESI (m/z): 214 $[M+H]^+$.

Step 5. Synthesis of 2-(6-isopropylpyridin-3-yl)acetonitrile

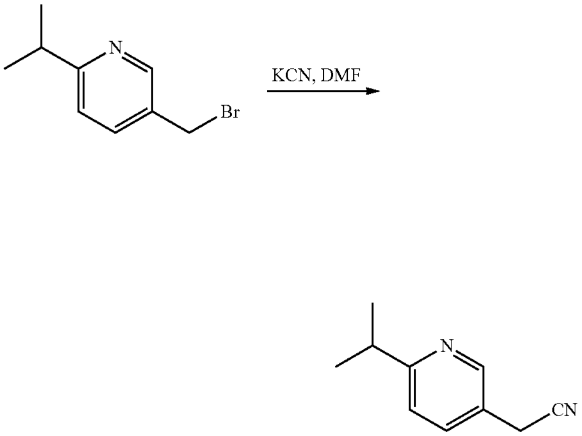

To a solution of 5-(bromomethyl)-2-isopropylpyridine (1.1 g) in DMF (15 mL) was added KCN (1.67 g). The mixture was stirred 50° C. for 3 hrs. LC/MS and TLC showed the reaction was complete. The reaction mixture was quenched by ice-water and then extracted with EtOAc twice. The combined extracts were concentrated, and the residue was purified by column chromatography on silica gel (PE:EA=5:1) to give 2-(6-isopropylpyridin-3-yl)acetonitrile (120 mg) as a colorless oil. $^1H$ NMR (400 MHz, $CDCl_3$) δ 8.49 (d, J=1.7 Hz, 1H), 7.65 (d, J=8.1 Hz, 1H), 7.23 (d, J=8.1 Hz, 1H), 3.74 (s, 2H), 3.21-2.91 (m, 1H), 1.31 (d, J=6.9 Hz, 6H) ppm; LC/MS ESI (m/z): 161 $[M+H]^+$.

Step 6. Synthesis of 2-(6-isopropylpyridin-3-yl)acetic acid hydrochloride

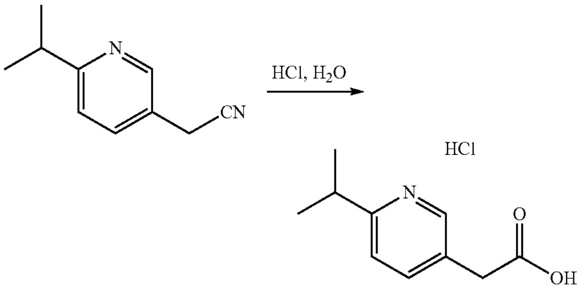

To a solution of 2-(6-isopropylpyridin-3-yl)acetonitrile (120 mg) in water (3.0 mL) was added 12N HCl (1.4 g). The mixture was stirred at 100° C. for 2 hrs, and LC/MS showed that the reaction was complete. The reaction mixture was quenched by ice-water and then extracted with EtOAc twice. The water phase was evaporated to dryness to give 2-(6-isopropylpyridin-3-yl)acetic acid hydrochloride (130 mg) as a brown solid, which was used next step; LC/MS ESI (m/z): 180 $[M+H]^+$.

Step 7. Synthesis of (R)-2-(6-isopropylpyridin-3-yl)-N-(1-(1-(2,2,2-trifluoroethyl)-1H-pyrazolo[3,4-c]pyridin-5-yl)ethyl)acetamide

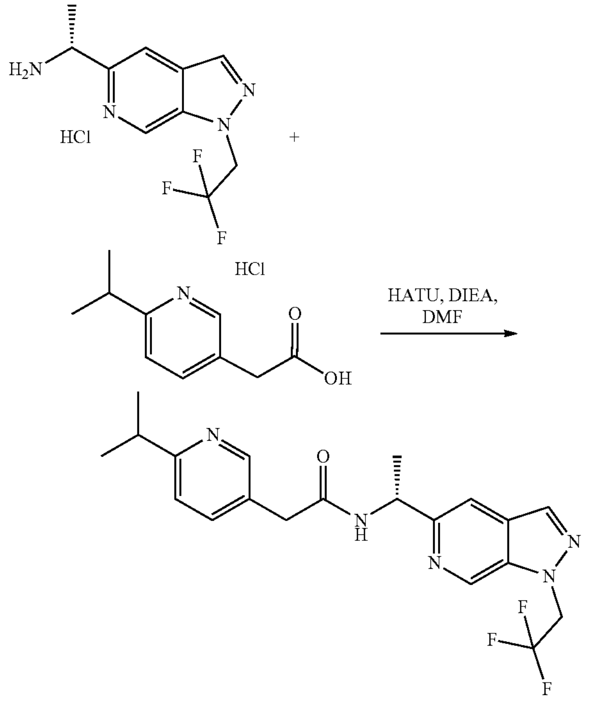

A solution of (1R)-1-[1-(2,2,2-trifluoroethyl)-1H-pyrazolo[3,4-c]pyridin-5-yl]ethan-1-amine hydrochloride (140 mg), 2-(6-isopropylpyridin-3-yl)acetic acid hydrochloride (102.0 mg), HATU (239.8 mg) and DIEA (0.28 mL) in DMF (4.0 mL) was stirred at 25° C. for 1 hr. The mixture was diluted with water and DCM. The two phases were separated, and the aqueous phase was extracted with DCM (10 mL×3). The combined organic layers were dried over $Na_2SO_4$, filtered, and concentrated to give a residue, which was purified by prep-HPLC [Column: YMC-Actus Triart C18 250*21 mm; Mobile phase: from 10% to 85% MeCN with H2O (0.1% $NH_3H_2O$); flow rate: 15 mL/min; wavelength: 220 nm/254 nm] and SFC (Column:ChiralPak IA, 250×21.3 mm I.D., 5 μm; Mobile phase: A for $CO_2$ and B for MEOH+0.1% $NH_3H_2O$; Gradient: B 40%; Wavelength: 220 nm) to give (R)-2-(6-isopropylpyridin-3-yl)-N-(1-(1-(2,2,2-trifluoroethyl)-1H-pyrazolo[3,4-c]pyridin-5-yl)ethyl)acetamide (67.9 mg) as a white solid. LC/MS ESI (m/z): 406 $(M+H)^+$; $^1H$-NMR (400 MHz, $CDCl_3$) δ 8.87 (s, 1H), 8.50 (s, 1H), 8.09 (s, 1H), 7.81-7.74 (m, 1H), 7.56 (s, 1H), 7.27 (s, 1H), 6.98-6.90 (m, 1H), 5.29-5.22 (m, 1H), 5.11-5.02 (m, 2H), 3.60 (s, 2H), 3.27-3.17 (m, 1H), 1.50 (d, J=6.8 Hz, 3H), 1.34-1.32 (m, 6H); $^{19}F$-NMR (377 MHz, $CDCl_3$) δ -70.79.

Example 21. (R)-2-(6-(1-(difluoromethyl)cyclopropyl)pyridin-3-yl)-N-(1-(1-(2,2,2-trifluoroethyl)-1H-pyrazolo[3,4-c]pyridin-5-yl)ethyl)acetamide Step 1. 1-(5-bromopyridin-2-yl)cyclopropane-1-carbonitrile

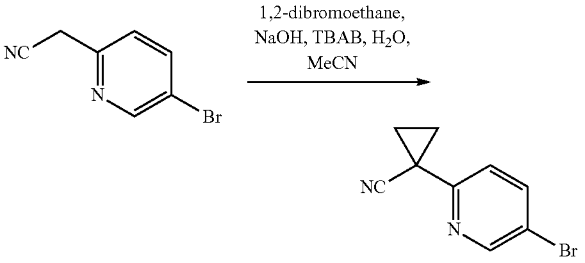

To a solution of NaOH (10.1 g) in $H_2O$ (20 mL) was added 2-(5-bromopyridin-2-yl)acetonitrile (5.0 g), 1,2-dibromoethane (2.2 mL), tetrabutylammonium bromide (7.9 mL) and $CH_3CN$ (80 mL). The mixture was stirred at 25° C. for 12 hr. The mixture was diluted with water and extracted with EtOAc. The combined extracts were dried, filtered and concentrated to give a residue, which was purified by chromatography on silica gel (PE:EA=1:0 to 50:1) to give 1-(5-bromopyridin-2-yl)cyclopropane-1-carbonitrile (4.5 g) as a white solid. $^1H$ NMR (400 MHz, DMSO-d6) δ 8.66-8.62 (m, 1H), 8.08 (dd, J=8.4, 2.4 Hz, 1H), 7.51 (dd, J=8.4, 0.6 Hz, 1H), 1.91-1.78 (m, 2H), 1.73-1.61 (m, 2H).

Step 2. 1-(5-bromopyridin-2-yl)cyclopropane-1-carbaldehyde

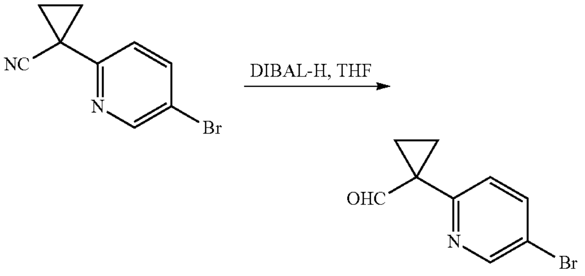

To a solution of 1-(5-bromopyridin-2-yl)cyclopropane-1-carbonitrile (4.5 g) in THE (80 mL) was added diisobutylaluminium hydride (1.0M in THF, 40.3 mL) at 0° C. and the reaction mixture was stirred at 0° C. for 2 hr. The reaction was quenched with MeOH (20 mL) and 1 N HCl (30 mL) and extracted with EtOAc. The combined extracts were dried, filtered and concentrated to give 1-(5-bromopyridin-2-yl)cyclopropane-1-carbaldehyde (1.8 g) as yellow oil. LC/MS ESI (m/z): 246 $[M+H]^+$.

Step 3. 5-bromo-2-(1-(difluoromethyl)cyclopropyl)pyridine

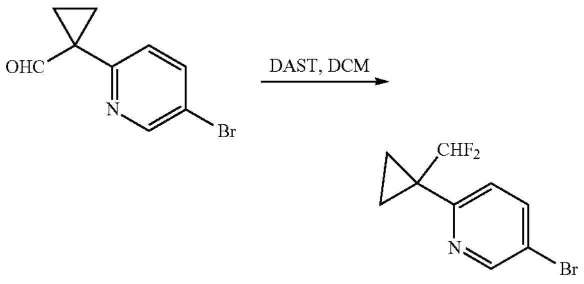

To a solution of 1-(5-bromopyridin-2-yl)cyclopropane-1-carbaldehyde (1.8 g) in DCM (30 mL) was added DAST (3.2 mL). The mixture was stirred at 25° C. for 12 hr. Then the reaction was quenched with $NaHCO_3$ solution at 0° C. and washed with water. The organic layer was dried, filtered and concentrated to give a residue, which was purified by chromatography on silica gel (PE:EtOAc=1:0 to 50:1) to give 5-bromo-2-[1-(difluoromethyl)cyclopropyl]pyridine (700 mg) as colorless oil. LC/MS ESI (m/z): 248 $[M+H]^+$.

Step 4. ethyl 2-(6-(1-(difluoromethyl)cyclopropyl)pyridin-3-yl)acetate

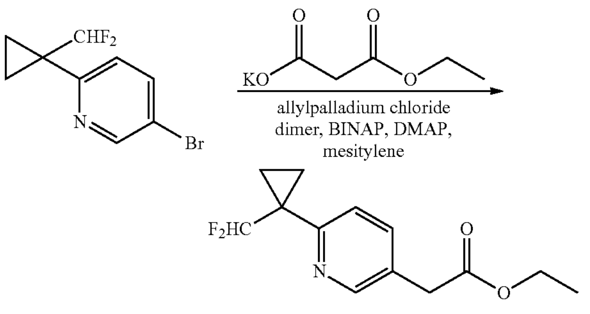

A solution of 5-bromo-2-[1-(difluoromethyl)cyclopropyl]pyridine (700 mg), 1-ethyl 3-potassium propanedioate (720 mg), allylpalladium chloride dimer (103.2 mg), BINAP (527.1 mg) and DMAP (344.7 mg) in mesitylene (10 mL) was charged with $N_2$ three times and stirred at 140° C. for 1 hr. The mixture was then stirred at 120° C. for an additional 12 hr. The mixture was concentrated to give a residue, which was purified by chromatography silica gel (PE:EtOAc=1:0 to 20:1) to give ethyl 2-{6-[1-(difluoromethyl)cyclopropyl]pyridin-3-yl}acetate (430 mg) as yellow oil. LC/MS ESI (m/z): 256 $[M+H]^+$.

Step 5. 2-(6-(1-(difluoromethyl)cyclopropyl)pyridin-3-yl)acetic acid

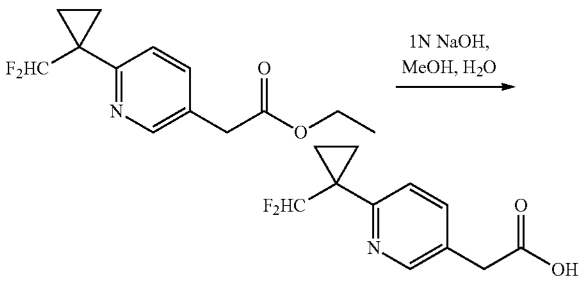

To a solution of ethyl 2-{6-[1-(difluoromethyl)cyclopropyl]pyridin-3-yl}acetate (430 mg) in MeOH (1.0 mL) was added NaOH (1 M in $H_2O$, 4.0 mL), and the mixture was stirred at 25° C. for 30 min. The mixture was then concentrated, diluted with water and extracted with EtOAc. The aqueous phase was adjusted to pH=4 with 1 N aqueous HCl and then lyophilized to give 2-(6-(1-(difluoromethyl)cyclopropyl)pyridin-3-yl)acetic acid (230 mg) as white solid. LC/MS ESI (m/z): 226 [M−H].

Step 6. (R)-2-(6-(1-(difluoromethyl)cyclopropyl)pyridin-3-yl)-N-(1-(1-(2,2,2-trifluoroethyl)-1H-pyrazolo[3,4-c]pyridin-5-yl)ethyl)acetamide

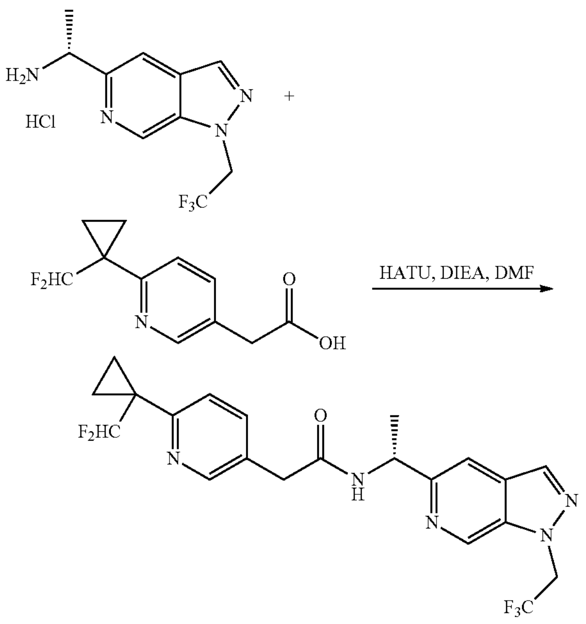

A solution of 2-(6-(1-(difluoromethyl)cyclopropyl)pyridin-3-yl)acetic acid (130 mg), (R)-1-[1-(2,2,2-trifluoroethyl)-1H-pyrazolo[3,4-c]pyridin-5-yl]ethan-1-amine hydrochloride (153.7 mg), HATU (239.3 mg) and DIEA (0.284 mL) in DMF (5 mL) was stirred at 25° C. for 12 hr. The mixture was diluted with water and extracted with DCM. The combined extracts were dried, filtered and concentrated to give a residue, which was purified by prep-HPLC [Column: Shim-pack GIST C18 250*20 mm; Mobile phase: from 10% to 95% MeCN with $H_2O$ (0.1% $NH_3H_2O$); flow rate: 15 mL/min; wavelength: 220 nm/254 nm] to give (R)-2-(6-(1-(difluoromethyl)cyclopropyl)pyridin-3-yl)-N-(1-(1-(2,2,2-trifluoroethyl)-1H-pyrazolo[3,4-c]pyridin-5-yl)ethyl)acetamide (89.4 mg) as a white solid. LC/MS ESI (m/z): 454 (M+H)+; $^1H$ NMR (400 MHz, $CDCl_3$) δ 8.90 (s, 1H), 8.43 (s, 1H), 8.11 (s, 1H), 7.62 (dd, J=8.2, 2.3 Hz, 1H), 7.58 (s, 1H), 7.32 (d, J=8.0 Hz, 1H), 6.82 (d, J=7.4 Hz, 1H), 6.18 (t, J=57.1 Hz, 1H), 5.27-5.24 (m, 1H), 5.06 (q, J=8.3 Hz, 2H), 3.55 (s, 2H), 1.51 (d, J=6.8 Hz, 3H), 1.40-1.11 (m, 4H); $^{19}F$ NMR (377 MHz, $CDCl_3$) δ −70.80, −119.76.

Example 22. (R)-2-(4-(1-(difluoromethyl)cyclopropyl)phenyl)-N-(1-(1-(2,2,2-trifluoroethyl)-1H-pyrazolo[3,4-c]pyridin-5-yl)ethyl)acetamide Synthesis of 1-(4-bromophenyl)cyclopropane-1-carbonitrile

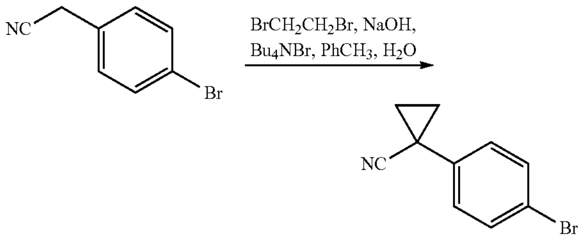

To a 250 mL round bottom flask containing a solution of 1,2-dibromoethane (6.17 mL) and 2-(4-bromophenyl)acetonitrile (10 g) in toluene (40 mL) were added 50% aqueous NaOH (40 mL) and tetrabutylammonium bromide (3.17 mL) at rt. The reaction mixture was stirred vigorously at rt for 24 h. Then the reaction was poured into 450 mL ice-water solution, and this solution was extracted with EA (130 mL×3). The combined extracts were washed with water (150 mL×2), washed with brine (150 mL), and finally dried over anhydrous $Na_2SO_4$, filtered. The solvent was removed under vacuo to provide a crude product, which was purified by silica gel flash chromatography to afford 1-(4-bromophenyl)cyclopropane-1-carbonitrile as a yellow oil (7.75 g). $^1H$-NMR (400 MHz, $CDCl_3$) δ 7.51-7.44 (m, 2H), 7.21-7.11 (m, 2H), 1.81-1.67 (m, 2H), 1.45-1.31 (m, 2H) ppm.

Synthesis of 1-(4-bromophenyl)cyclopropane-1-carbaldehyde

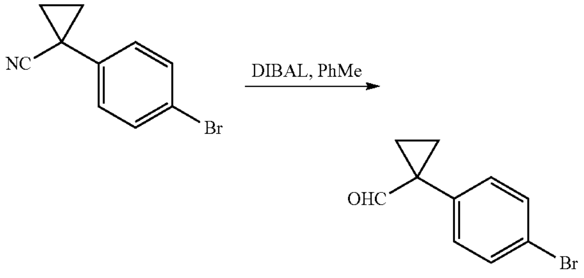

A mixture of 1-(4-bromophenyl)cyclopropane-1-carbonitrile (4.0 g) and diisobutylaluminum hydride (36.02 mL) in THE (30 mL) were stirred at 0° C. for 1 hour, and the reaction mixture was allowed to warm to room temperature. Upon completion of the reaction, the reaction mixture was cooled to 0° C. and quenched with MeOH. The reaction was slowly warmed to room temperature over 15 min and then 1 M HCl was added. The reaction was extracted with EA and washed with NaCl solution. The organic phase was concentrated to provide the 1-(4-bromophenyl)cyclopropane-1-carbaldehyde as a yellow oil (3.79 g, crude). $^1H$-NMR (400 MHz, $CDCl_3$) δ 9.16 (s, 1H), 7.51-7.46 (m, 2H), 7.20-7.15 (m, 2H), 1.60-1.56 (m, 2H), 1.41-1.37 (m, 2H) ppm.

Synthesis of 1-bromo-4-(1-(difluoromethyl)cyclopropyl)benzene

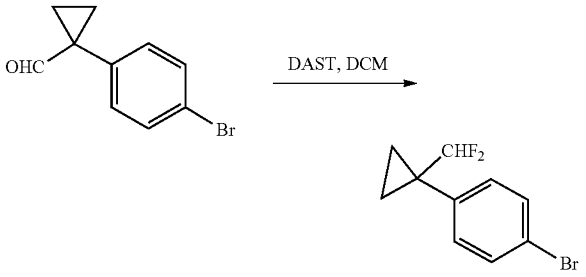

To a solution of 1-(4-bromophenyl)cyclopropane-1-carbaldehyde (3.79 g) in DCM (40 mL) was added DAST (22 g), and the reaction was stirred at room temperature overnight. The reaction was diluted with DCM and water. The two phases were separated, and the aqueous phase was extracted with DCM (10 mL×3). The combined organic layers were dried over $Na_2SO_4$, filtered, and concentrated to give a residue, which was purified by silica gel column chromatography (PE:EA=10:1) to give 1-bromo-4-[1-(difluoromethyl)cyclopropyl]benzene as a yellow oil (2.2 g). $^1H$-NMR (400 MHz, $CDCl_3$) δ 7.56-7.35 (m, 2H), 7.29-7.26 (m, 2H), 5.58 (t, J=56.0 Hz, 1H), 1.21-1.07 (m, 2H), 0.99-0.86 (m, 2H) ppm. $^{19}F$-NMR (377 MHz, $CDCl_3$) δ −117.06 ppm.

Synthesis of ethyl 2-(4-(1-(difluoromethyl)cyclopropyl)phenyl)acetate

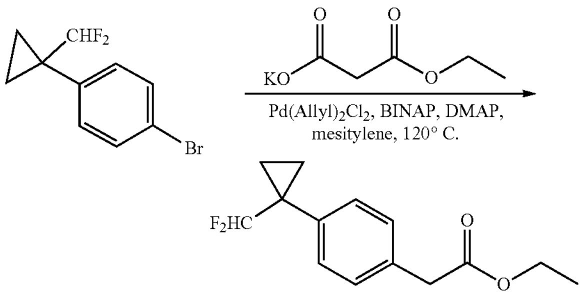

To a solution of 1-bromo-4-[1-(difluoromethyl)cyclopropyl]benzene (636 mg) in Mesitylene (10 mL) were added diallylpalladium dichloride (18.8 mg,), BINAP (96.2 mg), DMAP (31.4 mg) and ethyl potassium malonate (657.2 mg). The reaction was charged with $N_2$ for three times and stirred at 120° C. overnight. The reaction was diluted with EA and water. The two phases were separated, and the aqueous phase was extracted with DCM (10 mL×3). The combined organic layers were dried over $Na_2SO_4$, filtered, and concentrated to give a residue, which was purified by silica gel column chromatography (PE:EA=10:1) to give ethyl 2-(4-(1-(difluoromethyl)cyclopropyl)phenyl)acetate (267 mg) as a yellow oil. $^1$H-NMR (400 MHz, $CDCl_3$) δ 7.36 (d, J=8.0 Hz, 2H), 7.26-7.20 (m, 2H), 5.64 (t, J=56.0 Hz, 1H), 4.20-4.10 (m, 2H), 3.60 (s, 2H), 1.26 (t, J=4.0 Hz, 3H), 1.16-1.12 (m, 2H), 0.98-0.92 (m, 2H) ppm. $^{19}$F-NMR (377 MHz, $CDCl_3$) δ −117.51 ppm.

Synthesis of 2-(4-(1-(difluoromethyl)cyclopropyl)phenyl)acetic acid

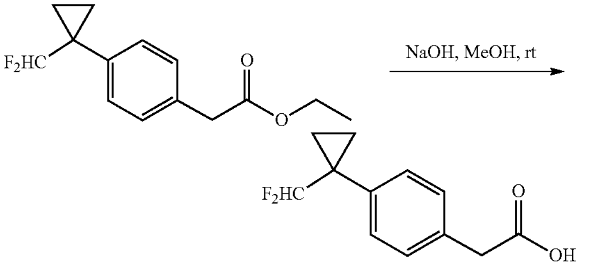

In a 25 mL round-bottomed flask were combined ethyl 2-(4-(1-(difluoromethyl)cyclopropyl)phenyl)acetate (66 mg) and 1M aqueous NaOH (2.0 mL) and MeOH (2.0 mL) to provide a colorless solution. The reaction mixture was stirred at rt for 1 hour. Water (20 mL) was then added and the aqueous layer was washed with EA. The aqueous layer was acidified to pH<3 with 1M aqueous HCl, and the mixture was extracted with EA. The combined EtOAc extracts from the acidic water layer were washed with saturated NaCl, dried with $Na_2SO_4$, filtered, and concentrated to provide 2-(4-(1-(difluoromethyl)cyclopropyl)phenyl)acetic acid as a white solid (244 mg, crude). $^1$H-NMR (400 MHz, $CDCl_3$) δ 7.37 (d, J=8.0 Hz, 2H), 7.25 (d, J=8.0 Hz, 2H), 5.63 (t, J=56.0 Hz, 1H), 3.64 (s, 2H), 1.16-1.11 (m, 2H), 0.97-0.92 (m, 2H) ppm; $^{19}$F-NMR (377 MHz, $CDCl_3$) δ −117.43 ppm.

Synthesis of (R)-2-(4-(1-(difluoromethyl)cyclopropyl)phenyl)-N-(1-(1-(2,2,2-trifluoroethyl)-1H-indazol-5-yl)ethyl)acetamide

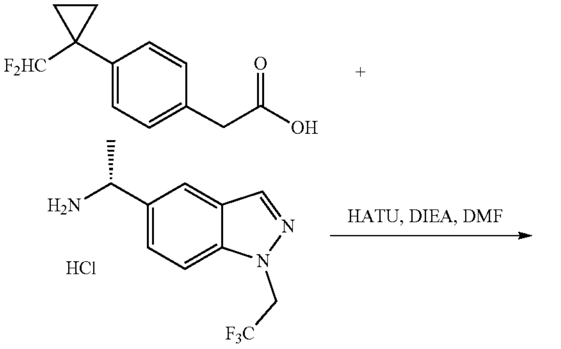

-continued

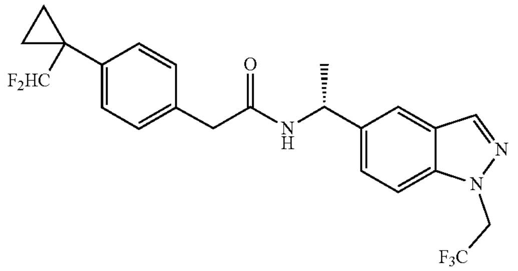

A solution of 2-(4-(1-(difluoromethyl)cyclopropyl)phenyl)acetic acid (164 mg) and HATU (413.5 mg) in DMF (5.0 mL) was stirred at room temperature for 15 min. Then (R)-1-(1-(2,2,2-trifluoroethyl)-1H-indazol-5-yl)ethan-1-amine hydrochloride (230.2 mg) and DIEA (0.72 mL) were added. The reaction was stirred for 1 hour, and LC/MS indicated that the reaction was complete. The reaction was diluted with EA and water. The two phases were separated, and the aqueous phase was extracted with DCM (10 mL×3). The combined organic phase was dried over $Na_2SO_4$, filtered, and concentrated to give a residue, which was purified by prep-HPLC [Column: YMC-Actus Triart C18 250*20 mm; Mobile phase: from 25% to 95% MeCN with H2O (0.1% FA); flow rate: 15 mL/min; wavelength: 220 nm/254 nm] to afford (R)-2-(4-(1-(difluoromethyl)cyclopropyl)phenyl)-N-(1-(1-(2,2,2-trifluoroethyl)-1H-indazol-5-yl)ethyl)acetamide (160 mg) as a brown-yellow solid. LC/MS ESI (m/z): 453 $(M+H)^+$; $^1$H-NMR (400 MHz, $CDCl_3$): δ 8.88 (s, 1H), 8.11 (s, 1H), 7.57 (s, 1H), 7.36 (d, J=8.1 Hz, 2H), 7.23 (d, J=8.2 Hz, 2H), 6.75 (s, 1H), 5.63 (t, J=57.3 Hz, 1H), 5.26-5.23 (m, 1H), 5.04 (q, J=8.3 Hz, 2H), 3.57 (s, 2H), 1.49 (d, J=6.8 Hz, 3H), 1.14 (dd, J=6.3, 4.7 Hz, 2H), 0.95 (d, J=2.1 Hz, 2H); $^{19}$F-NMR (377 MHz, $CDCl_3$) δ −70.81, −117.15.

Example 23. (R)-2-(6-cyclopropylnyridin-3-yl)-N-(1-(1-(4-fluorophenyl)-1H-pyrazolo[3,4-c]pyridin-5-yl)ethyl)acetamide Synthesis of 5-bromo-1-(4-fluorophenyl)-1H-pyrazolo[3,4-c]pyridine

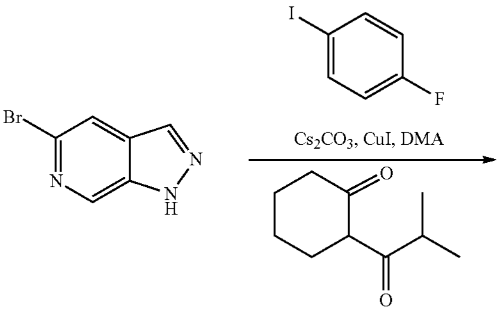

-continued

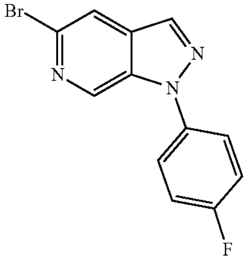

A suspension of 5-bromo-1H-pyrazolo[3,4-c]pyridine (4.0 g), 4-fluoro-1-iodobenzene (6.95 g), 2-Isobutyrylcyclohexanone (1.69 mL), CuI (0.77 g) and $Cs_2CO_3$ (12.5 g) in 30 mL of DMA was degassed with nitrogen for 15 min. The reaction mixture was then warmed to 100° C. and stirred overnight. The reaction mixture was then cooled and diluted with DCM. The organic phase was washed with 1 N aqueous NaOH and water, dried with $Na_2SO_4$ and concentrated to dryness. The solid residue was suspended in ether, stirred for 30 min, and filtered to collect the desired product 5-bromo-1-(4-fluorophenyl)-1H-pyrazolo[3,4-c]pyridine (1.66 g) as a white solid. LC/MS ESI (m/z): 292 $(M+H)^+$; $^1$H-NMR (400 MHz, $CDCl_3$) δ 8.93 (s, 1H), 8.24-8.14 (m, 1H), 7.91 (d, J=4.0 Hz, 1H), 7.76-7.63 (m, 2H), 7.33-7.27 (m, 2H) ppm; $^{19}$F-NMR (377 MHz, $CDCl_3$) δ −113.02.

Synthesis of 1-(4-fluorophenyl)-5-vinyl-1H-pyrazolo[3,4-c]pyridine

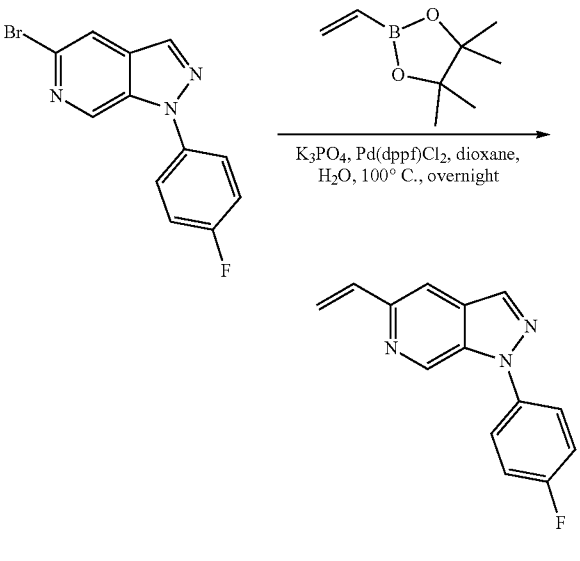

To a solution of 5-bromo-1-(4-fluorophenyl)-1H-pyrazolo[3,4-c]pyridine (2.24 g) in dioxane/water 5:1 (100 mL) were added 2-ethenyl-4,4,5,5-tetramethyl-1,3,2-dioxaborolane (1.95 mL), $K_3PO_4$ (4.07 g), and Pd(dppf)$Cl_2$ (0.56 g). The reaction was charged with $N_2$ (3×) and stirred at 100° C. overnight. The reaction was diluted with EA and water. The two phases were separated, and the aqueous phase was extracted with DCM (10 mL×3). The combined extracts were dried over $Na_2SO_4$, filtered, and concentrated to give a residue, which was purified using silica gel column chromatography eluting with 10% ethyl acetate in petroleum ether to afford 1-(4-fluorophenyl)-5-vinyl-1H-pyrazolo[3,4-c]pyridine (1.21 g). LC/MS ESI (m/z): 240 $(M+H)^+$; $^1$H-NMR: (400 MHz, $CDCl_3$) δ 9.17 (s, 1H), 8.26 (d, J=10.0 Hz, 1H), 7.76-7.65 (m, 3H), 7.32-7.27 (m, 2H), 7.03-6.88 (m, 1H), 6.31 (d, J=16.0 Hz, 1H), 5.50 (d, J=12.0 Hz, 1H) ppm.

Synthesis of 1-(4-fluorophenyl)-1H-pyrazolo[3,4-c]pyridine-5-carbaldehyde

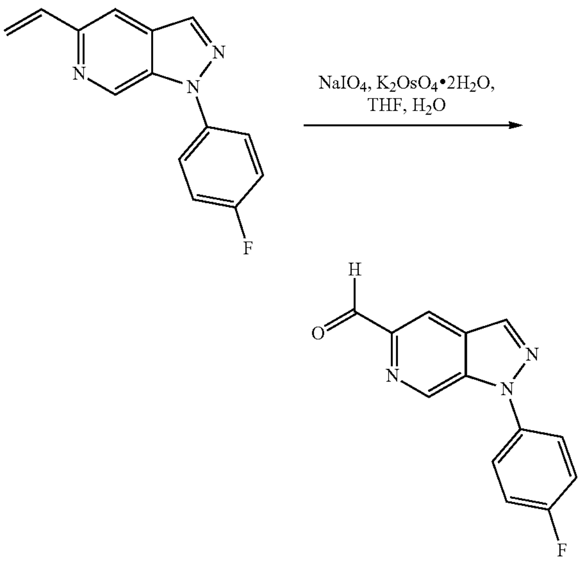

To a solution of 1-(4-fluorophenyl)-5-vinyl-1H-pyrazolo[3,4-c]pyridine (1.2 g) in THF (80 mL) and $H_2O$ (10 mL) were added sodium periodate (6.4 g) and potassium osmate dihydrate (0.18 g). The reaction was stirred at room temperature for 0.5 h and then diluted with EA and water. The two phases were separated, and the aqueous phase was extracted with DCM (10 mL×3). The combined organic layers were dried over $Na_2SO_4$, filtered, and concentrated to give a residue which was purified using silica gel column chromatography eluting with 14% ethyl acetate in petroleum ether to afford 1-(4-fluorophenyl)-1H-pyrazolo[3,4-c]pyridine-5-carbaldehyde (701 mg). LC/MS ESI (m/z): 242 $(M+H)^+$.

Synthesis of (R,E)-N-((1-(4-fluorophenyl)-1H-pyrazolo[3,4-c]pyridin-5-yl)methylene)-2-methylpropane-2-sulfinamide

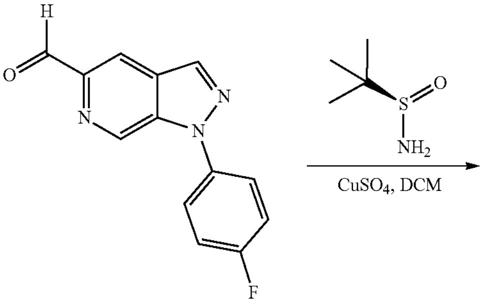

-continued

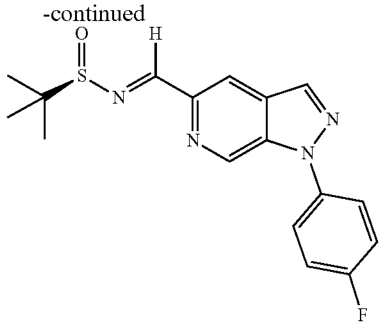

A mixture of 1-(4-fluorophenyl)-1H-pyrazolo[3,4-c]pyridine-5-carbaldehyde (700 mg), (R)-(+)-2-methyl-2-propanesulfinamide (457 mg) and $CuSO_4$ (1.4 g) in DCM (20 mL) were stirred at room temperature overnight. LC/MS showed that the reaction was complete. The reaction mixture was diluted with DCM and water. The two phases were separated, and the aqueous phase was extracted with DCM (10 mL×3). The combined organic layers were dried over $Na_2SO_4$, filtered, and concentrated to give a residue, which was purified by chromatography on silica gel (PE:EA=5:1) to provide (R,E)-N-((1-(4-fluorophenyl)-1H-pyrazolo[3,4-c]pyridin-5-yl)methylene)-2-methylpropane-2-sulfinamide (811 mg); LC/MS ESI (m/z): 345 $(M+H)^+$.

Step 5. Synthesis of (R)—N—((R)-1-(1-(4-fluorophenyl)-1H-pyrazolo[3,4-c]pyridin-5-yl)ethyl)-2-methylpropane-2-sulfinamide

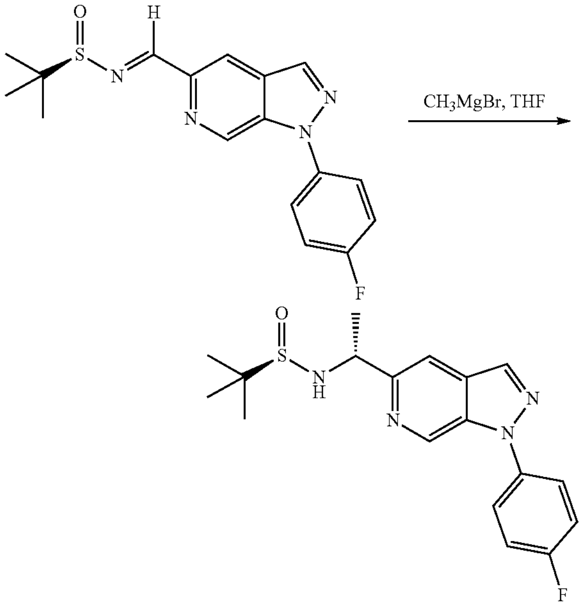

To a solution of (R,E)-N-((1-(4-fluorophenyl)-1H-pyrazolo[3,4-c]pyridin-5-yl)methylene)-2-methylpropane-2-sulfinamide (300 mg) in THE (10 mL) was added $CH_3MgBr$ (4.1 mL, 3.0 M in $Et_2O$). The reaction was stirred at −78° C. for 2 hr. The reaction was diluted with DCM and water. The two phases were separated, and the aqueous phase was extracted with DCM (10 mL×3). The combined organic layers were dried over $Na_2SO_4$, filtered, and concentrated to give a residue, which was purified by chromatography on silica gel (DCM:MeOH=15:1) afford (R)—N—((R)-1-(1-(4-fluorophenyl)-1H-pyrazolo[3,4-c]pyridin-5-yl)ethyl)-2-methylpropane-2-sulfinamide as a yellow solid (602 mg); LC/MS ESI (m/z): 361 $(M+H)^+$.

Step 6. Synthesis of (R)-1-(1-(4-fluorophenyl)-1H-pyrazolo[3,4-c]pyridin-5-yl)ethan-1-amine hydrochloride

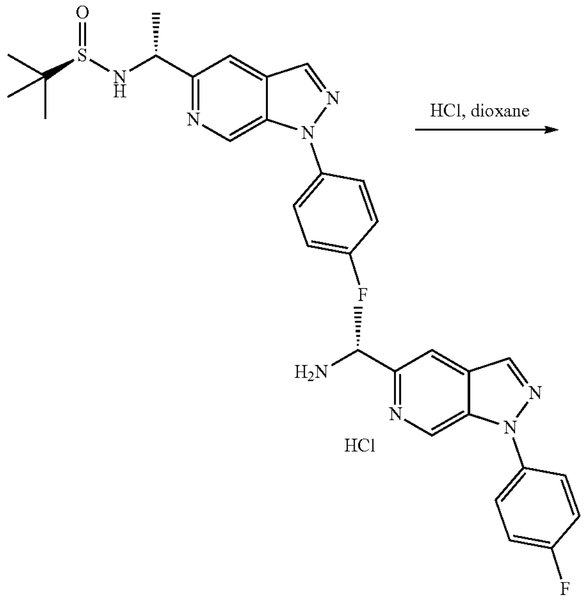

To a solution of (R)—N—((R)-1-(1-(4-fluorophenyl)-1H-pyrazolo[3,4-c]pyridin-5-yl)ethyl)-2-methylpropane-2-sulfinamide (602 mg,) in dioxane (10 mL) was added 4N HCl-Dioxane (5.0 mL), and the reaction was stirred at rt for 30 min. The reaction was evaporated in vacuo. The resulting solid was filtered, washed with EtOAc and then dried under vacuum to provide (R)-1-(1-(4-fluorophenyl)-1H-pyrazolo[3,4-c]pyridin-5-yl)ethan-1-amine hydrochloride as a white solid (545 mg, crude). LC/MS ESI (m/z): 257 $(M+H)^+$.

Step 7. Synthesis of (R)-2-(6-cyclopropylpyridin-3-yl)-N-(1-(1-(4-fluorophenyl)-1H-pyrazolo[3,4-c]pyridin-5-yl)ethyl)acetamide

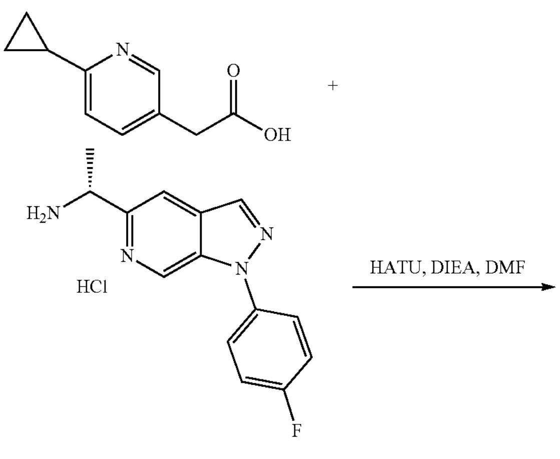

-continued

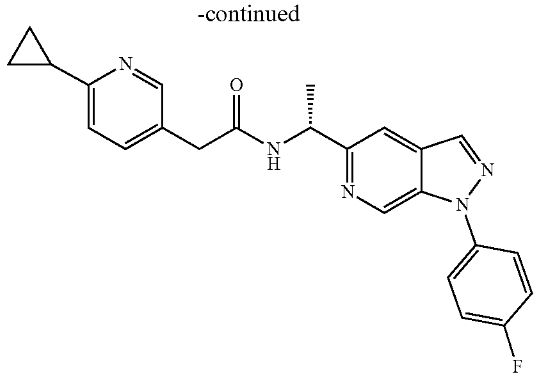

A mixture of 2-(6-cyclopropylpyridin-3-yl)acetic acid (250 mg, crude) and HATU (321.9 mg) in DMF (5.0 mL) was stirred at room temperature for 15 min. Then, (R)-1-(1-(4-fluorophenyl)-1H-pyrazolo[3,4-c]pyridin-5-yl)ethan-1-amine hydrochloride (205.4 mg, crude) and DIEA (0.56 mL) were added until the pH of the solution was higher than 7 by using pH paper. After stirring for 1 hour, LC/MS showed the reaction was complete. The reaction was diluted with EA and water, and the two phases were separated. The aqueous phase was extracted with DCM (10 mL×3). The combined organic layers were dried over $Na_2SO_4$, filtered and concentrated to give a residue. The residue was precipitated in $CH_3CN$ and washed by $CH_3CN$ to provide 149.8 mg of the product as white solid. LC/MS ESI (m/z): 416 $(M+H)^+$. $^1$H-NMR (400 MHz, $CDCl_3$) δ 9.07 (s, 1H), 8.34 (s, 1H), 8.20 (s, 1H), 7.74-7.67 (m, 2H), 7.58-7.50 (m, 2H), 7.33-7.26 (m, 2H), 7.10 (d, J=8.0 Hz, 1H), 6.74 (d, J=7.0 Hz, 1H), 5.35-5.17 (m, 1H), 3.53 (s, 2H), 2.11-2.02 (m, 1H), 1.49 (d, J=6.8 Hz, 3H), 1.04-0.97 (m, 4H). $^{19}$F-NMR (377 MHz, $CDCl_3$) δ −113.66.

Example 24. (R)-2-(4-cyclopropylphenyl)-N-(1-(3-(2,2,2-trifluoroethyl)-3H-[1,2,3]triazolo[4,5-c]pyridin-6-yl)ethyl)acetamide

Synthesis of 2-chloro-5-fluoropyridine 1-oxide

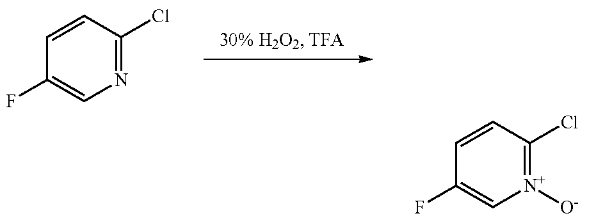

To a solution of 2-chloro-5-fluoropyridine (19.28 mL) in 30% $H_2O_2$ (96 mL) was added TFA (175 mL), and the reaction was stirred at 70° C. overnight. The reaction was concentrated in vacuo and diluted with toluene. Then the reaction solution was concentrated in vacuo again and diluted with DCM and water. The two phases were separated, and the aqueous phase was extracted with DCM (10 mL×3). The combined organic layers were dried over $Na_2SO_4$, filtered, concentrated to give 2-chloro-5-fluoropyridine 1-oxide (26.2 g) as a crude product. LC/MS ESI (m/z): 148 [M+H]. $^1$H NMR (400 MHz, $CDCl_3$) δ 8.35-8.28 (m, 1H), 7.52-7.43 (m, 1H), 7.11-7.01 (m, 1H) ppm.

Synthesis of 2-chloro-5-fluoro-4-nitropyridine 1-oxide

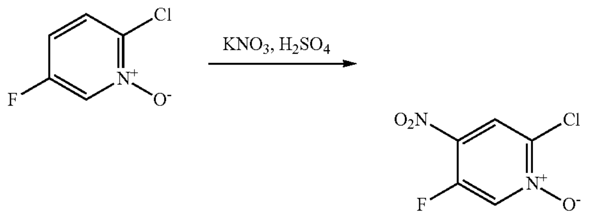

To a solution of 2-chloro-5-fluoropyridine 1-oxide (10 g) in $H_2SO_4$ (102 mL) were slowly added $KNO_3$ (27.4 g) at rt. The reaction was stirred at 110° C. under nitrogen for 16 hr. The reaction was poured into ice at 0° C. and neutralized by addition of 30% ammonium hydroxide dropwise while maintaining the temperature below 15° C. with an ice bath. The pale yellow crystals precipitated was collected by filtration. The precipitate was then purified by flash chromatography on silica gel to give 2-chloro-5-fluoro-4-nitropyridine 1-oxide (1.6 g). LC/MS ESI (m/z): 193 $[M+H]^+$. $^1$H NMR (400 MHz, $CDCl_3$) δ 8.41 (d, J=5.7 Hz, 1H), 8.31 (d, J=8.4 Hz, 1H).

Synthesis of 2-chloro-4-nitro-5-((2,2,2-trifluoroethyl)amino)pyridine 1-oxide

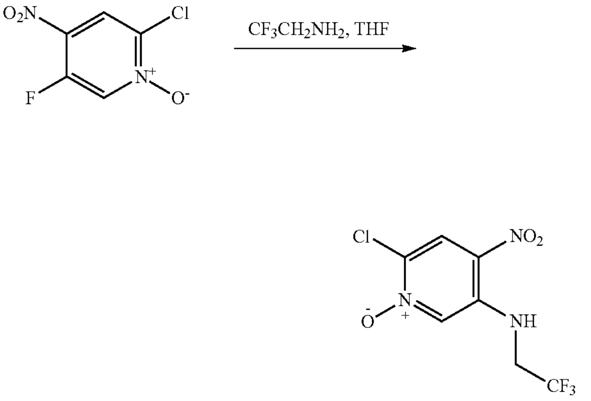

To a solution of 2-chloro-5-fluoro-4-nitropyridine 1-oxide (1.89 g) in THF (24 mL) was added 2,2,2-trifluoroethan-1-amine (1.568 mL), and the reaction was stirred at rt overnight. The reaction was then diluted with DCM and water. The two phases were separated, and the aqueous phase was extracted with DCM (10 mL×3). The combined organic layers were dried over $Na_2SO_4$, filtered, and concentrated to give a residue, which was further concentrated under high vacuum to give 2-chloro-4-nitro-5-((2,2,2-trifluoroethyl)amino)pyridine 1-oxide (2.1 g). LC/MS ESI (m/z): 272 $[M+H]^+$. $^1$H NMR (400 MHz, $CDCl_3$): δ 8.33 (s, 1H), 8.16 (s, 1H), 7.98 (brs, 1H), 3.98-3.87 (m, 2H).

Synthesis of 6-chloro-$N^3$-(2,2,2-trifluoroethyl)pyridine-3,4-diamine

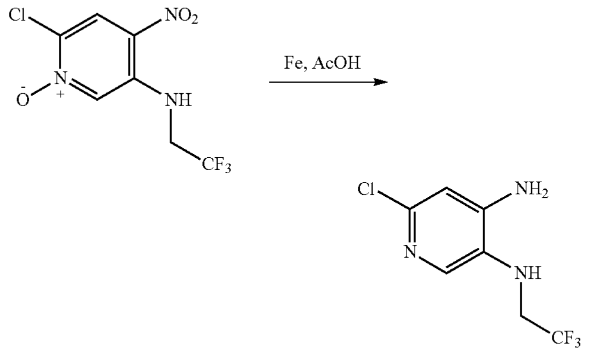

To a solution of 2-chloro-4-nitro-5-((2,2,2-trifluoroethyl)amino)pyridine 1-oxide (2.0 g) in glacial acetic acid (21 mL) was slowly added Fe (0.209 mL) at 0° C. The reaction was stirred at rt for 1 hr and the reaction diluted with EA and water. The two phases were separated, and the aqueous phase was extracted with DCM (10 mL×3). The combined organic layers were dried over $Na_2SO_4$, filtered, and concentrated to give a residue, which was concentrated in vacuo to give 6-chloro-$N^3$-(2,2,2-trifluoroethyl)pyridine-3,4-diamine (2.28 g, crude). LC/MS ESI (m/z): 226 $[M+H]^+$.

Synthesis of 6-chloro-3-(2,2,2-trifluoroethyl)-3H-[1,2,3]triazolo[4,5-c]pyridine

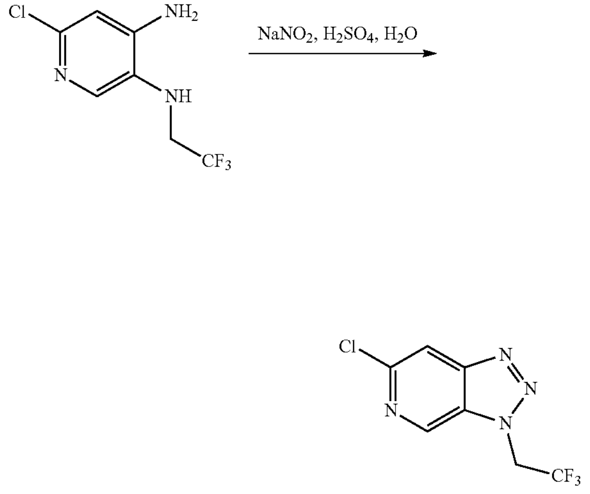

To a solution of 6-chloro-$N^3$-(2,2,2-trifluoroethyl)pyridine-3,4-diamine (2.67 g) and $H_2SO_4$ (1.8 mL) in 30 mL of water was slowly added $NaNO_2$ (1.63 g) in water (17 mL) under nitrogen at 0° C. The reaction mixture was stirred at 0° C. for 4 h, and then the reaction was neutralized to pH 8 with saturated $NaHCO_3$. The resulting solid was collected and purified by silica gel column to afford 6-chloro-3-(2,2,2-trifluoroethyl)-3H-[1,2,3]triazolo[4,5-c]pyridine (872 mg). LC/MS ESI (m/z): 237 $[M+H]^+$. $^1H$ NMR (400 MHz, $CDCl_3$) δ 8.96 (s, 1H), 8.06 (s, 1H), 5.38-5.32 (m, 2H). $^{19}F$ NMR (377 MHz, CDCl3) δ −70.30 (s).

Synthesis of 3-(2,2,2-trifluoroethyl)-6-vinyl-3H-[1,2,3]triazolo[4,5-c]pyridine

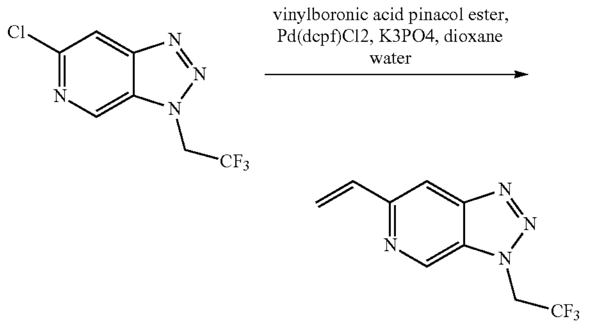

To a solution of 6-chloro-3-(2,2,2-trifluoroethyl)-3H-[1,2,3]triazolo[4,5-c]pyridine (872 mg) in dioxane-water (25 mL) were added vinylboronic acid pinacol ester (149.55 mg), $K_3PO_4$ (1.9 g) and $Pd(dcpf)Cl_2$ (276.38 mg). The reaction was charged with $N_2$ and stirred at 100° C. under nitrogen overnight. The reaction was diluted with EA and water and filtered through Celite. The two phases were separated, and the aqueous phase was extracted with DCM (10 mL×3). The combined organic layers were dried over $Na_2SO_4$, filtered, and concentrated to give a residue, which was purified by silica gel column chromatography to give 3-(2,2,2-trifluoroethyl)-6-vinyl-3H-[1,2,3]triazolo[4,5-c]pyridine (807 mg). LC/MS ESI (m/z): 229 $[M+H]^+$; $^1H$ NMR (400 MHz, $CDCl_3$) δ 9.12 (s, 1H), 7.93 (d, J=0.9 Hz, 1H), 7.01-6.94 (m, 1H), 6.38-6.33 (m, 1H), 5.57-5.54 (m, 1H), 5.38-5.32 (m, 2H).

Synthesis of 3-(2,2,2-trifluoroethyl)-3H-[1,2,3]triazolo[4,5-c]pyridine-6-carbaldehyde

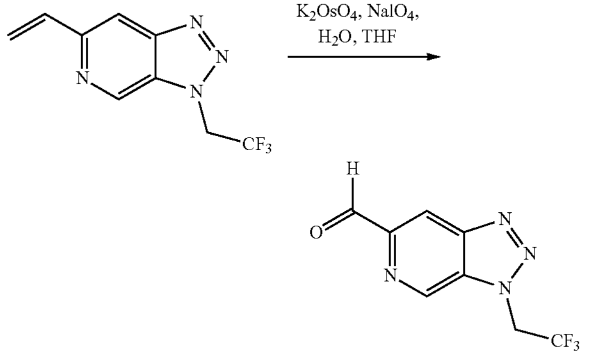

To a solution of 3-(2,2,2-trifluoroethyl)-6-vinyl-3H-[1,2,3]triazolo[4,5-c]pyridine (802 mg) in THE-Water (8:1, 30 mL) were added $NaIO_4$ (4.5 g) and potassium osmate (1.3 g), and the reaction was stirred at rt for 1 hr. The reaction was filtered through Celite and diluted with DCM and water. The two phases were separated, and the aqueous phase was extracted with DCM (10 mL×3). The combined organic layers were dried over $Na_2SO_4$, filtered, and concentrated to give a residue, which was purified by silica gel column chromatography to give 3-(2,2,2-trifluoroethyl)-3H-[1,2,3]triazolo[4,5-c]pyridine-6-carbaldehyde (584 mg). LC/MS ESI (m/z): 231 $[M+H]^+$; $^1H$ NMR (400 MHz, $CDCl_3$) δ 10.29 (s, 1H), 9.29 (s, 1H), 8.72 (s, 1H), 5.46-5.40 (m, 2H).

Synthesis of (R,E)-2-methyl-N-((3-(2,2,2-trifluoroethyl)-3H-[1,2,3]triazolo[4,5-c]pyridin-6-yl)methylene)propane-2-sulfinamide

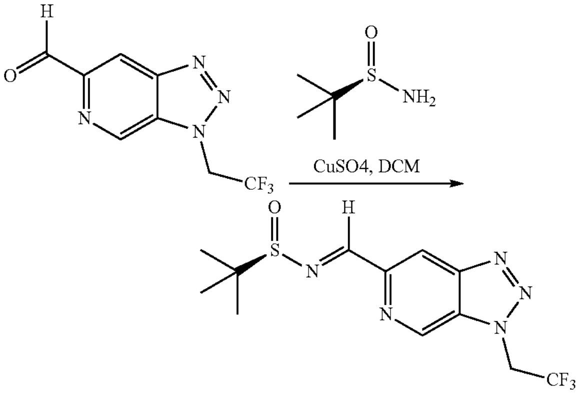

To a solution of 3-(2,2,2-trifluoroethyl)-3H-[1,2,3]triazolo[4,5-c]pyridine-6-carbaldehyde (584 mg) in anhydrous DCM (15 mL) were added $CuSO_4$ (1.2 g) and (R)-2-methylpropane-2-sulfinamide (399.8 mg). The reaction was stirred at rt overnight. The solution was filtered through a pad of Celite, and the filtrate was concentrated. The residue was purified by silica gel column to give (R,E)-2-methyl-N-((3-(2,2,2-trifluoroethyl)-3H-[1,2,3]triazolo[4,5-c]pyridin-6-yl)methylene)propane-2-sulfinamide (840 mg). LC/MS ESI (m/z): 334 $[M+H]^+$; $^1H$ NMR (400 MHz, $CDCl_3$) δ 9.26 (s, 1H), 8.90 (s, 1H), 8.74 (d, J=0.8 Hz, 1H), 5.45-5.36 (m, 2H), 1.32 (s, 9H).

Synthesis of (R)-2-methyl-N—((R)-1-(3-(2,2,2-trifluoroethyl)-3H-[1,2,3]triazolo[4,5-c]pyridin-6-yl)ethyl)propane-2-sulfinamide

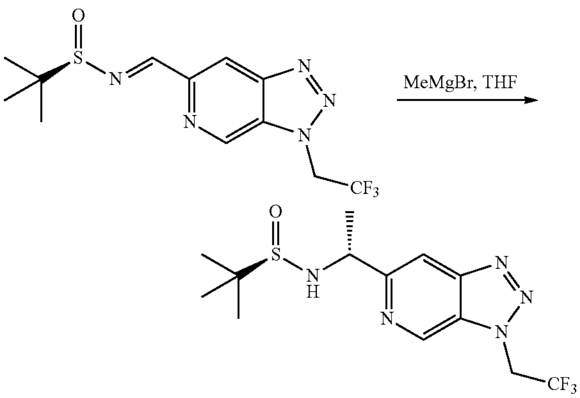

To a solution of (R,E)-2-methyl-N-((3-(2,2,2-trifluoroethyl)-3H-[1,2,3]triazolo[4,5-c]pyridin-6-yl)methylene)propane-2-sulfinamide in anhydrous THE (26 mL) was added MeMgBr (4.20 mL, 3.0M in ether) dropwise at −78° C. under nitrogen. The reaction was stirred at −78° C. for 2 hr. The reaction solution was then quenched with aqueous $NH_4Cl$ and extracted with EA. The combined extracts were separated, washed with brine, and concentrated in vacuo. Then the residue was purified by silica gel column chromatography to give (R)-2-methyl-N—((R)-1-(3-(2,2,2-trifluoroethyl)-3H-[1,2,3]triazolo[4,5-c]pyridin-6-yl)ethyl)propane-2-sulfinamide (690 mg). LC/MS ESI (m/z): 350 $[M+H]^+$; $^1H$ NMR (400 MHz, $CDCl_3$) δ 9.12 (s, 1H), 7.98 (d, J=0.7 Hz, 1H), 5.43-5.31 (m, 2H), 4.80-4.72 (m, 1H), 4.51 (d, J=6.7 Hz, 1H), 1.61 (d, J=6.7 Hz, 3H), 1.25 (s, 9H).

Synthesis of (R)-1-(3-(2,2,2-trifluoroethyl)-3H-[1,2,3]triazolo[4,5-c]pyridin-6-yl)ethan-1-amine hydrochloride

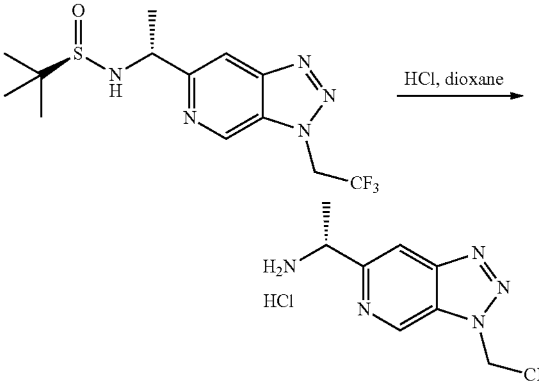

To a solution of (R)-2-methyl-N—((R)-1-(3-(2,2,2-trifluoroethyl)-3H-[1,2,3]triazolo[4,5-c]pyridin-6-yl)ethyl)propane-2-sulfinamide (680 mg) in dioxane (6.0 mL) was added 4N HCl-dioxane (2.0 mL), and the reaction was stirred at rt for 1 hr. Then the mixture was concentrated in vacuo and directly used in the next step. LC/MS ESI (m/z): 246 $[M+H]^+$.

Synthesis of (R)-2-(4-cyclopropylphenyl)-N-(1-(3-(2,2,2-trifluoroethyl)-3H-[1,2,3]triazolo[4,5-c]pyridin-6-yl)ethyl)acetamide (N201201-361)

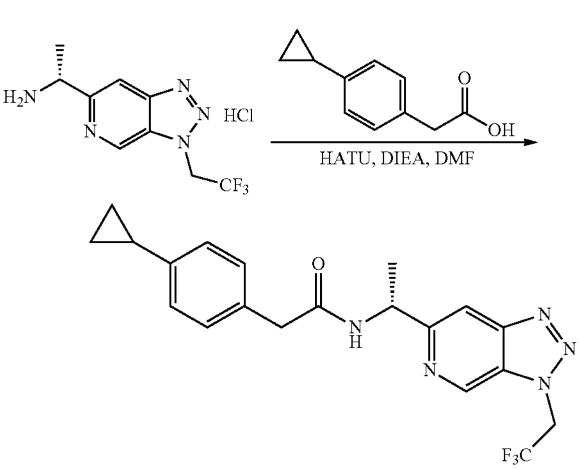

To a solution of (R)-1-[3-(2,2,2-trifluoroethyl)-3H-[1,2,3]triazolo[4,5-c]pyridin-6-yl]ethan-1-amine hydrochloride (150 mg) in anhydrous DMF was added DIEA (0.607 mL)

to provide Solution A. To a solution of 2-(4-cyclopropylphenyl)acetic acid (129.3 mg) in DMF (1 mL) was added HATU (255.85 mg) and stirred 15 min at RT to provide Solution B. Solution B was added to the solution A, and the mixture was stirred at rt for 1 h. The reaction was diluted with EA and water. The two phases were separated, and the aqueous phase was extracted with DCM (10 mL×3). The combined organic layers dried over $Na_2SO_4$, filtered, and concentrated to give a residue, which was purified by prep-HPLC [Column: YMC-Actus Triart C18 250*21 mm; Mobile phase: from 20% to 95% MeCN with $H_2O$ (1% $NH_3H_2O$); flow rate: 15 mL/min; wavelength: 220 nm/254 nm] and SFC (Column: ChiralPak IA, 250×21.3 mm I.D., 5 μm; Mobile phase: A for $CO_2$ and B for MEOH+0.1% $NH_3$H2O; Gradient: B 35%; Wavelength: 220 nm) to give (R)-2-(4-cyclopropylphenyl)-N-(1-(3-(2,2,2-trifluoroethyl)-3H-[1,2,3]triazolo[4,5-c]pyridin-6-yl)ethyl)acetamide (89.3 mg). LC/MS ESI (m/z): 404 $[M+H]^+$; $^1H$ NMR (400 MHz, $CDCl_3$): δ 9.06 (s, 1H), 7.90 (s, 1H), 7.16 (d, J=8.1 Hz, 2H), 7.05 (d, J=8.1 Hz, 2H), 6.48 (d, J=7.6 Hz, 1H), 5.37-5.31 (m, 3H), 3.56 (s, 2H), 1.92-1.86 (m, 1H), 1.48 (d, J=6.9 Hz, 3H), 0.98-0.96 (m, 2H), 0.70-0.68 (m, 2H) ppm; 19F NMR (377 MHz, $CDCl_3$) δ −70.30 (s).

Example 25. (R)-2-(6-cyclopropylpyridin-3-yl)-N-(1-(1-(2,2,2-trifluoroethyl)-1H-pyrazolo[3,4-c]pyridin-5-yl)ethyl)acetamide

Synthesis of ethyl 2-(6-cyclopropylpyridin-3-yl)acetate

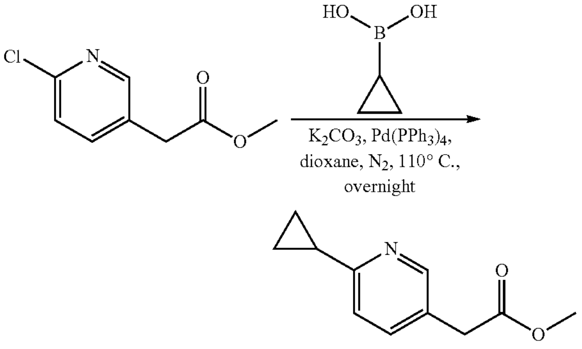

To a solution of ethyl 2-(6-chloropyridin-3-yl)acetate (1.5 g), cyclopropylboronic acid (1.94 g) and potassium carbonate (1.04 g) in dioxane (40 mL) was added $Pd(PPh_3)_4$ (0.87 g) and the mixture was charged with $N_2$ for three times and stirred at 110° C. overnight. After cooling to room temperature, the reaction was diluted with EA (30 mL) and water (40 mL), and the two layers were separated. The aqueous layer was then extracted with EA (30 mL). The combined organic layers were washed with water and brine (40 mL each), dried over $Na_2SO_4$, filtered, and concentrated. The crude product was purified by silica gel chromatography (5-18% EA/PE) to give ethyl 2-(6-cyclopropylpyridin-3-yl)acetate (1.21 g) as a colorless oil. LC/MS ESI (m/z): 192 $(M+H)^+$. $^1H$ NMR (400 MHz, $CDCl_3$) δ 8.33 (d, J=4.0 Hz, 1H), 7.51-7.48 (m, 1H), 7.09 (d, J=8.0 Hz, 1H), 3.70 (s, 3H), 3.57 (s, 2H), 2.06-2.01 (m, 1H), 1.05-0.92 (m, 4H).

Synthesis of 2-(6-cyclopropylpyridin-3-yl)acetic acid

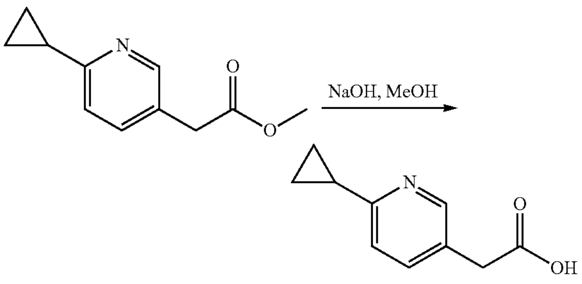

To a 250 mL round-bottomed flask was added methyl 2-(6-cyclopropylpyridin-3-yl)acetate (1.2 g) and 50 mL of MeOH. Aqueous NaOH (1N, 50 mL) was added to the mixture resulting in a colorless solution. The reaction mixture was stirred at room temperature for 1 hour, and the aqueous layer was extracted with EA. The aqueous layer was acidified to pH<3 with 1N aqueous HCl. The aqueous phase was then extracted with EA. The EtOAc extract from the acidified aqueous phase was washed with saturated NaCl solution, filtered, and concentrated to provide 2-(6-cyclopropylpyridin-3-yl)acetic acid as a white solid (2.31 g, crude).

Synthesis of (R)-2-(6-cyclopropylpyridin-3-yl)-N-(1-(1-(2,2,2-trifluoroethyl)-1H-pyrazolo[3,4-c]pyridin-5-yl)ethyl)acetamide

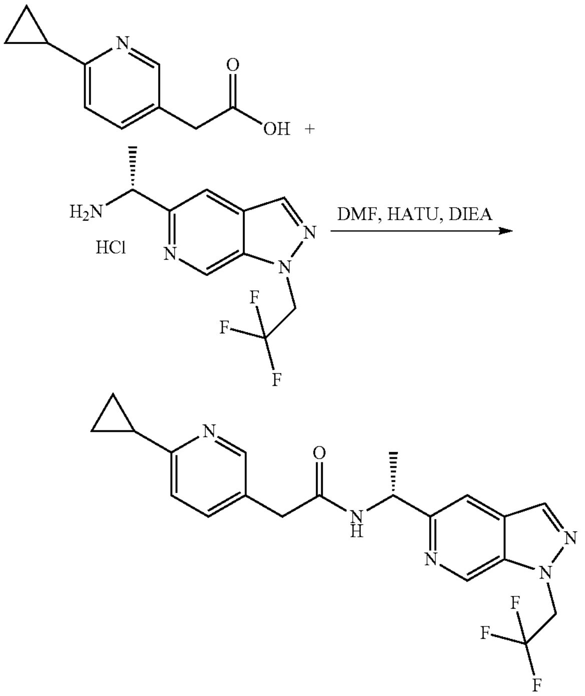

A solution of 2-(6-cyclopropylpyridin-3-yl)acetic acid (250 mg, crude) and HATU (321.9 mg) in DMF (5.0 mL) was stirred at room temperature for 15 min. Then (R)-1-(1-

(2,2,2-trifluoroethyl)-1H-pyrazolo[3,4-c]pyridin-5-yl) ethan-1-amine hydrochloride (179.2 mg) and DIEA (0.56 mL) were added. The mixture was stirred for 1 hour, and LC/MS showed the reaction was complete. The reaction was diluted with EA and water. The two phases were separated, the aqueous phase was extracted with DCM (10 mL×2). The combined organic layers were dried over $Na_2SO_4$, filtered, and concentrated in vacuo to provide a residue, which was purified by prep-HPLC [Column: YMC-Actus Triart C18 250*20 mm; Mobile phase: from 10% to 95% MeCN with H2O (1% $NH_3 \cdot H_2O$); flow rate: 15 mL/min; wavelength: 220 nm/254 nm] to afford (R)-2-(6-cyclopropylpyridin-3-yl)-N-(1-(1-(2,2,2-trifluoroethyl)-1H-pyrazolo[3,4-c]pyridin-5-yl)ethyl)acetamide (141.8 mg) as a white solid. LC/MS ESI (m/z): 404 $(M+H)^+$; $^1$H-NMR (400 MHz, $CDCl_3$): δ 8.86 (s, 1H), 8.38 (s, 1H), 8.08 (s, 1H), 7.64 (s, 1H), 7.54 (d, J=4.0 Hz, 1H), 7.10 (d, J=8.0 Hz, 1H), 6.84 (s, 1H), 5.32-5.20 (m, 1H), 5.14-4.95 (m, 2H), 3.65-3.47 (m, 2H), 2.17 (s, 1H), 1.49 (d, J=8.0 Hz, 3H), 1.11-1.01 (m, 4H); $^{19}$F-NMR (377 MHz, $CDCl_3$) δ −70.78.

Example 26. (R)—N-(1-(1-(2,2,2-trifluoroethyl)-1H-pyrazolo[3,4-c]pyridin-5-yl)ethyl)-2-(6-(1-(trifluoromethyl)cyclopropyl)pyridin-3-yl)acetamide

Synthesis of methyl 6-(3,3,3-trifluoroprop-1-en-2-yl)nicotinate

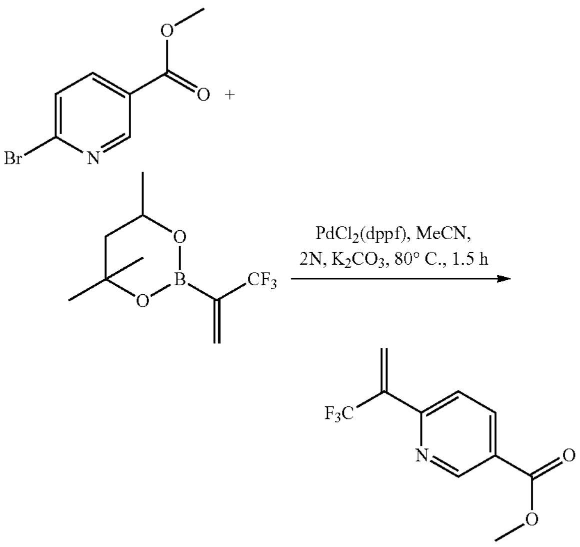

A mixture of methyl 6-bromonicotinate (5.47 g), 4,4,6-trimethyl-2-(3,3,3-trifluoroprop-1-en-2-yl)-1,3,2-dioxaborinane (7.87 g), $PdCl_2$(dppf) (1.85 g), $K_2CO_3$ (26.8 mL of 2 M in water) in acetonitrile (104 mL) was charged three times with $N_2$ and heated at 80° C. for 90 minutes. LC/MS showed formation of the desired product. The reaction mixture was cooled to room temperature and partitioned between water and ethyl acetate. The two phases were separated, and the aqueous phase was extracted with DCM (10 mL×3). The combined organic layers were dried over $Na_2SO_4$, filtered, and concentrated to give a residue, which was purified by Silica gel column chromatography (0-20% ethyl acetate/PE) to provide methyl 6-(3,3,3-trifluoroprop-1-en-2-yl)nicotinate as a colorless oil (3.6 g). LC/MS ESI (m/z): 232 $[M+H]^+$; $^1$HNMR (400 MHz, $CDCl_3$): δ 9.22 (d, J=2.4 Hz, 1H), 8.75-8.74 (m, 1H), 8.34-8.31 (m, 1H), 8.25 (d, J=1.2 Hz, 1H), 7.58 (d, J=11.6 Hz, 1H), 3.97 (s, 3H); $^{19}$FNMR (376.48 MHz, $CDCl_3$): −63.98 ppm.

Synthesis of methyl 6-(1-(trifluoromethyl)cyclopropyl)nicotinate

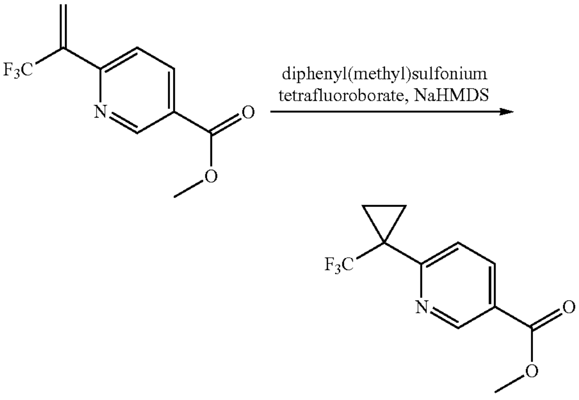

To a suspension of methyl 6-(3,3,3-trifluoroprop-1-en-2-yl)nicotinate (2.47 g) and methyldiphenylsulfonium tetrafluoroborate (4.0 g) in anhydrous tetrahydrofuran (30 mL) was added sodium bis(trimethylsilyl)amide (2 M in THF) at 0° C. under nitrogen. The reaction mixture was stirred at 0° C. for 10 min and then at room temperature for 1 h. Methanol (250 μL) of was added to quench the reaction. The crude mixture was concentrated in vacuo to get a residue, which was purified by silica gel column chromatography (10% EA in PE) to provide methyl 6-(1-(trifluoromethyl) cyclopropyl)nicotinate as a white solid (1.3 mg). LC/MS ESI (m/z): 246$[M+H]^+$; $^1$HNMR (400 MHz, $CDCl_3$): δ 9.09 (d, J=2.4 Hz, 1H), 8.26-8.23 (m, 1H), 7.64 (d, J=8.4 Hz, 1H), 3.95 (s, 3H), 1.54-1.53 (m, 2H), 1.50-1.49 (m, 2H) ppm; $^{19}$FNMR (376.48 MHz, $CDCl_3$): δ −67 ppm.

Synthesis of 6-(1-(trifluoromethyl)cyclopropyl)nicotinic acid

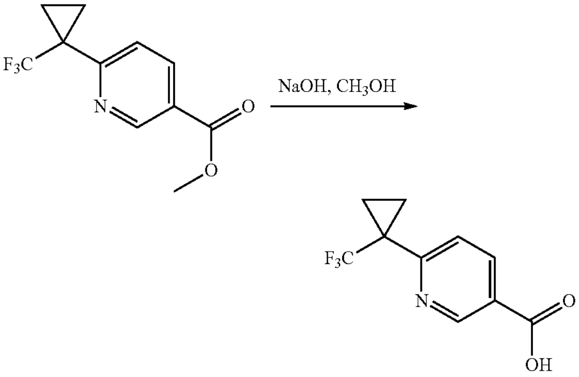

To a solution of methyl 6-(1-(trifluoromethyl)cyclopropyl)nicotinate (345 mg) in MeOH (20 mL) was added 4.0 mL of NaOH (2.0 M). The mixture was stirred at 65° C. for 2 hours, and TLC indicated the reaction was complete. The solvent was concentrated in vacuo and the reaction mixture was adjusted pH to 2-3 with 1 N HCl. The reaction was extracted with EA (50 mL), washed with brine, dried with anhydrous $Na_2SO_4$, filtered, and concentrated to give 6-(1-(trifluoromethyl)cyclopropyl)nicotinic acid as a white solid (300 mg). LC/MS ESI (m/z): 232 $[M+H]^+$.

Synthesis of 2-diazo-1-(6-(1-(trifluoromethyl)cyclopropyl)pyridin-3-yl)ethanone

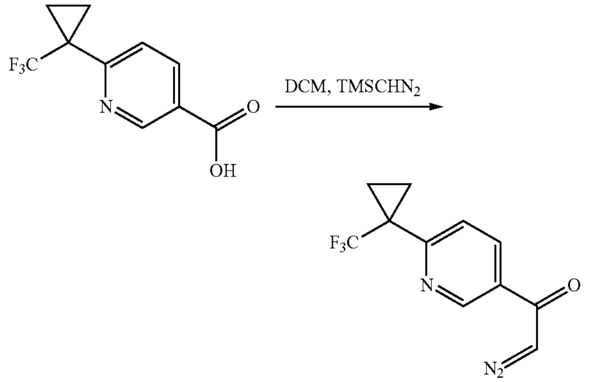

6-(1-(trifluoromethyl)cyclopropyl)nicotinic acid (300 mg) in DCM (10 mL) was cooled to 0° C. Oxaly chloride (1.1 mL) and DMF (2 drops) were added and the resulting solution was stirred at rt for 2 hours. The volatiles were then removed under vacuum. The residue was redissolved in DCM (10 mL) and cooled to 0° C. $TMSCHN_2$ (1.28 mL, 2 M solution in hexane) and TEA (0.33 mL) were added slowly, and the resulting solution was maintained at 5° C. for 12 hours. The reaction was then filtered, and the filtrate was concentrated under reduced pressure to give 2-diazo-1-(6-(1-(trifluoromethyl)cyclopropyl)pyridin-3-yl)ethenone as brown residue, which was directly used in the next step. LC/MS ESI (m/z): 256 $[M+H]^+$.

Step 5. Synthesis of methyl 2-(6-(1-(trifluoromethyl)cyclopropyl)pyridin-3-yl)acetate

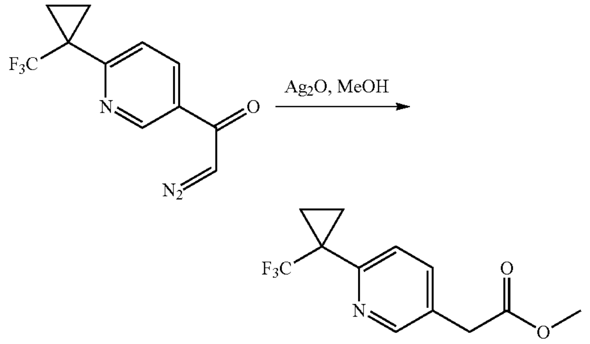

To a mixture of 2-diazo-1-(6-(1-(trifluoromethyl)cyclopropyl)pyridin-3-yl)ethanone (600 mg, crude) in methanol (20 mL) was added $Ag_2O$ (175 mg). The reaction was stirred at 65° C. for 2 hours. TLC showed trace product had formed, and an additional 142 mg of $Ag_2O$ was added. The mixture was stirred at 65° C. for another 2 hours. The reaction was concentrated under vacuo and the residue was purified by silica gel column chromatography (10% EA-20% EA in PE) to give methyl 2-(6-(1-(trifluoromethyl)cyclopropyl)pyridin-3-yl)acetate as yellow oil (100 mg). LC/MS ESI (m/z): 260 $[M+H]^+$.

Step 6. Synthesis of 2-(6-(1-(trifluoromethyl)cyclopropyl)pyridin-3-yl)acetic acid

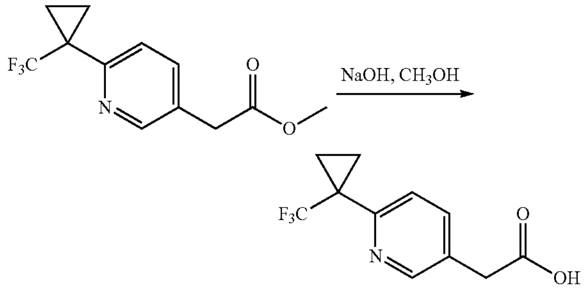

To a solution of methyl 2-(6-(1-(trifluoromethyl)cyclopropyl)pyridin-3-yl)acetate (100 mg) in MeOH (10 mL) was added 2.0 mL of NaOH (2.0 M). The mixture was stirred at 65° C. for 2 hours. After completion, the reaction was removed under reduced pressure and the reaction was adjusted pH to 2-3 by 1 N HCl. The reaction mixture was extracted with EA (50 mL×3). The combined extracts were washed with brine, dried with anhydrous $Na_2SO_4$, filtered and concentrated to give 2-(6-(1-(trifluoromethyl)cyclopropyl)pyridin-3-yl)acetic acid as white solid (70 mg). LC/MS ESI (m/z): 246 $[M+H]^+$. $^1$HNMR (400 MHz, $CDCl_3$): δ 8.43 (d, J=1.6 Hz, 1H), 7.78-7.75 (m, 1H), 7.59-7.56 (m, 1H), 3.69 (s, 2H), 1.43-1.40 (m, 2H), 1.32-1.29 (m, 2H) ppm. $^{19}$FNMR (CDCl3, −376.48): 6-69.78 ppm.

Step 7. Synthesis of (R)—N-(1-(1-(2,2,2-trifluoroethyl)-1H-pyrazolo[3,4-c]pyridin-5-yl)ethyl)-2-(6-(1-(trifluoromethyl)cyclopropyl)pyridin-3-yl)acetamide

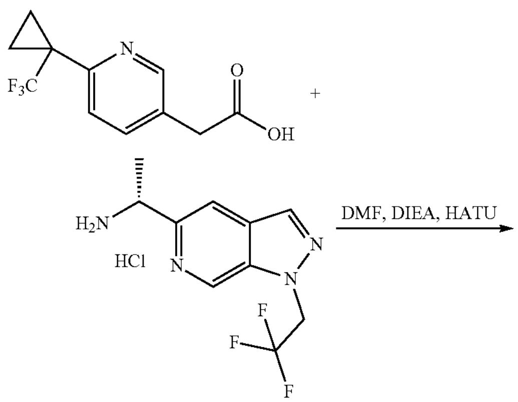

-continued

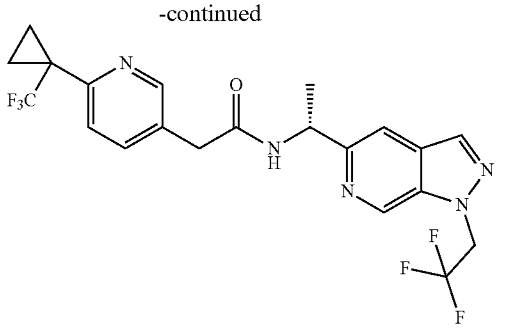

To a mixture of 2-(6-(1-(trifluoromethyl)cyclopropyl) pyridin-3-yl)acetic acid (125.0 mg) in DMF (1.0 mL) was added HATU (213 mg), and the mixture was stirred at rt for 5 min to provide Solution A. To another round flask containing (R)-1-(1-(2,2,2-trifluoroethyl)-1H-pyrazolo[3,4-c] pyridin-5-yl)ethanamine hydrochloride (186 mg) was added DMF (1.0 mL) and DIEA (197 mg), and the mixture was stirred for 1 min (Solution B). Solution B was added to Solution A, and the reaction mixture was stirred at rt for 2 hours. EA (50 mL) and water (40 mL) were added, and the organic layer was washed with water and brine, dried over $Na_2SO_4$, filtered and concentrated. The residue was purified by prep-HPLC [Column: YMC-Actus Triart C18 250*21 mm; Mobile phase: from 10% to 85% MeCN with $H_2O$ (0.1% FA); flow rate: 15 mL/min; wavelength: 220 nm/254 nm] to give a white solid (106.9 mg). LC/MS ESI (m/z): 472 $(M+H)^+$; $^1H$ NMR (400 MHz, $CDCl_3$): δ 8.90 (s, 1H), 8.43 (d, J=2.0 Hz, 1H), 8.11 (s, 1H), 7.64-7.62 (m, 1H), 7.58 (s, 1H), 7.52-7.49 (m, 1H), 6.84 (d, J=7.6 Hz, 1H), 5.30-5.23 (m, 1H), 5.08-5.02 (m, 2H), 3.56 (s, 2H), 1.51 (d, J=6.4 Hz, 3H), 1.41-1.37 (m, 4H); $^{19}F$NMR (377 MHz, $CDCl_3$): δ −67.70, −70.79.

Example 27. (R)-2-(4-cyclopropylphenyl)-N-(1-(1-(4-fluorophenyl)-1H-Pyrazolo[3,4-c]pyridin-5-yl) ethyl)acetamide Synthesis of ethyl 2-(4-cyclopropylphenyl)acetate

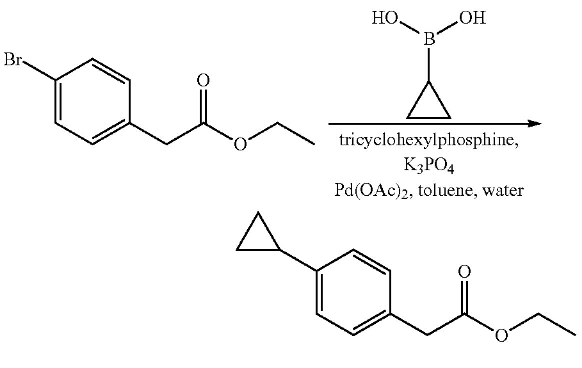

To a solution of ethyl 4-bromophenylacetate (2.0 g), cyclopropylboronic acid (0.92 g), tricyclohexylphosphine (0.23 g) and $K_3PO_4$ (6.11 g) in toluene/water (40 mL, 20:1) was added palladium (II) acetate (0.09 g). The reaction mixture was charged with $N_2$ and stirred at 100° C. overnight. After cooling to room temperature, the reaction was diluted with EA and water and the two layers were separated. The aqueous layer was extracted with EA (20 mL). The combined organic layers were washed with water and brine (40 mL each), dried over $Na_2SO_4$, filtered, and concentrated. The residue was purified by silica gel chromatography (5-18% EA/PE) to give ethyl 2-(4-cyclopropylphenyl) acetate (1.368 g) as a pale-yellow oil. 1H NMR (400 MHz, $CDCl_3$) δ 7.16 (d, J=8.0 Hz, 1H), 7.02 (d, J=8.0 Hz, 1H), 4.15 (q, J=8.0 Hz, 2H), 3.56 (s, 2H), 1.90-1.84 (m, 1H), 1.24 (t, J=8.0 Hz, 3H), 0.95-0.92 (m, 2H), 0.7-0.63 (m, 2H).

Step 2. Synthesis of 2-(4-cyclopropylphenyl)acetic acid

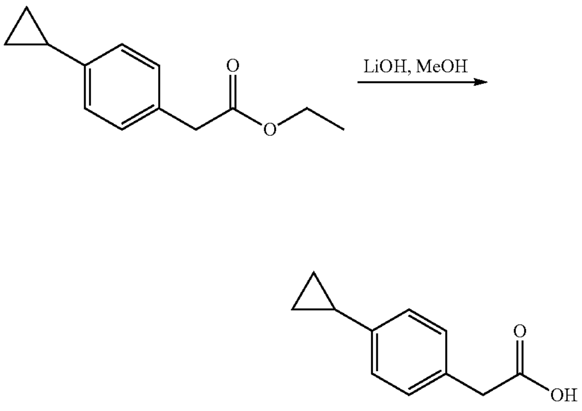

To a solution of ethyl 2-(4-cyclopropylphenyl)acetate (1.24 g) in THF (20.0 mL) and MeOH (8.0 mL) was added 2.5 M aqueous LiOH (12 mL), and the resulting solution was stirred at room temperature for 2 hours. After completion, the mixture was acidified with aqueous 1N HCl, and the aqueous phase was extracted with DCM. The combined organic layers were dried over $NaSO_4$, filtered, and concentrated to provide 2-(4-cyclopropylphenyl)acetic acid (1.04 g) as a yellow solid, which used for next step.

Step 3. Synthesis of (R)-2-(4-cyclopropylphenyl)-N-(1-(1-(4-fluorophenyl)-1H-pyrazolo[3,4-c]pyridin-5-yl)ethyl)acetamide

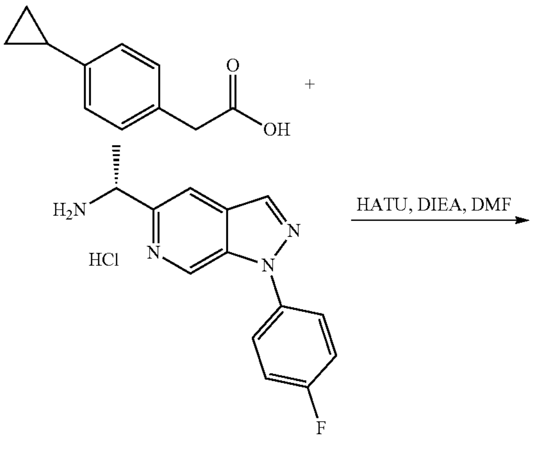

-continued

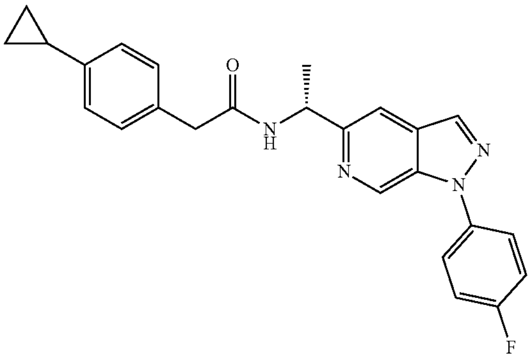

A solution of 2-(4-cyclopropylphenyl)acetic acid (100 mg) and HATU (323.7 mg) in DMF (5.0 mL) was stirred at room temperature for 15 min. Then (R)-1-(1-(4-fluorophenyl)-1H-pyrazolo[3,4-c]pyridin-5-yl)ethan-1-amine hydrochloride (206.6 mg) and DIEA (0.56 mL) was added. The reaction was stirred at rt for 1 hour, and LC/MS showed the reaction was complete. The reaction was diluted with EA and water. The two phases were then separated. The aqueous phase was extracted with EA (10 mL×3). The combined organic layers were dried over $Na_2SO_4$, filtered, and concentrated in vacuo. The residue was purified by prep-HPLC [Column: YMC-Actus Triart C18 250*20 mm; Mobile phase: from 20% to 80% MeCN with $H_2O$ (0.1% FA); flow rate: 15 mL/min; wavelength: 220 nm/254 nm] to afford the compound (R)-2-(4-cyclopropylphenyl)-N-(1-(1-(4-fluorophenyl)-1H-pyrazolo[3,4-c]pyridin-5-yl)ethyl)acetamide (140 mg) as a white solid. LC/MS ESI (m/z): 415 $(M+H)^+$; $^1$H-NMR (400 MHz, $CDCl_3$) δ 9.06 (s, 1H), 8.20 (s, 1H), 7.76-7.65 (m, 2H), 7.60 (s, 1H), 7.32-7.26 (m, 2H), 7.15 (d, J=8.1 Hz, 2H), 7.07-7.01 (m, 2H), 6.61 (s, 1H), 5.29-5.24 (m, 1H), 3.64-3.44 (m, 2H), 1.93-1.82 (m, 1H), 1.48 (d, J=6.8 Hz, 3H), 1.02-0.88 (m, 2H), 0.75-0.61 (m, 2H). $^{19}$F-NMR (377 MHz, $CDCl_3$) δ −113.57.

Example 28. (R)-2-(4-cyclopropylphenyl)-N-(1-(1-(2,2,2-trifluoroethyl)-1H-pyrazolo[3,4-c]pyridin-5-yl)ethyl)acetamide Synthesis of (R)-2-(4-cyclopropylphenyl)-N-(1-(1-(2,2,2-trifluoroethyl)-1H-pyrazolo[3,4-c]pyridin-5-yl)ethyl)acetamide

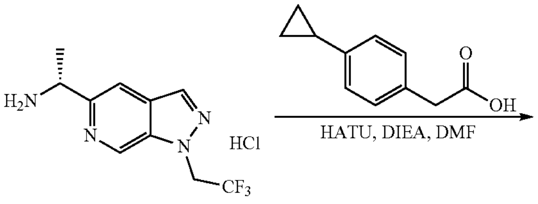

-continued

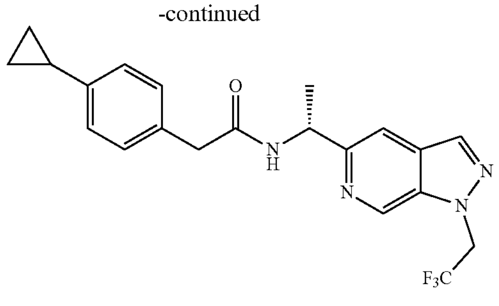

To a solution of (R)-1-(1-(2,2,2-trifluoroethyl)-1H-pyrazolo[3,4-c]pyridin-5-yl)ethan-1-amine hydrochloride (151 mg) in anhydrous DMF (1 mL) was added DIEA (0.61 mL, 3.71 mmol) to get Solution A. To a solution of 2-(4-cyclopropylphenyl)acetic acid (130.8 mg) in DMF were added HATU (258.6 mg) and stirred 5 min at RT to get Solution B. Solution B was added to the solution A and stirred at RT for 1 h. The reaction was diluted with EA and water, the two phases were separated, and the aqueous phase was extracted with DCM (10 mL×3). The combined organic layers were dried over $Na_2SO_4$, filtered and concentrated to give a residue, which was purified by prep-HPLC [Column: YMC-Actus Triart C18 250*20 mm; Mobile phase: from 20% to 95% MeCN with $H_2O$ (0.1% FA); flow rate: 15 mL/min; wavelength: 220 nm/254 nm] and SFC (Column: ChiralPak IA, 250×21.3 mm I.D., 5 μm; Mobile phase: A for $CO_2$ and B for MEOH+0.1% $NH_3$H2O; Gradient: B 40%; Wavelength:220 nm) to give (R)-2-(4-cyclopropylphenyl)-N-(1-(1-(2,2,2-trifluoroethyl)-1H-pyrazolo[3,4-c]pyridin-5-yl)ethyl)acetamide as a white solid (97 mg). LC/MS ESI (m/z): 403 $[M+H]^+$; $^1$H NMR (400 MHz, $CDCl_3$) δ 8.86 (s, 1H), 8.08 (s, 1H), 7.53 (s, 1H), 7.16-7.03 (m, 4H), 6.53 (d, J=7.6 Hz, 1H), 5.30-5.23 (m, 1H), 5.06-5.00 (m, 2H), 3.54-3.53 (m, 2H), 1.93-1.86 (m, 1H), 1.45 (d, J=6.8 Hz, 3H), 1.03-0.90 (m, 2H), 0.69-0.68 (m, 2H); $^{19}$F NMR (377 MHz, $CDCl_3$) δ −70.81 (s).

Example 29. (R)-2-(4-(1-fluorocyclopropyl)phenyl)-N-(1-(1-(2,2,2-trifluoroethyl)-1H-pyrazolo[3,4-c]pyridin-5-yl)ethyl)acetamide Synthesis of 1-(2-bromo-1-fluoroethyl)-4-methylbenzene

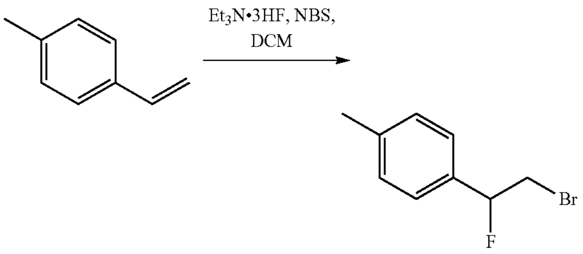

To an ice cooled solution of 1-ethenyl-4-methylbenzene (9.45 g,) in DCM (80.0 mL) were added triethylamine trihydrofluoride (40 mL) and N-bromosuccinimide (17.0 g). After stirring 30 min at 0° C., the reaction mixture was warmed to room temperature and stirred overnight. The reaction mixture was poured into ice water (500 mL) and neutralized with aqueous NH40H. The two phases were separated, and the aqueous phase was extracted with DCM (600 mL). The combined organic layers were washed with 0.1 M HCl (600 mL), 5% $NaHCO_3$ and water (200 mL), and dried over $Na_2SO_4$. The organic layer was then filtered and concentrated in vacuo. The residue was purified by silica gel column (5% EA in PE) to give 1-(2-bromo-1-fluoroethyl)-4-methylbenzene (13.69 g) as colorless oil. $^1H$ NMR (400 MHz, $CDCl_3$) δ 7.26 (d, J=8.0, 2H), 7.16 (d, J=8.0 Hz, 2H), 5.66-5.63 (m, 1H), 5.54-5.51 (m, 1H), 3.70-3.61 (m, 3H), 2.35-2.32 (m, 1H); $^{19}F$ NMR (377 MHz, $CDCl_3$) δ −172.35 (s).

Synthesis of 1-(1-fluorovinyl)-4-methylbenzene

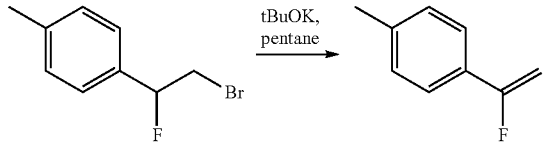

1-(2-bromo-1-fluoroethyl)-4-methylbenzene (2.0 g) was dissolved in pentane (60 ml), and tBuOK (2.09 g) was added slowly at 0° C. The reaction mixture was stirred under reflux for 1 h. After cooling to room temperature, the mixture was poured into ice water (50 ml). After separation of the phases, the aqueous phase was extracted with pentane (300 ml). The combined organic layers were washed with 5% $NaHCO_3$ (50 ml), 0.05 M HCl (25 ml), and water (50 ml). The organic phase was dried ($NaSO_4$) and filtered. The filtrate was concentrated in vacuo to get a residue, which was purified by silica gel column (5% EA in PE) to give 1-(1-fluorovinyl)-4-methylbenzene (711 mg) as a colorless liquid. $^1H$-NMR: (400 MHz, DMSO-d6) δ 7.51 (d, J=8.0 Hz, 2H), 7.26 (d, J=8.0 Hz, 2H), 5.36-5.22 (m, 1H), 4.90-4.85 (m, 1H), 2.33 (s, 3H); $^{19}F$-NMR (377 MHz, DMSO) δ −107.97.

Synthesis of 1-(2,2-dichloro-1-fluorocyclopropyl)-4-methylbenzene

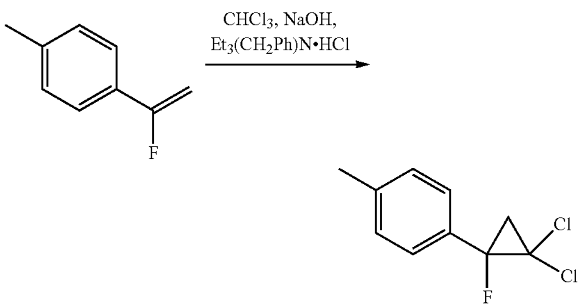

A mixture of 1-(1-fluorovinyl)-4-methylbenzene (500 mg), $CHCl_3$ (10 mL), NaOH (40%, 10 mL) and benzyltriethylammonium chloride (30 mg) was stirred at rt overnight. The mixture was poured into $H_2O$ (50 mL) and then extracted with $CHCl_3$ (3×20 mL). The $CHCl_3$ layer was washed with $H_2O$ (3×20 mL), dried ($MgSO_4$) and filtered. The filtrate was concentrated under reduced pressure to provide crude 1-(2,2-dichloro-1-fluorocyclopropyl)-4-methylbenzene (500 mg) as colorless liquid, which was used directly in the next reaction. $^1H$-NMR: (400 MHz, DMSO-d6) δ 7.40 (t, J=12.7 Hz, 2H), 7.28 (d, J=8.0 Hz, 2H), 2.86-2.63 (m, 1H), 2.39-2.35 (m, 1H), 2.33 (s, 3H).

Synthesis of 1-(1-fluorocyclopropyl)-4-methylbenzene

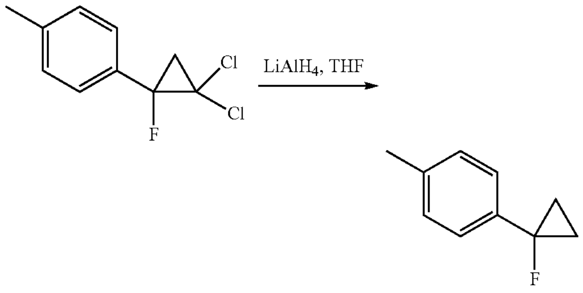

To a mixture of 1-(2,2-dichloro-1-fluorocyclopropyl)-4-methylbenzene (500 mg) in THF (10 mL) was added lithium aluminium tetrahydride (436 mg) at 0° C., and the resulting mixture was stirred at rt overnight. The mixture was poured into $H_2O$ (50 mL) and then extracted with EA (3×20 mL). The combined EA layers were washed with $H_2O$ (3×20 mL), dried ($MgSO_4$) and filtered. The filtrate was concentrated under reduced pressure to provide crude 1-(1-fluorocyclopropyl)-4-methylbenzene (250 mg) as colorless liquid, which was used directly in the next step. $^1H$-NMR: (400 MHz, DMSO-d6) δ 7.25-7.04 (m, 4H), 2.38-2.25 (m, 3H), 1.51-1.33 (m, 2H), 1.10-1.01 (m, 2H).

Step 5. Synthesis of 1-(bromomethyl)-4-(1-fluorocyclopropyl)benzene

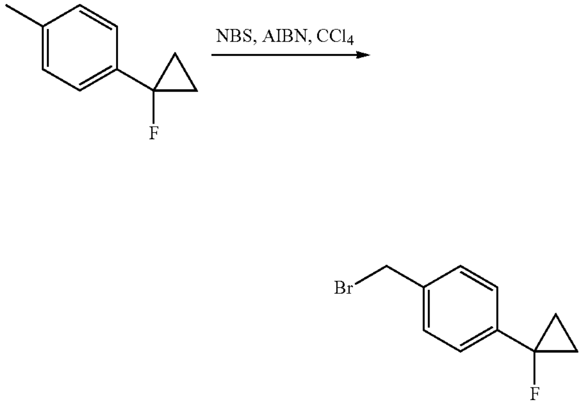

To a solution of 1-(1-fluorocyclopropyl)-4-methylbenzene (200 mg) in $CCl_4$ (4 mL) were added AIBN (0.02 mL) and NBS (355.5 mg). The reaction was stirred at 80° C. for 16 hr. The reaction was the diluted with DCM and water. The organic layer was separated and concentrated in vacuo to give an oil, which was purified by column chromatography to give 1-(bromomethyl)-4-(1-fluorocyclopropyl)benzene (170 mg) as colorless oil. $^1H$ NMR (400 MHz, $CD_3OD$) δ 7.40 (d, J=8.2 Hz, 2H), 7.23 (d, J=8.2 Hz, 2H), 4.55 (s, 2H), 1.52-1.37 (m, 2H), 1.14-1.04 (m, 2H).

Step 6. Synthesis of 2-(4-(1-fluorocyclopropyl)phenyl)acetonitrile

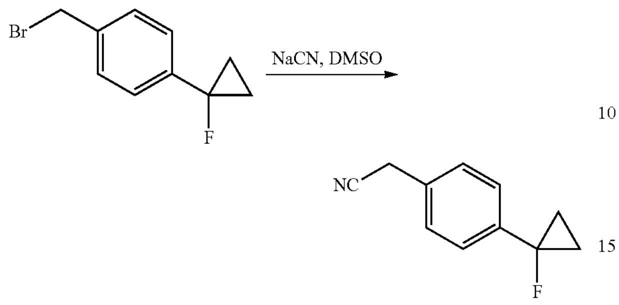

To a solution of 1-(bromomethyl)-4-(1-fluorocyclopropyl)benzene (100.0 mg, crude) in DMSO (5.0 mL) was added NaCN (107.0 mg), and the reaction mixture was stirred at 40° C. overnight. The reaction mixture was then poured into water (10 mL) and extracted with EA (20 mL). The organic layer was separated, dried ($NaSO_4$), filtered and concentrated in vacuo to get a residue, which was purified by silica gel column (5% EA in PE) to afford 2-(4-(1-fluorocyclopropyl)phenyl)acetonitrile (30 mg) as colorless oil. $^1H$ NMR (400 MHz, $CDCl_3$) δ 7.30 (dd, J=22.6, 8.2 Hz, 4H), 3.75 (s, 2H), 1.55-1.43 (m, 2H), 1.11-1.00 (m, 2H).

Step 7. Synthesis of 2-(4-(1-fluorocyclopropyl)phenyl)acetic acid

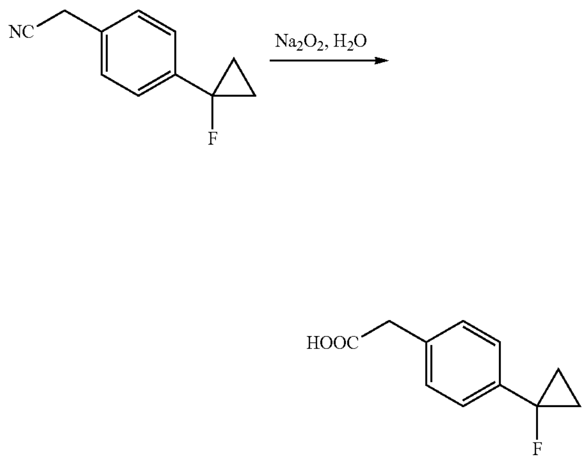

To a solution of 2-[4-(1-fluorocyclopropyl)phenyl]acetonitrile (30 mg) in $H_2O$ (3 mL) was added sodium peroxide (40 mg). The mixture was stirred at 50° C. for 24 hr. Then the mixture was stirred at 60° C. for 24 hr. The pH of the mixture was adjusted to 4 with 1N HCl solution and extracted with EtOAc. The combined organic layers were dried, filtered and concentrated to give 2-[4-(1-fluorocyclopropyl)phenyl]acetic acid (30 mg) as a white solid. LC/MS ESI (m/z): 193 [M−H]; $^1H$ NMR (400 MHz, $CDCl_3$) δ 7.29 (d, J=8.2 Hz, 2H), 7.24 (d, J=8.2 Hz, 2H), 3.66 (s, 1H), 1.53-1.48 (m, 1H), 1.48-1.42 (m, 2H), 1.10-1.01 (m, 2H).

Step 8. Synthesis of (R)-2-(4-(1-fluorocyclopropyl)phenyl)-N-(1-(1-(2,2,2-trifluoroethyl)-1H-pyrazolo[3,4-c]pyridin-5-yl)ethyl)acetamide

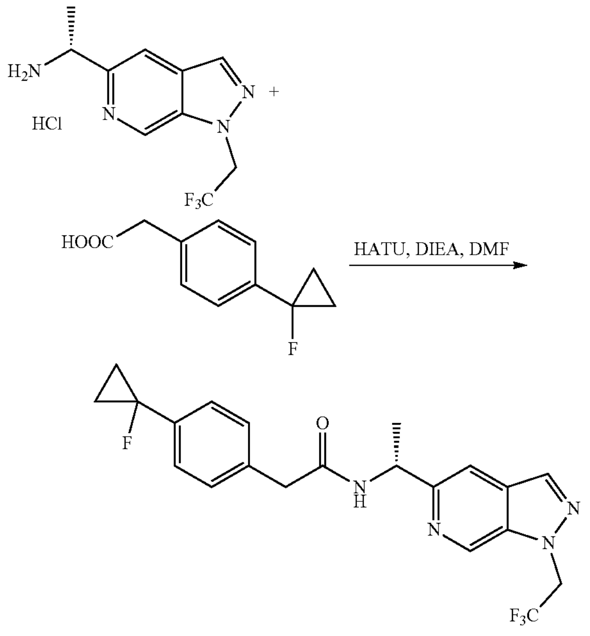

A solution of 2-[4-(1-fluorocyclopropyl)phenyl]acetic acid (30 mg), (R)-1-[1-(2,2,2-trifluoroethyl)-1H-pyrazolo[3,4-c]pyridin-5-yl]ethan-1-amine hydrochloride (49.0 mg), HATU (64.6 mg) and DIEA (0.077 mL) in DMF (5 mL) was stirred at 25° C. for 12 hr. The mixture was diluted with water and extracted with DCM. The combined organic extracts were dried, filtered, and concentrated to give a residue. The residue was purified by prep-HPLC (Column: YMC-Actus Triart C18 250*21 mm; Mobile phase: from 25% to 95% MeCN with $H_2O$ (0.1% FA); flow rate: 15 mL/min; wavelength: 220 nm/254 nm) to give (R)-2-(4-(1-fluorocyclopropyl)phenyl)-N-(1-(1-(2,2,2-trifluoroethyl)-1H-pyrazolo[3,4-c]pyridin-5-yl)ethyl)acetamide (26.9 mg) as a white solid. LCMS ESI (m/z): 421 $(M+H)^+$; $^1H$ NMR (400 MHz, $CDCl_3$) δ 8.90 (s, 1H), 8.12 (s, 1H), 7.59 (s, 1H), 7.31-7.27 (m, 2H), 7.24 (d, J=8.4 Hz, 2H), 6.71 (s, 1H), 5.35-5.20 (m, 1H), 5.18-4.93 (m, 2H), 3.59 (s, 2H), 1.52-1.46 (m, 5H), 1.10-1.02 (m, 2H). $^{19}F$ NMR (377 MHz, $CDCl_3$) δ −70.78, −179.26.

Example 30. 2-(4-(2,2-difluorocyclopropyl)phenyl)-N—((R)-1-(1-(2,2,2-trifluoroethyl)-1H-pyrazolo[3,4-c]pyridin-5-yl)ethyl)acetamide diastereomer A Step 1. 1-bromo-4-(2,2-difluorocyclopropyl)benzene

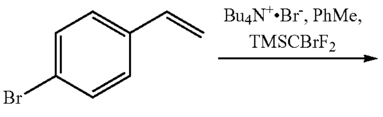

-continued

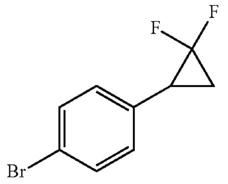

A solution of 1-bromo-4-ethenylbenzene (2.50 mL), trimethyl(bromodifluoromethyl)silane (4.46 mL) and tetrabutylammonium bromide (0.178 mL) in toluene (50 mL) was stirred at 110° C. for 12 hr. The mixture was concentrated to a residue, and the residue was purified by chromatography on silica gel (PE:EA=1:0 to 50:1) to give racemic 1-bromo-4-(2,2-difluorocyclopropyl)benzene (4.2 g) as colorless oil. $^1$H NMR (400 MHz, $CDCl_3$) δ 7.50-7.43 (d, J=8.5 Hz, 2H), 7.10 (d, J=8.5 Hz, 2H), 2.78-2.61 (m, 1H), 1.92-1.74 (m, 1H), 1.66-1.56 (m, 1H).

Step 2. ethyl 2-(4-(2,2-difluorocyclopropyl)phenyl)acetate

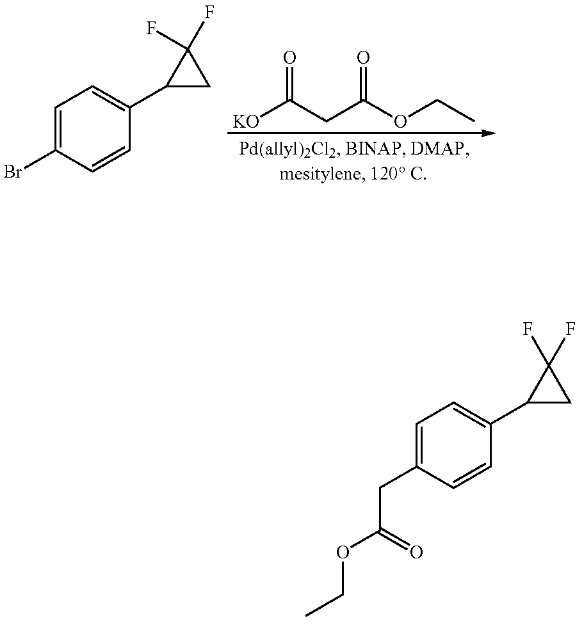

A solution of 1-bromo-4-(2,2-difluorocyclopropyl)benzene (4 g), 1-ethyl 3-potassium propanedioate (4.38 g), allylpalladium chloride dimer (0.13 g), BINAP (0.64 g) and DMAP (2.10 g) in mesitylene (10 mL) was charged with $N_2$. The mixture was stirred at 140° C. for 1 hr and then at 120° C. for 12 hr. The mixture was concentrated to give a residue, and the residue was purified by chromatography on silica gel (PE:EtOAc=1:0 to 50:1) to give ethyl 2-[4-(2,2-difluorocyclopropyl)phenyl]acetate as a white solid (1.54 g) as a white solid. LCMS ESI (m/z): 241 $(M+H)^+$.

Step 3. 2-(4-(2,2-difluorocyclopropyl)phenyl)acetic acid

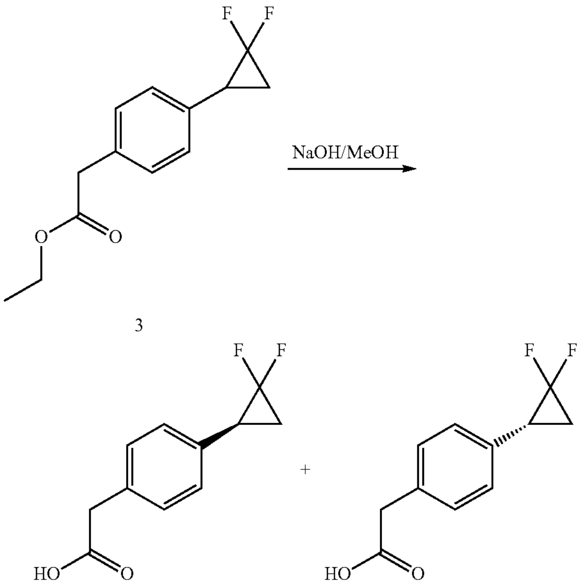

3 or enantiomer P1 or enantiomer P2

To a solution of racemic ethyl 2-[4-(2,2-difluorocyclopropyl)phenyl]acetate (1.3 g) in MeOH (4.0 mL) was added NaOH (1 M in $H_2O$, 30 mL), and the mixture was stirred at 25° C. for 12 hr. The reaction mixture was then concentrated, diluted with $H_2O$ and washed with EtOAc. The aqueous phase was adjusted pH=3 with 1N HCl and extracted with EtOAc. The combined organic extracts were dried, filtered and concentrated to give racemic 2-(4-(2,2-difluorocyclopropyl)phenyl)acetic acid as a white solid. [LC/MS ESI (m/z): 211 $[M-H]^-$; $^1$H NMR (400 MHz, $CDCl_3$) δ 7.27-7.23 (d, J=8.4 Hz, 2H), 7.20 (d, J=8.4 Hz, 2H), 3.64 (s, 2H), 2.81-2.64 (m, 1H), 1.90-1.71 (m, 1H), 1.65-1.60 (m, 1H). Racemic 2-(4-(2,2-difluorocyclopropyl)phenyl)acetic was resolved by chiral prep-SFC (Column: ChiralPak AD, 250×21.2 mm I.D., 5 μm; Mobile phase: A for $CO_2$ and B for MeOH; Gradient: B 15%; wavelength: 220 nm) to give 2-[4-(2,2-difluorocyclopropyl)phenyl]acetic acid enantiomer P1 (200 mg) and 2-[4-(2,2-difluorocyclopropyl)phenyl]acetic acid enantiomer P2 (240 mg) as white solids.

Step 4A. 2-(4-((R or S)-2,2-difluorocyclopropyl)phenyl)-N—((R)-1-(1-(2,2,2-trifluoroethyl)-1H-pyrazolo[3,4-c]pyridin-5-yl)ethyl)acetamide

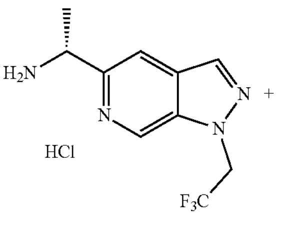

-continued

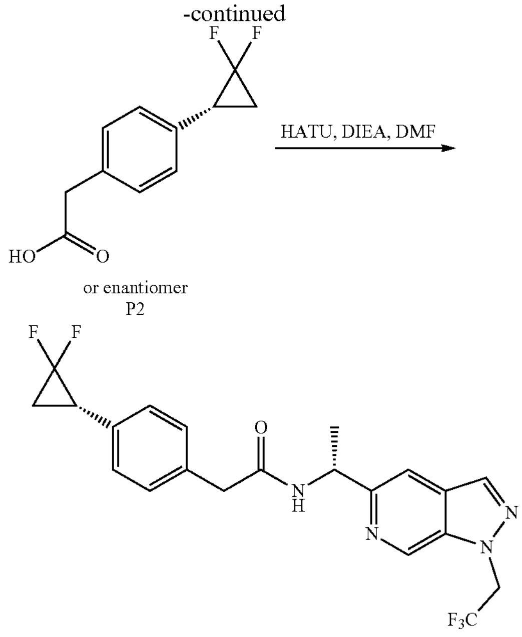

or enantiomer
P2 or diasteriomer

A solution of 2-[4-(2,2-difluorocyclopropyl)phenyl]acetic acid enantiomer P2 (120 mg), (R)-1-[1-(2,2,2-trifluoroethyl)-1H-pyrazolo[3,4-c]pyridin-5-yl]ethan-1-amine hydrochloride (165.7 mg), HATU (236.5 mg) and DIEA (0.28 mL) in DMF (5 mL) was stirred at 25° C. for 12 hr. The mixture was diluted with water and extracted with DCM. The combined organic extracts were dried, filtered and concentrated to give a residue. The residue was purified by prep-HPLC (Column: GEMINI C18 250*21.2 mm 5 um; Mobile phase: from 25% to 95% MeCN with $H_2O$ (0.1% FA); flow rate: 15 mL/min; wavelength: 220 nm/254 nm) to give 2-(4-((R or S)-2,2-difluorocyclopropyl)phenyl)-N—((R)-1-(1-(2,2,2-trifluoroethyl)-1H-pyrazolo[3,4-c]pyridin-5-yl)ethyl)acetamide (79.6 mg) as a white solid. LCMS ESI (m/z): 439 $(M+H)^+$; $^1H$ NMR (400 MHz, $CDCl_3$) δ 8.88 (s, 1H), 8.12 (s, 1H), 7.59 (s, 1H), 7.25 (d, J=8.4 Hz, 2H), 7.19 (d, J=8.4 Hz, 2H), 6.70 (d, J=7.2 Hz, 1H), 5.33-5.16 (m, 1H), 5.15-4.93 (m, 2H), 3.58 (s, 2H), 2.88-2.60 (m, 1H), 1.92-1.75 (m, 1H), 1.70-1.58 (m, 1H), 1.50 (d, J=6.8 Hz, 3H). $^{19}F$ NMR (377 MHz, $CDCl_3$) δ −70.79, −125.90, −142.41.

Example 31. 2-(4-(2,2-difluorocyclopropyl)phenyl)-N—((R)-1-(1-(2,2,2-trifluoroethyl)-1H-pyrazolo[3,4-c]pyridin-5-yl)ethyl)acetamide diastereomer B

Step 4B. 2-(4-((R or S)-2,2-difluorocyclopropyl)phenyl)-N—((R)-1-(1-(2,2,2-trifluoroethyl)-1H-pyrazolo[3,4-c]pyridin-5-yl)ethyl)acetamide

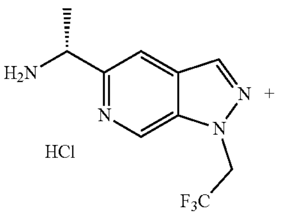

-continued

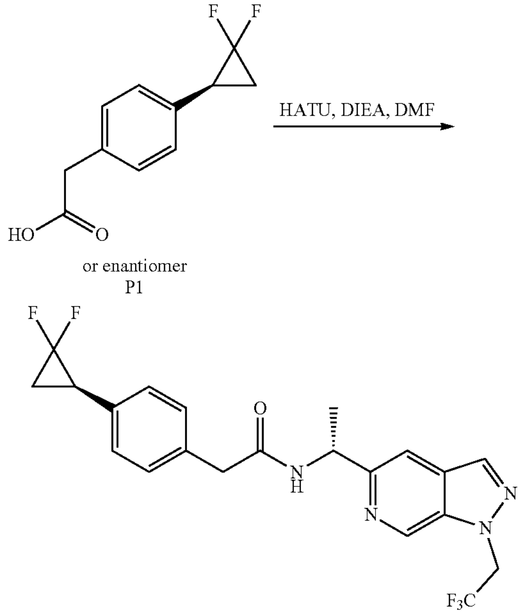

or enantiomer
P1 or diasteriomer

A solution of 2-[4-(2,2-difluorocyclopropyl)phenyl]acetic acid enantiomer P1 (100 mg), (R)-1-[1-(2,2,2-trifluoroethyl)-1H-pyrazolo[3,4-c]pyridin-5-yl]ethan-1-amine hydrochloride (138.1 mg), HATU (197.1 mg) and DIEA (0.23 mL) in DMF (5 mL) was stirred at 25° C. for 12 hr. The mixture was diluted with water and extracted with DCM. The combined organic extracts were dried, filtered and concentrated to give a residue, which was purified by prep-HPLC (Column: YMC-Actus Triart C18 250*21 mm; Mobile phase: from 55% to 95% MeCN with $H_2O$ (0.1% FA); flow rate: 20 mL/min; wavelength: 220 nm/254 nm) to give 2-(4-((R or S)-2,2-difluorocyclopropyl)phenyl)-N—((R)-1-(1-(2,2,2-trifluoroethyl)-1H-pyrazolo[3,4-c]pyridin-5-yl)ethyl)acetamide (50.7 mg, white solid). LCMS ESI (m/z): 439 $(M+H)^+$; $^1H$ NMR (400 MHz, $CDCl_3$) δ 8.88 (s, 1H), 8.12 (s, 1H), 7.58 (s, 1H), 7.25 (d, J=8.4 Hz, 2H), 7.20 (d, J=8.4 Hz, 2H), 6.72 (s, 1H), 5.38-5.20 (m, 1H), 5.14-4.95 (m, 2H), 3.58 (s, 2H), 2.86-2.62 (m, 1H), 1.95-1.76 (m, 1H), 1.70-1.58 (m, 1H), 1.49 (d, J=6.8 Hz, 3H). $^{19}F$ NMR (377 MHz, CDC13) δ −70.80, −125.92, −142.30.

Example 32. (R)-2-(4-isopropylphenyl)-N-(1-(3-methyl-1-(2,2,2-trifluoroethyl)-1H-pyrazolo[3,4-c]pyridin-5-yl)ethyl)acetamide

Synthesis of 2-bromo-5-fluoro-N-methoxy-N-methylisonicotinamide

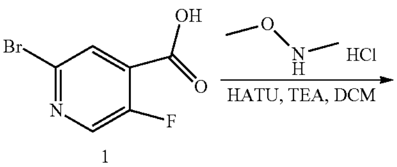

1

-continued

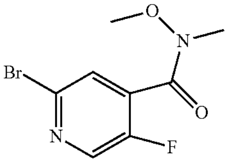

2

To a solution of 2-bromo-5-fluoroisonicotinic acid (10 g) in DCM (400 mL) were added HATU (22.47 g), TEA (18.9 mL) and N,O-dimethylhydroxylamine hydrochloride (4.88 g). The reaction was stirred at 20° C. for 16 h under nitrogen atmosphere. The solvent was evaporated under reduced pressure to provide a residue. The residue was dissolved in EA (500 mL), washed twice with water (500 mL) and then brine (500 mL). The organic layer was separated, dried with $Na_2SO_4$, filtered, and concentrated to get a residue, which was purified via Biotage (from 0% to 15% EA with PE) to give 2-bromo-5-fluoro-N-methoxy-N-methylisonicotinamide (10.3 g) as yellow oil: LCMS ESI (m/z): 262.9 $(M+H)^+$.

Synthesis of 1-(2-bromo-5-fluoropyridin-4-yl)ethan-1-one

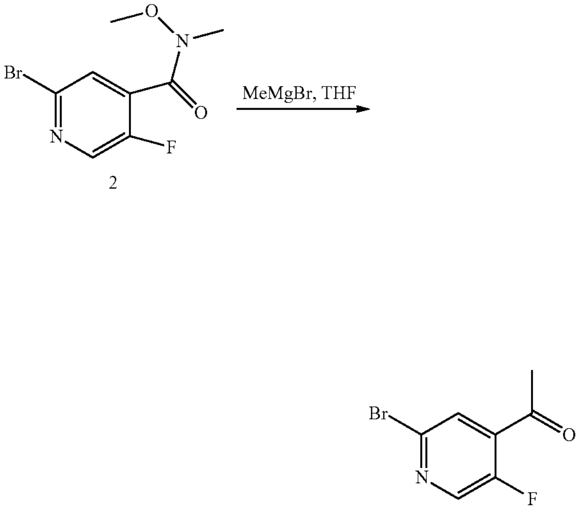

2-bromo-5-fluoro-N-methoxy-N-methylisonicotinamide (10.3 g) was suspended in THF (200 mL) and stirred at 0° C. for 5 min. Methylmagnesium bromide (19.58 mL, 3.0 M in ether) was slowly added to the reaction mixture under a nitrogen atmosphere, and the reaction was stirred at 20° C. for 16 h. The reaction was quenched with saturated ammonium chloride. The two phases were separated, and the aqueous phase was extracted with ethyl acetate. The combined organic phase was washed with brine, dried over $Na_2SO_4$, filtered, and concentrated to provide a residue, which was purified via Biotage (from 0% to 10% EA with PE) to give 1-(2-bromo-5-fluoropyridin-4-yl)ethan-1-one (8.3 g) as colorless oil. LCMS ESI (m/z): 218.0 $(M+H)^+$.

Synthesis of 5-bromo-3-methyl-1H-pyrazolo[3,4-c]pyridine

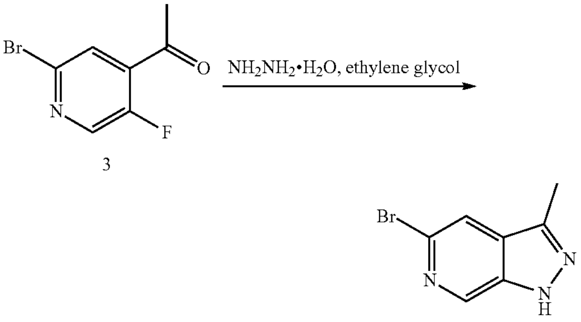

To a solution of 1-(2-bromo-5-fluoropyridin-4-yl)ethan-1-one (8.3 g) in ethylene glycol (50 mL) were added hydrazine hydrate (4.793 mL) and the reaction was stirred at 120° C. for 72 hr under a nitrogen atmosphere. Upon completion, the reaction was diluted with EA (200 mL), and the resulting mixture was washed twice with water (2 L) and brine (500 mL). The organic layer was separated, dried with $Na_2SO_4$, filtered, and evaporated to provide a residue, which was purified via Biotage (from 0% to 20% EA with PE) to give 5-bromo-3-methyl-1H-pyrazolo[3,4-c]pyridine (2.7 g) as a white solid. LCMS ESI (m/z): 212 $(M+H)^+$; H NMR (400 MHz, $CDCl_3$): δ 8.80 (d, J=0.9 Hz, 1H), 7.80 (d, J=0.9 Hz, 1H), 2.60 (s, 3H).

Synthesis of 5-bromo-3-methyl-1-(2,2,2-trifluoroethyl)-1H-pyrazolo[3,4-c]pyridine

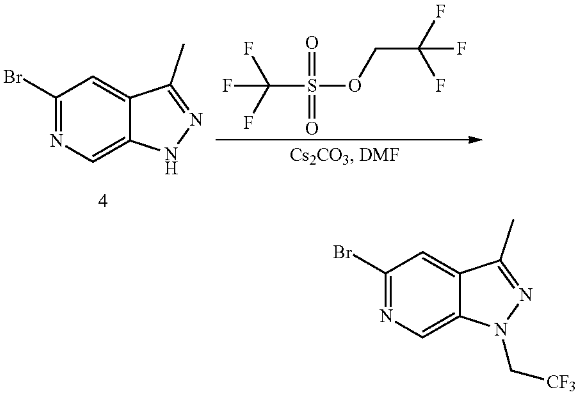

To a solution of 5-bromo-3-methyl-1H-pyrazolo[3,4-c]pyridine (5.30 g) in anhydrous DMF (26 mL) were added 2,2,2-trifluoroethyl trifluoromethanesulfonate (4.3 mL) and $Cs_2CO_3$ (9.82 g). The reaction was stirred at 25° C. for 16 hr under a nitrogen atmosphere. Upon completion, the reaction mixture was poured into $H_2O$ and extracted with EA three times. The combined organic layers were washed with brine, dried with $Na_2SO_4$, filtered and evaporated in vacuo. The residue was purified via Biotage (from 0% to 10% EA with PE; 80 g Cartridge column) to give 5-bromo- 3-methyl-1-(2,2,2-trifluoroethyl)-1H-pyrazolo[3,4-c]pyridine (5.72 g) as a white solid. LCMS ESI (m/z): 294 $(M+H)^+$; $^1H$ NMR (400 MHz, $CDCl_3$) δ 8.69 (s, 1H), 7.79 (d, J=0.9 Hz, 1H), 5.02-4.87 (m, 2H), 2.57 (s, 3H). $^{19}F$ NMR (377 MHz, $CDCl_3$) δ −70.91 (s).

Synthesis of 3-methyl-1-(2,2,2-trifluoroethyl)-1H-pyrazolo[3,4-c]pyridine-5-carbaldehyde

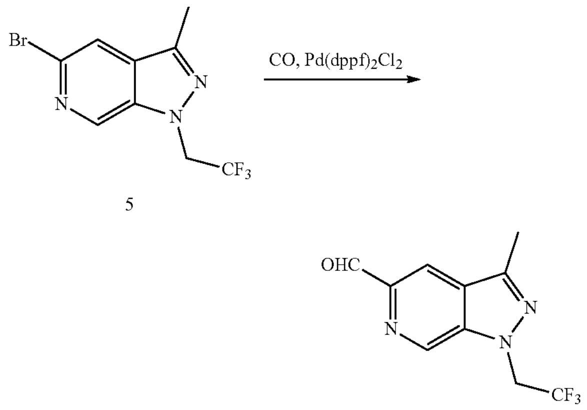

5

6

To a solution of 5-bromo-3-methyl-1-(2,2,2-trifluoroethyl)-1H-pyrazolo[3,4-c]pyridine (2 g) in anhydrous DMF (60 mL) were added $Na_2CO_3$ (1.082 g), $Pd(dppf)_2Cl_2$ (498 mg) and $Et_3SiH$ (2.2 mL). The reaction was charged with $N_2$ and stirred at 100° C. under CO (7 bar) atmosphere for 16 hr. After completion, water was added into the reaction. The reaction mixture was extracted with Ethyl Acetate. The combined organic extracts were washed with brine, dried over $Na_2SO_4$, filtered and concentrated to give as a black oil, which was purified via Biotage (from 0% to 20% EA with PE; 40 g Cartridge column). Collected fractions and evaporated to get 3-methyl-1-(2,2,2-trifluoroethyl)-1H-pyrazolo[3,4-c]pyridine-5-carbaldehyde (1.2 g) as a yellow solid. LCMS ESI (m/z): 244 $(M+H)^+$ $^1H$ NMR (400 MHz, $CDCl_3$): δ 10.24 (s, 1H), 9.04 (s, 1H), 8.37 (d, J=0.6 Hz, 1H), 5.10-4.98 (m, 2H), 2.66 (s, 3H). $^{19}F$ NMR (377 MHz, $CDCl_3$) δ −70.80 (s).

Synthesis of (R,E)-2-methyl-N-((3-methyl-1-(2,2,2-trifluoroethyl)-1H-pyrazolo[3,4-c]pyridin-5-yl)methylene)propane-2-sulfinamide

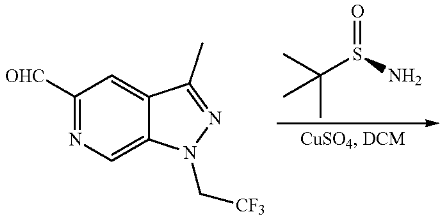

6

-continued

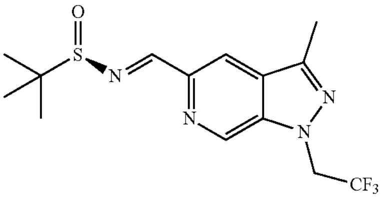

7

To a solution of 3-methyl-1-(2,2,2-trifluoroethyl)-1H-pyrazolo[3,4-c]pyridine-5-carbaldehyde (1.2 g) in anhydrous DCM (15 mL) were added $CuSO_4$ (2.36 g) and (R)-2-methylpropane-2-sulfinamide (0.78 g). The reaction mixture was stirred at rt overnight. The solution was filtered through a pad of Celite and the filtrate was concentrated. The residue was purified by silica gel column to give (R,E)-2-methyl-N-((3-methyl-1-(2,2,2-trifluoroethyl)-1H-pyrazolo[3,4-c]pyridin-5-yl)methylene)propane-2-sulfinamide (1.5 g). LCMS ESI (m/z): 347 $(M+H)^+$. $^1H$ NMR (400 MHz, $CDCl_3$) δ 9.02 (s, 1H), 8.85 (s, 1H), 8.31 (d, J=1.1 Hz, 1H), 5.07-4.95 (m, 2H), 2.66 (s, 3H), 1.31 (s, 9H).

Synthesis of (R)-2-methyl-N—((R)-1-(3-methyl-1-(2,2,2-trifluoroethyl)-1H-pyrazolo[3,4-c]pyridin-5-yl)ethyl)propane-2-sulfinamide

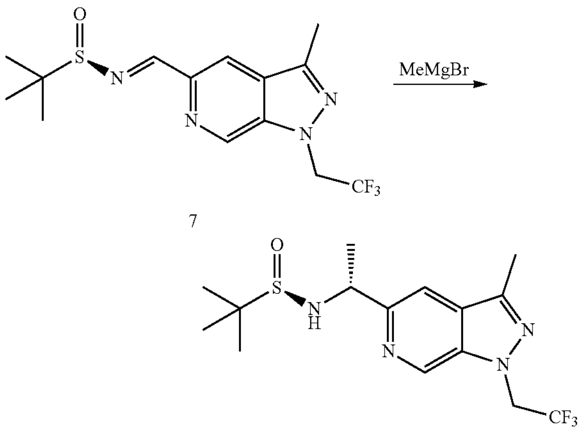

7

8

To a solution of (R,E)-2-methyl-N-((3-methyl-1-(2,2,2-trifluoroethyl)-1H-pyrazolo[3,4-c]pyridin-5-yl)methylene)propane-2-sulfinamide (1.6 g, 4.62 mmol) in anhydrous THE (17 mL) was added methylmagnesium bromide (7.699 mL, 3.0 M in ether) dropwise at −78° C. under nitrogen. The reaction was stirred at −78° C. for 2 hr. Then the reaction solution was quenched with aqueous $NH_4Cl$. The two phases were separated, and the aqueous phase was extracted with EA. The combined organic layers were washed with brine, dried over $Na_2SO_4$, filtered and concentrated in vacuo. Then the residue was purified by silica gel column chromatography, to give (R)-2-methyl-N—((R)-1-(3-methyl-1-(2,2,2-trifluoroethyl)-1H-pyrazolo[3,4-c]pyridin-5-yl)ethyl)propane-2-sulfinamide (1.5 g, 4.139 mmol) as a white solid. LCMS ESI (m/z): 363 (M+H)+

Synthesis of (R)-1-(3-methyl-1-(2,2,2-trifluoro-ethyl)-1H-pyrazolo[3,4-c]pyridin-5-yl)ethan-1-amine hydrochloride

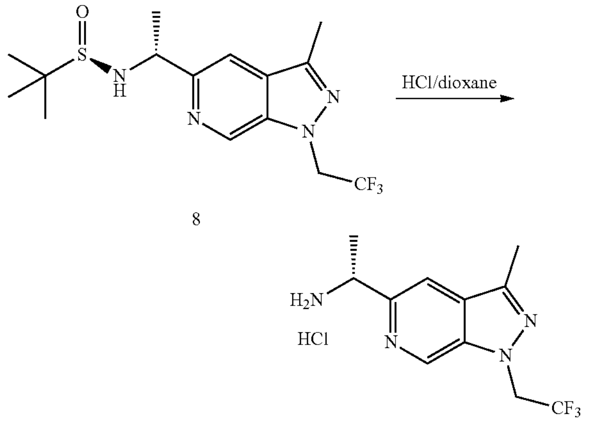

8

9

To a solution of (R)-2-methyl-N—[(R)-1-[3-methyl-1-(2,2,2-trifluoroethyl)-1H-pyrazolo[3,4-c]pyridin-5-yl]ethyl] propane-2-sulfinamide (1.0 g, 2.76 mmol) in dioxane (4.0 mL) was added 4 N HCl-Dioxane (2.0 mL), and the reaction was stirred at rt for 1 hr. Then the mixture was then concentrated to provide a residue, which was directly used in the next step. LCMS ESI (m/z): 259 $(M+H)^+$.

Synthesis of (R)-2-(4-isopropylphenyl)-N-(1-(3-methyl-1-(2,2,2-trifluoroethyl)-1H-pyrazolo[3,4-c]pyridin-5-yl)ethyl)acetamide

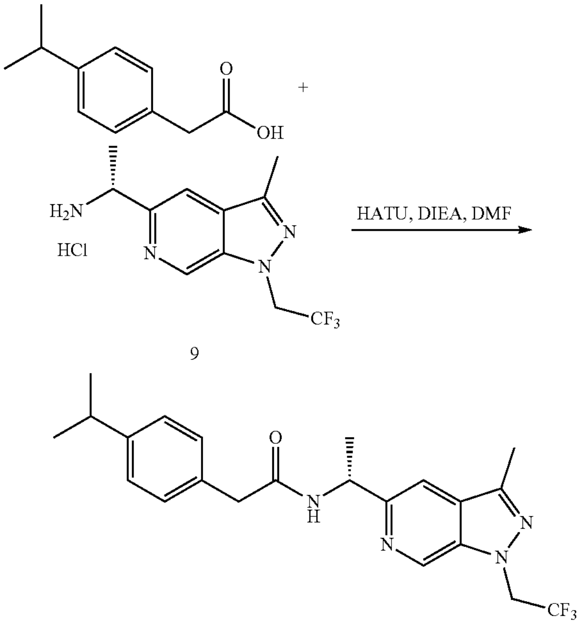

9

To a solution of (R)-1-(3-methyl-1-(2,2,2-trifluoroethyl)-1H-pyrazolo[3,4-c]pyridin-5-yl)ethan-1-amine hydrochloride (238 mg) in anhydrous DMF (1.5 mL) were added DIEA (0.6 mL) to provide solution A. To a solution of 2-(4-isopropylphenyl)acetic acid (126.4 mg) in DMF (1 mL) were added HATU (296.5 mg) and stirred 15 min at rt to provide solution B. Solution A was added to the solution B and stirred at rt for 1 h. The reaction was diluted with EA and water. The two phases were separated, and the organic layer was washed with brine, dried over $Na_2SO_4$, filtered, and concentrated in vacuo. The residue was purified by Prep-HPLC ((Column: AZZOTA C18 30*250 mm*10 um; Mobile phase: from 25% to 95% MeCN with $H_2O$ (1% FA); flow rate: 15 mL/min; wavelength: 220 nm/254 nm)) and SFC (Column: ChiralPak IG, 250×21.2 mm I.D., 5 μm; Mobile phase: A for $CO_2$ and B for MEOH+0.1% $NH_3H_2O$; Gradient: B 40%; wavelength: 220 nm) to give (R)-2-(4-isopropylphenyl)-N-(1-(3-methyl-1-(2,2,2-trifluoroethyl)-1H-pyrazolo[3,4-c]pyridin-5-yl)ethyl)acetamide as a white solid (100.2 mg). LCMS ESI (m/z): 419.5 $(M+H)^+$; $^1H$ NMR (400 MHz, $CDCl_3$) δ 8.78 (s, 1H), 7.47 (s, 1H), 7.19 (s, 4H), 6.58 (s, 1H), 5.34-5.20 (m, 1H), 5.01-4.87 (m, 2H), 3.55 (d, J=1.8 Hz, 2H), 2.95-2.85 (m, 1H), 2.56 (s, 3H), 1.48 (d, J=6.8 Hz, 3H), 1.25 (d, J=6.9 Hz, 6H); $^{19}F$ NMR (377 MHz, $CDCl_3$) δ −70.92.

Example 33. (R)-2-(4-cyclopropylphenyl)-N-(1-(3-methyl-1-(2,2,2-trifluoroethyl)-1H-pyrazolo[3,4-c]pyridin-5-yl)ethyl)acetamide Synthesis of (R)-2-(4-cyclopropylphenyl)-N-(1-(3-methyl-1-(2,2,2-trifluoroethyl)-1H-pyrazolo[3,4-c]pyridin-5-yl)ethyl)acetamide

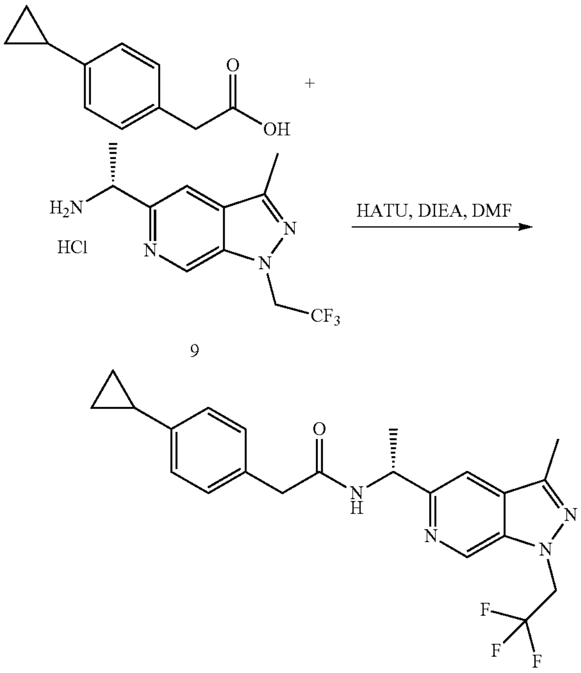

9

To a solution of (R)-1-[3-methyl-1-(2,2,2-trifluoroethyl)-1H-pyrazolo[3,4-c]pyridin-5-yl]ethan-1-amine hydrochloride (242 mg) in anhydrous DMF (1.5 mL) was added DIEA (0.6 mL) to provide Solution A. To a solution of 2-(4-cyclopropylphenyl)acetic acid (111.58 mg) in DMF (1.0 mL) was added HATU (264.83 mg) and stirred 15 min at rt to provide Solution B. Solution A was added to the Solution B and stirred at rt for 1 h. The reaction was diluted with EA and water. The organic layer was washed with aqueous NaCl, dried over $Na_2SO_4$, filtered, and concentrated in vacuo. The residue was purified by Prep-HPLC ((Column: YMC-Actus Triart C18 250*21 mm; Mobile phase: from 40% to 90% MeCN with $H_2O$ (0.1% $NH_3H_2O$); flow rate: 15 mL/min; wavelength: 220 nm/254 nm)) and SFC (Column: ChiralPak IG, 250×21.2 mm I.D., 5 μm; Mobile phase: A for $CO_2$ and B for MEOH+0.1% $NH_3H_2O$; Gradient: B 45%; Flow rate: 50 mL/min; wavelength: 220 nm) to give (R)-2-(4-cyclopropylphenyl)-N-(1-(3-methyl-1-(2,2,2-trifluoroethyl)-1H-pyrazolo[3,4-c]pyridin-5-yl)ethyl)acetamide as a white solid (86.7 mg). LCMS ESI (m/z): 417.5 $(M+H)^+$; $^1H$ NMR (400 MHz, $CDCl_3$) δ 8.78 (s, 1H), 7.44 (d, J=0.9 Hz, 1H), 7.15 (d, J=8.1 Hz, 2H), 7.04 (d, J=8.1 Hz, 2H), 6.52 (d, J=7.4 Hz, 1H), 5.31-5.22 (m, 1H), 5.00-4.87 (m, 2H), 3.54 (d, J=2.4 Hz, 2H), 2.55 (s, 3H), 1.93-1.84 (m, 1H), 1.46 (d, J=6.8 Hz, 3H), 1.00-0.92 (m, 2H), 0.72-0.64 (m, 2H); $^{19}F$ NMR (377 MHz, $CDCl_3$) δ −70.92 (s).

Example 34. (R)-2-(5-cyclopropylpyridin-2-yl)-N-(1-(1-(2,2,2-trifluoroethyl)-1H-pyrazolo[3,4-c]pyridin-5-yl)ethyl)acetamide Synthesis of methyl 2-(5-cyclopropylpyridin-2-yl)acetate

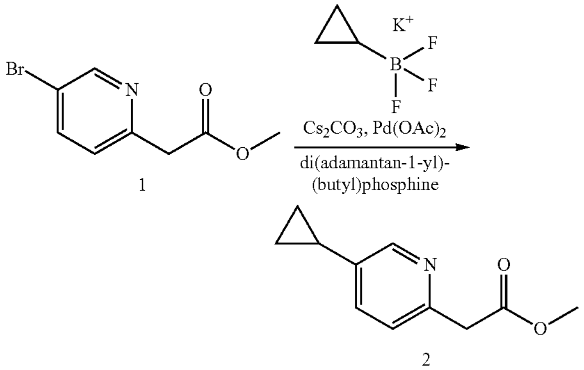

1

2

To a solution of methyl 2-(5-bromopyridin-2-yl)acetate (1 g) in toluene-water (10:1, 16.5 mL) were added potassium cyclopropyltrifluoroborate (1.29 g), $Cs_2CO_3$ (4.25 g), $Pd(OAc)_2$ (0.20 g) and di(adamantan-1-yl)(butyl)phosphine (0.31 g). The reaction was charged with $N_2$ and stirred at 110° C. overnight. The reaction was diluted with EA and water. The two phases were separated, and the organic layer was washed with saturated NaCl, dried over $Na_2SO_4$, filtered and concentrated in vacuo. The resulting residue was purified by silica gel column chromatography to provide methyl 2-(5-cyclopropylpyridin-2-yl)acetate (582 mg) as an oil. LCMS ESI (m/z): 192 $(M+H)^+$.

Synthesis of 2-(5-cyclopropylpyridin-2-yl)acetic acid

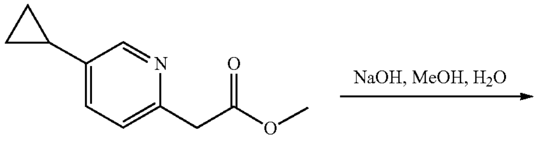

2

-continued

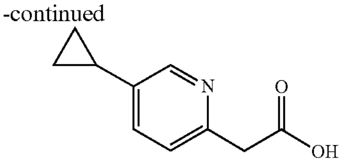

3

To a solution of methyl 2-(5-cyclopropylpyridin-2-yl) acetate (582 mg) in MeOH—$H_2O$ (2:1, 9.5 mL) was added NaOH (183 mg). The reaction was stirred at rt for 3 hr. Then the MeOH was removed under reduced pressure and the pH of the water layer adjusted to 5 with 2M HCl while cooling in an ice bath. Ethyl acetate was added to acidic water later, and the resulting precipitate was collected by filtration. The water layer was then extracted with DCM-MeOH (10:1), and the combined organic layers were concentrated in vacuum. Both the residue and the precipitate were combined to give 2-(5-cyclopropylpyridin-2-yl)acetic acid (354 mg) as a white solid. LCMS ESI (m/z): 178 $(M+H)^+$; $^1H$ NMR (400 MHz, DMSO-d6) δ 8.64 (d, J=2.0 Hz, 1H), 8.05-8.00 (m, 1H), 7.73 (d, J=8.3 Hz, 1H), 4.06 (s, 2H), 2.18-2.08 (m, 1H), 1.15-1.08 (m, 2H), 0.93-0.85 (m, 2H).

Synthesis of (R)-2-(5-cyclopropylpyridin-2-yl)-N-(1-(1-(2,2,2-trifluoroethyl)-1H-pyrazolo[3,4-c]pyridin-5-yl)ethyl)acetamide

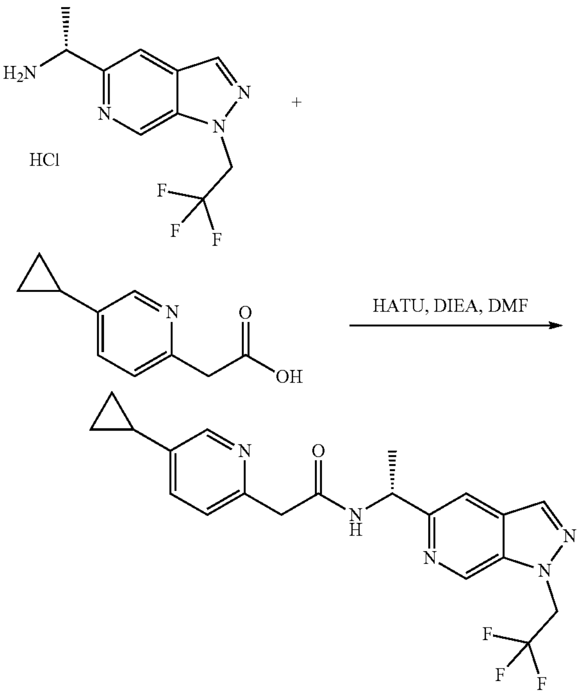

To a solution of (R)-1-(1-(2,2,2-trifluoroethyl)-1H-pyrazolo[3,4-c]pyridin-5-yl)ethan-1-amine hydrochloride (308 mg) in anhydrous DMF (1.5 mL) was added DIEA (1 mL) to provide Solution A. To a solution of 2-(5-cyclopropylpyridin-2-yl)acetic acid (150 mg) in DMF (1 mL) was added HATU (405.76 mg) and stirred 5 min at rt to provide Solution B. Solution A was added to the Solution B, and the reaction mixture was stirred at rt for 1 h. The reaction was then diluted with EA and water. The organic layer was washed with aqueous NaCl, dried over $Na_2SO_4$, filtered, and concentrated in vacuo. The residue was purified by Prep-HPLC ((Column: YMC-Actus Triart C18 250*21 mm; Mobile phase: from 10% to 90% MeCN with $H_2O$ (0.10% FA); flow rate: 15 mL/min; wavelength: 220 nm/254 nm)) to give (R)-2-(5-cyclopropylpyridin-2-yl)-N-(1-(1-(2,2,2-trifluoroethyl)-1H-pyrazolo[3,4-c]pyridin-5-yl)ethyl)acetamide as a white solid (135.4 mg). LCMS ESI (m/z): 404.4 $(M+H)^+$; $^1H$ NMR (400 MHz, $CDCl_3$) δ 8.94 (s, 1H), 8.36 (d, J=1.9 Hz, 1H), 8.09 (s, 1H), 7.82 (d, J=7.2 Hz, 1H), 7.60 (s, 1H), 7.52 (d, J=7.7 Hz, 1H), 7.40 (d, J=8.2 Hz, 1H), 5.32-5.18 (m, 1H), 5.11-4.98 (m, 2H), 3.87 (d, J=2.3 Hz, 2H), 2.00-1.90 (m, 1H), 1.53 (d, J=6.9 Hz, 3H), 1.17-1.06 (m, 2H), 0.81-0.72 (m, 2H); $^{19}F$ NMR (377 MHz, $CDCl_3$) δ −70.81 (s).

Example 35. (R)-2-(5-chloro-6-(1,1-difluoroethyl)pyridin-3-yl)-N-(1-(1-(2,2,2-trifluoroethyl)-1H-pyrazolo[3,4-c]pyridin-5-yl)ethyl)acetamide Synthesis of 5-bromo-3-chloro-N-methoxy-N-methylpicolinamide

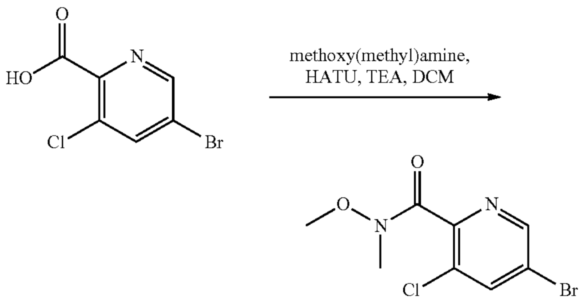

To a solution of 5-bromo-3-chloropyridine-2-carboxylic acid (4.76 g) in DCM (10 mL) were added HATU (9.94 g), methoxy(methyl)amine (3.396 mL) and TEA (8.4 mL). The reaction was stirred at room temperature for 2 hr. The reaction was then diluted with DCM and water, the two phases were separated. The organic phase was washed with saturated NaCl, dried over $Na_2SO_4$, filtered, and concentrated in vacuo. The residue was purified by using silica gel column chromatography eluting with ethyl acetate in petroleum ether (15%) to afford the 5-bromo-3-chloro-N-methoxy-N-methylpicolinamide (5.11 g) as a white solid. LCMS ESI (m/z): 281 $(M+H)^+$.

Synthesis of 1-(5-bromo-3-chloropyridin-2-yl)ethan-1-one

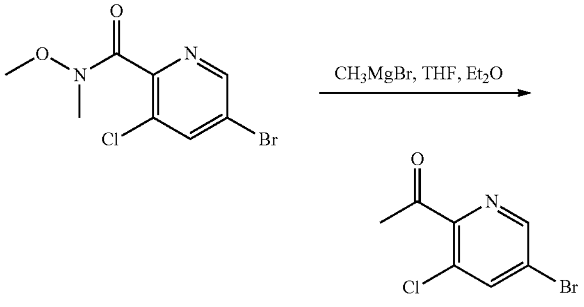

To a solution of 5-bromo-3-chloro-N-methoxy-N-methylpicolinamide (5.48 g) in THF (65 mL) was added methylmagnesium bromide (32.6 mL, 3.0 M in $Et_2O$) at −78° C. under $N_2$. The reaction was stirred at −78° C. for 2 hr. Upon completion, the reaction was diluted with DCM and water. The two phases were separated, and the aqueous phase was extracted with DCM (30 mL×3). The combined organic phase was dried over $Na_2SO_4$, filtered, and concentrated to give a residue. The residue was purified by silica gel column chromatography, eluting with ethyl acetate in petroleum ether (6%) to afford 1-(5-bromo-3-chloropyridin-2-yl)ethan-1-one as a white solid (602 mg). LCMS ESI (m/z): 234 $(M+H)^+$; $^1H$ NMR (400 MHz, $CDCl_3$) δ 8.59 (d, J=1.6 Hz, 1H), 7.98 (d, J=1.9 Hz, 1H), 2.67 (s, 3H).

Synthesis of 5-bromo-3-chloro-2-(1,1-difluoroethyl)pyridine

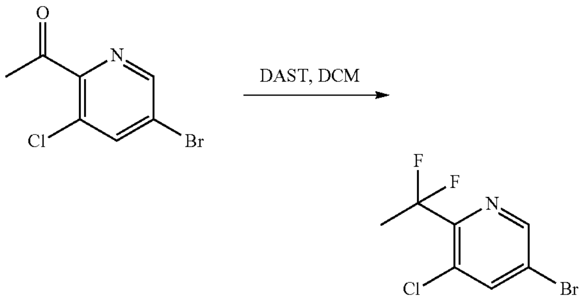

To a solution of 1-(5-bromo-3-chloropyridin-2-yl)ethan-1-one (2 g) in 1,2-dichloroethane (40 mL) was added DAST (11.27 mL). The mixture was stirred at 80° C. in a sealed tube for 12 hr. The mixture was quenched with saturated sodium bicarbonate and extracted with DCM. The combined organic layers were dried, filtered and concentrated to give a residue, which was purified by chromatography on silica gel (PE:EA=20:1) to give 5-bromo-3-chloro-2-(1,1-difluoroethyl)pyridine (1.0 g) as a yellow oil.

$^1H$ NMR (400 MHz, $CDCl_3$) δ 8.55 (d, J=2.0 Hz, 1H), 7.98 (d, J=2.0 Hz, 1H), 2.06 (t, J=18.8 Hz, 3H).

Synthesis of ethyl 2-(5-chloro-6-(1,1-difluoroethyl)pyridin-3-yl)acetate

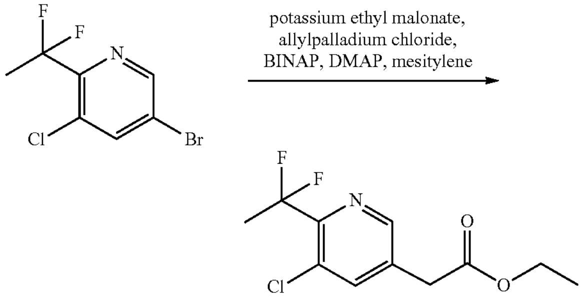

A solution of 5-bromo-3-chloro-2-(1,1-difluoroethyl)pyridine (200 mg), potassium ethyl malonate (199.1 mg), allylpalladium chloride dimer (34.24 mg), BINAP (97.11 mg) and DMAP (95.27 mg) in mesitylene (10 mL) was charged with $N_2$ and stirred at 140° C. for 1 hr. The mixture was then stirred at 120° C. for 12 hr. The mixture was concentrated to give a residue, which was purified by chromatography on silica gel (PE:EA=10:1) to provide ethyl 2-[5-chloro-6-(1,1-difluoroethyl)pyridin-3-yl]acetate (50 mg) as a yellow oil. LCMS ESI (m/z): 264 $(M+H)^+$.

Step 5. Synthesis of 2-(5-chloro-6-(1,1-difluoroethyl)pyridin-3-yl)acetic acid

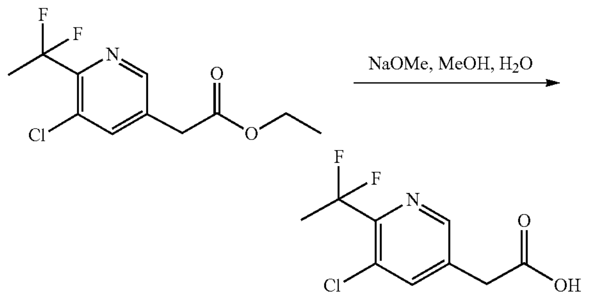

To a solution of ethyl 2-[5-chloro-6-(1,1-difluoroethyl) pyridin-3-yl]acetate (50 mg) in MeOH (1.0 mL) was added NaOH (1M in $H_2O$, 1.0 mL). The mixture was stirred at 25° C. for 12 hr. The mixture was then concentrated, diluted with water, and extracted with EtOAc. The aqueous layer was adjusted pH to 3 with 1 N HCl and extracted with DCM. The combined organic layers were dried, filtered and concentrated to give 2-[5-chloro-6-(1,1-difluoroethyl)pyridin-3-yl] acetic acid (25 mg) as a white solid. LCMS ESI (m/z): 234 (M−H).

Step 6. Synthesis of (R)-2-(5-chloro-6-(1,1-difluoroethyl)pyridin-3-yl)-N-(1-(1-(2,2,2-trifluoroethyl)-1H-pyrazolo[3,4-c]pyridin-5-yl)ethyl)acetamide

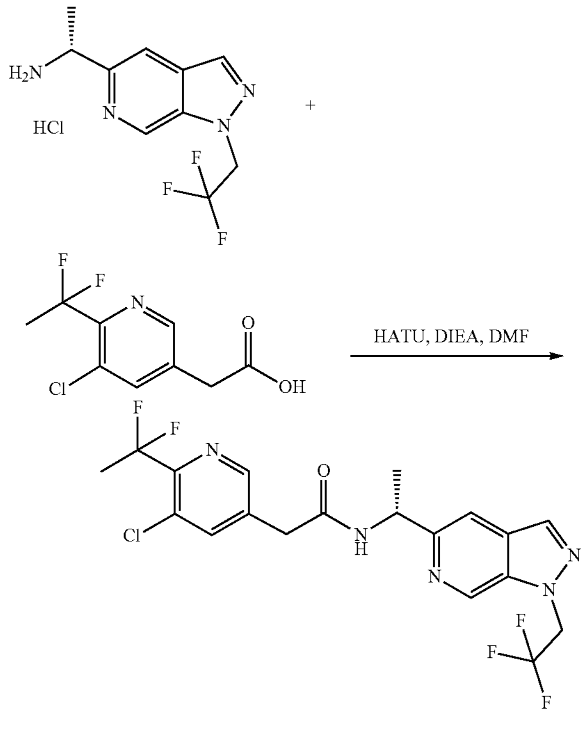

A solution of 2-[5-chloro-6-(1,1-difluoroethyl)pyridin-3-yl]acetic acid (80 mg), (1R)-1-[1-(2,2,2-trifluoroethyl)-1H-pyrazolo[3,4-c]pyridin-5-yl]ethan-1-amine hydrochloride (107.80 mg), HATU (142.0 mg) and DIEA (0.168 mL) in DMF (1.0 mL) was stirred at 25° C. for 2 hr. The reaction was diluted with water and extracted with DCM. The combined organic layers were dried, filtered and concentrated to give a residue. The residue was purified by prep-HPLC (Column: YMC-Actus Triart C18 250*20 mm; Mobile phase: from 30% to 95% MeCN with $H_2O$ (0.1% FA); flow rate: 15 mL/min; wavelength: 220 nm/254 nm) to give (R)-2-(5-chloro-6-(1,1-difluoroethyl)pyridin-3-yl)-N-(1-(1-(2,2,2-trifluoroethyl)-1H-pyrazolo[3,4-c]pyridin-5-yl) ethyl)acetamide (82.3 mg) as a white solid. LCMS ESI (m/z): 462 $(M+H)^+$. $^1H$ NMR (400 MHz, $CDCl_3$) δ 8.97 (s, 1H), 8.40 (s, 1H), 8.17 (s, 1H), 7.80 (d, J=1.6 Hz, 1H), 7.67 (s, 1H), 7.02 (d, J=14.4 Hz, 1H), 5.38-5.24 (m, 1H), 5.19-5.00 (m, 2H), 3.61 (s, 2H), 2.07 (t, J=18.8 Hz, 3H), 1.57 (d, J=6.8 Hz, 3H). $^{19}F$ NMR (377 MHz, $CDCl_3$) δ −70.73, −89.61.

Example 36. (R)-2-(5-chloro-6-cyclopropylpyridin-3-yl)-N-(1-(1-(2,2,2-trifluoroethyl)-1H-pyrazolo[3,4-c]pyridin-5-yl)ethyl)acetamide

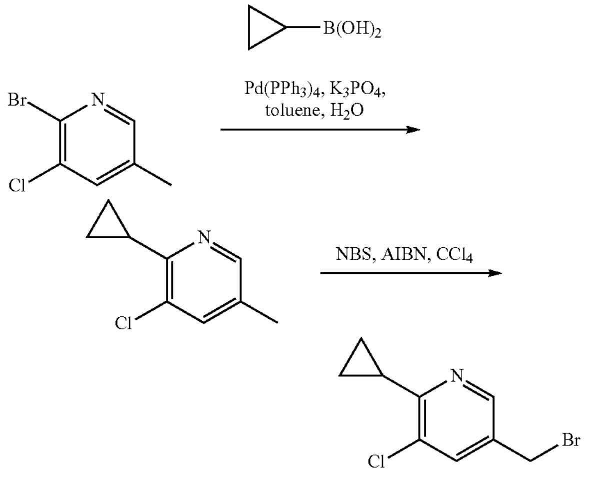

Step 1: 3-chloro-2-cyclopropyl-5-methylpyridine. A solution of 2-bromo-3-chloro-5-methylpyridine (4.2 g), cyclopropylboronic acid (1.92 g), $Pd(PPh_3)_4$ (2.35 g) and $K_3PO_4$ (12.95 g) in toluene (80 mL)/$H_2O$ (8 mL) was stirred at 110° C. for 12 hours under $N_2$. The reaction was complete monitored by LCMS. The mixture was concentrated under vacuo to give a residue, and the residue was purified by column chromatography on silica gel (PE:EA=10:1) to give 3-chloro-2-cyclopropyl-5-methylpyridine (1.4 g) as colorless oil. LCMS ESI (m/z): 168 $(M+H)^+$.

Step 2: 5-(bromomethyl)-3-chloro-2-cyclopropylpyridine. A solution of 3-chloro-2-cyclopropyl-5-methylpyridine (960 mg), NBS (1.12 g) and AIBN (0.042 mL,) in carbon tetrachloride (15 mL) was stirred at 80° C. for 12 hours under $N_2$. The reaction was filtered and concentrated to give a residue. The residue was purified by column chromatography on silica gel (PE:EA=30:1) to give 5-(bromomethyl)-3-chloro-2-cyclopropylpyridine (700 mg) as colorless oil. LCMS ESI (m/z): 246 $(M+H)^+$.

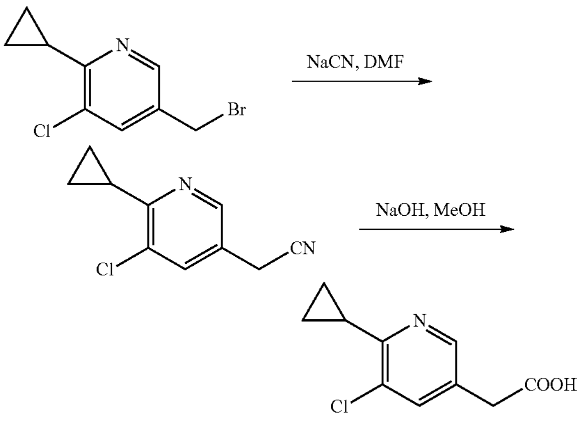

Step 3: 2-(5-chloro-6-cyclopropylpyridin-3-yl)acetonitrile. A solution of 5-(bromomethyl)-3-chloro-2-cyclopropylpyridine (600 mg, 2.43 mmol) and NaCN (239 mg) in DMF (5 mL) was stirred at 25° C. for 12 hours. The reaction was complete monitored by LCMS. The mixture was diluted with water and extracted with DCM. The mixture was dried, filtered and concentrated to give 2-(5-chloro-6-cyclopropylpyridin-3-yl)acetonitrile (380 mg) as a yellow oil. LCMS ESI (m/z): 193 $(M+H)^+$.

Step 4: 2-(5-chloro-6-cyclopropylpyridin-3-yl)acetic acid. To a solution of 2-(5-chloro-6-cyclopropylpyridin-3-yl)acetonitrile (380 mg) in MeOH (2 mL) was added NaOH (10 mL, 20.0 mmol, 2N). The mixture was stirred at 25° C. for 12 hours, and the reaction was complete by LCMS. The reaction was then extracted with EtOAc. The aqueous layer was adjusted pH=3 with 1 N HCl solution and lyophilized to give a white solid. The white solid was dissolved in MeOH/DCM (10:1), filtered and concentrated to give 2-(5-chloro-6-cyclopropylpyridin-3-yl)acetic acid (150 mg) as a white solid. LCMS ESI (m/z): 210 (M−H).

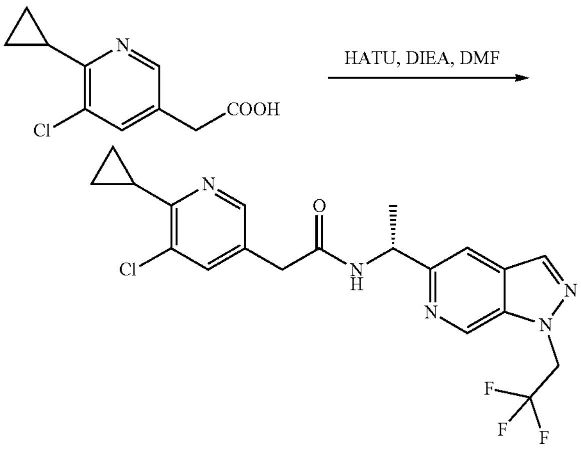

Step 5: (R)-2-(5-chloro-6-cyclopropylpyridin-3-yl)-N-(1-(1-(2,2,2-trifluoroethyl)-1H-pyrazolo[3,4-c]pyridin-5-yl)ethyl)acetamide. A solution of 2-(5-chloro-6-cyclopropylpyridin-3-yl)acetic acid (150 mg), (R)-1-[1-(2,2,2-trifluoroethyl)-1H-pyrazolo[3,4-c]pyridin-5-yl]ethan-1-amine hydrochloride (258.89 mg), HATU (296 mg) and DIEA (0.35 mL) in DMF (5 mL) was stirred at 25° C. for 12 hours. The mixture was diluted with water and extracted with DCM. The organic layer was dried, filtered and concentrated to give a residue. The residue was purified by prep-HPLC (Column: YMC-Actus Triart C18 250*21 mm; Mobile phase: from 20% to 95% MeCN with $H_2O$ (0.1% FA); flow rate: 15 mL/min; wave length: 220 nm/254 nm) to give (R)-2-(5-chloro-6-cyclopropylpyridin-3-yl)-N-(1-(1-(2,2,2-trifluoroethyl)-1H-pyrazolo[3,4-c]pyridin-5-yl)ethyl)acetamide (203 mg) as a white solid: LCMS ESI (m/z): 438 $(M+H)^+$. $^1H$ NMR (400 MHz, $CDCl_3$) δ 8.97 (s, 1H), 8.22 (d, J=2.0 Hz, 1H), 8.15 (s, 1H), 7.64 (s, 1H), 7.61 (d, J=2.0 Hz, 1H), 7.03-6.89 (m, 1H), 5.36-5.21 (m, 1H), 5.16-5.01 (m, 2H), 3.51 (s, 2H), 2.56-2.42 (m, 1H), 1.54 (d, J=6.8 Hz, 3H), 1.12-1.07 (m, 2H), 1.06-1.01 (m, 2H). $^{19}F$ NMR (377 MHz, $CDCl_3$) δ −70.73.

Example 37. (R)-2-(3-chloro-4-(1,1-difluoroethyl)phenyl)-N-(1-(1-(2,2,2-trifluoroethyl)-1H-pyrazolo[3,4-c]pyridin-5-yl)ethyl)acetamide

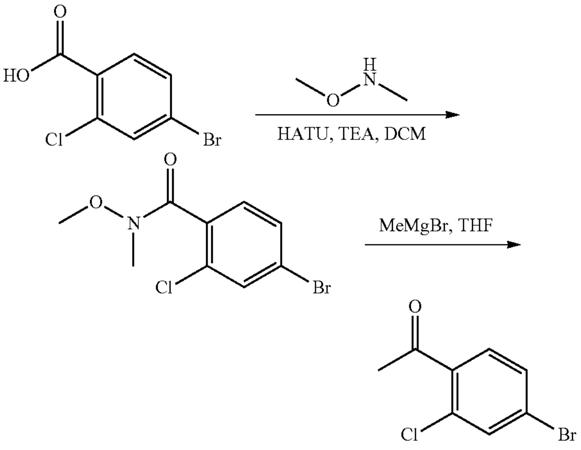

Step 1: 4-bromo-2-chloro-N-methoxy-N-methylbenzamide. To a solution of 4-bromo-2-chlorobenzoic acid (2.0 g) in DCM (25 mL) were added HATU (4.20 g), methoxy(methyl)amine hydrochloride (4.54 g), and TEA (3.5 mL). The reaction was then stirred at room temperature overnight, and the reaction was complete as monitored by LCMS. The reaction was diluted with DCM and water, and the organic layer was separated, washed with saturated NaCl solution, and concentrated in vacuo. The residue was purified by silica gel column chromatography eluting with 25% ethyl acetate in petroleum ether to afford 4-bromo-2-chloro-N-methoxy-N-methylbenzamide (2.209 g) as a pale-yellow oil. LCMS ESI (m/z): $279[M+H]^+$.

Step 2: 1-(4-bromo-2-chlorophenyl)ethan-1-one. To a solution of 4-bromo-2-chloro-N-methoxy-N-methylbenzamide (1.07 g) in THF (10 mL) was added MeMgBr (6.4 mL, 3.0 M in $Et_2O$). The reaction was stirred at −78° C. for 2 h and then stirred at room temperature overnight. The reaction was diluted with DCM and water, and the two phases were separated. The aqueous phase was further extracted with DCM (30 mL×3). The combined organic phases were dried over anhydrous $Na_2SO_4$, filtered, and concentrated to give a residue, which was purified by column chromatography on silica gel (PE:EA=10:1) to afford 1-(4-bromo-2-chlorophenyl)ethan-1-one as a pale-yellow solid (820 mg). $^1H$ NMR (400 MHz, $CDCl_3$) δ 7.61 (s, 1H), 7.50-7.44 (m, 2H), 2.64 (s, 3H). $^{19}F$ NMR (377 MHz, $CDCl_3$) δ −87.65.

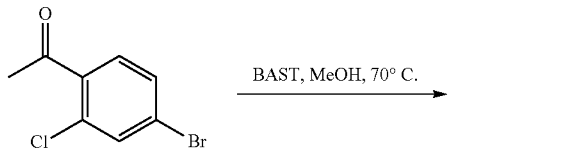

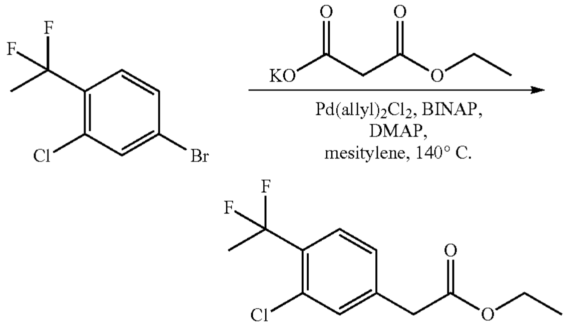

Step 3: 4-bromo-2-chloro-1-(1,1-difluoroethyl)benzene. To a solution of 1-(4-bromo-2-chlorophenyl)ethan-1-one (2.2 g) in BAST (2.6 mL) was added two drops of methanol. Upon completion of the addition, the reaction mixture was placed under a nitrogen atmosphere and heated to 70° C. overnight. The reaction mixture was cooled to room temperature and quenched with 50 ml of water. The resulting mixture was extracted twice with 50 ml of ether. The combined ether phases were washed twice with water, twice with aqueous sodium bicarbonate, once with 10% aqueous citric acid, once with brine, and then dried over magnesium sulfate. The solvent was removed under reduced pressure and was purified by column chromatography on silica gel (2% EA in PE) to afford 4-bromo-2-chloro-1-(1,1-difluoroethyl)benzene (1.71 g) as a colorless oil. $^{1}$H NMR (400 MHz, $CDCl_3$) δ 7.62 (d, J=4.0 Hz, 1H), 7.50-7.43 (m, 2H), 2.02 (t, J=18.4 Hz, 3H). $^{19}$F NMR (377 MHz, $CDCl_3$) δ −87.65.

Step 4: ethyl 2-(3-chloro-4-(1,1-difluoroethyl)phenyl)acetate. To a solution of 4-bromo-2-chloro-1-(1,1-difluoroethyl)benzene (1.5 g) in mesitylene (2 mL) were added diallylpalladium dichloride (1.56 mg), BINAP (0.22 g), DMAP (0.72 g) and ethyl potassium malonate (1.50 g). The reaction was charged with $N_2$ and stirred at 120° C. overnight. The reaction was diluted with EA and water, the two phases were separated, and the aqueous phase was extracted with DCM (30 mL×3). The combined organic phases were dried over $Na_2SO_4$, filtered, and concentrated to give a residue, which was purified by silica gel column chromatography (PE:EA=20:1) to give ethyl 2-(3-chloro-4-(1,1-difluoroethyl)phenyl)acetate (590 mg, 2.246 mmol) as a pale-yellow oil. $^{1}$H NMR (400 MHz, $CDCl_3$) δ 7.56 (d, J=8.0 Hz, 1H), 7.38 (s, 1H), 7.24 (d, J=8.0 Hz, 1H), 4.17 (q, J=20.0 Hz, 2H), 3.61 (s, 2H), 2.03 (t, J=36.0 Hz, 3H), 1.27 (t, J=16.0 Hz, 3H). $^{19}$F NMR (377 MHz, $CDCl_3$) δ −87.45.

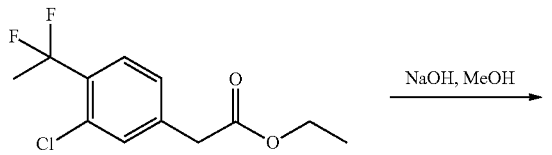

-continued

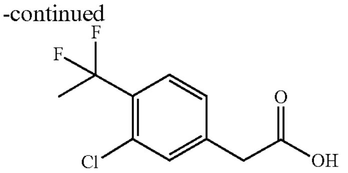

Step 5. 2-(3-chloro-4-(1,1-difluoroethyl)phenyl)acetic acid. In a 25 mL round-bottomed flask were added ethyl 2-(3-chloro-4-(1,1-difluoroethyl)phenyl) acetate (590 mg), 1M aqueous NaOH (10 mL) and MeOH (10 mL). The reaction mixture was stirred at rt for 1 hour. The reaction was complete monitored by LCMS. Water (50 mL) was then added, and the aqueous layer was washed with EA. The aqueous layer was acidified to pH<3 with 1M aqueous HCl, and the mixture was extracted with EA. The combined organic phases were washed with saturated NaCl, dried with $Na_2SO_4$, filtered, and concentrated to provide 2-(3-chloro-4-(1,1-difluoroethyl)phenyl)acetic acid (465 mg) as a green-yellow solid. $^{1}$H NMR (400 MHz, $CDCl_3$) δ 7.58 (d, J=8.0 Hz, 1H), 7.39 (s, 1H), 7.23 (d, J=8.0 Hz, 1H), 3.67 (s, 2H), 2.03 (t, J=36.0 Hz, 3H). $^{19}$F NMR (377 MHz, $CDCl_3$) δ −87.53. LCMS ESI (m/z): 233 $(M-H)^+$.

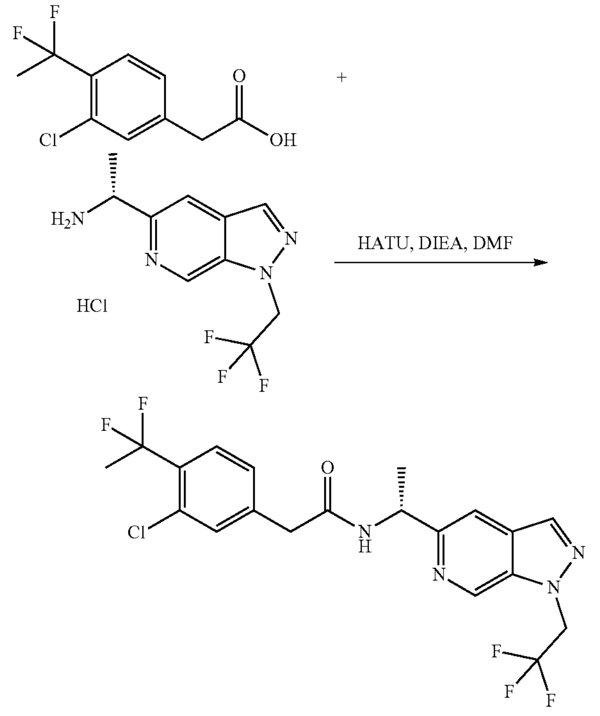

Step 6. (R)-2-(3-chloro-4-(1,1-difluoroethyl)phenyl)-N-(1-(1-(2,2,2-trifluoroethyl)-1H-pyrazolo[3,4-c]pyridin-5-yl)ethyl)acetamide. A solution of 2-(3-chloro-4-(1,1-difluoroethyl) phenyl) acetic acid (120 mg) and HATU (292 mg) in 2 mL DMF was stirred at room temperature for 15 min (Solution A). To another vessel was added (R)-1-(1-(2,2,2-trifluoroethyl)-1H-pyrazolo[3,4-c]pyridin-5-yl)ethan-1-amine hydrochloride (186 mg) and DMF (2.0 mL). DIEA (0.566 mL) was added until the pH of the solution higher than 7 by wet pH paper (Solution B). Solution B was added to Solution A, and the reaction was stirred for 1 hour, at which time LCMS showed the reaction was complete. The reaction was diluted with EA and water, the two phases were separated, and the aqueous phase was extracted with EA (10 mL×2). The combined organic phases were dried over anhydrous $Na_2SO_4$, filtered, and concentrated under vacuo. The residue was purified by prep-HPLC (Column: AZZOTA C18 30*250 mm*10 um; Mobile phase: from 35% to 95% MeCN with $H_2O$ (0.1% FA); flow rate: 20 mL/min; wave length: 220 nm/254 nm) to give (R)-2-(3-chloro-4-(1,1-difluoroethyl)phenyl)-N-(1-(1-(2,2,2-trifluoroethyl)-1H-pyrazolo[3,4-c]pyridin-5-yl)ethyl)acetamide (130 mg) as a white solid. $^1$H NMR (400 MHz, $CDCl_3$) δ 8.93 (s, 1H), 8.14 (s, 1H), 7.62 (s, 1H), 7.55 (d, J=8.0 Hz, 1H), 7.36 (s, 1H), 7.24 (d, J=8.0 Hz, 1H), 6.85 (d, J=8.0 Hz, 1H), 5.32-5.25 (m, 1H), 5.10-5.03 (m, 2H), 3.57 (s, 2H), 2.02 (t, J=16.0 Hz, 3H), 1.53 (d, J=8.0 Hz, 3H). $^{19}$F NMR (377 MHz, $CDCl_3$) δ −70.76, −87.39. LC/MS ESI (m/z): 461 $[M+H]^+$.

Example 38. (R)-2-(4-(1,1-difluoroethyl)-3-fluorophenyl)-N-(1-(1-(2,2,2-trifluoroethyl)-1H-pyrazolo[3,4-c]pyridin-5-yl)ethyl)acetamide

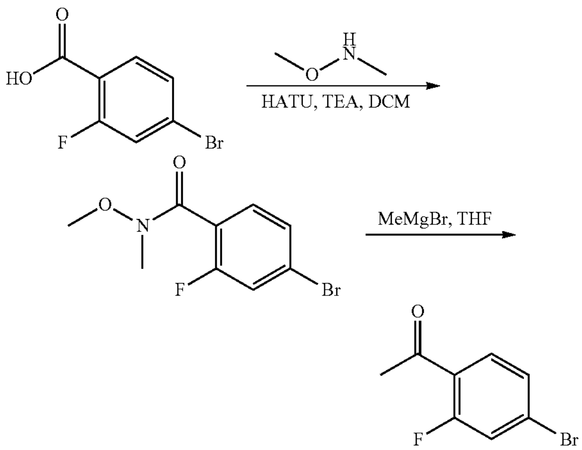

4-bromo-2-fluoro-N-methoxy-N-methylbenzamide. To a solution of 4-bromo-2-fluorobenzoic acid (1.0 g) in DCM (15 mL) were added HATU (2.26 g), methoxy(methyl)amine hydrochloride (4.54 g), and TEA (1.9 mL). The reaction mixture was stirred at room temperature overnight and then diluted with DCM and water. The organic layer was separated, washed with saturated NaCl solution, and concentrated in vacuo. The residue was purified by silica gel column chromatography eluting with 17% ethyl acetate in petroleum ether to afford the title compound 4-bromo-2-fluoro-N-methoxy-N-methylbenzamide (1.166 g) as a yellow oil. $^1$H NMR (400 MHz, $CDCl_3$) δ 7.37-7.29 (m, 3H), 3.55 (s, 3H), 3.34 (s, 3H). $^{19}$F NMR (377 MHz, $CDCl_3$) δ −110.95. LCMS ESI (m/z): 262 $(M+H)^+$.

1-(4-bromo-2-fluorophenyl)ethan-1-one. To a solution of 4-bromo-2-fluoro-N-methoxy-N-methylbenzamide (1.116 g) in THE (10 mL) was added MeMgBr (7.1 mL, 3.0 M in $Et_2O$). The reaction was stirred at −78° C. for 2 hours and then stirred at room temperature overnight. The reaction was complete as monitored by LCMS. The reaction was diluted with DCM and water, the two phases were separated, and the aqueous phase was extracted with DCM (30 mL×3). The combined organic phases were dried over $Na_2SO_4$, filtered, and concentrated to give a residue, which was purified by column chromatography on silica gel (PE:EA=10:1) to afford 1-(4-bromo-2-fluorophenyl)ethan-1-one (667 mg) as a pale-yellow solid. $^1$H NMR (400 MHz, $CDCl_3$) δ 7.77 (t, J=8.0 Hz, 1H), 7.40-7.34 (m, 2H), 2.63 (d, J=4.0 Hz, 3H). $^{19}$F NMR (377 MHz, $CDCl_3$) δ −107.01 (s).

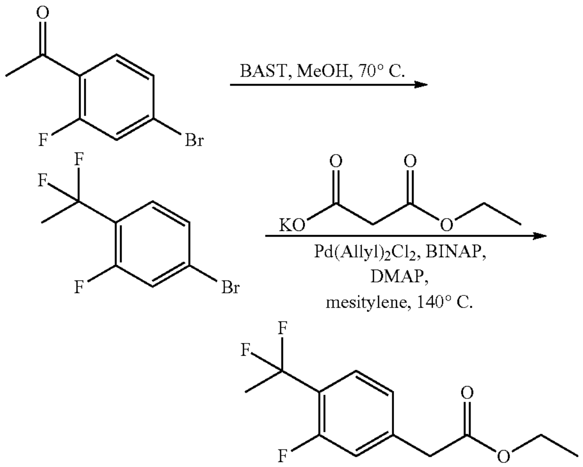

Synthesis of 4-bromo-1-(1,1-difluoroethyl)-2-fluorobenzene. To a solution of 1-(4-bromo-2-fluorophenyl)ethan-1-one (667 mg) in BAST (0.8 mL) was added two drops of methanol. Upon completion of the addition, the reaction mixture was placed under a nitrogen atmosphere and heated to 70° C. overnight. The reaction mixture was cooled to room temperature and quenched with 10 ml of water. The resulting mixture was extracted twice with 20 ml of ether. The combined ether phases were washed twice with water, twice with aqueous sodium bicarbonate, once with 10% aqueous citric acid, once with brine, and then dried over magnesium sulfate. The solvent was removed under reduced pressure and was purified by a gel silica column (3% EA in PE) to afford 4-bromo-1-(1,1-difluoroethyl)-2-fluorobenzene (294 mg) as a colorless oil. $^1$H NMR (400 MHz, $CDCl_3$) δ 7.44-7.40 (m, 1H), 7.36-7.31 (m, 2H), 2.02-1.93 (m, 3H). $^{19}$F NMR (377 MHz, $CDCl_3$) δ −87.13, −112.27.

Ethyl 2-(4-(1,1-difluoroethyl)-3-fluorophenyl)acetate. To a solution of 4-bromo-1-(1,1-difluoroethyl)-2-fluorobenzene (290 mg) in mesitylene (5 mL) were added BINAP (45 mg), 1-ethyl 3-potassium propanedioate (310 mg), DMAP (148 mg, 1.21 mmol) and diallylpalladium dichloride (1.6 mg). The reaction was charged with $N_2$ and stirred at 120° C. overnight. The reaction was complete as monitored by LCMS. The reaction was diluted with EA and water, the two phases were separated, and the aqueous phase was extracted with DCM (10 mL×3). The combined organic phases were dried over $Na_2SO_4$, filtered, and concentrated to give a residue, which was purified by silica gel column chromatography (4% ethyl acetate in petroleum ether) to give ethyl 2-(4-(1,1-difluoroethyl)-3-fluorophenyl)acetate (121 mg) as a pale-yellow oil. H NMR (400 MHz, $CDCl_3$) δ 7.451-7.47 (m, 1H), 7.11-1.07 (m, 2H), 4.17 (q, J=8.0 Hz, 2H), 3.63 (s, 2H), 2.03-1.94 (m, 3H), 1.27 (t, J=8.0 Hz, 3H). $^{19}$F NMR (377 MHz, $CDCl_3$) δ −86.88, −114.99.

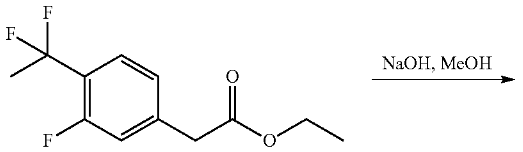

-continued

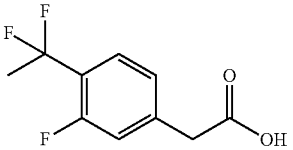

2-(4-(1,1-difluoroethyl)-3-fluorophenyl)acetic acid. To a 25 mL round-bottomed flask were added ethyl 2-(4-(1,1-difluoroethyl)-3-fluorophenyl)acetate (121 mg), 1M aqueous NaOH (3 mL) and MeOH (3 mL). The reaction mixture was stirred at room temperature for 1 hour. Water (10 mL) was then added, and the aqueous layer was washed with EA. The aqueous layer was acidified to pH<3 with 1M aqueous HCl, and the mixture was extracted with EA. The combined organic phases were washed with saturated NaCl, dried with $Na_2SO_4$, filtered, and concentrated to product 2-(4-(1,1-difluoroethyl)-3-fluorophenyl)acetic acid (100 mg) as a yellow solid. LCMS ESI (m/z): 217 $(M-H)^+$.

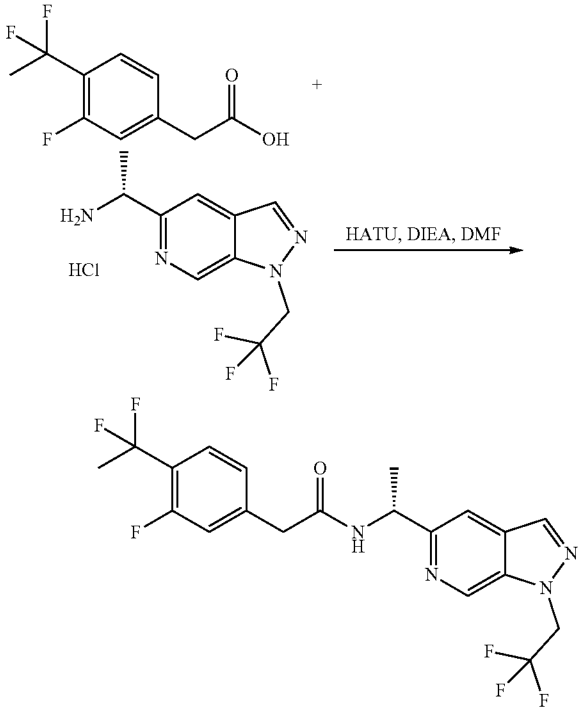

(R)-2-(4-(1,1-difluoroethyl)-3-fluorophenyl)-N-(1-(1-(2,2,2-trifluoroethyl)-1H-pyrazolo[3,4-c]pyridin-5-yl)ethyl)acetamide. A solution of 2-(4-(1,1-difluoroethyl)-3-fluorophenyl)acetic acid (100 mg) and HATU (261 mg) in 2 mL DMF was stirred at room temperature for 15 min (Solution A). DIEA (0.46 mL) was added to (R)-1-(1-(2,2,2-trifluoroethyl)-1H-pyrazolo[3,4-c]pyridin-5-yl)ethan-1-amine hydrochloride (167 mg) in 2 mL DMF, and the pH of the solution higher than 7 by wet pH paper (Solution B). Solution B was added to Solution A, and the reaction was stirred at room temperature for 1 hour, at which time LCMS showed the reaction was complete. The reaction was diluted with EA and water. The two phases were separated, and the aqueous phase was extracted with EA (10 mL×2). The combined organic phases were dried over $Na_2SO_4$, filtered, and concentrated under vacuo. The residue was purified by prep-HPLC (Column: AZZOTA C18 30*250 mm*10 um; Mobile phase: from 30% to 95% MeOH with $H_2O$ (0.1% FA); flow rate: 20 mL/min; wave length: 220 nm/254 nm) to give (R)-2-(4-(1,1-difluoroethyl)-3-fluorophenyl)-N-(1-(1-(2,2,2-trifluoroethyl)-1H-pyrazolo[3,4-c]pyridin-5-yl)ethyl)acetamide (59 mg) as a white solid. 1H NMR (400 MHz, $CDCl_3$) δ 8.91 (s, 1H), 8.12 (s, 1H), 7.60 (s, 1H), 7.48 (t, J=8.0 Hz, 1H), 7.09 (t, J=8.0 Hz, 2H), 6.83 (d, J=4.0 Hz, 1H), 5.31-5.24 (m, 1H), 5.09-5.03 (m, 2H), 3.59 (s, 2H), 1.98 (t, J=16.0 Hz, 3H), 1.51 (d, J=4.0 Hz, 3H). $^{19}F$ NMR (377 MHz, $CDCl_3$) δ −70.78, −86.83, −114.72. LC/MS ESI (m/z): 445 $[M+H]^+$.

Example 39. (R)-2-(6-cyclopropyl-5-fluoropyridin-3-yl)-N-(1-(1-(2,2,2-trifluoroethyl)-1H-pyrazolo[3,4-c]pyridin-5-yl)ethyl)acetamide

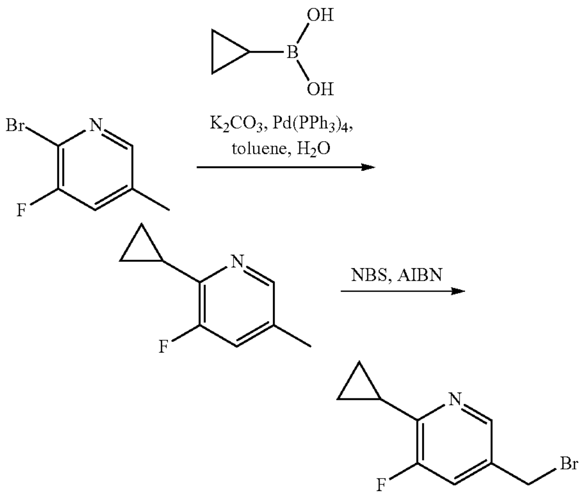

2-cyclopropyl-3-fluoro-5-methylpyridine. To a solution of 2-bromo-3-fluoro-5-methylpyridine (3.75 g) in toluene: $H_2O$ (50 mL, 10:1) were added $K_3PO_4$ (12.57 g), cyclopropylboronic acid (2.54 g) and $Pd(PPh_3)_4$ (2.28 g). The reaction was stirred at 110° C. under $N_2$ overnight, and the reaction was diluted with EA and water. The organic layer was separated, washed with brine, dried over $Na_2SO_4$, and concentrated in vacuo. The residue was then purified by silica gel column chromatography to give 2-cyclopropyl-3-fluoro-5-methylpyridine (2.2 g) as a colorless oil: LCMS ESI (m/z): 152 $(M+H)^+$. $^1H$ NMR (400 MHz, $CDCl_3$) δ 8.06 (s, 1H), 7.13-7.06 (m, 1H), 2.30-2.24 (m, 4H), 1.12-0.92 (m, 4H). $^{19}F$ NMR (377 MHz, $CDCl_3$) δ −131.54 (s).

5-(bromomethyl)-2-cyclopropyl-3-fluoropyridine. To a solution of 2-cyclopropyl-3-fluoro-5-methylpyridine (2.2 g) in $CCl_4$ (55 mL) were added NBS (3.63 g) and AIBN (0.22 mL), and the reaction was stirred at 80° C. under nitrogen overnight. The reaction was diluted with DCM and water, and the organic layer was separated, washed with brine, dried over $Na_2SO_4$, and concentrated in vacuo at 30° C. The reaction was complete monitored by LCMS. The residue was purified by silica gel column chromatography to give 5-(bromomethyl)-2-cyclopropyl-3-fluoropyridine (897 mg) as a purple oil. LCMS ESI (m/z): 230.0 $(M+H)^+$. $^1H$ NMR (400 MHz, $CDCl_3$) δ 8.23 (s, 1H), 7.36-7.29 (m, 1H), 4.43 (s, 2H), 2.36-2.29 (m, 1H), 1.16-1.00 (m, 4H). $^{19}F$ NMR (377 MHz, $CDCl_3$) δ −129.72 (s).

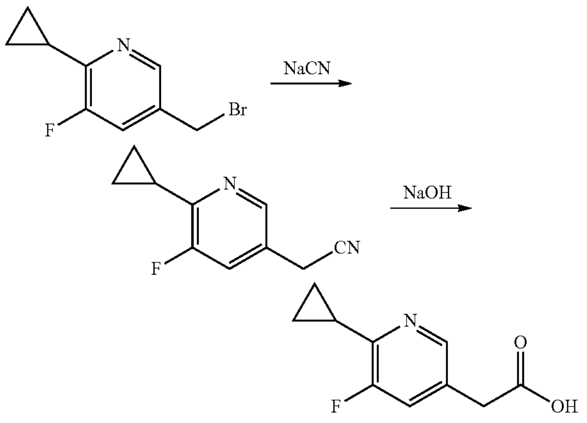

2-(6-cyclopropyl-5-fluoropyridin-3-yl)acetonitrile. To a solution of 5-(bromomethyl)-2-cyclopropyl-3-fluoropyridine (897 mg) in DMF (5 mL) were added NaCN (385 mg), and the reaction was stirred at RT for 30 min. The reaction was complete as monitored by LCMS. The reaction was then diluted with DCM and water, and the organic layer was separated, washed with brine, dried over $Na_2SO_4$, and concentrated in vacuo. The residue was purified by silica gel column chromatography to give 2-(6-cyclopropyl-5-fluoropyridin-3-yl)acetonitrile (513 mg) as a yellow oil: LCMS ESI (m/z): 177 $(M+H)^+$. 1H NMR (400 MHz, $CDCl_3$) δ 8.23-8.14 (m, 1H), 7.36-7.28 (m, 1H), 3.73 (s, 2H), 2.40-2.25 (m, 1H), 1.15-1.09 (m, 2H), 1.09-1.01 (m, 2H). $^{19}F$ NMR (377 MHz, $CDCl_3$) δ −128.87 (s).

2-(6-cyclopropyl-5-fluoropyridin-3-yl)acetic acid. 2-(6-cyclopropyl-5-fluoropyridin-3-yl)acetonitrile (589 mg) was dissolved in 2M NaOH (5 mL) and stirred at 100° C. for 1 hr. The reaction solution was acidified to pH=1 with 2 M HCl and extracted with EA (50 mL×3). The organic layer was concentrated to give the 2-(6-cyclopropyl-5-fluoropyridin-3-yl)acetic acid as yellow solid (553 mg) and used in the next step without further purification. LCMS ESI (m/z): 196 $(M+H)^+$. $^1H$ NMR (400 MHz, DMSO-d6) δ 12.53 (s, 1H), 8.15 (s, 1H), 7.56-7.48 (m, 1H), 3.63 (s, 2H), 2.32-2.21 (m, 1H), 1.04-0.93 (m, 4H). $^{19}F$ NMR (377 MHz, DMSO) δ −131.95 (s).

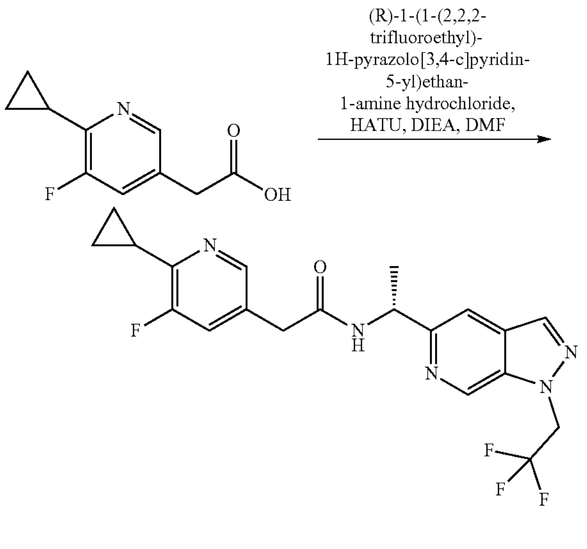

(R)-2-(6-cyclopropyl-5-fluoropyridin-3-yl)-N-(1-(1-(2,2,2-trifluoroethyl)-1H-pyrazolo[3,4-c]pyridin-5-yl)ethyl)acetamide. To a solution of (R)-1-(1-(2,2,2-trifluoroethyl)-1H-pyrazolo[3,4-c]pyridin-5-yl)ethan-1-amine hydrochloride (206 mg) in anhydrous DMF (1.5 mL) was added DIEA (1 mL) to provide Solution A. To a solution of 2-(6-cyclopropyl-5-fluoropyridin-3-yl)acetic acid (110 mg) in anhydrous DMF (1.5 mL) was added HATU (236 mg), and the mixture was stirred for 15 min at RT to provide Solution B. Solution A was added to the Solution B, and the reaction was stirred at RT for 1 hr. The mixture was then diluted with EA and water, and the organic layer was washed with brine, dried over $Na_2SO_4$ and concentrated under vacuo. The residue was purified by prep-HPLC (Column: AZZOTA C18 30*250 mm*10 um; Mobile phase: from 20% to 95% MeCN with $H_2O$ (0.1% FA); flow rate: 20 mL/min; wave length: 220 nm/254 nm) to give (R)-2-(6-cyclopropyl-5-fluoropyridin-3-yl)-N-(1-(1-(2,2,2-trifluoroethyl)-1H-pyrazolo[3,4-c]pyridin-5-yl)ethyl)acetamide (145 mg) as a white solid. LCMS ESI (m/z): 422 $(M+H)^+$. $^1H$ NMR (400 MHz, $CDCl_3$) δ 8.90 (s, 1H), 8.11 (d, J=6.0 Hz, 2H), 7.56 (s, 1H), 7.30-7.27 (m, 1H), 6.74 (d, J=7.6 Hz, 1H), 5.30-5.23 (m, 1H), 5.08-5.02 (m, 2H), 3.52 (s, 2H), 2.31-2.27 (m, 1H), 1.49 (d, J=6.4 Hz, 3H), 1.12-0.97 (m, 4H). $^{19}F$ NMR (377 MHz, $CDCl_3$) δ −70.79 (s), −130.20 (s).

Example 40. (R)—N-(1-(1-(2,2-difluoropropyl)-1H-pyrazolo[3,4-c]pyridin-5-yl)ethyl)-2-(4-(trifluoromethyl)phenyl)acetamide

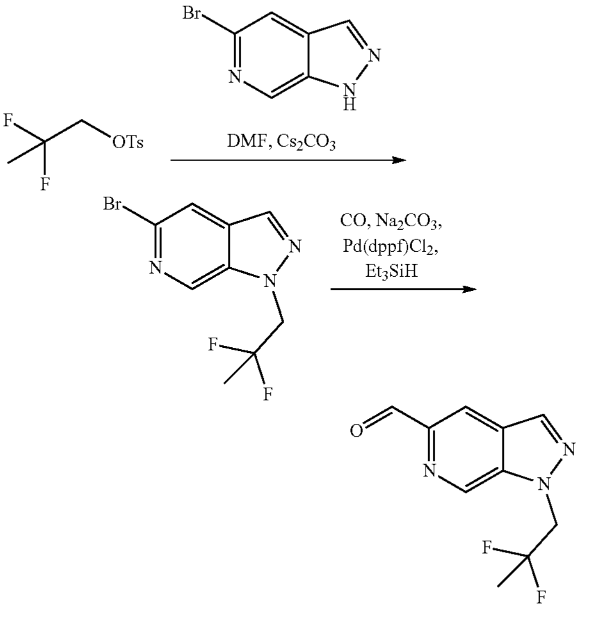

5-bromo-1-(2,2-difluoropropyl)-1H-pyrazolo[3,4-c]pyridine. To a solution of 2,2-difluoropropyl 4-methylbenzenesulfonate (3.0 g,) in DMF (30 mL) were added 5-bromo-1H-pyrazolo[3,4-c]pyridine (2.19 g) and $Cs_2CO_3$ (3.61 g). The reaction was stirred at 90° C. under nitrogen overnight. The reaction was then diluted with EA and water, and the organic layer was separated, washed with brine, dried over $Na_2SO_4$, and concentrated in vacuo. Then the residue was purified by silica gel column chromatography to give 5-bromo-1-(2,2-difluoropropyl)-1H-pyrazolo[3,4-c]pyridine (1.2 g) as a white solid. LCMS ESI (m/z): 276 $(M+H)^+$. $^1H$ NMR (400 MHz, $CDCl_3$) δ 8.79 (s, 1H), 8.05 (s, 1H), 7.84 (d, J=1.0 Hz, 1H), 4.79 (t, J=12.2 Hz, 2H), 1.63 (t, J=18.8 Hz, 3H). $^{19}F$ NMR (377 MHz, $CDCl_3$) δ −93.76 (s).

1-(2,2-difluoropropyl)-1H-pyrazolo[3,4-c]pyridine-5-carbaldehyde. To a solution of 5-bromo-1-(2,2-difluoropropyl)-1H-pyrazolo[3,4-c]pyridine (1.3 g) in anhydrous DMF (50 mL) were added $Na_2CO_3$ (0.75 g), Pd(dppf)$Cl_2$ (0.34 g) and $Et_3SiH$ (1.10 g). Then the reaction was stirred at 100° C. under CO (5 bar) overnight. The reaction was diluted with EA and water, and the organic layer was separated, washed with brine, dried over $Na_2SO_4$, and concentrated in vacuo. The residue was then purified by silica gel column chromatography to give 1-(2,2-difluoropropyl)-1H-pyrazolo[3,4-c]pyridine-5-carbaldehyde (828 mg) as yellow solid. LCMS ESI (m/z): 226 $(M+H)^+$. $^1H$ NMR (400 MHz, $CDCl_3$) δ 10.23 (s, 1H), 9.13 (s, 1H), 8.41 (d, J=1.2 Hz, 1H), 8.29 (s, 1H), 4.88 (t, J=12.2 Hz, 2H), 1.67 (t, J=18.8 Hz, 3H). $^{19}F$ NMR (377 MHz, $CDCl_3$) δ −93.83 (s).

(R)—N—((R)-1-(1-(2,2-difluoropropyl)-1H-pyrazolo[3,4-c]pyridin-5-yl)ethyl)-2-methylpropane-2-sulfinamide. To a solution of (R,E)-N-((1-(2,2-difluoropropyl)-1H-pyrazolo[3,4-c]pyridin-5-yl)methylene)-2-methylpropane-2-sulfinamide (1.4 g) in anhydrous THF (20 mL) was added MeMgBr (3.0 M in ether, 7.11 mL) dropwise at −78° C. under nitrogen. Then the reaction was stirred at −78° C. for 2 hr, and the reaction solution was then quenched with saturated ammonium chloride and extracted with EA. The organic layer was separated, washed with brine, dried over $Na_2SO_4$, and concentrated in vacuo. The residue was purified by silica gel column chromatography to give (R)—N—((R)-1-(1-(2,2-difluoropropyl)-1H-pyrazolo[3,4-c]pyridin-5-yl)ethyl)-2-methylpropane-2-sulfinamide (1.1 g) as a yellow oil. LCMS ESI (m/z): 264 $(M+H)^+$. $^1H$ NMR (400 MHz, $CDCl_3$) δ 8.97 (s, 1H), 8.06 (d, J=0.8 Hz, 1H), 7.62 (d, J=1.0 Hz, 1H), 4.79 (t, J=12.0 Hz, 2H), 4.72-4.66 (m, 1H), 1.65-1.58 (m, 6H), 1.25 (s, 9H). $^{19}F$ NMR (377 MHz, $CDCl_3$) δ −93.55 (d, J=5.6 Hz).

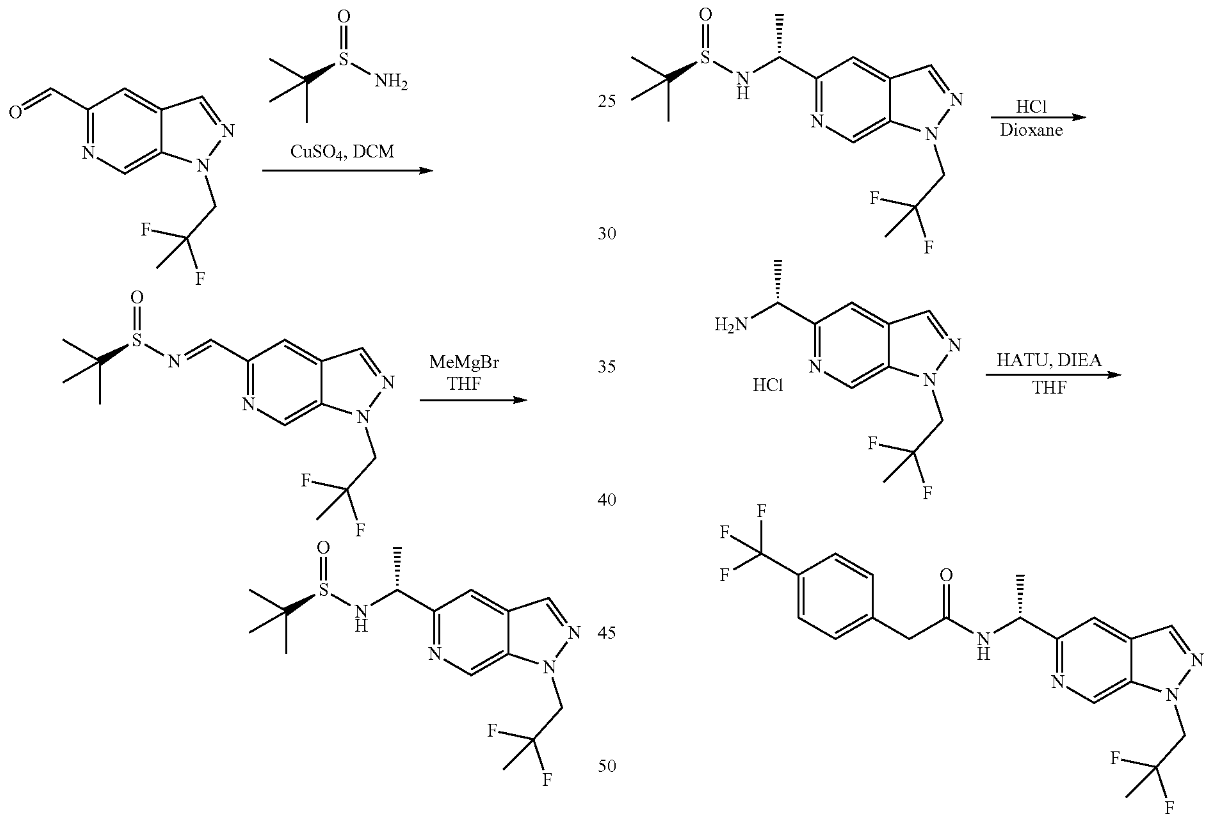

(R,E)-N-((1-(2,2-difluoropropyl)-1H-pyrazolo[3,4-c]pyridin-5-yl)methylene)-2-methylpropane-2-sulfinamide. To a solution of 1-(2,2-difluoropropyl)-1H-pyrazolo[3,4-c]pyridine-5-carbaldehyde (1.04 g) in anhydrous DCM (15 mL) were added $CuSO_4$ (2.21 g) and (R)-2-methylpropane-2-sulfinamide (0.73 g). Then the reaction mixture was stirred at RT overnight, and the solution was filtered through a pad of Celite and the filtrate concentrated. The residue was purified by silica gel column to give (R,E)-N-((1-(2,2-difluoropropyl)-1H-pyrazolo[3,4-c]pyridin-5-yl)methylene)-2-methylpropane-2-sulfinamide (1.4 g) as a white solid. LCMS ESI (m/z): 329 $(M+H)^+$. $^1H$ NMR (400 MHz, $CDCl_3$) δ 9.12 (s, 1H), 8.84 (s, 1H), 8.36 (d, J=1.0 Hz, 1H), 8.23 (s, 1H), 4.86 (t, J=12.2 Hz, 2H), 1.65 (t, J=18.8 Hz, 3H), 1.31 (s, 9H). $^{19}F$ NMR (377 MHz, $CDCl_3$) δ −93.82 (s).

(R)-1-(1-(2,2-difluoropropyl)-1H-pyrazolo[3,4-c]pyridin-5-yl)ethan-1-amine hydrochloride. To a solution of (R)—N—((R)-1-(1-(2,2-difluoropropyl)-1H-pyrazolo[3,4-c]pyridin-5-yl)ethyl)-2-methylpropane-2-sulfinamide (1.1 g) in dioxane (6 mL) was added HCl-dioxane (3 mL, 4N), and the reaction was stirred at rt for 1 hr. Then the mixture was concentrated, and the residue used directly in next step. LCMS ESI (m/z): 241 $(M+H)^+$.

(R)—N-(1-(1-(2,2-difluoropropyl)-1H-pyrazolo[3,4-c]pyridin-5-yl)ethyl)-2-(4-(trifluoromethyl)phenyl)acetamide. To a solution of (R)-1-(1-(2,2-difluoropropyl)-1H-pyrazolo[3,4-c]pyridin-5-yl)ethan-1-amine hydrochloride (264 mg) in anhydrous DMF was added DIEA (655 mg) to provide Solution A. To a solution of 2-(4-(trifluoromethyl)phenyl)

acetic acid (173 mg) in anhydrous DMF was added HATU (354 mg) and the mixture was stirred 15 min at RT to provide Solution B. Solution A was then added to the Solution B, and the mixture was stirred at RT for 1 hr. The reaction was diluted with EA and water, and the organic layer was washed brine, dried over $Na_2SO_4$ and concentrated in vacuo. The residue was purified by prep-HPLC (Column: YMC-Actus Triart C18 150*20 mm*5 um; Mobile phase: from 30% to 95% MeCN with $H_2O$ (0.1% $NH_3H_2O$); flow rate: 25 mL/min; wave length: 220 nm/254 nm) to give (R)—N-(1-(1-(2,2-difluoropropyl)-1H-pyrazolo[3,4-c]pyridin-5-yl)ethyl)-2-(4-(trifluoromethyl)phenyl)acetamide (188 mg) as a white solid. LCMS ESI (m/z): 427 $(M+H)^+$. $^1H$ NMR (400 MHz, DMSO-d6) δ 9.15 (s, 1H), 8.67 (d, J=8.0 Hz, 1H), 8.22 (s, 1H), 7.68-7.60 (m, 3H), 7.49 (d, J=8.0 Hz, 2H), 5.19-5.00 (m, 3H), 3.62 (s, 2H), 1.68 (t, J=19.2 Hz, 3H), 1.44 (d, J=7.2 Hz, 3H). $^{19}F$ NMR (377 MHz, $CDCl_3$) δ −62.53 (s), −93.63 (s).

Example 41. (R)-2-(4-(1,1-difluoroethyl)phenyl)-N-(1-(1-(2,2-difluoropropyl)-1H-pyrazolo[3,4-c]pyridin-5-yl)ethyl)acetamide

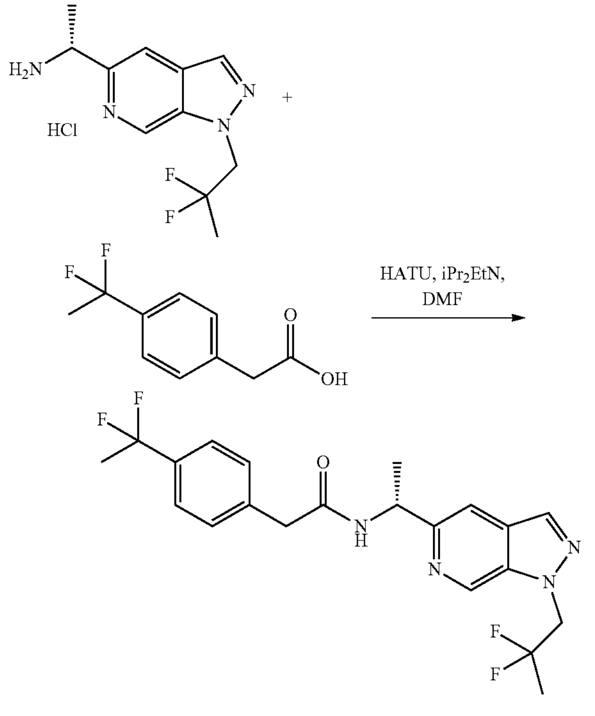

To a solution of (R)-1-(1-(2,2-difluoropropyl)-1H-pyrazolo[3,4-c]pyridin-5-yl)ethan-1-amine hydrochloride (359 mg) in anhydrous DMF was added DIEA (0.63 mL) to provide Solution A. To a solution of 2-(4-(1,1-difluoroethyl)phenyl)acetic acid (230 mg) in anhydrous DMF (3 mL) was added HATU (481 mg), and the mixture was stirred 15 min at RT to provide Solution B. Then Solution A was added to the Solution B, and the reaction was stirred at RT for 1 hr. The reaction was diluted with EA and water, and the organic layer was washed with brine, dried over $Na_2SO_4$ and concentrated in vacuo. The residue was purified by prep-HPLC (Column: AZZOTA C18 GEMINI 250*20 mm 10 um; Mobile phase: from 20% to 95% MeCN with $H_2O$ (0.1% $NH_3H_2O$); flow rate: 15 mL/min; wave length: 220 nm/254 nm) to give (R)-2-(4-(1,1-difluoroethyl)phenyl)-N-(1-(1-(2,2-difluoropropyl)-1H-pyrazolo[3,4-c]pyridin-5-yl)ethyl)acetamide (207 mg) as a white solid. LCMS ESI (m/z): 423 $(M+H)^+$. $^1H$ NMR (400 MHz, $CDCl_3$) δ 8.89 (s, 1H), 8.04 (s, 1H), 7.51-7.46 (m, 3H), 7.33 (d, J=8.2 Hz, 2H), 6.69 (d, J=8.0 Hz, 1H), 5.29-5.22 (m, 1H), 4.79 (t, J=12.0 Hz, 2H), 3.60 (s, 2H), 1.91 (t, J=18.4 Hz, 3H), 1.62-1.57 (m, 3H), 1.47 (d, J=6.8 Hz, 3H). $^{19}F$ NMR (377 MHz, $CDCl_3$) δ −87.38 (s), −93.61 (s).

Example 42. (R)-2-(3-fluoro-4-(trifluoromethyl)phenyl)-N-(1-(1-(2,2,2-trifluoroethyl)-1H-pyrazolo[3,4-c]pyridin-5-yl)ethyl)acetamide

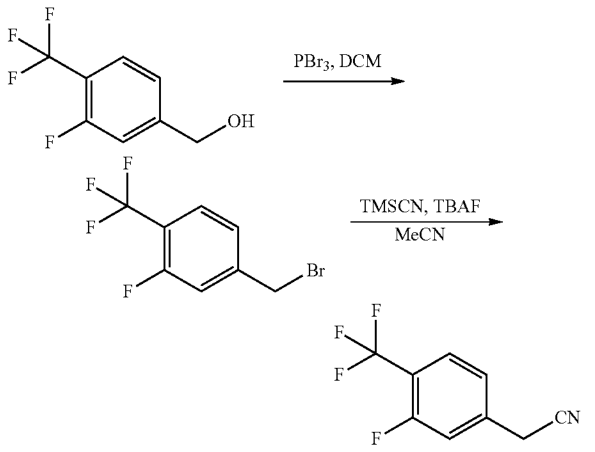

4-(bromomethyl)-2-fluoro-1-(trifluoromethyl)benzene. To a solution of (3-fluoro-4-(trifluoromethyl)phenyl)methanol (1 g) in DCM (10 mL) was added $PBr_3$ (1 mL) at 0° C., and the reaction was stirred at RT for 30 min. The reaction was diluted with EA and water. The organic layer was separated, washed with brine, and concentrated under vacuo. The residue was then purified by silica gel column chromatography to give 4-(bromomethyl)-2-fluoro-1-(trifluoromethyl)benzene (542 mg) as a colorless oil. LCMS ESI (m/z): no MS signal. $^1H$ NMR (400 MHz, $CDCl_3$) δ 7.58 (t, J=7.8 Hz, 1H), 7.26 (t, J=7.4 Hz, 2H), 4.45 (s, 2H). $^{19}F$ NMR (377 MHz, $CDCl_3$) δ −61.43, −113.43.

Synthesis of 2-(3-fluoro-4-(trifluoromethyl)phenyl)acetonitrile. To a solution of 4-(bromomethyl)-2-fluoro-1-(trifluoromethyl)benzene (542 mg) and TMSCN (0.32 mL) in anhydrous MeCN (5 mL) was added TBAF (2.5 mL, 1M in THF). The reaction mixture was stirred at RT for 18 hr and then diluted with DCM and water. The organic layer was separated, washed with brine, and concentrated in vacuo. Then the residue was purified by silica gel column chromatography, to give 2-(3-fluoro-4-(trifluoromethyl)phenyl)acetonitrile (262 mg) as a colorless oil. LCMS ESI (m/z): no MS signal. $^1H$ NMR (400 MHz, DMSO-d6) δ 7.85 (t, J=8.0 Hz, 1H), 7.53 (d, J=11.8 Hz, 1H), 7.44 (d, J=8.2 Hz, 1H), 4.22 (s, 2H). $^{19}F$ NMR (377 MHz, DMSO) δ −59.99, −115.24.

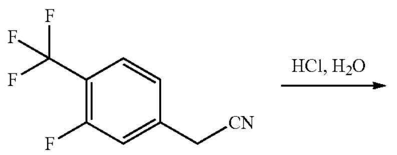

-continued

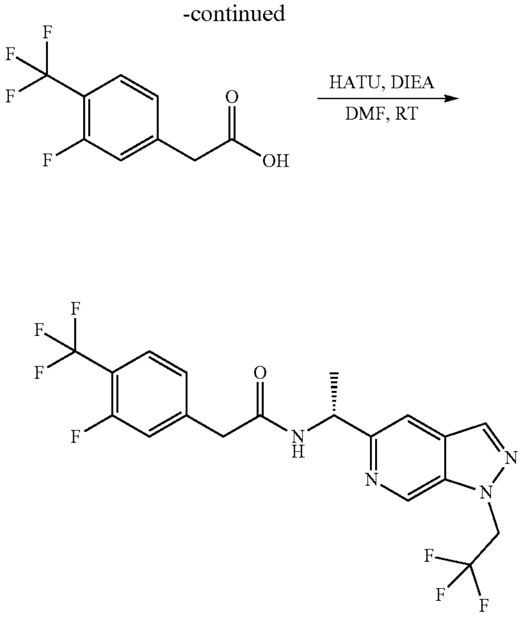

2-(3-fluoro-4-(trifluoromethyl)phenyl)acetic acid. 2-(3-fluoro-4-(trifluoromethyl)phenyl)acetonitrile (262 mg) was dissolved in conc. Hydrogen chloride (4.0 mL) and stirred at 100° C. for 1 h. The reaction solution was diluted with water and extracted with EA. The organic layer was separated and concentrated in vacuo to give 2-(3-fluoro-4-(trifluoromethyl)phenyl)acetic acid as a colorless oil (149 mg), which was used in the next step without further purification. LCMS ESI (m/z): 443 (2M−H). $^{1}$H NMR (400 MHz, DMSO-d6) δ 7.78 (t, J=8.0 Hz, 1H), 7.50 (d, J=12.2 Hz, 1H), 7.38 (d, J=8.0 Hz, 1H), 3.81 (s, 2H).

(R)-2-(3-fluoro-4-(trifluoromethyl)phenyl)-N-(1-(1-(2,2,2-trifluoroethyl)-1H-pyrazolo[3,4-c]pyridin-5-yl)ethyl)acetamide. To a solution of (R)-1-(1-(2,2,2-trifluoroethyl)-1H-pyrazolo[3,4-c]pyridin-5-yl)ethan-1-amine hydrochloride (196 mg) in anhydrous DMF was added DIPEA (0.53 mL) to provide Solution A. To a solution of 2-(3-fluoro-4-(trifluoromethyl)phenyl)acetic acid (119 mg) in anhydrous DMF was added HATU (224 mg), and the mixture was stirred for 15 min at RT to provide Solution B. Solution A was then added to the Solution B, and the reaction was stirred at RT for 1 hr. The reaction was diluted with EA and water, and the organic layer was washed with brine, dried over $Na_2SO_4$ and concentrated in vacuo. Then the residue was purified by silica gel column chromatography and prep-HPLC (Column: AZZOTA C18 30*250 mm*10 um; Mobile phase: from 25% to 95% MeCN with $H_2O$ (1% FA); flow rate: 28 mL/min; wave length: 220 nm/254 nm), to give (R)-2-(3-fluoro-4-(trifluoromethyl)phenyl)-N-(1-(1-(2,2,2-trifluoroethyl)-1H-pyrazolo[3,4-c]pyridin-5-yl)ethyl)acetamide (119 mg) as white solid. LCMS ESI (m/z): 449 $(M+H)^+$. $^{1}$H NMR (400 MHz, DMSO-d6) δ 9.25 (s, 1H), 8.71 (d, J=7.6 Hz, 1H), 8.31 (s, 1H), 7.72-7.68 (m, 2H), 7.40-7.29 (m, 2H), 5.66-5.59 (m, 2H), 5.10-5.07 (m, 1H), 3.64 (s, 2H), 1.45 (d, J=6.8 Hz, 3H). $^{19}$F NMR (377 MHz, DMSO) δ −59.72, −69.80, −116.73.

Example 43. (R)-2-(3-chloro-4-(trifluoromethyl)phenyl)-N-(1-(1-(2,2,2-trifluoroethyl)-1H-pyrazolo[3,4-c]pyridin-5-yl)ethyl)acetamide

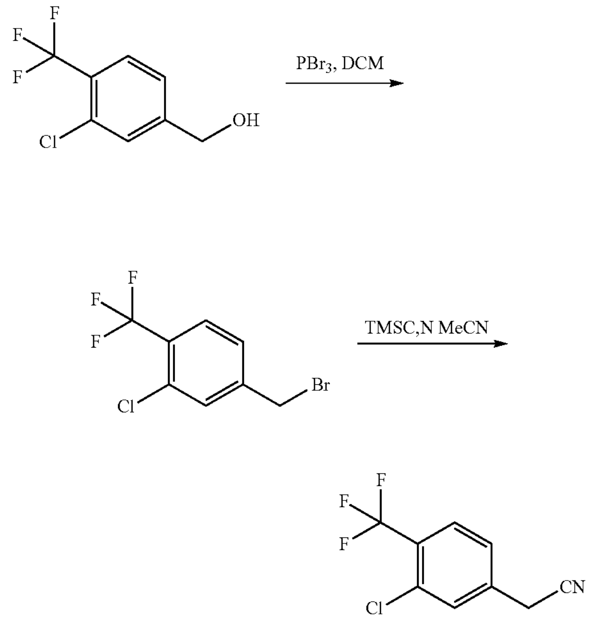

4-(bromomethyl)-2-chloro-1-(trifluoromethyl)benzene. To a solution of [3-fluoro-4-(trifluoromethyl)phenyl]methanol (1 g) in DCM (4 mL) was added $PBr_3$ (0.9 mL) at 0° C., and the reaction was stirred at RT for 30 min. The reaction was diluted with EA and water, and the organic layer was separated, washed with sat. brine, and concentrated in vacuo. The residue was then purified by silica gel column chromatography to give 4-(bromomethyl)-2-chloro-1-(trifluoromethyl)benzene as a colorless oil (690 mg). LCMS ESI (m/z): no MS signal. $^{1}$H NMR (400 MHz, DMSO-d6) δ 7.89-7.82 (m, 2H), 7.64 (d, J=8.0 Hz, 1H), 4.77 (s, 2H). $^{19}$F NMR (377 MHz, DMSO-d6) δ −61.16 (s).

Synthesis of 2-(3-chloro-4-(trifluoromethyl)phenyl)acetonitrile. 4-(bromomethyl)-2-chloro-1-(trifluoromethyl)benzene (700 mg) and TMSCN (0.384 mL) were dissolved in anhydrous MeCN (5 mL) and stirred at RT for 30 min. TBAF (3 mL, 1M in THF) was then added, and the reaction was stirred at RT for 3 h. The reaction was diluted with DCM and water and the organic layer was separated, washed with brine, and concentrated under vacuo. The residue was purified by silica gel column chromatography to give 2-(3-chloro-4-(trifluoromethyl)phenyl)acetonitrile (292 mg) as a colorless oil. LCMS ESI (m/z): 218 (M−H). $^{1}$H NMR (400 MHz, DMSO-d6) δ 7.92 (d, J=8.2 Hz, 1H), 7.74 (s, 1H), 7.57 (d, J=8.2 Hz, 1H), 4.21 (s, 2H). $^{19}$F NMR (377 MHz, DMSO-d6) δ −61.17 (s).

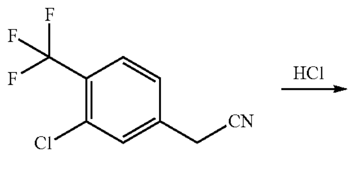

-continued

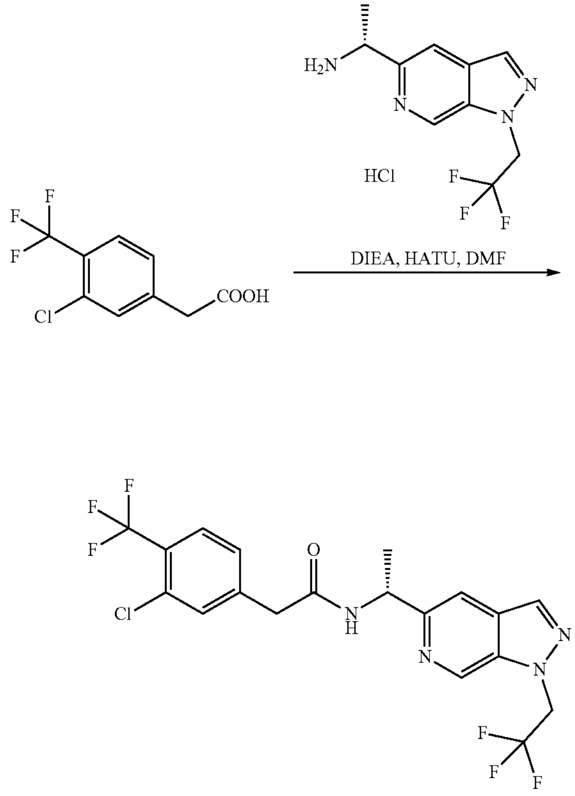

2-(3-chloro-4-(trifluoromethyl)phenyl)acetic acid. 2-(3-chloro-4-(trifluoromethyl)phenyl)acetonitrile (290 mg) was dissolved in conc. hydrochloric acid (2.5 mL) and stirred at 100° C. for 1 hr. The reaction solution was diluted with water and extracted with EA, and the organic layer was separated, and concentrated under vacuo to give 2-(3-chloro-4-(trifluoromethyl)phenyl)acetic acid as a colorless oil (250 mg) without further purification. $^1H$ NMR (400 MHz, DMSO-d6) δ 12.46 (s, 1H), 7.81 (d, J=8.0 Hz, 1H), 7.66 (s, 1H), 7.46 (d, J=8.0 Hz, 1H), 3.75 (s, 2H).

(R)-2-(3-chloro-4-(trifluoromethyl)phenyl)-N-(1-(1-(2,2,2-trifluoroethyl)-1H-pyrazolo[3,4-c]pyridin-5-yl)ethyl)acetamide. To a solution of (R)-1-(1-(2,2,2-trifluoroethyl)-1H-pyrazolo[3,4-c]pyridin-5-yl)ethan-1-amine hydrochloride (353 mg) in anhydrous DMF was added DIEA (0.96 mL) to provide Solution A. To a solution of 2-(3-chloro-4-(trifluoromethyl)phenyl)acetic acid (230 mg) in anhydrous DMF was added HATU (403 mg), and the mixture was stirred 15 min at RT to provide Solution B. Solution A was then added to the Solution B, and the reaction was stirred at RT for 2 h. The reaction was diluted with EA and water, and the organic layer was separated, washed with brine, dried over $Na_2SO_4$, and concentrated in vacuo. The residue was purified by silica gel column chromatography (Column: AZZOTA C18 GEMINI 250*20 mm 10 um; Mobile phase: from 20% to 95% MeCN with $H_2O$ (0.1% FA); flow rate: 15 mL/min; wave length: 220 nm/254 nm), to give (R)-2-(3-chloro-4-(trifluoromethyl)phenyl)-N-(1-(1-(2,2,2-trifluoroethyl)-1H-pyrazolo[3,4-c]pyridin-5-yl)ethyl)acetamide (347 mg) as a white solid. LCMS ESI (m/z): 465 $(M+H)^+$. $^1H$ NMR (400 MHz, $CDCl_3$) δ 8.90 (s, 1H), 8.11 (s, 1H), 7.63 (d, J=8.0 Hz, 1H), 7.58 (s, 1H), 7.44 (s, 1H), 7.29 (d, J=8.6 Hz, 1H), 6.81 (d, J=7.6 Hz, 1H), 5.31-5.23 (m, 1H), 5.08-5.02 (m, 2H), 3.59 (s, 2H), 1.51 (d, J=6.8 Hz, 3H). $^{19}F$ NMR (377 MHz, $CDCl_3$) δ −62.46 (s), −70.79 (s).

Example 44. (R)—N-(1-(1-(2,2,2-trifluoroethyl)-1H-pyrazolo[3,4-c]pyridin-5-yl)ethyl)-2-(4-(1-(trifluoromethyl)cyclopropyl)phenyl)acetamide

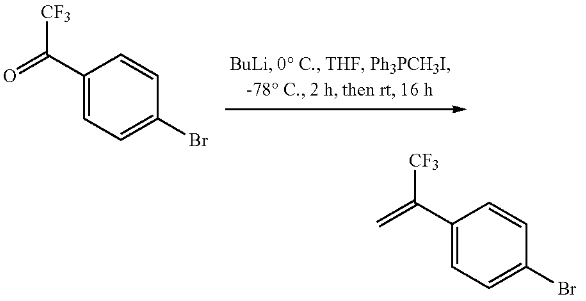

Synthesis of 1-bromo-4-(3,3,3-trifluoroprop-1-en-2-yl)benzene. To a flame dried flask with methyl triphenylphosphonium iodine $Ph_3PCH_3I$ (15.2 g, 0.04 mol) was added THF (60 mL) under an argon atmosphere. Cool the resulting suspension to 0° C. and add n-BuLi (15.6 mL, 2.5 N) dropwise. The mixture was stirred at 0° C. for 10 minutes, then cooled to −78° C. 1-(4-bromophenyl)-2,2,2-trifluoroethan-1-one (8.2 g, 0.03 mol) in THF (10 mL) was added and the mixture was stirred at −78° C. for 30 min and then stirred at rt overnight. It was quenched with sat. $NH_4Cl$ and extracted with PE (300 mL). The organic layer was washed with sat. NaCl, dried with anhydrous $Na_2SO_4$, filtered and the filtrate was concentrated. The residue was purified by column chromatography on silica gel (PE:EA=10:1) to give 1-bromo-4-(3,3,3-trifluoroprop-1-en-2-yl)benzene as a colorless oil (6.1 g, 74%). $^1$HNMR (400 MHz, $CDCl_3$): 7.53-7.50 (m, 2H), 7.31 (d, J=8.4 Hz, 2H), 5.97 (d, J=1.2 Hz, 1H), 5.77-5.76 (m, 1H) ppm. $^{19}$FNMR (376.48 MHz, $CDCl_3$): −64.9 ppm.

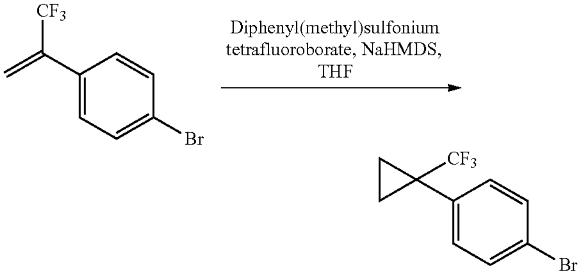

1-bromo-4-(1-(trifluoromethyl)cyclopropyl)benzene. To an oven dried 100 mL vessel containing 1-bromo-4-(3,3,3-trifluoroprop-1-en-2-yl)benzene (2.2 g) and methyldiphenylsulfonium tetrafluoroborate (3.3 g) in anhydrous tetrahydrofuran (40 mL) was added sodium bis(trimethylsilyl) amide 2 M in THF (7.0 mL) at 0° C. under nitrogen. The reaction mixture was stirred at 0° C. for 10 min and then at room temperature for 1 h. To the solution was added 2.5 mL of methanol, and the crude mixture was concentrated in vacuo. The residue was dissolved in PE (100 mL) and washed with water (30 mL×2) and brine. The combined organic layers were collected and concentrated under vacuo. The crude residue was purified by automated flash chromatography on silica gel (PE 100%) to give 1-bromo-4-(1-(trifluoromethyl)cyclopropyl)benzene a colorless oil (1.4 g).

$^1$HNMR (400 MHz, CDCl3):7.49-7.44 (m, 2H), 7.34-7.32 (m, 2H), 1.42-1.33 (m, 2H), 1.02-0.95 (m, 2H). $^{19}$FNMR (376.48 MHz, $CDCl_3$): −70.2 ppm.

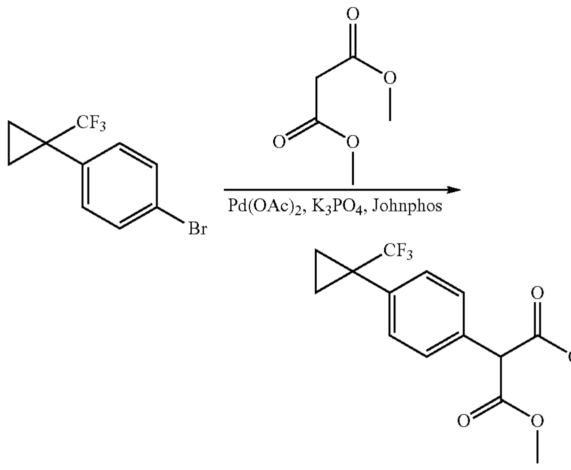

Dimethyl 2-(4-(1-(trifluoromethyl)cyclopropyl)phenyl) malonate. To a 100 mL round bottom flask containing diethylmalonate (0.77 g) and 1-bromo-4-(1-(trifluoromethyl)cyclopropyl)benzene (1.4 g) in PhMe (50 mL) were added $K_3PO_4$ (3.4 g), $Pd(OAc)_2$ (40 mg) and JohnPhos (CAS #224311-51-7, 90 mg). The reaction mixture was stirred at 125° C. for 4.0 h under $N_2$ and monitored by LCMS. After completion of the reaction, the crude mixture was filtered and concentrated in vacuo. The residue was purified by automated flash chromatography on silica gel eluting with 100% PE to 50% PE in EA to give the dimethyl 2-(4-(1-(trifluoromethyl)cyclopropyl)phenyl)malonate as a white solid (693 mg). LCMS ESI (m/z): 317 $(M+H)^+$. $^1$NMR (400 MHz, $CDCl_3$): 7.45 (d, J=8.4 Hz, 2H), 7.37 (d, J=8.0 Hz, 2H), 4.65 (s, 1H), 3.75 (s, 6H), 1.36-1.33 (m, 2H), 1.02 (m, 2H). $^{19}$FNMR (376.48 MHz, $CDCl_3$): −70.0 ppm.

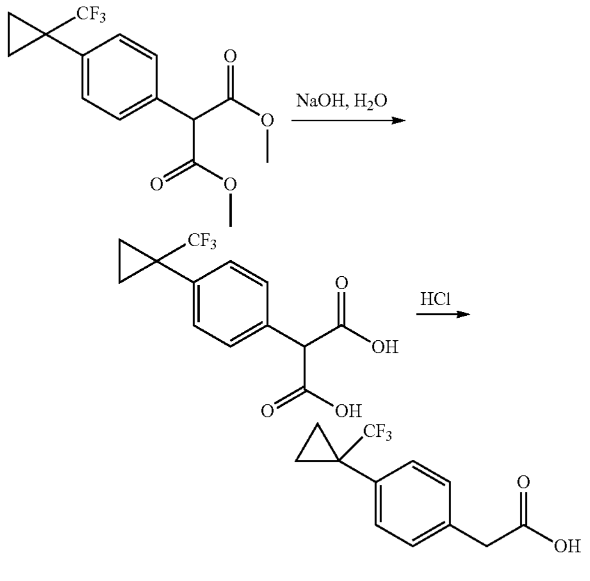

2-(4-(1-(trifluoromethyl)cyclopropyl)phenyl)malonic acid. To a solution of dimethyl 2-(4-(1-(trifluoromethyl) cyclopropyl)phenyl)malonate (540 mg) in toluene (10 mL) was added 8 mL of 32% NaOH. The mixture was stirred at 100° C. for 24 h. After cooling to rt, the aqueous layer was washed with toluene and adjusted pH=1 with 2 N HCl. The aqueous layer was extracted with EA and washed with brine. The combined organic layers were concentrated to give a yellow solid which was used in the next step without further purification (450 mg). LCMS ESI (m/z): 287 $(M-H)^+$;

2-(4-(1-(trifluoromethyl)cyclopropyl)phenyl)acetic acid. A mixture of 2-(4-(1-(trifluoromethyl)cyclopropyl)phenyl) malonic acid (400 mg) in toluene (6 mL) and 6 N HCl (6 mL) was stirred at 100° C. for 16 h. The organic layer was collected and washed with saturated brine and concentrated under vacuo to give 2-(4-(1-(trifluoromethyl)cyclopropyl) phenyl)acetic acid as a yellow solid (250 mg), which was used in the next step without further purification. $^1$NMR (400 MHz, $CD_3OD$): 7.41 (d, J=8.4 Hz, 2H), 7.27 (d, J=8.0 Hz, 2H), 3.60 (s, 2H), 1.34-1.31 (m, 2H), 1.06-1.03 (m, 2H) ppm. $^{19}$FNMR (376.48 MHz, $CD_3OD$): −71.5 ppm.

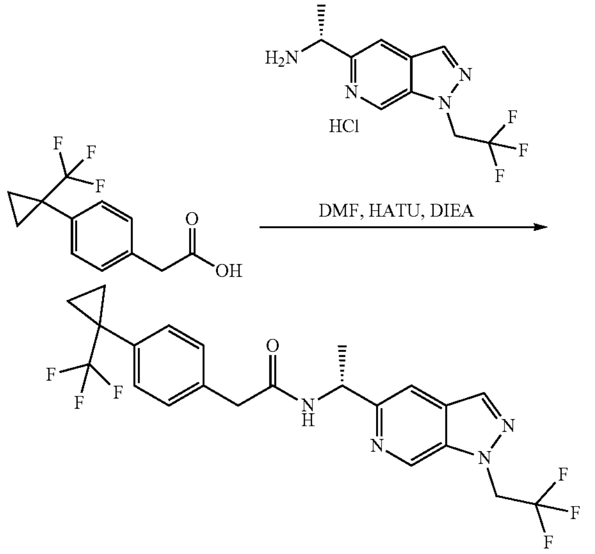

(R)—N-(1-(1-(2,2,2-trifluoroethyl)-1H-pyrazolo[3,4-c] pyridin-5-yl)ethyl)-2-(4-(1-(trifluoromethyl)cyclopropyl) phenyl)acetamide. To a solution of (R)-1-(1-(2,2,2-trifluoroethyl)-1H-pyrazolo[3,4-c]pyridin-5-yl)ethan-1-amine hydrochloride (272 mg) in anhydrous DMF (2.0 mL) was added DIEA (0.85 mL) to provide Solution A. To a mixture of 2-(4-(1-(trifluoromethyl)cyclopropyl)phenyl)acetic acid (209 mg) in DMF (1.5 mL) was added HATU (358 mg), and the reaction was stirred for 15 min at RT to provide Solution B. Solution A was added to Solution B, and the reaction was stirred at RT for 1 hr. The reaction was then diluted with EA and water, and the organic layer was washed with brine, dried over $Na_2SO_4$, and concentrated in vacuo. The residue was purified by silica gel column (Column: AZZOTA C18 GEMINI 250*20 mm 10 um; Mobile phase: from 20% to 95% MeCN with $H_2O$ (0.1% FA); flow rate: 15 mL/min; wave length: 220 nm/254 nm) to give (R)—N-(1-(1-(2,2,2-trifluoroethyl)-1H-pyrazolo[3,4-c]pyridin-5-yl)ethyl)-2-(4-(1-(trifluoromethyl)cyclopropyl)phenyl)acetamide (126 mg) as a white solid: LCMS ESI (m/z): 471 $(M+H)^+$. $^1$H NMR (400 MHz, $CDCl_3$) δ 8.84 (s, 1H), 8.11 (s, 1H), 7.57 (s, 1H), 7.41 (d, J=8.0 Hz, 2H), 7.24 (d, J=8.0 Hz, 2H), 6.71 (d, J=7.6 Hz, 1H), 5.27-5.24 (m, 1H), 5.07-5.01 (m, 2H), 3.58 (s, 2H), 1.49 (d, J=6.8 Hz, 3H), 1.38-1.31 (m, 2H), 1.01 (s, 2H). $^{19}$F NMR (377 MHz, $CDCl_3$) δ −70.11 (s), −70.82 (s).

Example 45. (R)—N-(1-(1-(2,2,2-trifluoroethyl)-1H-pyrazolo[3,4-c]pyridin-5-yl)propyl)-2-(4-(trifluoromethyl)phenyl)acetamide

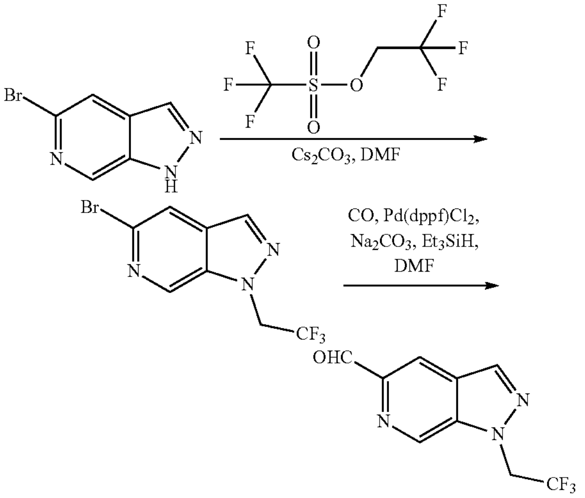

5-bromo-1-(2,2,2-trifluoroethyl)-1H-pyrazolo[3,4-c]pyridine. To a solution of 5-bromo-1H-pyrazolo[3,4-c]pyridine (10 g) in DMF (50 mL) were added 2,2,2-trifluoroethyl trifluoromethanesulfonate (8.7 mL) and $Cs_2CO_3$ (19.7 g). The reaction was stirred at rt overnight, and the reaction was then diluted with EA and water. The organic layer was separated, washed with saturated NaCl solution, and concentrated in vacuo. The residue was purified by silica gel column chromatography, eluting with 40% ethyl acetate in petroleum ether to afford the title compound 5-bromo-1-(2,2,2-trifluoroethyl)-1H-pyrazolo[3,4-c]pyridine (7.5 g) as a white solid. LC/MS ESI (m/z): 280 $[M+H]^+$. $^1$H NMR (400 MHz, $CDCl_3$) δ 8.78 (s, 1H), 8.11 (s, 1H), 7.87 (s, 1H), 5.05 (q, J=8.2 Hz, 2H). $^{19}$F NMR (377 MHz, $CDCl_3$) δ −70.79 (s).

1-(2,2,2-trifluoroethyl)-1H-pyrazolo[3,4-c]pyridine-5-carbaldehyde. To a solution of 5-bromo-1-(2,2,2-trifluoroethyl)-1H-pyrazolo[3,4-c]pyridine (5 g) in DMF (28 mL) were added $Na_2CO3$ (2.84 g), Pd(dppf)$Cl_2$ (0.52 g) and $Et_3SiH$ (5.8 mL). The reaction was then stirred at 80° C. under carbon monoxide for 3 hr. The reaction was diluted with EA and water, and the organic layer was separated, washed with brine, and concentrated in vacuo. Then the residue was purified by silica gel column chromatography to give 1-(2,2,2-trifluoroethyl)-1H-pyrazolo[3,4-c]pyridine-5-carbaldehyde (2.34 g) as white solid. LC/MS ESI (m/z): 230 $[M+H]^+$. $^1$H NMR (400 MHz, $CDCl_3$) δ 10.24 (s, 1H), 9.13 (s, 1H), 8.43 (s, 1H), 8.34 (s, 1H), 5.15 (q, J=8.2 Hz, 2H). $^{19}$F NMR (377 MHz, $CDCl_3$) δ −70.72 (s).

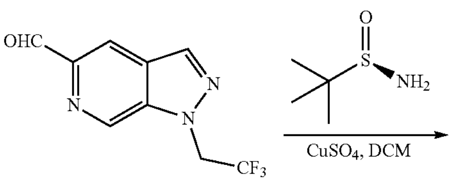

-continued

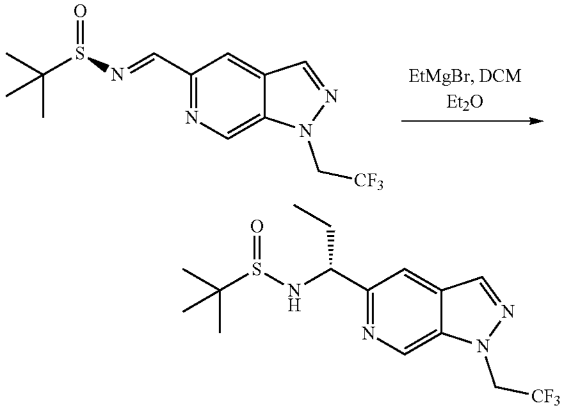

(R,E)-2-methyl-N-((1-(2,2,2-trifluoroethyl)-1H-pyrazolo[3,4-c]pyridin-5-yl)methylene)propane-2-sulfinamide. To a solution of 1-(2,2,2-trifluoroethyl)-1H-pyrazolo[3,4-c]pyridine-5-carbaldehyde (2.39 g) in DCM (15 mL) were added (R)-2-methylpropane-2-sulfinamide (1.64 g) and $CuSO_4$ (4.16 g). Then the reaction was stirred at 30° C. for 18 hr, and the mixture was filtered through Celite. The organic layer was concentrated in vacuo and purified by silica gel column chromatography to give (R,E)-2-methyl-N-((1-(2,2,2-trifluoroethyl)-1H-pyrazolo[3,4-c]pyridin-5-yl)methylene)propane-2-sulfinamide (3.23 g) as white solid. LC/MS ESI (m/z): 333 $[M+H]^+$.

(R)-1-(1-(2,2,2-trifluoroethyl)-1H-pyrazolo[3,4-c]pyridin-5-yl)propan-1-amine. To a solution of (R,E)-2-methyl-N-((1-(2,2,2-trifluoroethyl)-1H-pyrazolo[3,4-c]pyridin-5-yl)methylene)propane-2-sulfinamide (600 mg) in DCM (10.0 mL) at −45° C. was added EtMgBr (0.72 mL, 3 mol/L in ether) dropwise. The reaction mixture was stirred at −45° C. for 30 minutes and then quenched with water. The layers were separated, and the organic layer was concentrated under vacuo. The residue was purified by column chromatography on silica gel (0-10% MeOH in $CH_2C_2$) to give 2-methyl-N—((R)-1-(1-(2,2,2-trifluoroethyl)-1H-pyrazolo[3,4-c]pyridin-5-yl)propyl)propane-2-sulfinamide (350 mg) as an oil. LCMS ESI (m/z): 363 $[M+H]^+$. $^1$H NMR (400 MHz, $CDCl_3$) δ 8.95 (s, 1H), 8.10 (d, J=4.0 Hz, 1H), 7.57 (t, J=16.0 Hz, 1H), 5.08-4.94 (m, 2H), 4.51 (d, J=8.0 Hz, 1H), 4.38 (d, J=8.0 Hz, 1H), 1.96-1.87 (m, 2H), 1.26 (s, 9H), 0.91 (t, J=8.0 Hz, 3H).

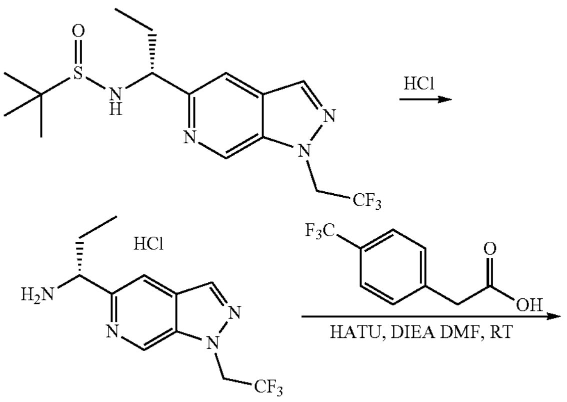

-continued

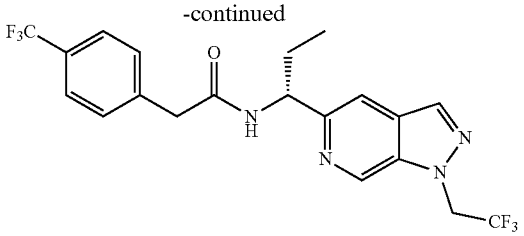

(R)-1-(1-(2,2,2-trifluoroethyl)-1H-pyrazolo[3,4-c]pyridin-5-yl)propan-1-amine. To a solution of 2-methyl-N—((R)-1-(1-(2,2,2-trifluoroethyl)-1H-pyrazolo[3,4-c]pyridin-5-yl)propyl)propane-2-sulfinamide (300 mg) in dioxane (5 mL) was added HCl (1 mL, 4N in dioxane). The mixture was stirred at room temperature for 2 hrs. LCMS showed the reaction was complete. The reaction mixture was quenched with ice-water and extracted with EA twice. The combined extracts were concentrated to give (R)-1-(1-(2,2,2-trifluoroethyl)-1H-pyrazolo[3,4-c]pyridin-5-yl)propan-1-amine (200 mg) as a oil. LCMS ESI (m/z): 259 $[M+H]^+$.

(R)—N-(1-(1-(2,2,2-trifluoroethyl)-1H-pyrazolo[3,4-c]pyridin-5-yl)propyl)-2-(4-(trifluoromethyl)phenyl)acetamide. To a solution of 2-[4-(trifluoromethyl)phenyl]acetic acid (186 mg) in DMF (3.0 mL) were added HATU (347 mg) and N,N-diisopropylethylamine (0.41 mL). The solution was allowed to stir at room temperature for 10 min before the addition of (R)-1-[1-(2,2,2-trifluoroethyl)-1H-pyrazolo[3,4-c]pyridin-5-yl]propan-1-amine (214 mg). The mixture was stirred at RT overnight, and the reaction was diluted with water (5 mL) and extracted with EA (10 mL×2). The combined organic phases were dried over $Na_2SO_4$, filtered and concentrated to provide crude product, which was purified by prep-HPLC (Column: AZZOTA C18 GEMINI 250*20 mm 10 um; Mobile phase: from 30% to 95% MeCN with $H_2O$ (0.1% FA); flow rate: 15 mL/min; wave length: 205 nm/254 nm) to give (R)—N-(1-(1-(2,2,2-trifluoroethyl)-1H-pyrazolo[3,4-c]pyridin-5-yl)propyl)-2-(4-(trifluoromethyl)phenyl)acetamide (114 mg) as a white solid. LC/MS ESI (m/z): 445 $[M+H]^+$. $^1H$ NMR (400 MHz, $CDCl_3$) δ 8.88 (s, 1H), 8.11 (s, 1H), 7.59-7.55 (m, 3H), 7.40 (d, J=8.0 Hz, 2H), 6.68 (d, J=8.0 Hz, 1H), 5.05-5.03 (m, 3H), 3.63 (s, 2H), 2.42-1.65 (m, 2H), 0.81 (d, J=8.0 Hz, 3H). $^{19}F$ NMR (377 MHz, $CDCl_3$) δ −62.54, −70.80.

Example 46. (R)-2-(2,3-dimethyl-2H-indazol-6-yl)-N-(1-(1-(2,2,2-trifluoroethyl)-1H-pyrazolo[3,4-c]pyridin-5-yl)ethyl)acetamide

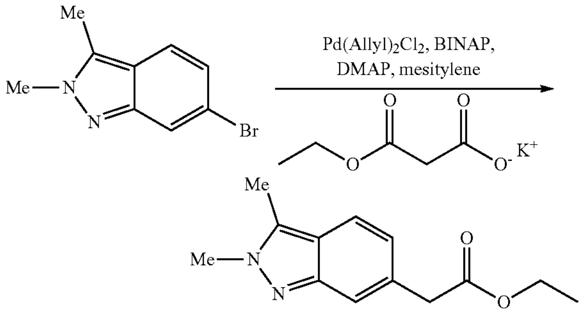

Ethyl 2-(2,3-dimethyl-2H-indazol-6-yl)acetate. To a solution of 6-bromo-2,3-dimethyl-2H-indazole (500 mg) in mesitylene (6 mL) were added BINAP (84 mg), potassium 3-ethoxy-3-oxopropanoate (570 mg), DMAP (273 mg) and allylpalladium(II) chloride (17 mg). The reaction was stirred at 140° C. during the day and 120° C. overnight. The solvent was removed under reduced pressure, and the residue was purified by silica gel column chromatography to afford ethyl 2-(2,3-dimethyl-2H-indazol-6-yl)acetate (240 mg) as a yellow solid. LCMS ESI (m/z): 233.2 $(M+H)^+$. $^1H$ NMR (400 MHz, $CDCl_3$) δ 7.49 (d, J=11.2 Hz, 2H), 6.97 (d, J=8.6 Hz, 1H), 4.19-4.11 (m, 2H), 4.08 (s, 3H), 3.69 (s, 2H), 2.59 (s, 3H), 1.24 (t, J=7.1 Hz, 3H).

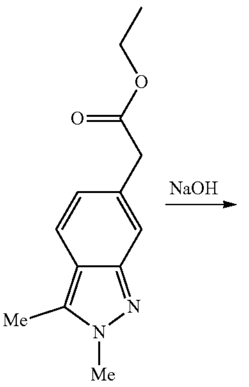

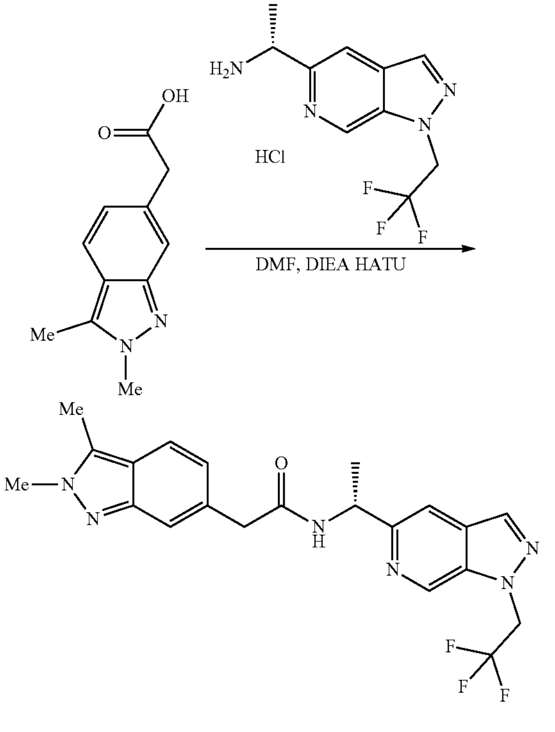

2-(2,3-dimethyl-2H-indazol-6-yl)acetic acid. To a solution of ethyl 2-(2,3-dimethyl-2H-indazol-6-yl)acetate (120 mg) in EtOH (2 mL) was added 2M NaOH (1 mL), and the reaction was stirred at RT for 1 hr. The reaction was diluted with water (0.5 mL) and EA. The aqueous phase was adjusted to pH=1 with 2M HCl, and extracted with EA. The product was found to be dissolved in the aqueous phase. The aqueous phase was separated and concentrated in vacuo to give 2-(2,3-dimethyl-2H-indazol-6-yl)acetic acid and NaCl as a crude white solid (174 mg) that was used in the next step without purification. LCMS ESI (m/z): 205.2 $(M+H)^+$.

(R)-2-(2,3-dimethyl-2H-indazol-6-yl)-N-(1-(1-(2,2,2-trifluoroethyl)-1H-pyrazolo[3,4-c]pyridin-5-yl)ethyl)acetamide. To a solution of (R)-1-(1-(2,2,2-trifluoroethyl)-1H-pyrazolo[3,4-c]pyridin-5-yl)ethan-1-amine hydrochloride (310 mg) in anhydrous DMF was added DIEA (0.845 mL) to provide Solution A. To a solution of crude 2-(2,3-dimethyl-2H-indazol-6-yl)acetic acid (174 mg) in anhydrous DMF was added HATU (356 mg), and the reaction was stirred 15 min at RT to provide Solution B. Solution A was added to solution B, and the mixture stirred at RT for 1 hr. The reaction was diluted with EA and water, and the organic layer was washed with brine, dried over $Na_2SO_4$ and concentrated in vacuo. The residue was purified by prep-HPLC (Column: YMC-Actus Triart C18 250*21 mm; Mobile phase: from 20% to 95% MeCN with $H_2O$ (0.1% FA); flow rate: 15 mL/min; wave length: 220 nm/254 nm), to give (R)-2-(2,3-dimethyl-2H-indazol-6-yl)-N-(1-(1-(2,2,2-trifluoroethyl)-1H-pyrazolo[3,4-c]pyridin-5-yl)ethyl)acetamide (117 mg) as a white solid. LCMS ESI (m/z): 431.3 $(M+H)^+$. $^1H$ NMR (400 MHz, DMSO-d6): δ 9.22 (s, 1H), 8.53 (d, J=8.0 Hz, 1H), 8.24 (s, 1H), 7.63 (s, 1H), 7.53 (d, J=8.4 Hz, 1H), 7.34 (s, 1H), 6.89 (d, J=8.8 Hz, 1H), 5.64-5.57 (m, 2H), 5.10-5.06 (m, 1H), 4.01 (s, 3H), 3.53 (s, 2H), 2.57 (s, 3H), 1.43 (d, J=7.2 Hz, 3H). $^{19}F$ NMR (377 MHz, DMSO-d6) δ −69.77 (s).

Example 47. (R)-2-(4-(1-cyanocyclopropyl)phenyl)-N-(1-(1-(2,2,2-trifluoroethyl)-1H-pyrazolo[3,4-c]pyridin-5-yl)ethyl)acetamide

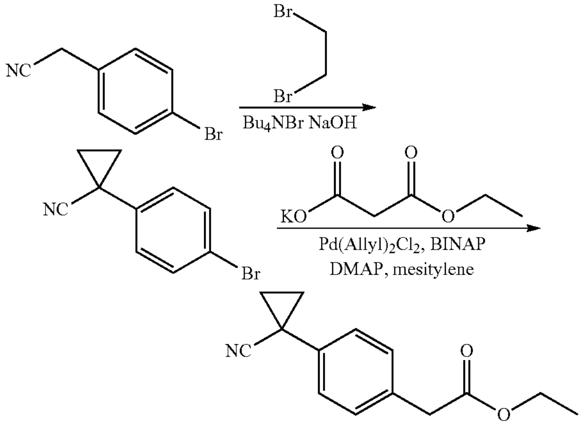

1-(4-bromophenyl)cyclopropane-1-carbonitrile. To a 250 mL round bottom flask containing a solution of 1,2-dibromoethane (1.24 mL) and 2-(4-bromophenyl)acetonitrile (2 g) in toluene (20 mL) were added 50% aqueous NaOH (20 mL) and tetrabutylammonium bromide (0.63 mL) at room temperature. The reaction mixture was stirred vigorously at room temperature overnight, and the reaction was then poured into 450 mL of ice-water. The resulting mixture was extracted with EA (130 mL×3). The combined organic layers were washed with water (150 mL×2) and brine (150 mL), and finally dried over anhydrous $Na_2SO_4$. The solvent was removed under vacuo, and the residue was purified by silica gel flash chromatography (PE:EA=5:1) to afford 1-(4-bromophenyl)cyclopropane-1-carbonitrile as a yellow oil (1.5 g). $^1H$ NMR (400 MHz, $CDCl_3$) δ 7.48 (d, J=8.4 Hz, 2H), 7.16 (d, J=8.4 Hz, 2H), 1.74 (q, J=5.2 Hz, 2H), 1.38 (q, J=5.2 Hz, 2H).

Ethyl 2-(4-(1-cyanocyclopropyl)phenyl)acetate. To a solution of 1-(4-bromophenyl)cyclopropane-1-carbonitrile (500 mg) in mesitylene (10 mL) were added diallylpalladium dichloride (1.56 mg), BINAP (95 mg), DMAP (311.58 mg) and ethyl potassium malonate (651 mg). The reaction was charged with $N_2$ and stirred at 120° C. overnight. The reaction was diluted with EA and water, and the two phases were separated. The aqueous phase was extracted with DCM (10 mL×3), and the combined organic phases were dried over $Na_2SO_4$, filtered, and concentrated to give a residue. The residue was purified by silica gel column chromatography (PE:EA=5:1) to give ethyl 2-(4-(1-cyanocyclopropyl)phenyl)acetate (200 mg) as a yellow oil. $^1H$ NMR (400 MHz, $CDCl_3$) δ 7.32-7.23 (m, 4H), 4.15 (q, J=7.2 Hz, 2H), 3.60 (s, 2H), 1.71 (q, J=5.2 Hz, 2H), 1.39 (q, J=5.2 Hz, 2H), 1.25 (t, J=7.2 Hz, 3H).

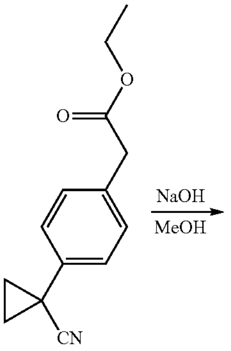

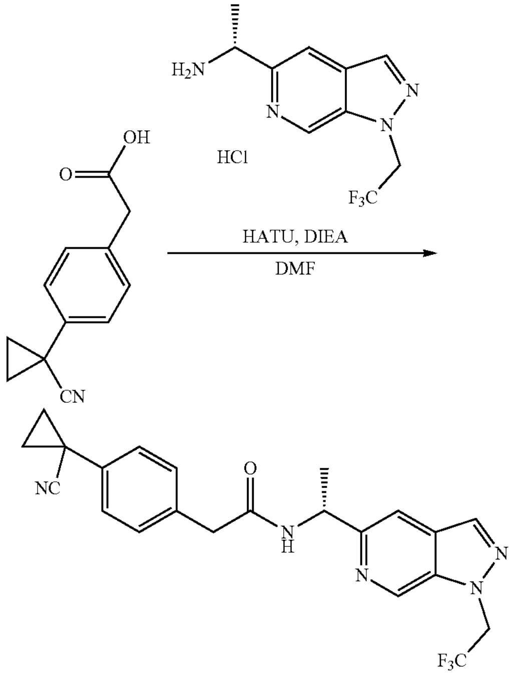

2-(4-(1-cyanocyclopropyl)phenyl)acetic acid. In a 25 mL round-bottomed flask were added ethyl 2-(4-(1-cyanocyclopropyl)phenyl)acetate (330 mg), 2M aqueous NaOH (2.0 mL) and MeOH (2.0 mL). The reaction mixture was stirred at room temperature for 1 hour. Water (20 mL) was then added, and the aqueous layer was washed with EA. The aqueous layer was acidified to pH<3 with 1M aqueous HCl, and the mixture was extracted with EA. The combined organic phases were washed with saturated NaCl, dried with $Na_2SO_4$, filtered, and concentrated to provide 2-(4-(1-cyanocyclopropyl)phenyl)acetic acid as a crude white solid (280 mg) which can be used in the next step without purification.

(R)-2-(4-(1-cyanocyclopropyl)phenyl)-N-(1-(1-(2,2,2-trifluoroethyl)-1H-pyrazolo[3,4-c]pyridin-5-yl)ethyl)acetamide. A solution of 2-(4-(1-cyanocyclopropyl)phenyl)acetic acid (200 mg) and HATU (567 mg) in 4 mL DMF was stirred at room temperature for 15 min to provide Solution A. DIEA (1.0 mL) was added to (R)-1-(1-(2,2,2-trifluoroethyl)-1H-pyrazolo[3,4-c]pyridin-5-yl)ethan-1-amine hydrochloride (362 mg) in 2 mL DMF until the pH of the solution higher than 7 by wet pH paper (Solution B). Solution B was added to Solution A, and the reaction was stirred at room temperature for 1 hour, at which time LCMS indicated complete reaction. The reaction mixture was diluted with EA and water. The two phases were separated, and the aqueous phase was extracted with EA (10 mL×2). The combined organic phases were dried over $Na_2SO_4$, filtered, and concentrated to give a residue. The residue was purified by prep-HPLC (Column: AZZOTA C18 30*250 mm*10 um; Mobile phase: from 25% to 95% MeCN with $H_2O$ (0.1% FA); flow rate: 30 mL/min; wave length: 220 nm/254 nm) to afford (R)-2-(4-(1-cyanocyclopropyl)phenyl)-N-(1-(1-(2,2,2-trifluoroethyl)-1H-pyrazolo[3,4-c]pyridin-5-yl)ethyl)acetamide (256 mg) as a white solid. LCMS ESI (m/z): 428 $(M+H)^+$. $^1H$ NMR (400 MHz, $CDCl_3$) δ 8.93 (s, 1H), 8.14 (s, 1H), 7.62 (s, 1H), 7.30-7.22 (m, 4H), 6.80 (d, J=6.8 Hz, 1H), 5.29-5.25 (m, 1H), 5.07 (q, J=8.0 Hz, 2H), 3.57 (s, 2H), 1.73-1.70 (m, 2H), 1.51 (d, J=6.8 Hz, 3H), 1.43-1.34 (m, 2H). $^{19}F$ NMR (377 MHz, $CDCl_3$) δ −70.76 ppm.

Example 48. (R)-2-(2,2-difluorobenzo[d][1,3]dioxol-5-yl)-N-(1-(1-(2,2,2-trifluoroethyl)-1H-pyrazolo[3,4-c]pyridin-5-yl)ethyl)acetamide

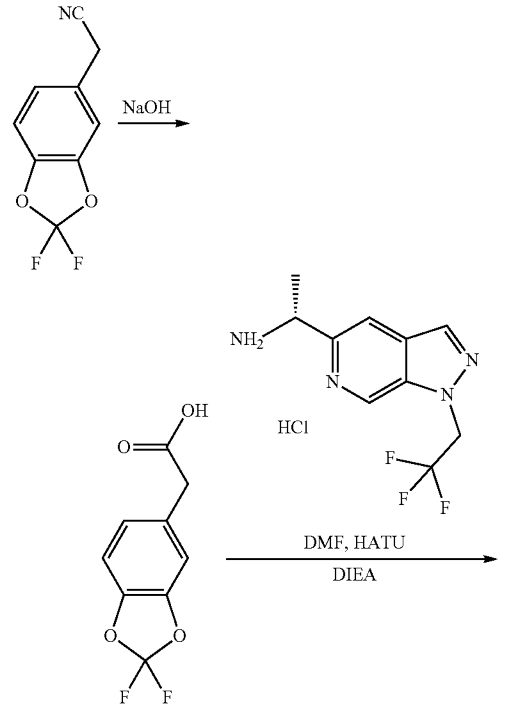

-continued

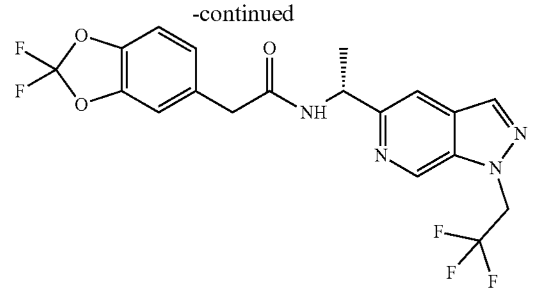

2-(2,2-difluorobenzo[d][1,3]dioxol-5-yl)acetic acid. To a 25 mL round bottom flask were added 2-(2,2-difluorobenzo[d][1,3]dioxol-5-yl)acetonitrile (200 mg), 6 M aqueous NaOH (2.0 mL) and EtOH (2.0 mL), and the mixture was stirred at 80° C. overnight. The reaction was cooled to room temperature, and the ethanol was evaporated under vacuum. Water (20 mL) was added, and the aqueous layer was washed with EA. The aqueous layer was acidified to pH<3 with 1M aqueous HCl, and the mixture was extracted with EA. The combined organic phases were washed with saturated NaCl, dried with $Na_2SO_4$, filtered, and concentrated to provide 2-(2,2-difluorobenzo[d][1,3]dioxol-5-yl)acetic acid (200 mg, crude) which was used directly in the next step.

(R)-2-(2,2-difluorobenzo[d][1,3]dioxol-5-yl)-N-(1-(1-(2,2,2-trifluoroethyl)-1H-pyrazolo[3,4-c]pyridin-5-yl)ethyl)acetamide. A solution of 2-(2,2-difluorobenzo[d][1,3]dioxol-5-yl)acetic acid (200 mg) and HATU (528 mg) in DMF (5.0 mL) was stirred at room temperature for 15 min. (R)-1-(1-(2,2,2-Trifluoroethyl)-1H-pyrazolo[3,4-c]pyridin-5-yl)ethan-1-amine hydrochloride (337 mg) and DIEA (0.92 mL) were added. The reaction was stirred for 1 hour, and LC/MS indicated that the reaction was complete. The reaction was diluted with EA and water. The two phases were separated, and the aqueous phase was extracted with EA (10 mL×3). The combined organic phases were dried over $Na_2SO_4$, filtered, and concentrated to give a residue, which was purified by prep-HPLC (Column: AZZOTA C18 30*250 mm*10 um; Mobile phase: from 30% to 95% MeCN with $H_2O$ (0.1% FA); flow rate: 30 mL/min; wave length: 220 nm/254 nm) to afford (R)-2-(2,2-difluorobenzo[d][1,3]dioxol-5-yl)-N-(1-(1-(2,2,2-trifluoroethyl)-1H-pyrazolo[3,4-c]pyridin-5-yl)ethyl)acetamide (263 mg) as a white solid. LCMS ESI (m/z): 443 $(M+H)^+$. $^1H$ NMR (400 MHz, $CDCl_3$) δ 8.92 (s, 1H), 8.13 (s, 1H), 7.61 (s, 1H), 7.02-6.96 (m, 3H), 6.82 (d, J=8.0 Hz, 1H), 5.31-5.24 (m, 1H), 5.06 (q, J=8.0 Hz, 2H), 3.56 (s, 2H), 1.51 (d, J=8.0 Hz, 3H). $^{19}F$ NMR (377 MHz, $CDCl_3$) δ −49.97 ppm, −70.78 ppm.

Example 49. (R)-2-(1,3-dimethyl-1H-indazol-5-yl)-N-(1-(1-(2,2,2-trifluoroethyl)-1H-pyrazolo[3,4-c]pyridin-5-yl)ethyl)acetamide

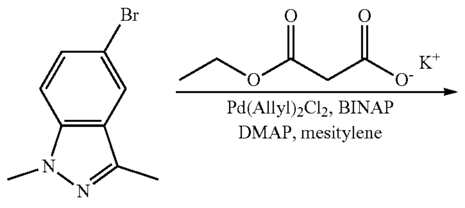

-continued

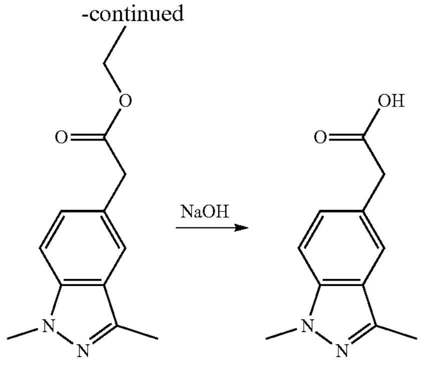

Ethyl 2-(1,3-dimethyl-1H-indazol-5-yl)acetate. To a solution of 5-bromo-1,3-dimethyl-1H-indazole (500 mg) in mesitylene (5 mL) were added BINAP (84 mg), potassium 3-ethoxy-3-oxopropanoate (572 mg), DMAP (274 mg) and allylpalladium(II) chloride (16 mg). The reaction was stirred at 140° C. during the day and 120° C. overnight under nitrogen. The reaction was concentrated in vacuo, and the residue was purified by silica gel column chromatography to afford the title compound ethyl 2-(1,3-dimethyl-1H-indazol-5-yl)acetate (342 mg) as a colorless oil: LCMS ESI (m/z): 233.2 $(M+H)^+$. $^1H$ NMR (400 MHz, $CDCl_3$) δ 7.53 (s, 1H), 7.33-7.26 (m, 2H), 4.21-4.08 (m, 2H), 3.98 (s, 3H), 3.72 (s, 2H), 2.55 (s, 3H), 1.26 (t, J=7.2 Hz, 3H).

2-(1,3-dimethyl-1H-indazol-5-yl)acetic acid. To a solution of ethyl 2-(1,3-dimethyl-1H-indazol-5-yl)acetate (385 mg) in EtOH (4.0 mL) was added 2M NaOH (2 mL), and the reaction was stirred at 100° C. for 1 hr. The reaction was diluted with water (0.5 mL) and washed with EA. The water phase was adjusted to pH=1 with 2M HCl, extracted with EA, and the resulting organic phase was concentrated in vacuo to give 2-(1,3-dimethyl-1H-indazol-5-yl)acetic acid as a white solid (320 mg). LCMS ESI (m/z): 205.2 $(M+H)^+$. $^1H$ NMR (400 MHz, DMSO-d6) δ 7.47 (s, 1H), 7.41 (d, J=8.6 Hz, 1H), 7.20 (d, J=8.6 Hz, 1H), 3.86 (s, 3H), 3.58 (s, 2H), 2.38 (s, 3H).

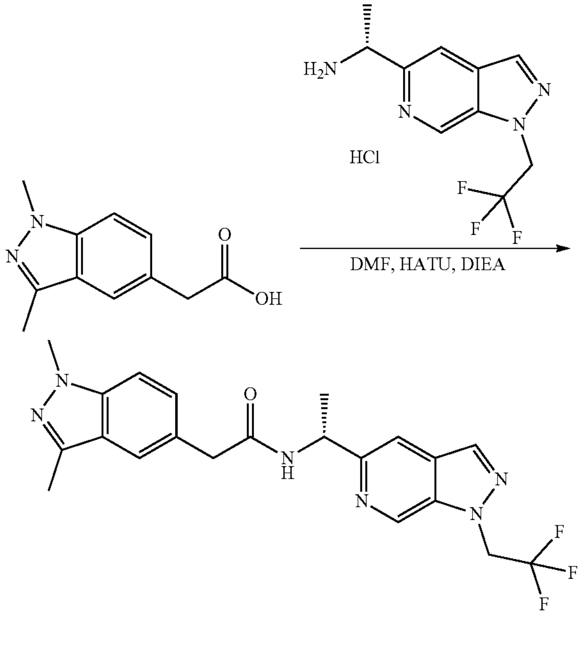

(R)-2-(1,3-dimethyl-1H-indazol-5-yl)-N-(1-(1-(2,2,2-trifluoroethyl)-1H-pyrazolo[3,4-c]pyridin-5-yl)ethyl)acetamide. To a solution of (R)-1-(1-(2,2,2-trifluoroethyl)-1H-pyrazolo[3,4-c]pyridin-5-yl)ethan-1-amine hydrochloride (232 mg) in anhydrous DMF was added DIEA (0.63 mL) to provide Solution A. To a solution of 2-(1,3-dimethyl-1H-indazol-5-yl)acetic acid (130 mg) in anhydrous DMF was added HATU (266 mg), and the reaction was stirred for 15 min at RT to provide solution B. Solution A was added to the Solution B and stirred at RT for 1 h. The reaction was diluted with EA and water. The organic layer was washed with brine, dried over $Na_2SO_4$ and concentrated in vacuo. Then the residue was purified by prep-HPLC (Column: AZZOTA C18 GEMINI 250*20 mm 10 um; Mobile phase: from 15% to 80% MeCN with $H_2O$ (0.1% $NH_3H_2O$); flow rate: 15 mL/min; wave length: 220 nm/254 nm), to give (R)-2-(1,3-dimethyl-1H-indazol-5-yl)-N-(1-(1-(2,2,2-trifluoroethyl)-1H-pyrazolo[3,4-c]pyridin-5-yl)ethyl)acetamide (109 mg) as a white solid. LCMS ESI (m/z): 431.5 $(M+H)^+$. $^1H$ NMR (400 MHz, $CDCl_3$) δ 8.82 (s, 1H), 8.08 (s, 1H), 7.53 (d, J=8.8 Hz, 2H), 7.29 (d, J=2.4 Hz, 2H), 6.59 (d, J=7.6 Hz, 1H), 5.30-5.27 (m, 1H), 5.05-4.99 (m, 2H), 4.00 (s, 3H), 3.69 (s, 2H), 2.54 (s, 3H), 1.45 (d, J=6.8 Hz, 3H). $^{19}F$ NMR (377 MHz, $CDCl_3$) δ −70.81 (s).

Example 50. (R)-2-(3-cyano-1-methyl-1H-indol-5-yl)-N-(1-(1-(2,2,2-trifluoroethyl)-1H-pyrazolo[3,4-c]pyridin-5-yl)ethyl)acetamide

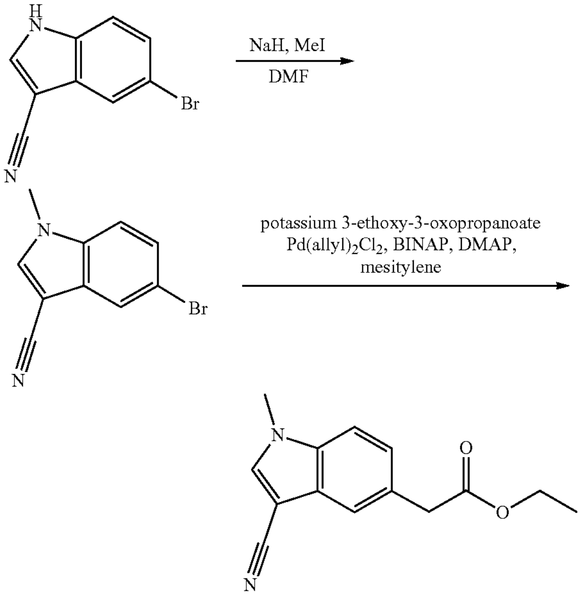

5-bromo-1-methyl-1H-indole-3-carbonitrile. To a solution of 5-bromo-1H-indole-3-carbonitrile (500 mg) in DMF (8 mL) was added NaH (273 mg, 60% in mineral oil) at 0° C., and the reaction was stirred at the same temperature for 30 min. Then iodomethane (0.2 mL) was added to the reaction, and the reaction was stirred at room temperature for 1 h. The reaction was quenched with water and extracted with EA. The organic layer was separated, washed with brine, dried over $Na_2SO_4$ and concentrated in vacuo. The residue was purified by silica gel column chromatography to afford 5-bromo-1-methyl-1H-indole-3-carbonitrile (507 mg) as a white solid. LCMS ESI (m/z): 235.3 $(M+H)^+$. $^1H$ NMR (400 MHz, DMSO-d6) δ 8.23 (s, 1H), 7.74 (d, J=1.6 Hz, 1H), 7.57 (d, J=8.8 Hz, 1H), 7.48-7.35 (m, 1H), 3.80 (s, 3H).

Ethyl 2-(3-cyano-1-methyl-1H-indol-5-yl)acetate. To a solution of 5-bromo-1-methyl-1H-indole-3-carbonitrile (507 mg) in mesitylene (10 mL) were added BINAP (81 mg), potassium 3-ethoxy-3-oxopropanoate (554 mg), DMAP (265 mg) and allylpalladium(II) chloride (15.6 mg), and the reaction was stirred under nitrogen at 140° C. during the day and 120° C. overnight. The reaction was concentrated in vacuo, and the residue was purified by silica gel column chromatography to afford ethyl 2-(3-cyano-1-methyl-1H-indol-5-yl)acetate (270 mg) as a colorless oil. LCMS ESI (m/z): 243.4 $(M+H)^+$. $^1$H NMR (400 MHz, $CDCl_3$) δ 7.65 (s, 1H), 7.54 (s, 1H), 7.35 (d, J=8.6 Hz, 1H), 7.32-7.27 (m, 1H), 4.16 (q, J=7.2 Hz, 2H), 3.84 (s, 3H), 3.74 (s, 2H), 1.26 (t, J=7.2 Hz, 3H).

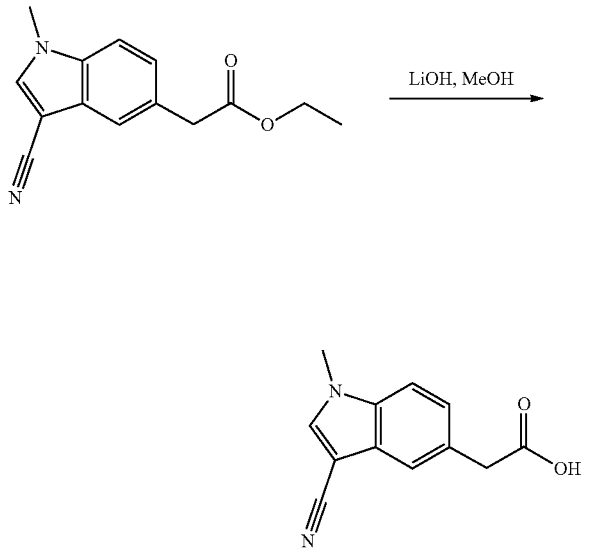

2-(3-cyano-1-methyl-1H-indol-5-yl)acetic acid. To a solution of ethyl 2-(3-cyano-1-methyl-1H-indol-5-yl)acetate (270 mg) in MeOH:THF:$H_2O$ (1:1:1, 9 mL) was added aqueous LiOH (234 mg), and the reaction was stirred at room temperature for 2 hr. The reaction was diluted with water (0.5 mL) and washed with EA. The water phase was separated, the pH adjusted 1 with 2M HCl, and extracted with EA. The organic layer was dried over $Na_2SO_4$ and concentrated in vacuo, to give 2-(3-cyano-1-methyl-1H-indol-5-yl)acetic acid (246 mg) as a grey solid. LCMS ESI (m/z): 215.4 $(M+H)^+$. $^1$H NMR (400 MHz, DMSO-d6) δ 8.14 (s, 1H), 7.53-7.43 (m, 2H), 7.17 (d, J=8.4 Hz, 1H), 3.78 (s, 3H), 3.63 (s, 2H).

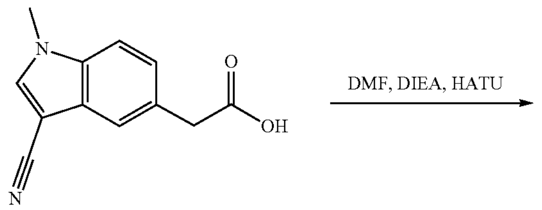

-continued

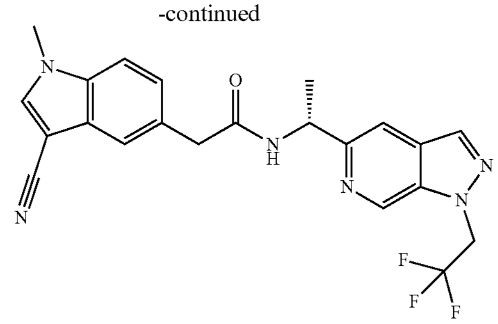

(R)-2-(3-cyano-1-methyl-1H-indol-5-yl)-N-(1-(1-(2,2,2-trifluoroethyl)-1H-pyrazolo[3,4-c]pyridin-5-yl)ethyl)acetamide. To a solution of (R)-1-(1-(2,2,2-trifluoroethyl)-1H-pyrazolo[3,4-c]pyridin-5-yl)ethan-1-amine hydrochloride (204 mg) in anhydrous DMF was added DIEA (0.56 mL) to provide Solution A. To a solution of 2-(3-cyano-1-methyl-1H-indol-5-yl)acetic acid (120 mg) in DMF was added HATU (234 mg) and stirred 15 min at room temperature to provide Solution B. Solution A was added to Solution B and stirred at room temperature for 1 h. The reaction was diluted with EA and water. The organic layer was washed with brine, dried over $Na_2SO_4$ and concentrated in vacuo. The residue was purified by prep-HPLC (AZZOTA C18 GEMINI 250*20 mm 10 um; Mobile phase: from 15% to 75% MeCN with $H_2O$ (0.1% $NH_3H_2O$); flow rate: 15 mL/min; wave length: 220 nm/254 nm) and SFC (Column: ChiralPak IA, 250×21.3 mm I.D., 5 μm; Mobile phase: A for $CO_2$ and B for MEOH+0.1% $NH_3H_2O$; Gradient: B 35%; flow rate: 45 mL/min; wave length: 220 nm) to give (R)-2-(3-cyano-1-methyl-1H-indol-5-yl)-N-(1-(1-(2,2,2-trifluoroethyl)-1H-pyrazolo[3,4-c]pyridin-5-yl)ethyl)acetamide (142 mg) as white solid. LCMS ESI (m/z): 441.5 $(M+H)^+$. $^1$H NMR (400 MHz, $CDCl_3$) δ 8.93 (s, 1H), 8.08 (s, 1H), 7.61 (s, 1H), 7.57-7.55 (m, 2H), 7.35-7.30 (m, 1H), 7.30 (d, J=8.4 Hz 1H), 6.65 (d, J=7.2 Hz, 1H), 5.34-5.22 (m, 1H), 5.14-4.97 (m, 2H), 3.85 (s, 3H), 3.71 (s, 2H), 1.46 (d, J=6.8 Hz, 3H). $^{19}$F NMR (377 MHz, $CDCl_3$) δ −70.81 (s).

Example 51. (R)—N-(1-(1-(2,2,2-trifluoroethyl)-1H-pyrrolo[2,3-c]pyridin-5-yl)ethyl)-2-(4-(trifluoromethyl)phenyl)acetamide

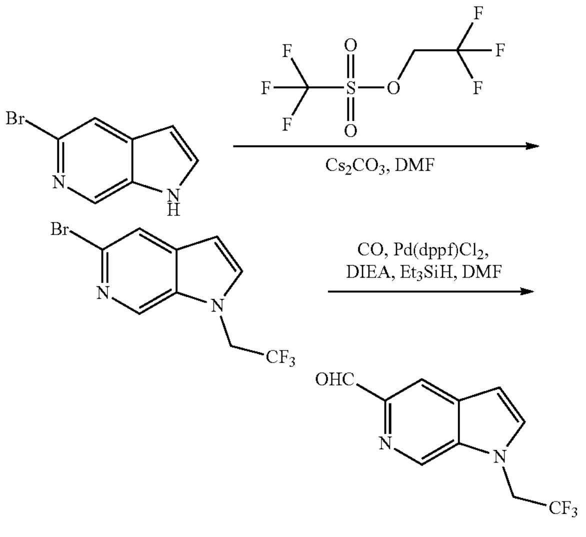

5-bromo-1-(2,2,2-trifluoroethyl)-1H-pyrrolo[2,3-c]pyridine. To a solution of 5-bromo-1H-pyrrolo[2,3-c]pyridine (1.50 g) in DCM (10.0 mL) were added 2,2,2-trifluoroethyl trifluoromethanesulfonate (1.21 mL) and $Cs_2CO_3$ (2.98 g), and the reaction was stirred at room temperature overnight. The reaction was diluted with EA and water. The organic layer was separated, washed with brine, and concentrated in vacuo. The residue was purified by silica gel column chromatography eluting with 40% ethyl acetate in petroleum ether to give 5-bromo-1-(2,2,2-trifluoroethyl)-1H-pyrrolo[2,3-c]pyridine (2.00 g) as a white solid. LCMS ESI (m/z): 279 $[M+H]^+$. $^1H$ NMR (400 MHz, DMSO-d6) δ 8.74 (s, 1H), 7.76 (s, 1H), 7.65 (d, J=4.0 Hz, 1H), 6.57 (d, J=4.0 Hz, 1H), 5.29 (q, J=8.0 Hz, 2H). $^{19}F$ NMR (377 MHz, DMSO-d6) δ −70.45 (s).

1-(2,2,2-trifluoroethyl)-1H-pyrrolo[2,3-c]pyridine-5-carbaldehyde. To a solution of 5-bromo-1-(2,2,2-trifluoroethyl)-1H-pyrrolo[2,3-c]pyridine (800 mg) in DMF (15 mL) were added triethylsilane (0.69 mL), 1,1'-bis(diphenylphosphino)ferrocene palladium(II)dichloride (210 mg), and DIEA (0.95 mL) under CO atmosphere, and the reaction was stirred at 100° C. overnight. The reaction was diluted with EA and water. The organic layer was separated, washed with saturated NaCl solution, and concentrated in vacuo. The residue was purified by silica gel column chromatography, eluting with 20% ethyl acetate in petroleum ether to afford 1-(2,2,2-trifluoroethyl)-1H-pyrrolo[2,3-c]pyridine-5-carbaldehyde (400 mg) as white solid.

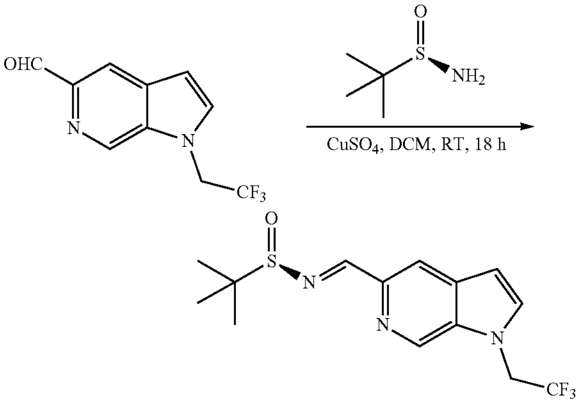

(R,E)-2-methyl-N-((1-(2,2,2-trifluoroethyl)-1H-pyrrolo[2,3-c]pyridin-5-yl)methylene)propane-2-sulfinamide. To a solution of 1-(2,2,2-trifluoroethyl)-1H-pyrrolo[2,3-c]pyridine-5-carbaldehyde (400 mg) in DCM (5.0 mL) were added $CuSO_4$ (839 mg) and 2-methylpropane-2-sulfinamide (276 mg), and the reaction was stirred at room temperature overnight. The reaction was diluted with EA and water. The organic layer was separated, washed with saturated brine solution, and concentrated in vacuo. The residue was purified by silica gel column chromatography, eluting with 40% ethyl acetate in petroleum ether. The organic layer was collected, concentrated in vacuo, and dried to afford (R,E)-2-methyl-N-((1-(2,2,2-trifluoroethyl)-1H-pyrrolo[2,3-c]pyridin-5-yl)methylene)propane-2-sulfinamide (440 mg) as white solid. LCMS ESI (m/z): 332[M+H]. $^1H$ NMR (400 MHz, DMSO-d6) δ 9.10 (d, J=2.4 Hz, 1H), 8.52 (s, 1H), 8.32 (s, 1H), 7.70 (d, J=4.0 Hz, 1H), 6.77 (d, J=4.0 Hz, 1H), 5.39-5.37 (m, 2H), 1.14 (s, 9H). $^{19}F$ NMR (377 MHz, DMSO-d6) δ −70.39 ppm.

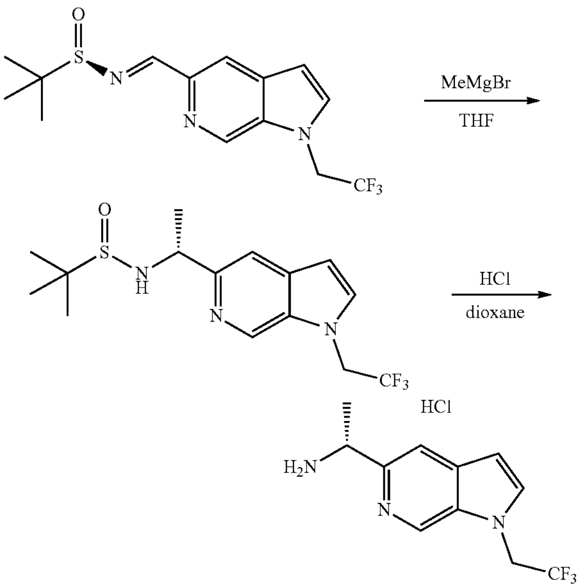

2-methyl-N—((R)-1-(1-(2,2,2-trifluoroethyl)-1H-pyrrolo[2,3-c]pyridin-5-yl)ethyl)propane-2-sulfinamide. To a solution of (R,E)-2-methyl-N-((1-(2,2,2-trifluoroethyl)-1H-pyrrolo[2,3-c]pyridin-5-yl)methylene)propane-2-sulfinamide (400 mg) in THE (10.0 mL) at −45° C. was added MeMgBr (0.400 mL, 3 M in ether) dropwise. The reaction mixture was stirred at −78° C. for 30 minutes and then diluted with water. The layers were separated, and the organic layer was concentrated. The residue was purified by column chromatography on silica gel (0-10% MeOH in DCM) to give 2-methyl-N—((R)-1-(1-(2,2,2-trifluoroethyl)-1H-pyrrolo[2,3-c]pyridin-5-yl)ethyl)propane-2-sulfinamide (320 mg) as a colorless oil. LCMS ESI (m/z): $348[M+H]^+$.

(R)-1-(1-(2,2,2-trifluoroethyl)-1H-pyrrolo[2,3-c]pyridin-5-yl)ethan-1-amine hydrochloride. To a solution of 2-methyl-N—((R)-1-(1-(2,2,2-trifluoroethyl)-1H-pyrrolo[2,3-c]pyridin-5-yl)ethyl)propane-2-sulfinamide (320 mg) in dioxane (2.00 mL) was added 4 N HCl in dioxane (1.00 mL). The mixture was stirred at room temperature for 2 hours, and LCMS showed the reaction was complete. The reaction mixture was quenched by ice-water and extracted with EA twice. The combined extracts were concentrated to give (R)-1-(1-(2,2,2-trifluoroethyl)-1H-pyrrolo[2,3-c]pyridin-5-yl)ethan-1-amine hydrochloride (220 mg) as a white solid. LCMS ESI (m/z): $244[M+H]^+$.

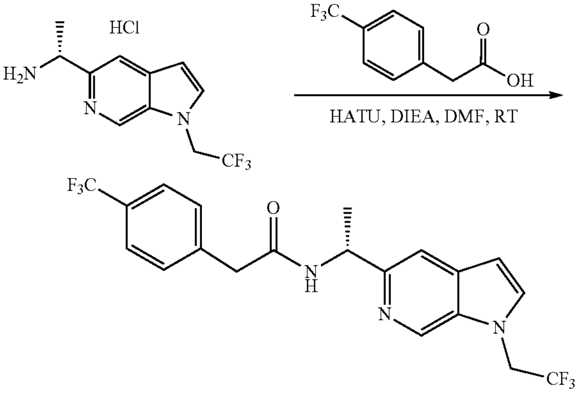

(R)—N-(1-(1-(2,2,2-trifluoroethyl)-1H-pyrrolo[2,3-c]pyridin-5-yl)ethyl)-2-(4-(trifluoromethyl)phenyl)acetamide. To a solution of 2-(4-(trifluoromethyl)phenyl)acetic acid (227 mg) in DMF (5 mL) were added HATU (422 mg) and DIEA (358 mg). The solution was allowed to stir at room temperature for 10 min before the addition of (R)-1-(1-(2,2,2-trifluoroethyl)-1H-pyrrolo[2,3-c]pyridin-5-yl)ethan-1-amine hydrochloride (225 mg). The mixture was stirred at room temperature overnight, and LCMS showed the desired MS was detected. The reaction was diluted with water (5 mL) and extracted with EA (10 mL×2). The combined organic phases were dried over $Na_2SO_4$, filtered and concentrated. The residue was purified by prep-HPLC (Column: YMC TA C18 250*21.2 mm Sum; Mobile phase: from 5% to 95% MeCN with $H_2O$ (0.1% FA); flow rate: 20 mL/min; wave length: 205 nm/254 nm) to give (R)—N-(1-(1-(2,2,2-trifluoroethyl)-1H-pyrrolo[2,3-c]pyridin-5-yl)ethyl)-2-(4-(trifluoromethyl)phenyl)acetamide (200 mg) as a white solid. LC/MS ESI (m/z): 430 $[M+H]^+$. 1H NMR (400 MHz, $CDCl_3$) δ 8.70 (s, 1H), 7.56 (d, J=8.0 Hz, 2H), 7.51 (s, 1H), 7.41 (d, J=8.0 Hz, 2H), 7.39-7.29 (m, 2H), 6.67-6.58 (m, 1H), 5.25-5.21 (m, 1H), 4.74 (q, J=8.0 Hz, 2H), 3.63 (s, 2H), 1.51 (d, J=8.0 Hz, 3H). $^{19}F$ NMR (377 MHz, $CDCl_3$) δ −62.52, −71.50.

Example 52. (R)-2-(3-cyano-4-(1,1-difluoroethyl)phenyl)-N-(1-(1-(2,2,2-trifluoroethyl)-1H-pyrazolo[3,4-c]pyridin-5-yl)ethyl)acetamide

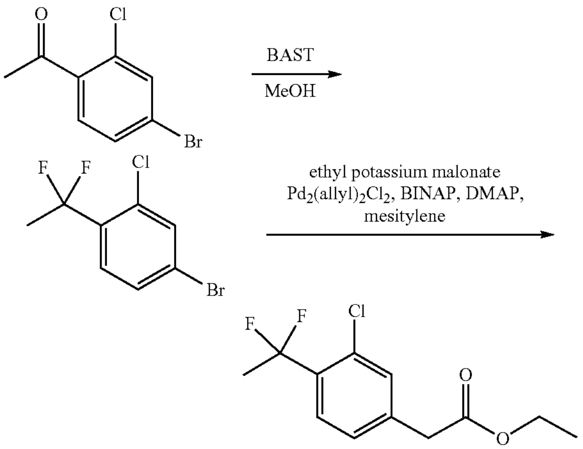

Synthesis of 4-bromo-2-chloro-1-(1,1-difluoroethyl)benzene. To a solution of 1-(4-bromo-2-chlorophenyl)ethan-1-one (4 g) in BAST (15 mL) was added MeOH (0.3 mL). The mixture was stirred at 70° C. for 12 hours in a microwave tube. The mixture was quenched with $NaHCO_3$ solution and extracted with DCM. The organic layer was dried, filtered and concentrated to give a residue. The residue was purified by chromatography on silica gel (100% PE) to give 4-bromo-2-chloro-1-(1,1-difluoroethyl)benzene (3.5 g) as a colorless oil. H NMR (400 MHz, $CDCl_3$) δ 7.61 (s, 1H), 7.53-7.41 (m, 2H), 2.01 (t, J=18.4 Hz, 3H). $^{19}F$ NMR (377 MHz, $CDCl_3$) δ −87.64 ppm.

Synthesis of ethyl 2-(3-chloro-4-(1,1-difluoroethyl)phenyl)acetate. A solution of 4-bromo-2-chloro-1-(1,1-difluoroethyl)benzene (3.5 g), potassium 3-ethoxy-3-oxopropanoate (3.50 g), $Pd_2(allyl)_2Cl_2$ (0.10 g), BINAP (0.51 g) and DMAP (1.67 g) in mesitylene (40 mL) was stirred at 140° C. for 1 hr. The mixture was then stirred at 120° C. for 12 hours, and the mixture was concentrated to give a residue. The residue was purified by column chromatography on silica gel (PE:EA=10:1) to give ethyl 2-(3-chloro-4-(1,1-difluoroethyl)phenyl)acetate (1.8 g) as colorless oil. $^1H$ NMR (400 MHz, $CDCl_3$) δ 7.56 (d, J=8.0 Hz, 1H), 7.38 (s, 1H), 7.24 (d, J=8.0 Hz, 1H), 4.17 (q, J=7.2 Hz, 2H), 3.61 (s, 2H), 2.03 (t, J=18.4 Hz, 3H), 1.27 (t, J=7.2 Hz, 3H).

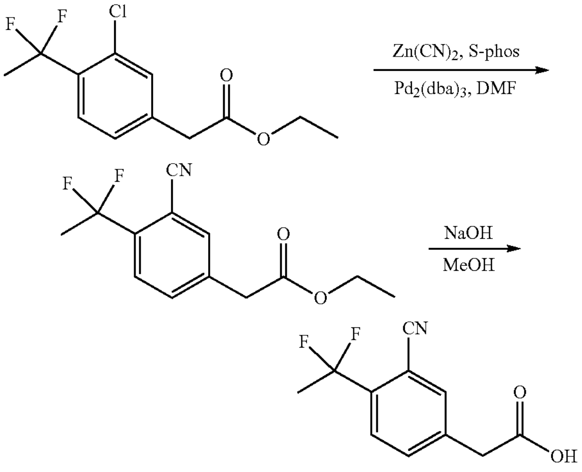

Synthesis of ethyl 2-(3-cyano-4-(1,1-difluoroethyl)phenyl)acetate. A solution of ethyl 2-(3-chloro-4-(1,1-difluoroethyl)phenyl)acetate (1.0 g), $Zn(CN)_2$ (1.02 g), S-Phos (0.32 g) and $Pd_2(dba)_3$ (0.36 g) in DMF (2.0 mL) was stirred at 150° C. for 30 min in a microwave. The mixture was concentrated and purified by column chromatography on silica gel (PE:EA=10:1) to give ethyl 2-(3-cyano-4-(1,1-difluoroethyl)phenyl)acetate (400 mg, 1.579) as a yellow oil.

Synthesis of 2-(3-cyano-4-(1,1-difluoroethyl)phenyl)acetic acid. To a solution of ethyl 2-(3-cyano-4-(1,1-difluoroethyl)phenyl)acetate (400 mg) in MeOH (2.0 mL) was added 1 M NaOH (3 mL), and the mixture was stirred at 25° C. for 12 hr. MeOH was removed under vacuum, and the aqueous residue was washed with EA. The aqueous phase was adjusted pH=4 with 1 N HCl solution and extracted with EA. The organic layer was dried, filtered and concentrated to give 2-(3-cyano-4-(1,1-difluoroethyl)phenyl)acetic acid (50 mg) as colorless oil which was used in the next step without further purification. LCMS ESI (m/z): 449 (2M−H).

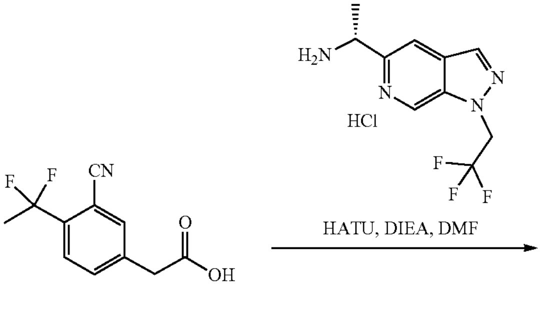

-continued

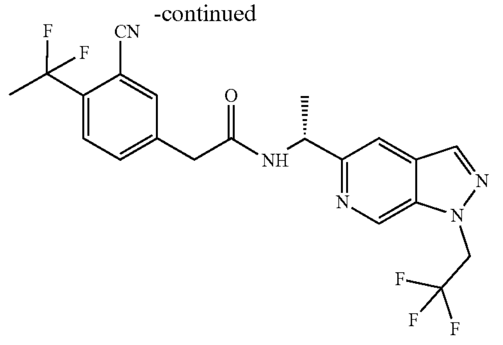

Synthesis of (R)-2-(3-cyano-4-(1,1-difluoroethyl)phenyl)-N-(1-(1-(2,2,2-trifluoroethyl)-1H-pyrazolo[3,4-c]pyridin-5-yl)ethyl)acetamide. A solution of 2-(3-cyano-4-(1,1-difluoroethyl)phenyl)acetic acid (50 mg) and HATU (110 mg) in DMF (2.0 mL) was stirred at 25° C. for 10 min. (R)-1-(1-(2,2,2-trifluoroethyl)-1H-pyrazolo[3,4-c]pyridin-5-yl)ethan-1-amine hydrochloride (70.5 mg) and DIEA (0.110 mL) were added to the mixture. The mixture was stirred at 25° C. for 2 hours, and the mixture was diluted with water and extracted with EA. The organic layer was dried, filtered, and concentrated to give a residue. The residue was purified by prep-HPLC (YMC-Actus Triart C18 150*20 mm*5 um; Mobile phase: from 30% to 95% MeCN with $H_2O$ (0.1% FA) to give (R)-2-(3-cyano-4-(1,1-difluoroethyl)phenyl)-N-(1-(1-(2,2,2-trifluoroethyl)-1H-pyrazolo[3,4-c]pyridin-5-yl)ethyl)acetamide (57.4 mg) as a white solid. LCMS ESI (m/z): 452 $(M+H)^+$. $^1H$ NMR (400 MHz, $CDCl_3$) δ 8.94 (s, 1H), 8.12 (s, 1H), 7.67 (s, 1H), 7.64-7.57 (m, 3H), 6.86 (d, J=7.6 Hz, 1H), 5.31-5.22 (m, 1H), 5.07 (q, J=8.4 Hz, 2H), 3.62 (s, 2H), 2.04 (t, J=18.4 Hz, 3H), 1.53 (d, J=6.8 Hz, 3H). $^{19}F$ NMR (400 MHz, $CDCl_3$) δ −70.78, −87.16 ppm.

Example 53. (R)-2-(1,2-dimethyl-1H-benzo[d]imidazol-5-yl)-N-(1-(1-(2,2,2-trifluoroethyl)-1H-pyrazolo[3,4-c]pyridin-5-yl)ethyl)acetamide

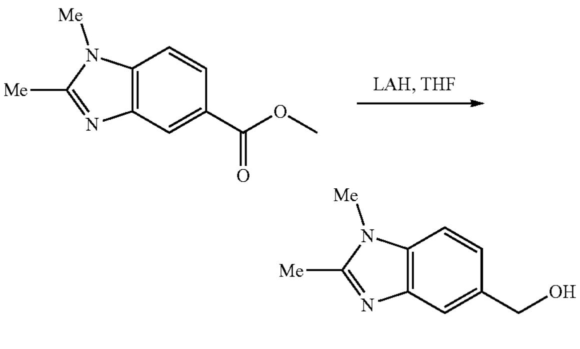

(1,2-dimethyl-1H-benzo[d]imidazol-5-yl)methanol. To a solution of methyl 1,2-dimethyl-1H-1,3-benzodiazole-5-carboxylate (1.0 g) in THF (40 mL) was added 4.90 mL 1M lithium aluminum hydride at 0° C. After 2 hours sodium sulfate decahydrate and citric acid were added to the reaction to destroy the excess of lithium aluminum hydride. After 1 hour, methanol (25 ml) was added and the fine suspension was filtered off. The filtrate was evaporated under reduced pressure to afford a brown solid. EA (50 ml) was added and the suspension was treated in an ultra sonic bath. The solid was filtered off and this procedure was repeated twice. The yellow filtrate was evaporated under reduced pressure to afford crude (1,2-dimethyl-1H-1,3-benzodiazol-5-yl)methanol (700 mg) as white solid. LC/MS ESI (m/z):177 $[M+H]^+$.

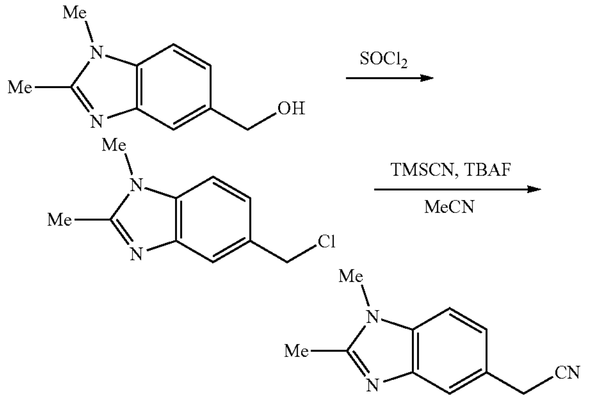

5-(chloromethyl)-1,2-dimethyl-1H-benzo[d]imidazole. A solution of (1,2-dimethyl-1H-1,3-benzodiazol-5-yl)methanol (700 mg) in $SOCl_2$ (5.0 mL) was stirred at room temperature for 2 hours. The mixture was concentrated to dryness to give the crude product as a yellow oil which was used for the next step without further purification. LC/MS ESI (m/z):195 $[M+H]^+$. $^1H$ NMR (400 MHz, $CDCl_3$) δ 7.86 (s, 1H), 7.55 (s, 2H), 4.67 (s, 2H), 3.84 (s, 3H), 3.07 (s, 3H).

2-(1,2-dimethyl-1H-benzo[d]imidazol-5-yl)acetonitrile. To a solution of 5-(chloromethyl)-1,2-dimethyl-1H-1,3-benzodiazole (230 mg) in $CH_3CN$ (2.0 mL) was added 1.4 mL 1 M TBAF in THF and TMSCN (0.18 mL). The resulting solution was stirred 2 h at room temperature. TLC, and LCMS showed the reaction was complete. The reaction mixture was quenched by ice-water and then extracted with EA twice. The combined extracts were concentrated, and the residue was purified by column chromatography on silica gel (DCM/MeOH=10/1) to give 2-(1,2-dimethyl-1H-benzo[d]imidazol-5-yl)acetonitrile (170 mg) as a colorless oil. LC/MS ESI (m/z):186 $[M+H]^+$. $^1H$ NMR (400 MHz, $CDCl_3$) δ 7.60 (s, 1H), 7.29 (d, J=8.0 Hz, 1H), 7.22 (d, J=8.0 Hz, 1H), 3.86 (s, 2H), 3.74 (s, 3H), 2.62 (s, 3H).

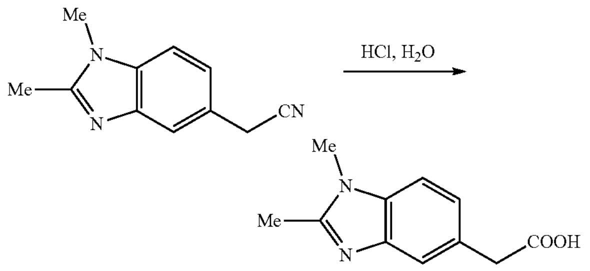

2-(1,2-dimethyl-1H-benzo[d]imidazol-5-yl)acetic acid. A solution of 2-(1,2-dimethyl-1H-1,3-benzodiazol-5-yl)acetonitrile (100 mg) in conc. HCl (0.5 mL) was stirred at 90° C. for 2 hours until the reaction was complete by LC/MS. The mixture was then concentrated to dryness to give crude 2-(1,2-dimethyl-1H-benzo[d]imidazol-5-yl)acetic acid as an oil, which was used for the next step without further purification. LC/MS ESI (m/z):205 $[M+H]^+$.

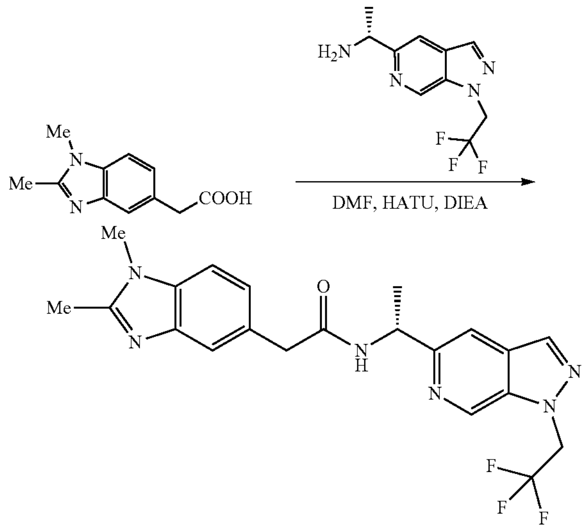

(R)-2-(1,2-dimethyl-1H-benzo[d]imidazol-5-yl)-N-(1-(1-(2,2,2-trifluoroethyl)-1H-pyrazolo[3,4-c]pyridin-5-yl)ethyl) acetamide. To a solution of 2-(1,2-dimethyl-1H-1,3-benzodiazol-5-yl) acetic acid (80 mg,) and HATU (193 mg) in DMF (2.0 mL) was added DIEA (152 mg). The solution was allowed to stir at room temperature for 10 min before the addition of (R)-1-[1-(2,2,2-trifluoroethyl)-1H-pyrazolo[3,4-c]pyridin-5-yl]ethan-1-amine hydrochloride (124 mg). The mixture was stirred at room temperature for 16 h, and LCMS detected the desired mass. The reaction was diluted with water (5 mL) and extracted with EA (10 mL×2). The combined organic phases were dried over $Na_2SO_4$, filtered and concentrated to give a residue, which was purified by prep-HPLC (Column: YMC-Actus Triart C18 250*21 mm; Mobile phase: from 20% to 95% MeCN with $H_2O$ (0.1% $NH_3H_2O$); flow rate: 15 mL/min; wave length: 220 nm/254 nm) to give (R)-2-(1,2-dimethyl-1H-benzo[d]imidazol-5-yl)-N-(1-(1-(2,2,2-trifluoroethyl)-1H-pyrazolo[3,4-c]pyridin-5-yl)ethyl)acetamide as a white solid (77.5 mg). LC/MS ESI (m/z):431 $[M+H]^+$. $^1$H NMR (400 MHz, $CDCl_3$) δ 8.88 (s, 1H), 8.07 (s, 1H), 7.60 (s, 1H), 7.52 (s, 1H), 7.30-7.21 (m, 2H), 6.55 (d, J=8.0 Hz, 1H), 5.30-5.23 (m, 1H), 5.06-5.03 (m, 2H), 3.76 (s, 3H), 3.71 (d, J=4.0 Hz, 2H), 2.67 (s, 3H), 1.42 (d, J=8.0 Hz, 3H). $^{19}$F NMR (377 MHz, $CDCl_3$) δ −70.80 (s).

Example 54. (R)-2-(3-cyano-1,2-dimethyl-1H-indol-5-yl)-N-(1-(1-(2,2,2-trifluoroethyl)-1H-pyrazolo[3,4-c]pyridin-5-yl)ethyl)acetamide

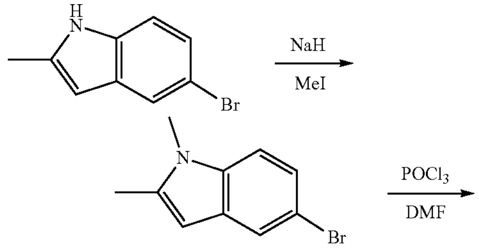

-continued

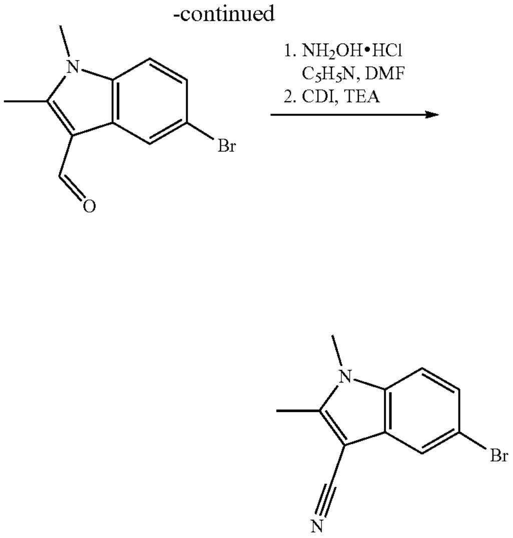

5-bromo-1,2-dimethyl-1H-indole. To a solution of 5-bromo-2-methyl-1H-indole (3.0 g) in DMF (15 mL) was added NaH (60% suspension in mineral oil, 1.71 g) at 0° C. The mixture was stirred at 0° C. for 30 min before addition of iodomethane (3.04 g). The reaction was allowed to warm to room temperature and stirred overnight. The reaction was then quenched with $H_2O$ and extracted by $Et_2O$ (3×40 mL). The combined organic layers were washed with $H_2O$ (50 mL) then dried over $Na_2SO_4$. The crude material was purified by column on silica gel (PE:EA=5:1) to afford 5-bromo-1,2-dimethyl-1H-indole (3.142 g) as a yellow solid. $^1$H NMR (400 MHz, $CDCl_3$) δ 7.61 (d, J=1.6 Hz, 1H), 7.23-7.17 (m, 1H), 7.09 (d, J=8.6 Hz, 1H), 6.17 (s, 1H), 3.62 (s, 3H), 2.40 (s, 3H). LC/MS ESI (m/z): 224$[M+H]^+$.

5-bromo-1,2-dimethyl-1H-indole-3-carbaldehyde. $POCl_3$ (1.66 mL) was added to the DMF (5 mL) at 0° C. and stirred for 30 min. Then 5-bromo-1,2-dimethyl-1H-indole (2 g) in DMF (5 mL) was added to the above mixture while cooling in an ice water bath. The reaction was then and stirred at 50° C. overnight. The reaction was cooled to the room temperature and poured into ice water. Aqueous NaOH (2 M) was added to the mixture to adjust the pH to 9, followed by extraction with ethyl acetate. The organic layer was washed with water and dried over $Na_2SO_4$. Concentration under reduced pressure gave crude 5-bromo-1,2-dimethyl-1H-indole-3-carbaldehyde (2.17 g, crude) as a yellow solid which was used in the next step without further purification. LC/MS ESI (m/z): 252$[M+H]^+$.

5-bromo-1,2-dimethyl-1H-indole-3-carbonitrile. To a solution of 5-bromo-1,2-dimethyl-1H-indole-3-carbaldehyde (2.17 g, crude) in DMF (10 mL) were added pyridine (0.84 mL) and $NH_2OH$—HCl (712 mg) and the reaction was stirred at 60° C. for 30 min. LCMS and TLC indicated that the reaction was complete, and the mixture was then cooled to 0° C. CDI (4.2 g) and TEA (1.44 mL) were sequentially added. The reaction was stirred at 60° C. overnight and then diluted with EA and water. The organic layer was separated, washed with saturated aqueous NaCl, and concentrated in vacuo. The residue was purified by silica gel column chromatography (23% EA in PE) to give 5-bromo-1,2-dimethyl-1H-indole-3-carbonitrile (1.57 g) as a yellow solid. $^1$H NMR (400 MHz, $CDCl_3$) δ 7.71 (d, J=1.2 Hz, 1H), 7.29 (dd, J=8.8, 1.8 Hz, 1H), 7.11 (d, J=8.8 Hz, 1H), 3.63 (s, 3H), 2.51 (s, 3H). LC/MS ESI (m/z): 249$[M+H]^+$.

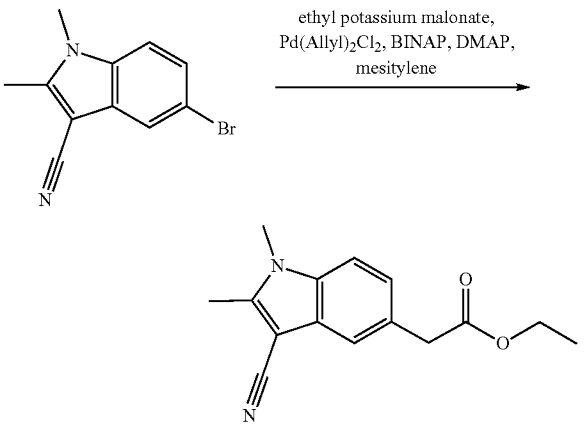

Ethyl 2-(3-cyano-1,2-dimethyl-1H-indol-5-yl)acetate. To a solution of 5-bromo-1,2-dimethyl-1H-indole-3-carbonitrile (1.57 g) in mesitylene (15 mL) were added diallylpalladium dichloride (0.10 g), BINAP (0.24 g), DMAP (0.72 g) and ethyl potassium malonate (1.61 g). The reaction was charged with $N_2$ and stirred at 120° C. overnight. The reaction was concentrated to give a residue, which was purified by silica gel column chromatography (PE:EA=5:1) to give ethyl 2-(3-cyano-1,2-dimethyl-1H-indol-5-yl)acetate (884 mg) as a white solid. LC/MS ESI (m/z): 257[M+H]$^+$.

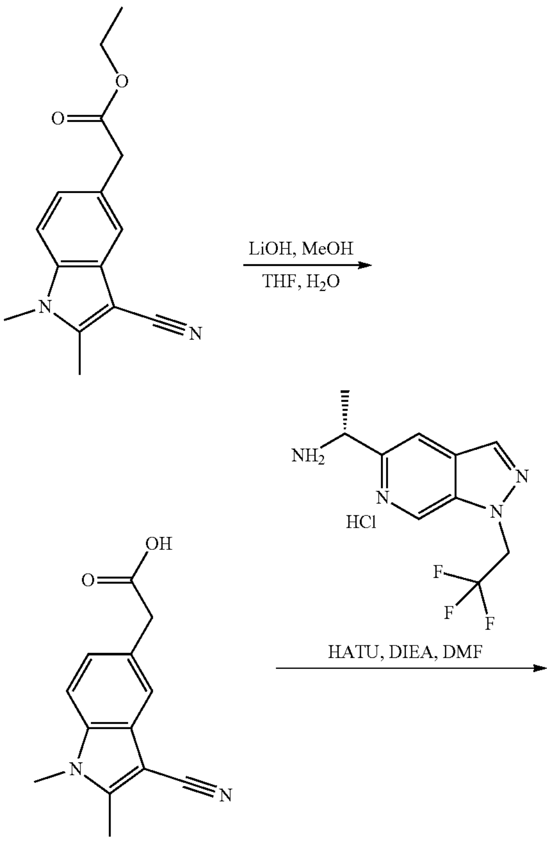

-continued

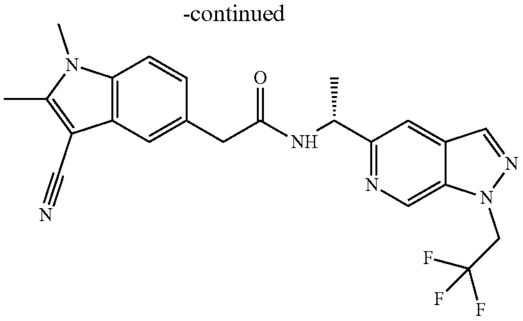

2-(3-cyano-1,2-dimethyl-1H-indol-5-yl)acetic acid. To a solution of ethyl 2-(3-cyano-1,2-dimethyl-1H-indol-5-yl)acetate (884 mg) in MeOH (3 mL) and THF (3 mL) was added LiOH (724 mg) in $H_2O$ (3 mL). The reaction mixture was stirred at room temperature for 1 hour, water (15 mL) was then added, and the aqueous layer was washed with EA. The aqueous layer was acidified to pH<3 with 1 M aqueous HCl, the mixture was extracted with EA, and the combined organic phases from were washed with saturated NaCl, dried with $Na_2SO_4$, filtered, and concentrated to give crude 2-(3-cyano-1,2-dimethyl-1H-indol-5-yl)acetic acid (530 mg) as a white solid. LC/MS ESI (m/z): 229[M+H]$^+$.

(R)-2-(3-cyano-1,2-dimethyl-1H-indol-5-yl)-N-(1-(1-(2,2,2-trifluoroethyl)-1H-pyrazolo[3,4-c]pyridin-5-yl)ethyl) acetamide. A solution of crude 2-(3-cyano-1,2-dimethyl-1H-indol-5-yl)acetic acid (200 mg) and HATU (500 mg) in 2 mL DMF was stirred at room temperature for 15 min (Solution A). DIEA (0.87 mL) was added to (R)-1-(1-(2,2,2-trifluoroethyl)-1H-pyrazolo[3,4-c]pyridin-5-yl)ethan-1-amine hydrochloride (319 mg) in 2 mL DMF until the pH of the solution higher than 7 by wet pH paper (Solution B). Solution B was added to Solution A, and the reaction was stirred at room temperature for 1 hour, at which time LCMS showed the reaction was complete. The reaction was diluted with EA and water. The two phases were separated, and the aqueous phase was extracted with EA (10 mL×2). The combined organic phases were dried over $Na_2SO_4$, filtered, and concentrated in vacuo. The residue was purified by prep-HPLC (Column: AZZOTA C18 30*250 mm*10 um; Mobile phase: from 20% to 95% MeCN with $H_2O$ (0.1% FA); flow rate: 30 mL/min; wave length: 220 nm/254 nm) to give (R)-2-(3-cyano-1,2-dimethyl-1H-indol-5-yl)-N-(1-(1-(2,2,2-trifluoroethyl)-1H-pyrazolo[3,4-c]pyridin-5-yl)ethyl) acetamide (63.3 mg) as a white solid. LC/MS ESI (m/z): 455[M+H]$^+$. $^1$H NMR (400 MHz, $CDCl_3$) δ 8.97 (s, 1H), 8.11 (s, 1H), 7.59 (s, 1H), 7.49 (s, 1H), 7.30-7.27 (m, 1H), 7.20 (d, J=8.0 Hz, 1H), 6.72 (d, J=7.6 Hz, 1H), 5.35-5.25 (m, 1H), 5.16-4.99 (m, 2H), 3.71 (s, 3H), 3.69 (d, J=3.2 Hz, 2H), 2.59 (s, 3H), 1.48 (d, J=6.8 Hz, 3H). $^{19}$F NMR (377 MHz, $CDCl_3$) δ −70.78 (s).

Example 55. (R)—N-(1-(1-(2,2,2-trifluoroethyl)-1H-pyrazolo[3,4-c]pyridin-5-yl)ethyl-1-d)-2-(4-(trifluoromethyl)phenyl)acetamide

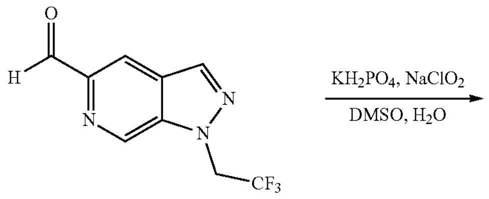

-continued

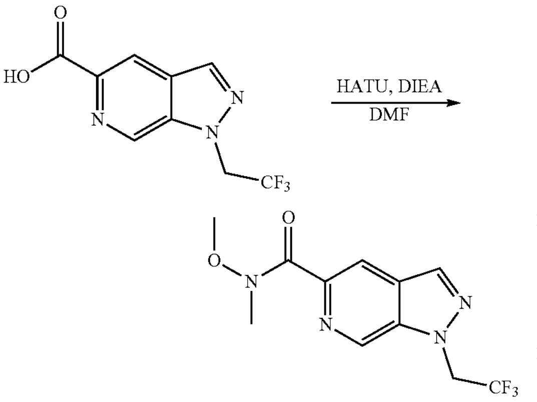

1-(2,2,2-trifluoroethyl)-1H-pyrazolo[3,4-c]pyridine-5-carboxylic acid. To a solution of 1-(2,2,2-trifluoroethyl)-1H-pyrazolo[3,4-c]pyridine-5-carbaldehyde (1.8 g) in DMSO (20 mL) were added a solution of $KH_2PO_4$ (1.4 mL) in $H_2O$ (10 mL) and a solution of sodium chlorite (2.13 g) in $H_2O$ (10 mL). The mixture was stirred at 25° C. for 12 hr. The mixture was diluted with 1N NaOH solution and extracted with EA. Then the aqueous phase was adjusted pH=4 with 1 N HCl and extracted with EA. The organic layer was dried, filtered and concentrated to give 1-(2,2,2-trifluoroethyl)-1H-pyrazolo[3,4-c]pyridine-5-carboxylic acid (2.2 g, crude) as a yellow solid. LCMS ESI (m/z): 246 $(M+H)^+$.

N-methoxy-N-methyl-1-(2,2,2-trifluoroethyl)-1H-pyrazolo[3,4-c]pyridine-5-carboxamide. A solution of 1-(2,2,2-trifluoroethyl)-1H-pyrazolo[3,4-c]pyridine-5-carboxylic acid (2.2 g), N,O-dimethylhydroxylamine hydrochloride (0.96 g), HATU (4.43 g) and TEA (3.8 mL) in DMF (20 mL) was stirred at 25° C. for 12 hr. The reaction was diluted with water and extracted with EA. The organic layer was dried, filtered and concentrated and the residue was purified by column chromatography on silica gel (DCM:MeOH=20:1) to give N-methoxy-N-methyl-1-(2,2,2-trifluoroethyl)-1H-pyrazolo[3,4-c]pyridine-5-carboxamide (2 g) as a yellow solid. LCMS ESI (m/z): 289 $(M+H)^+$. $^1H$ NMR (400 MHz, $CDCl_3$) δ 9.01 (s, 1H), 8.24 (s, 1H), 8.19 (s, 1H), 5.12 (q, J=8.4 Hz, 2H), 3.78 (s, 3H), 3.46 (s, 3H).

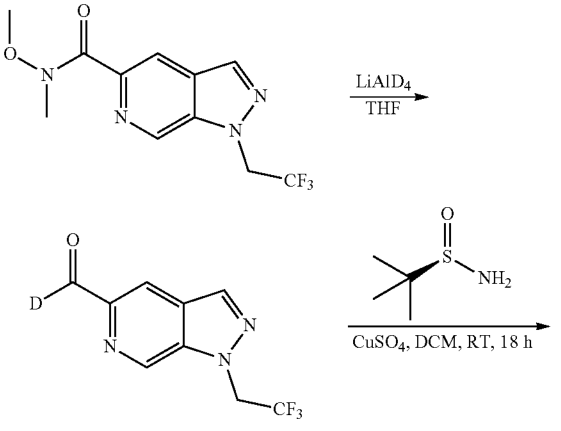

-continued

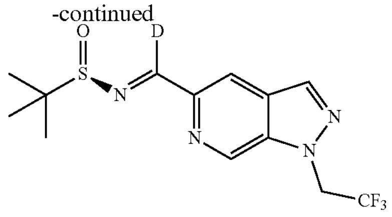

1-(2,2,2-trifluoroethyl)-1H-pyrazolo[3,4-c]pyridine-5-carbaldehyde-d. To a solution of N-methoxy-N-methyl-1-(2,2,2-trifluoroethyl)-1H-pyrazolo[3,4-c]pyridine-5-carboxamide (2000 mg) in THE (30 mL) was added $LiAlD_4$ (437 mg). The mixture was stirred at 25° C. for 12 hr. The mixture was quenched with water and 2 N aqueous NaOH solution, and extracted with EA. The organic layer was dried, filtered and concentrated to give a residue. The residue was purified by column chromatography on silica gel (DCM:MeOH=20:1) to give 1-(2,2,2-trifluoroethyl)-1H-pyrazolo[3,4-c]pyridine-5-carbaldehyde-d (820 mg) as a white solid. LCMS ESI (m/z): 231 (M+H)+

(R,E)-2-methyl-N-((1-(2,2,2-trifluoroethyl)-1H-pyrazolo[3,4-c]pyridin-5-yl)methylene-d)propane-2-sulfinamide. To a solution of 1-(2,2,2-trifluoroethyl)-1H-pyrazolo[3,4-c]pyridine-5-carbaldehyde-d (820 mg) in DCM (10 mL) was added (R)-2-methylpropane-2-sulfinamide (561 mg) and copper(II) sulfate pentahydrate (209 mg). The mixture was stirred at 25° C. for 12 hr. The mixture was filtered and concentrated to give a residue. The residue was purified by column chromatography on silica gel (DCM:MeOH=20:1) to give (R,E)-2-methyl-N-((1-(2,2,2-trifluoroethyl)-1H-pyrazolo[3,4-c]pyridin-5-yl)methylene-d)propane-2-sulfinamide (740 mg) as a yellow solid. LCMS ESI (m/z): 234 $(M+H)^+$

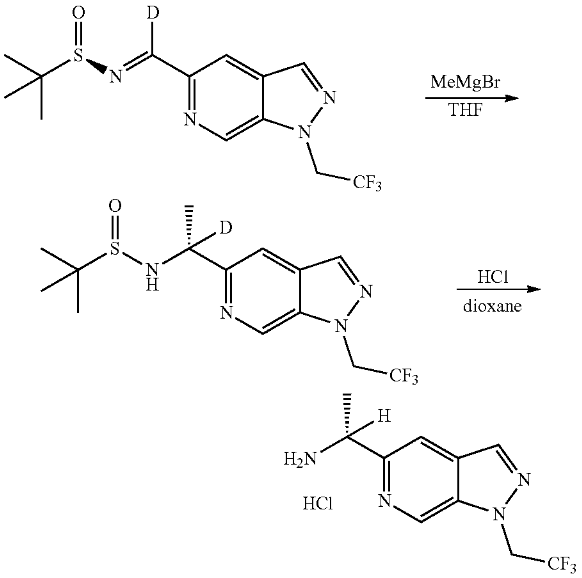

2-methyl-N-(1-(1-(2,2,2-trifluoroethyl)-1H-pyrazolo[3,4-c]pyridin-5-yl)ethyl-1-d)propane-2-sulfinamide. To a solution of (R,E)-2-methyl-N-((1-(2,2,2-trifluoroethyl)-1H-pyrazolo[3,4-c]pyridin-5-yl)methylene-d)propane-2-sulfinamide (640 mg) in THF (15 mL) was added Methylmagnesium bromide (3.200 mL, 3.0 M in $Et_2O$) at −78° C. The mixture was stirred at −78° C. for 2 hr. The mixture was quenched with aqueous $NH_4Cl$ solution and extracted with EA. The organic layer was dried, filtered and concentrated to give a yellow solid. The yellow solid was purified by column chromatography on silica gel (DCM: MeOH=20:1) to give 2-methyl-N-(1-(1-(2,2,2-trifluoroethyl)-1H-pyrazolo[3,4-c]pyridin-5-yl)ethyl-1-d)propane-2-sulfinamide (380 mg) as a white solid. LCMS ESI (m/z): 350 $(M+H)^+$.

(R)-1-(1-(2,2,2-trifluoroethyl)-1H-pyrazolo[3,4-c]pyridin-5-yl)ethan-1-amine hydrochloride. To a solution of 2-methyl-N-(1-(1-(2,2,2-trifluoroethyl)-1H-pyrazolo[3,4-c]pyridin-5-yl)ethyl-1-d)propane-2-sulfinamide (280 mg) in dioxane (2 mL) was added HCl/dioxane (2 mL, 4M in dioxane). The mixture was stirred at 25° C. for 2 hr. The mixture was concentrated to give (R)-1-(1-(2,2,2-trifluoroethyl)-1H-pyrazolo[3,4-c]pyridin-5-yl)ethan-1-amine hydrochloride (300 mg, crude) as a white solid. LCMS ESI (m/z): 246 $(M+H)^+$

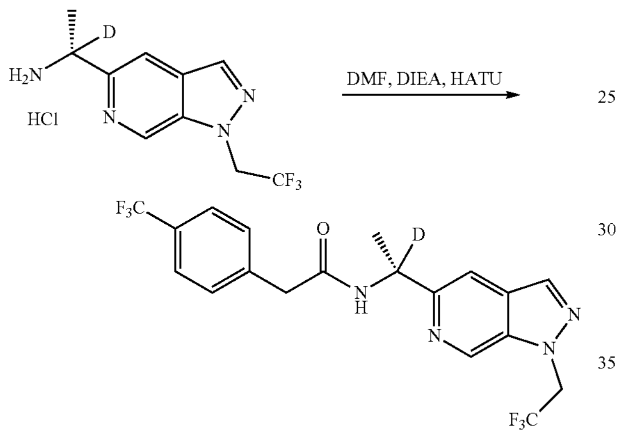

(R)—N-(1-(1-(2,2,2-trifluoroethyl)-1H-pyrazolo[3,4-c]pyridin-5-yl)ethyl-1-d)-2-(4-(trifluoromethyl)phenyl)acetamide. To a solution of 1-(1-(2,2,2-trifluoroethyl)-1H-pyrazolo[3,4-c]pyridin-5-yl)ethan-1-d-1-amine hydrochloride (300 mg) and 2-[4-(trifluoromethyl)phenyl]acetic acid (300 mg) in DMF (5 mL) was added HATU (558 mg) and DIEA (0.6 mL). The mixture was stirred at 25° C. for 3 hr. The reaction was diluted with water and extracted with EA. The organic layer was dried, filtered and concentrated to give a residue. The residue was purified by prep-HPLC (YMC-Actus Triart C18 150*20 mm*5 um; Mobile phase: from 30% to 95% MeCN with $H_2O$ (0.1% FA); flow rate: 25 mL/min; wave length: 205 nm/254 nm) to give (R)—N-(1-(1-(2,2,2-trifluoroethyl)-1H-pyrazolo[3,4-c]pyridin-5-yl)ethyl-1-d)-2-(4-(trifluoromethyl)phenyl)acetamide (241.8 mg) as a white solid. LCMS ESI (m/z): 432 $(M+H)^+$. $^1$HNMR (400 MHz, $CDCl_3$) δ 8.88 (s, 1H), 8.11 (s, 1H), 7.61-7.56 (m, 3H), 7.41 (d, J=8.0 Hz, 2H), 6.69 (s, 1H), 5.05 (q, J=8.4 Hz, 2H), 3.64 (s, 2H), 1.48 (s, 3H). $^{19}$F NMR (377 MHz, $CDCl_3$) δ −62.54, −70.81 ppm.

Example 56. 2-(4-isopropylphenyl)-N-[(1R)-1-(5-(2,2,2-trifluoroethoxy)pyridin-2-yl)ethyl]acetamide The title compound was synthesized according to Example 16 of U.S. Pat. No. 7,875,636.

Example 57. (R)—N-(1-(2,2-difluoro-[1,3]dioxolo[4,5-c]pyridin-6-yl)ethyl)-2-(4-isopropylphenyl)acetamide

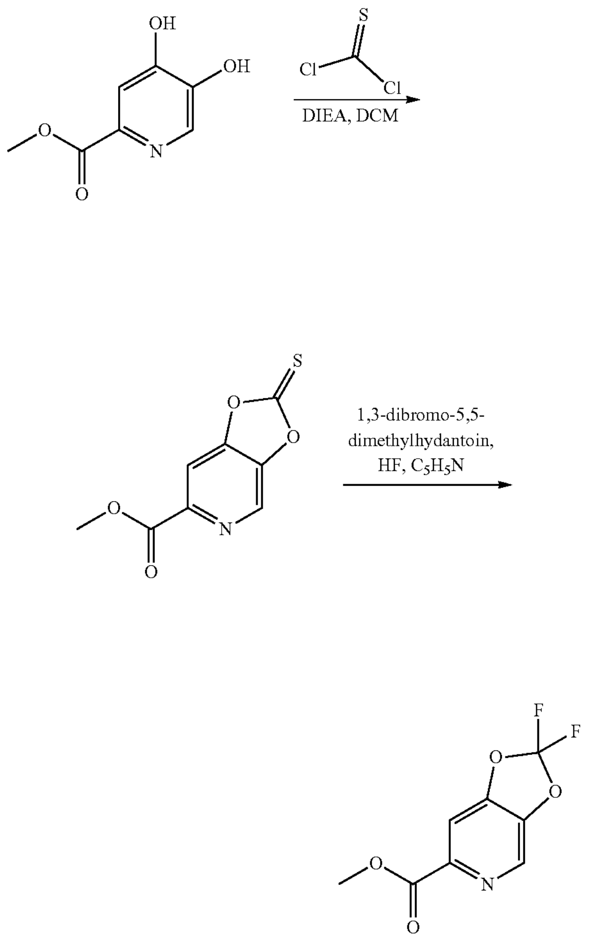

Synthesis of methyl 2-thioxo-[1,3]dioxolo[4,5-c]pyridine-6-carboxylate. To a solution of methyl 4,5-dihydroxypyridine-2-carboxylate (1.0 g) and DIEA (1.95 mL) in DCM (15 mL) was added thiophosgene (0.90 mL) at 0° C., and the mixture was stirred at 25° C. for 2 hours. The mixture was concentrated to give a brown oil, which was purified by column chromatography on silica gel (PE:EA=5:1) to give methyl 2-thioxo-[1,3]dioxolo[4,5-c]pyridine-6-carboxylate (1.0 g) as a white solid.

Synthesis of methyl 2,2-difluoro-[1,3]dioxolo[4,5-c]pyridine-6-carboxylate. To a solution of 2-thioxo-[1,3]dioxolo[4,5-c]pyridine-6-carboxylate (1.0 g) in DCM (30 mL) was added Hydrogen fluoride-pyridine (70% HF) (3.0 mL), followed by 1,3-dibromo-5,5-dimethylhydantoin (4.1 g) at −78° C. The mixture was stirred at −78° C. for 20 min, and the cooling bath was then replaced with ice-NaCl and the mixture stirred at −10° C. for 1 hour. The mixture was quenched with 50% NaOH solution (10 mL) until the pH was neutral. Then $Na_2S_2O_3$ (10% solution, 20 mL) was added, and the mixture was extracted with DCM (20 mL×3). The combined organic layers were dried, filtered and concentrated to give a yellow oil. The yellow oil was purified by column chromatography on silica gel (PE:EA=5:1) to give methyl 2,2-difluoro-2H-[1,3]dioxolo[4,5-c]pyridine-6-carboxylate (850 mg) as a white solid.

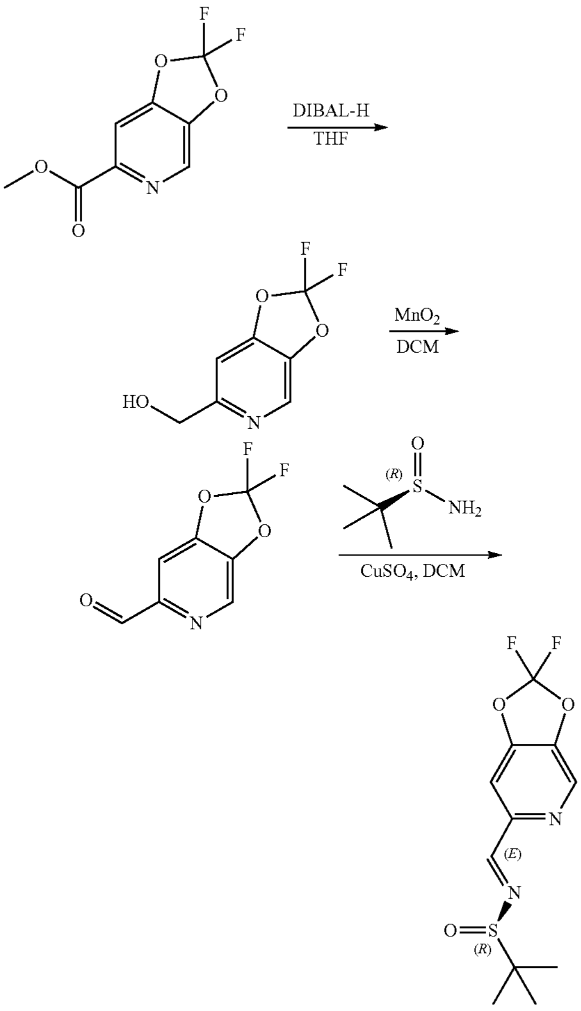

Synthesis of (2,2-difluoro-[1,3]dioxolo[4,5-c]pyridin-6-yl)methanol. To a solution of methyl 2,2-difluoro-2H-[1,3]dioxolo[4,5-c]pyridine-6-carboxylate (480 mg) in THF (10 mL) was added diisobutylaluminium hydride (6.6 mL, 1 M) at 0° C. The mixture was stirred at 0° C. for 2 hours, and the mixture was quenched with saturated aqueous ammonium chloride (5 mL) and extracted with DCM (5 mL×3). The combined organic layers were dried, filtered and concentrated to give crude {2,2-difluoro-2H-[1,3]dioxolo[4,5-c]pyridin-6-yl}methanol (230 mg) as colorless oil, which was used in the next step without further purification.

Synthesis of 2,2-difluoro-[1,3]dioxolo[4,5-c]pyridine-6-carbaldehyde. To a solution of {2,2-difluoro-2H-[1,3]dioxolo[4,5-c]pyridin-6-yl}methanol (230 mg) in DCM (5.0 mL) was added manganese oxide (106 mg), and the mixture was stirred at 25° C. for 12 hours. The mixture was then filtered, and the filtrate was concentrated to give crude 2,2-difluoro-[1,3]dioxolo[4,5-c]pyridine-6-carbaldehyde, which was used for the next step without further purification.

Synthesis of (R,E)-N-((2,2-difluoro-[1,3]dioxolo[4,5-c]pyridin-6-yl)methylene)-2-methylpropane-2-sulfinamide. To a solution of 2,2-difluoro-2H-[1,3]dioxolo[4,5-c]pyridine-6-carbaldehyde (250 mg) in DCM (10 mL) was added $CuSO_4$ (640 mg) and (R)-2-methylpropane-2-sulfinamide (210 mg). The reaction was stirred at 25° C. for 36 hours, and the mixture was filtered and the filtrate concentrated to give a brown oil. The brown oil was purified by column chromatography on silica gel (PE:EA=5:1) to give (R,E)-N-((2,2-difluoro-[1,3]dioxolo[4,5-c]pyridin-6-yl)methylene)-2-methylpropane-2-sulfinamide (240 mg) as a white solid.

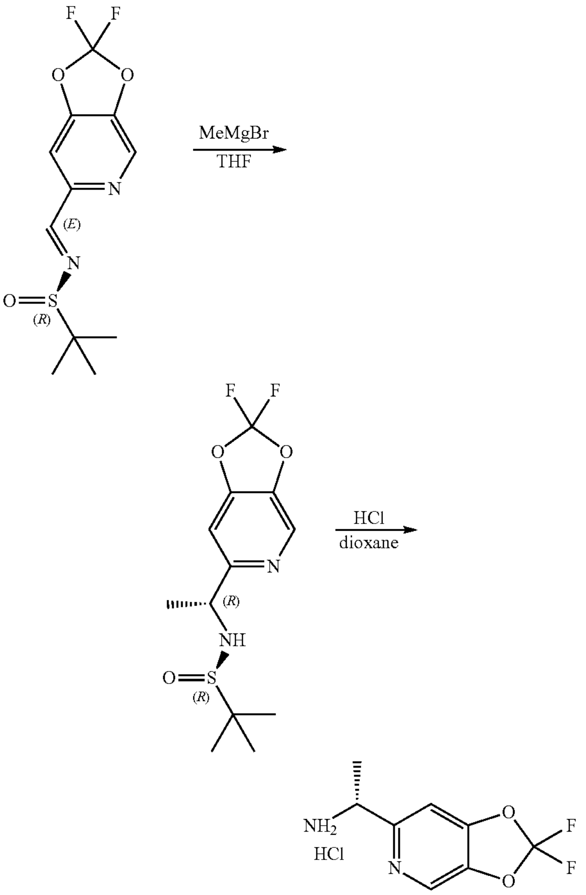

Synthesis of (R)—N—((R)-1-(2,2-difluoro-[1,3]dioxolo[4,5-c]pyridin-6-yl)ethyl)-2-methylpropane-2-sulfinamide. To a solution of (R,E)-N-((2,2-difluoro-[1,3]dioxolo[4,5-c]pyridin-6-yl)methylene)-2-methylpropane-2-sulfinamide (240 mg) in THF (5 mL) was added methylmagnesium bromide (1.1 mL, 3 M in THF) at −78° C. The mixture was stirred at −78° C. for 1 hour, and the mixture was quenched with saturated aqueous ammonium chloride (5 mL) and extracted with EtOAc (10 mL×2). The organic layer was dried, filtered and concentrated to give a yellow oil. The yellow oil was purified by column chromatography on silica gel (PE:EA=5:1 to 1:1) to give (R)—N—((R)-1-(2,2-difluoro-[1,3]dioxolo[4,5-c]pyridin-6-yl)ethyl)-2-methylpropane-2-sulfinamide (190 mg) as a white solid.

Synthesis of (R)-1-(2,2-difluoro-[1,3]dioxolo[4,5-c]pyridin-6-yl)ethan-1-amine hydrochloride. To a solution of (R)—N—((R)-1-(2,2-difluoro-[1,3]dioxolo[4,5-c]pyridin-6-yl)ethyl)-2-methylpropane-2-sulfinamide (100 mg) in dioxane (1.0 mL) was added HCl/dioxane (4 N, 1 mL). The mixture was stirred at 25° C. for 1 hour, and the mixture was concentrated to give (R)-1-(2,2-difluoro-[1,3]dioxolo[4,5-c]pyridin-6-yl)ethan-1-amine hydrochloride (70 mg, crude) as a white solid.

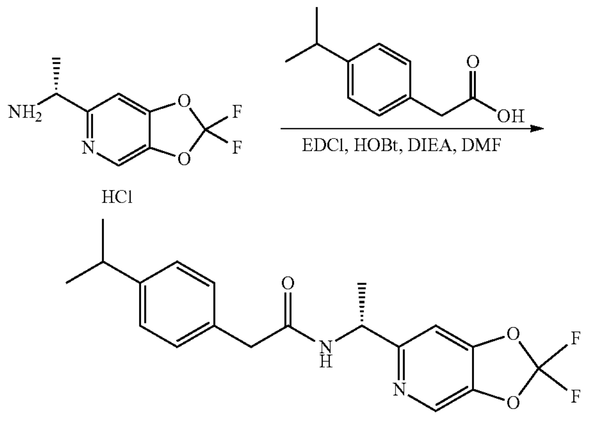

(R)—N-(1-(2,2-difluoro-[1,3]dioxolo[4,5-c]pyridin-6-yl)ethyl)-2-(4-isopropylphenyl)acetamide. To a solution of (R)-1-(2,2-difluoro-[1,3]dioxolo[4,5-c]pyridin-6-yl)ethan-1-amine hydrochloride (70 mg) in DMF (5.0 mL) was added 2-[4-(propan-2-yl)phenyl]acetic acid (67.9 mg), EDCI HCl (79.6 mg), HOBT (56.1 mg) and DIEA (0.23 mL). The reaction was stirred at 25° C. for 3 hours, and the mixture was diluted with water and extracted with EtOAc. The organic layer was dried, filtered and concentrated to give a yellow oil. The yellow oil was purified by prep-HPLC [YMC-Actus Triart C180250*21 mm; Mobile phase: from 30% to 95% MeCN with $H_2O$ (0.10% FA)] to give (R)—N-(1-(2,2-difluoro-[1,3]dioxolo[4,5-c]pyridin-6-yl)ethyl)-2-(4-isopropylphenyl)acetamide (51.6 mg) as a white solid. LCMS ESI (m/z): 363 $(M+H)^+$. $^1H$ NMR (400 MHz, $CDCl_3$) δ 8.18 (s, 1H), 7.24-7.15 (m, 4H), 6.98 (s, 1H), 6.53 (d, J=6.8 Hz, 1H), 5.18-4.97 (m, 1H), 3.56 (s, 2H), 2.98-2.80 (m, 1H), 1.40 (d, J=6.8 Hz, 3H), 1.26 (s, 3H), 1.24 (s, 3H).

Example 58. (R)—N-(1-(5-chlorothiazol-2-yl)ethyl)-2-(6-(1-(trifluoromethyl)cyclopropyl)pyridin-3-yl)acetamide

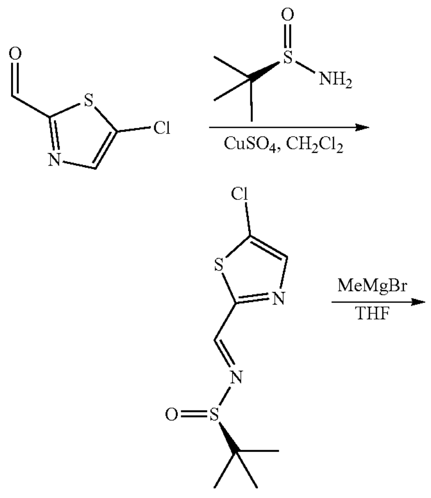

-continued

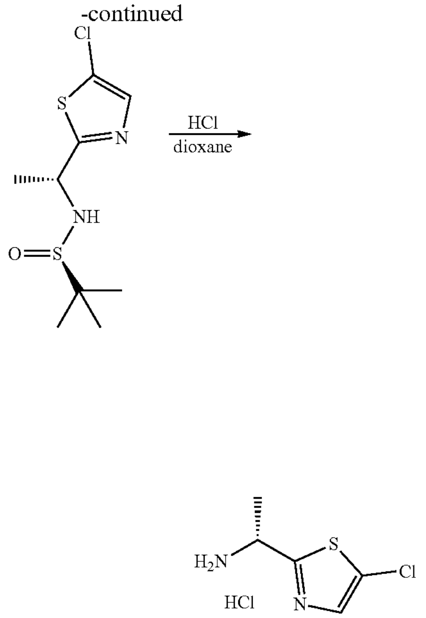

Synthesis of (R,E)-N-((5-chlorothiazol-2-yl)methylene)-2-methylpropane-2-sulfinamide. To the solution of 5-chloro-1,3-thiazole-2-carbaldehyde (160 mg) in $CH_2Cl_2$ (3.0 mL) were added (R)-2-methylpropane-2-sulfinamide (131 mg) and $CuSO_4$ (865 mg) at room temperature. The mixture was stirred at room temperature for 2 hours, and LCMS showed the reaction was complete. The reaction mixture was quenched by ice-water and then extracted twice with EtOAc. The combined extracts were concentrated and the residue was purified by column chromatography on silica gel (PE:EA=3:1) to give (R,E)-N-((5-chlorothiazol-2-yl)methylene)-2-methylpropane-2-sulfinamide (246 mg) as a yellow solid.

Synthesis of (R)—N—((R)-1-(5-chlorothiazol-2-yl)ethyl)-2-methylpropane-2-sulfinamide. To the solution of (R,E)-N-((5-chlorothiazol-2-yl)methylene)-2-methylpropane-2-sulfinamide (246 mg) in THF (5.0 mL) was added methylmagnesium bromide (0.98 mL, 2.5 mol/L in THF) dropwise at −78° C. under $N_2$. The mixture was stirred at −78° C. for 1 hour, and LCMS indicated the reaction was complete. The reaction mixture was quenched by ice-water and then extracted twice with EtOAc. The combined extracts were concentrated and the residue was purified by column chromatography on silica gel (PE:EA=1:1) to give (R)—N—((R)-1-(5-chlorothiazol-2-yl)ethyl)-2-methylpropane-2-sulfinamide (220 mg) as a yellow oil. LC/MS ESI (m/z): 267 $[M+H]^+$.

Synthesis of (R)-1-(5-chlorothiazol-2-yl)ethanamine hydrochloride. To the solution of (R)—N—((R)-1-(5-chlorothiazol-2-yl)ethyl)-2-methylpropane-2-sulfinamide (220 mg) in dioxane (5.0 mL) was added HCl in dioxane (0.82 mL, 4 M) at room temperature. The mixture was stirred at room temperature for 2 hours, and LCMS indicated the reaction was complete. The solvent was removed to give crude (R)-1-(5-chlorothiazol-2-yl)ethanamine hydrochloride (117 mg) as a yellow oil. LC/MS ESI (m/z): 163 $[M+H]^+$.

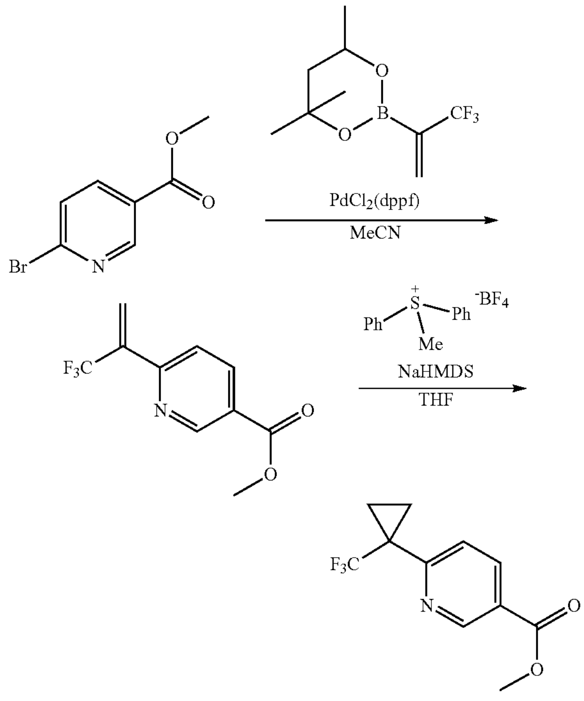

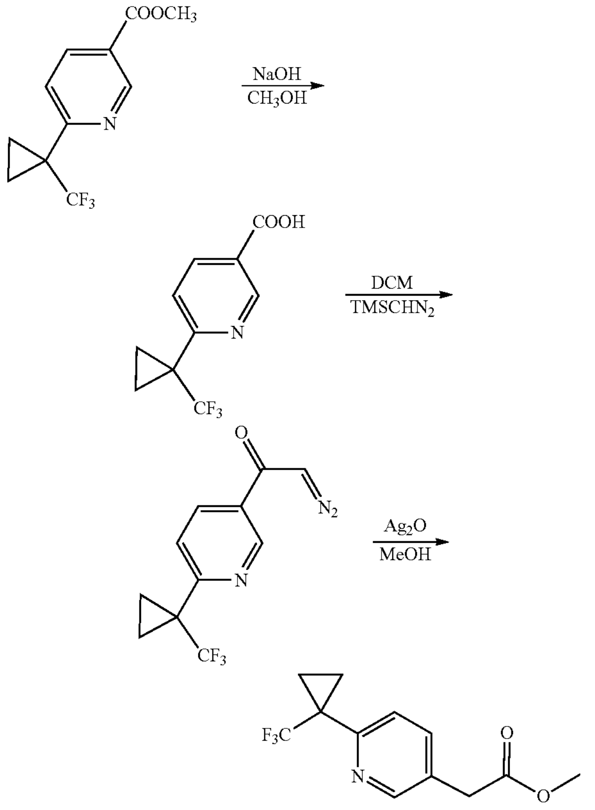

Synthesis of methyl 6-(3,3,3-trifluoroprop-1-en-2-yl) nicotinate. A mixture of methyl 6-bromonicotinate (5.47 g), 4,4,6-trimethyl-2-(3,3,3-trifluoroprop-1-en-2-yl)-1,3,2-dioxaborinane (7.87 g), Pd(dppf)$Cl_2$ (1.85 g), $K_2CO_3$ (26.8 mL of 2 M in water) in acetonitrile (104 mL) was charged with $N_2$ and heated at 80° C. for 90 minutes. The reaction mixture was cooled to room temperature and partitioned between water and ethyl acetate. The two phases were separated, and the aqueous phase was extracted with DCM (10 mL×3). The combined organic phases were dried over $Na_2SO_4$, filtered and concentrated to give a residue, which was purified by silica gel column chromatography (0-20% ethyl acetate/PE) to provide methyl 6-(3,3,3-trifluoroprop-1-en-2-yl)nicotinate as a colorless oil (3.0 g): LC/MS ESI (m/z): 232 $[M+H]^+$; $^1$H NMR (400 MHz, $CDCl_3$): δ 9.22 (d, J=2.4 Hz, 1H), 8.75-8.74 (m, 1H), 8.34-8.31 (m, 1H), 8.25 (d, J=1.2 Hz, 1H), 7.58 (d, J=11.6 Hz, 1H), 3.97 (s, 3H); $^{19}$F NMR (376.48 MHz, $CDCl_3$): −63.98 ppm.

Synthesis of methyl 6-(1-(trifluoromethyl)cyclopropyl) nicotinate. To a suspension of methyl 6-(3,3,3-trifluoroprop-1-en-2-yl)nicotinate (2.47 g) and methyldiphenylsulfonium tetrafluoroborate (4.0 g) in anhydrous tetrahydrofuran (30 mL) was added 4.27 mL NaHMDS (2 M in THF) at 0° C. under nitrogen. The reaction mixture was stirred at 0° C. for 10 min and then at room temperature for 1 h. Methanol (0.25 mL) was then added to quench the reaction. The crude mixture was concentrated in vacuo and the residue was purified by silica gel column chromatography (10% EA in PE) to give methyl 6-(1-(trifluoromethyl)cyclopropyl)nicotinate as a white solid (345 mg). LC/MS ESI (m/z): 246 $[M+H]^+$. $^1$HNMR (400 MHz, $CDCl_3$): δ 9.09 (d, J=2.4 Hz, 1H), 8.26-8.23 (m, 1H), 7.64 (d, J=8.4 Hz, 1H), 3.95 (s, 3H), 1.54-1.53 (m, 2H), 1.50-1.49 (m, 2H) ppm. $^{19}$FNMR (376.48 MHz, $CDCl_3$): δ −67 ppm.

Synthesis of 6-(1-(trifluoromethyl)cyclopropyl)nicotinic acid. To a solution of methyl 6-(1-(trifluoromethyl)cyclopropyl)nicotinate (345 mg) in MeOH (20 mL) was added 4.0 mL of 2.0 M NaOH. The mixture was stirred at 65° C. for 2 hours, and TLC showed total consumption of starting material. The MeOH was removed under vacuo and the reaction was adjusted pH to 2-3 with 1 N HCl. The reaction was extracted with EA (50 mL). The EA extract was washed with brine, dried with anhydrous $Na_2SO_4$, filtered and concentrated to give crude 6-(1-(trifluoromethyl)cyclopropyl)nicotinic acid (300 mg) as a white solid. LC/MS ESI (m/z): 232 $[M+H]^+$.

Synthesis of 2-diazo-1-(6-(1-(trifluoromethyl)cyclopropyl)pyridin-3-yl)ethanone. 6-(1-(trifluoromethyl)cyclopropyl)nicotinic acid (300 mg) in DCM (10 mL) was cooled to 0° C. Oxaly chloride (1.1 mL) and DMF (2 drops) were added, and the resulting solution was stirred at rt for 2 hours. The mixture was concentrated under vacuo, and the residue was redissolved in DCM (10 mL) and cooled to 0° C. (Diazomethyl)trimethylsilane (1.28 mL, 2 M solution in hexane) and TEA (0.33 mL) were added slowly, and the resulting solution was maintained at 5° C. for 12 hours. The reaction was then filtered, and the filtrate was concentrated under reduced pressure to give ~600 mg 2-diazo-1-(6-(1-(trifluoromethyl)cyclopropyl)pyridin-3-yl)ethanone as a brown residue, which was directly used in the next step directly. LC/MS ESI (m/z): 256 $[M+H]^+$.

Synthesis of methyl 2-(6-(1-(trifluoromethyl)cyclopropyl)pyridin-3-yl)acetate. To a mixture of 2-diazo-1-(6-(1-(trifluoromethyl)cyclopropyl)pyridin-3-yl)ethanone (600 mg, crude) in methanol (20 mL) was added $Ag_2O$ (175 mg). The reaction was stirred at 65° C. for 2 hours, and TLC showed formation of trace product. Additional $Ag_2O$ (142 mg) was added, and the mixture was stirred at 65° C. for another 2 hours. The reaction was concentrated under vacuo and the residue purified by silica gel column chromatography (10% EA-20% EA in PE) to give 100 mg methyl 2-(6-(1-(trifluoromethyl)cyclopropyl)pyridin-3-yl)acetate as a yellow oil. LC/MS ESI (m/z): 260 $[M+H]^+$.

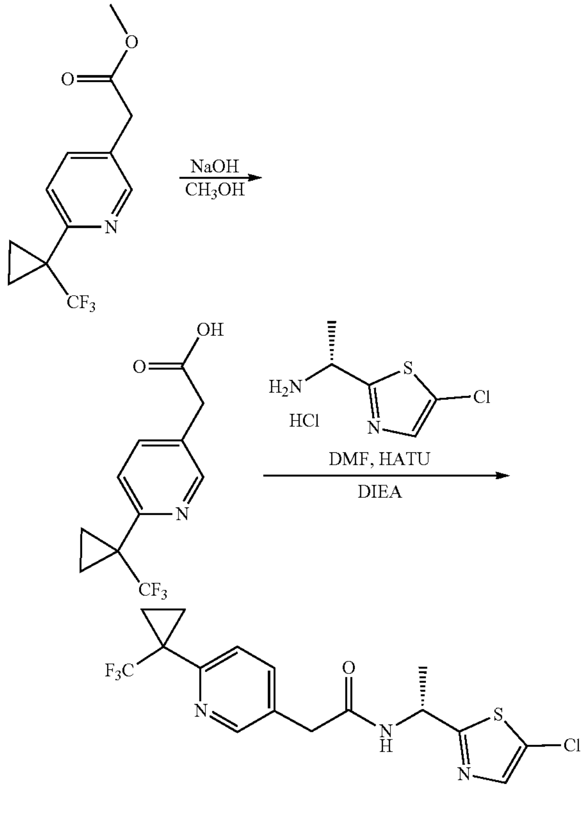

Synthesis of 2-(6-(1-(trifluoromethyl)cyclopropyl)pyridin-3-yl)acetic acid. To a solution of methyl 2-(6-(1-(trifluoromethyl)cyclopropyl)pyridin-3-yl)acetate (100 mg) in MeOH (10 mL) was added 2.0 mL of 2.0 M NaOH. After stirring the mixture at 65° C. for 2 hours, some of the volatiles were removed under reduced pressure, and the reaction was adjusted pH to 2-3 by 1 N HCl. The mixture was then extracted with EA (50 mL×3), and the combined organic phases were washed with brine, dried with anhydrous $Na_2SO_4$, filtered and concentrated to give crude 2-(6-(1-(trifluoromethyl)cyclopropyl)pyridin-3-yl)acetic acid (50 mg) as a white solid, which was used in the next step without further purification. LC/MS ESI (m/z): 246 $[M+H]^+$. T HNMR (400 MHz, $CDCl_3$): δ 8.43 (d, J=1.6 Hz, 1H), 7.78-7.75 (m, 1H), 7.59-7.56 (m, 1H), 3.69 (s, 2H), 1.43-1.40 (m, 2H), 1.32-1.29 (m, 2H) ppm. $^{19}$FNMR ($CDCl_3$, -376.48): δ -69.78 ppm.

Synthesis of (R)—N-(1-(5-chlorothiazol-2-yl)ethyl)-2-(6-(1-(trifluoromethyl)cyclopropyl)pyridin-3-yl)acetamide. To a mixture of 2-(6-(1-(trifluoromethyl)cyclopropyl)pyridin-3-yl)acetic acid (50 mg) in DMF (1.0 mL) was added HATU (85 mg), and the mixture was stirred at room temperature for 5 min (Solution A). To another flask was added (R)-1-(5-chlorothiazol-2-yl)ethanamine hydrochloride (40 mg) and DMF (0.5 mL). DIEA was then added until the (R)-1-(5-chlorothiazol-2-yl)ethanamine was dissolved in DMF and the pH was about 8 (Solution B). Solution B was added to Solution A, and the mixture was stirred at room temperature for 2 hours. EA (50 mL) and $H_2O$ (30 mL) were then added, and the two phases were separated. The aqueous phase was further extracted with DCM (10 mL×3), and the combined organic phases were dried over $Na_2SO_4$, filtered and concentrated to give a residue, which was purified by prep-HPLC (Column: Xbudge prep C18 250*19 mm Sum OBD; Mobile phase: from 10% to 55% MeCN with $H_2O$ (0.1% NH40H); flow rate: 20 mL/min; wave length: 205 nm/254 nm) and SFC (Column: Mobile phase: A for $CO_2$ and B for MEOH+0.1% $NH_3H_2O$; Gradient: B 40%; flow rate: 50 mL/min; wave length: 220 nm) to provide 25 mg (R)—N-(1-(5-chlorothiazol-2-yl)ethyl)-2-(6-(1-(trifluoromethyl)cyclopropyl)pyridin-3-yl)acetamide was obtained as a white solid. $^1$HNMR (400 MHz, $CDCl_3$): δ 8.43 (d, J=2.0 Hz, 1H), 7.65-7.63 (m, 1H), 7.55-7.53 (m, 1H), 7.46 (s, 1H), 6.24-6.23 (m, 1H), 5.32-5.25 (m, 1H), 3.57 (s, 2H), 1.56 (d, J=6.8 Hz, 3H), 1.43-1.41 (m, 2H), 1.40-1.39 (m, 2H) ppm. $^{19}$FNMR (376.48, $CDCl_3$): δ -67.8 ppm.

Example 59. (R)—N-(1-(5-(2,2,2-trifluoroethoxy)pyridin-2-yl)ethyl)-2-(6-(1-(trifluoromethyl)cyclopropyl)pyridin-3-yl)acetamide

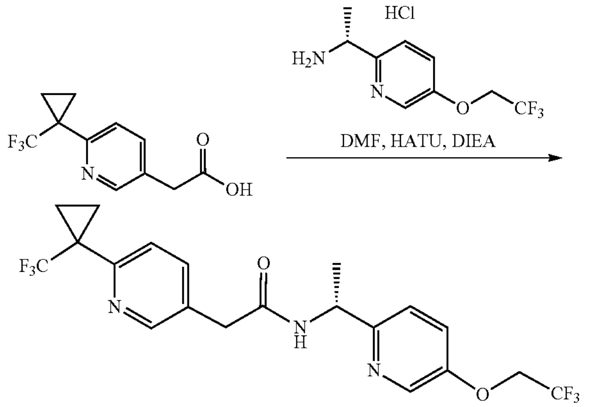

To a mixture of 2-(6-(1-(trifluoromethyl)cyclopropyl)pyridin-3-yl)acetic acid (40 mg) in DMF (1.5 mL) was added HATU (68 mg), and the mixture was stirred at room temperature for 5 min (Solution A). To (R)-1-(5-(2,2,2-trifluoroethoxy)pyridin-2-yl)ethanamine hydrochloride (49 mg) in DMF (0.5 mL) was added DIEA until (R)-1-(5-(2,2,2-trifluoroethoxy)pyridin-2-yl)ethanamine was dissolved in DMF and the pH was about 8 (Solution B). Solution B was added to Solution A, and the mixture was stirred at room temperature for 2 hours. EA (50 mL) and $H_2O$ (40 mL) were added, and the organic layer was washed by sat. NaCl, dried over $Na_2SO_4$, filtered and concentrated. The residue was purified by prep-HPLC (Column: Xbudge prep C18 250*19 mm Sum OBD; Mobile phase: from 10% to 55% MeCN with $H_2O$ (0.1% FA); flow rate: 20 mL/min; wave length: 205 nm/254 nm) to give (R)—N-(1-(5-(2,2,2-trifluoroethoxy)pyridin-2-yl)ethyl)-2-(6-(1-(trifluoromethyl)cyclopropyl)pyridin-3-yl)acetamide as a yellow solid (23.3 mg). LC/MS ESI (m/z): 448 $[M+H]^+$. $^1$HNMR (400 MHz, $CDCl_3$): δ 8.43 (d, J=2.0 Hz, 1H), 8.23 (d, J=2.8 Hz, 1H), 7.65-7.62 (m, 1H), 7.52-7.50 (m, 1H), 7.25-7.18 (m, 2H), 6.87 (d, J=7.2 Hz, 1H), 5.13-5.06 (m, 1H), 4.38 (q, J=8.0 Hz, 2H), 3.55 (s, 2H), 1.43-1.38 (m, 5H), 1.36-1.35 (m, 2H) ppm. $^{19}$FNMR (376.48, $CDCl_3$): δ -67.7 ppm, -73.9 ppm.

Example 60. In Vitro Patch Clamp Data for T-type Calcium Channel Antagonists

Patch clamp assays were performed at Charles River. HEK293 cells were cultured in Dulbecco's Modified Eagle Medium/Nutrient Mixture F-12 (D-MEM/F-12) supplemented with 10% fetal bovine serum, 100 U/mL penicillin G sodium, 100 μg/mL streptomycin sulfate and 500 μg/mL G418. Before testing, cells in culture dishes were washed twice with Hank's Balanced Salt Solution, treated with Accutase™ and re-suspended in the culture media (~$20\times10^6$ cells in 20 mL). Cells in suspension were allowed to recover for 10 minutes in tissue culture incubator set at 37° C. in a humidified 95% air: 5% CO2 atmosphere. Immediately before use in the SyncroPatch 384PE system (SP384PE), the cells were washed twice in extracellular buffer (HB-PS) to remove the culture medium and re-suspended in 20 mL of HB-PS. Extracellular buffer was loaded into the wells of Nanion 384-well Patch Clamp (NPC-384, 4×M) chip (60 μL per well). Then, cell suspension was pipetted into the wells (20 μL per well) of the chip. After establishment of the whole-cell configuration, membrane currents were recorded using patch clamp amplifier in the SP384PE system.

The illustrative compounds of the present disclosure showed inhibition of a T-type calcium channel in a patch clamp assay.

TABLE 4

| Cav3.2 Activity | |
|---|---|
| Example | $Ca_v3.2\ IC_{50}$ (μM) |
| 1 | 0.522 |
| 2 | 6.450 |
| 3 | >10 |
| 4 | >10 |
| 5 | 1.218 |
| 6 | 7.841 |
| 7 | 0.110 |
| 8 | 0.126 |
| 9 | 0.044 |
| 10 | >10 |
| 11 | 2.422 |
| 12 | 0.647 |
| 13 | 0.710 |
| 14 | 0.085 |
| 15 | 0.163 |
| 16 | 1.272 |
| 17 | 0.292 |
| 18 | 0.343 |
| 19 | 0.132 |
| 20 | 1.050 |
| 21 | 0.637 |
| 22 | 0.194 |
| 23 | 4.019 |
| 24 | 0.333 |
| 25 | 2.593 |
| 26 | 7.030 |
| 27 | 0.861 |
| 28 | 0.089 |
| 29 | 0.533 |
| 30 | 0.475 |
| 31 | 0.505 |
| 32 | 9.42 |
| 33 | 8.27 |
| 34 | >10 |
| 35 | 2.13 |
| 36 | 0.873 |
| 37 | 0.084 |
| 38 | 0.123 |
| 39 | 0.519 |
| 40 | 0.827 |
| 41 | 0.727 |
| 42 | 0.394 |

TABLE 4-continued

| Cav3.2 Activity | |
|---|---|
| Example | $Ca_v3.2\ IC_{50}$ (μM) |
| 43 | 0.214 |
| 44 | 0.071 |
| 45 | 0.113 |
| 46 | 0.806 |
| 47 | 0.220 |
| 48 | 0.260 |
| 49 | 0.352 |
| 50 | 0.850 |
| 51 | 0.411 |
| 52 | 0.389 |
| 53 | 0.919 |
| 54 | 0.529 |
| 55 | 0.335 |
| 56 | 0.037 |
| 57 | 0.868 |
| 58 | 4.9 |
| 59 | 0.097 |

Example 61. T-Type Calcium Channel Antagonists Reduce Miro1

Determination of Miro1 reduction after compound administration was performed according to the Western blot method described in: Hsieh C-H, Li L, Vanhauwaert R, Nguyen K T, Davis M D, Bu G, et al. Miro1 Marks Parkinson's Disease Subset and Miro1 Reducer Rescues Neuron Loss in Parkinson's Models. Cell Metab. 2019; 1131-1140.

Several known compounds were tested for Miro1 reducing ability, including benidipine (1,4-dihydro-2,6-dimethyl-4-(3-nitrophenyl)-3,5-pyridine-dicarboxylic acid methyl 1-(phenylmethyl)-3-piperidinyl ester); MK-8998 ((R)-2-(4-Isopropylphenyl)-N-(1-(5-(2,2,2-trifluoroethoxy)pyridin-2-yl)ethyl)acetamide); ABT-639 (5-[(8aR)-3,4,6,7,8,8a-hexahydro-1H-pyrrolo[1,2-a]pyrazine-2-carbonyl]-4-chloro-2-fluoro-N-(2-fluorophenyl)benzenesulfonamide); ACT-709478 (N-(1-((5-cyanopyridin-2-yl)methyl)-1H-pyrazol-3-yl)-2-(4-(1-(trifluoromethyl)cyclopropyl)phenyl) acetamide), and zonisamide (1,2-Benzisoxazole-3-methanesulfonamide). The results are shown below.

TABLE 5

| Miro1 Lowering Effects of Calcium Channel Antagonists | | |
|---|---|---|
| Compound | Ca Channel Selectivity | Miro1 Lowering |
| Benidipine | T-/L-/N-Type | YES |
| MK-8998 | T-Type | YES |
| ABT-639 | T-Type | YES |
| ACT-709478 | T-Type | YES |
| Zonisamide | T-Type | YES |
| Nimodipine | L-Type | NO |
| Isradipine | L-Type | NO |
| Nifedipine | L-Type | NO |
| Felodipine | L-Type | NO |
| Omega-Conotoxin | N-Type | NO |
| Levetiracetam | N-Type | NO |
| Gabapentin | N-Type | NO |
| Nicardipine | N-Type | NO |
| Cilnidipine | L-/N-Type | NO |
| Lamotrigene | L-/N-/P-Type | NO |

The compounds having T-type calcium channel activity demonstrated reduction of Miro1.

Example 62. Exemplary Compounds that Reduce Miro1 a) Miro1 Fibroblast Assay

Fibroblast Challenge and Miro1 Western blot: Skin fibroblasts were obtained from human Parkinson's disease (PD) patients. CCCP was applied at 40 μM for 24 hr to fibroblasts before cells were lysed in RIPA lysis buffer with 0.25 mM PMSF and protease inhibitors. Lysates were cleared by centrifugation at 17,000×g for 10 min at 4° C., and supernatants were run in an SDS-PAGE for Western blotting. After electrophoresis, nitrocellulose membranes (Bio-Rad) were used in wet transfer. Transferred membranes were first blocked for 1 hr in phosphate-buffered saline (PBS) containing 5% fat-free milk and 0.1% tween-20, and then incubated with the following primary antibodies: rabbit anti-Miro1 (HPA010687, Sigma-Aldrich) at 1:1,000, mouse anti-ATP50 (AB14730, Abcam) at 1:5,000, mouse anti-β-Actin (A00702, Genscript) at 1:3,000, or rabbit anti-VDAC (4661S, Cell Signaling Technology) at 1:1,000 at 4° C. overnight in blocking buffer. West Dura ECL reagents (GE Healthcare) were used for ECL immunoblotting with HRP-conjugated goat anti-mouse or anti-rabbit, anti-mouse IgG (Jackson ImmunoResearch Laboratories) at 1:5-10,000. Membranes were exposed to UltraCruz autoradiography films (Santa Cruz Biotechnology) and developed on a Konica Minolta SRX-101A developer.

T-type calcium channel antagonists that could reduce Miro1 level were tested in the above PD fibroblast assay. The following demonstrated dose-dependent Miro1 reduction.

TABLE 6

Miro1 Reduction in Fibroblast

| Compound | Fibroblast $IC_{50}$ (nM) |
|---|---|
| Benidipine | 2565 |
| ABT-639 | 5408 |
| ACT-709478 | 3932 |
| MK-8998 | 693 |

b) Miro1 Neuron Assay

Neuron Challenge and Mitochondria Western blot: iPSC-derived neuronal cells are homogenized, spun, and separated into a "cytosolic fraction" supernatant, and a "mitochondrial fraction" pellet. Samples are then run in an SDS-PAGE for Western blotting.

Example 63. In Vivo Miro1 Reduction with Benidipine

The Parkinson's disease (PD) fly model was used as described in Hsieh C-H, Li L, Vanhauwaert R, Nguyen K T, Davis M D, Bu G, et al. Miro1 Marks Parkinson's Disease Subset and Miro1 Reducer Rescues Neuron Loss in Parkinson's Models. Cell Metab. 2019; 1131-1140. The average Performance Index (PI) (negative geotaxis) was evaluated. Briefly, adult flies were gently tapped to the base of a modified 25 ml climbing tube and their climbing progress was recorded after 45 sec. Three populations of flies were assessed, and for each population, flies were examined 3 times per experiment. The recorded values were used to calculate the average PI.

Feeding PD Flies with a Calcium Channel Blocker Rescues Locomotion Deficits. Benidipine was tested in a PD fly model (mutant SNCA flies) and the flies examined for their locomotion. 2.5 μM Benidipine in feed for 10 days significantly improved locomotor decline, suggesting the involvement of Miro1 and calcium in PD mechanisms (FIG. 1).

Example 64. Miro1 Reduction in Patient-Derived Samples

The failure to clear Miro1 from patient-derived cells following depolarization has been associated with the risk of Parkinson's disease. The data herein supports the potential use of Miro1 for detecting a pre-symptomatic phase of Parkinson's disease.

Materials and Methods iPSCs were obtained under an MTA from the National Institute of Neurological Disorders and Stroke (NINDS) human and cell repository or Parkinson's Progression Markers Initiative (PPMI), which is in a partnership with multiple institutions that deposited iPSCs, approved study protocols, and ensured consent from donors.

Cell Culture and Western Blotting

Induced pluripotent stem cells were cultured in mTeSR Plus Kit (05825, Stemcell Technologies) and maintained in a 37° C., 5% CO2 incubator with humidified atmosphere. The media were refreshed every 1-2 days and split every 4-6 days. CCCP (C2759, Sigma-Aldrich) was prepared at 40 mM in dimethyl sulfoxide (DMSO) fresh every time and applied at 40 mM in fresh culture medium (1:1000 dilution) for 6 h. Cells were subsequently lysed in NP40 Cell lysis buffer (FNN0021, ThermoFisher Scientific) with protease inhibitor cocktail (539134, Calbiochem). Cell debris was removed by centrifugation at 17,000 g for 10 min at 4° C. Cell lysates were mixed 1:1 with 2× Laemmli buffer (4% SDS, 20% Glycerol, 120 mM Tris-HCl, 0.02% bromophenol blue, 700 mM 2-mercaptoethanol) and boiled for 5 min prior to being loaded into an SDS-PAGE. 10% polyacrylamide gels (acrylamide:bis-acrylamide=29:1) and Tris-Glycine-SDS buffer (24.8 mM Tris, 192 mM glycine, 0.1% SDS) were used for electrophoresis. After electrophoresis, nitrocellulose membranes (1620115, Bio-Rad) were used in semi-dry transfer with Bjerrum Schafer-Nielsen buffer [48 mM Tris, 39 mM glycine, 20% Methanol (v/v), pH 9.2]. Transferred membranes were first blocked overnight in phosphate-buffered saline containing 5% fat-free milk and 0.1% tween-20 at 4° C., and then incubated with the following primary antibodies: mouse anti-Miro1 (WH0055288M1, Sigma-Aldrich) at 1:1,000, mouse anti-ATP5b (AB14730, AbCam) at 1:1,000, or rabbit anti-GAPDH (5174S, Cell Signaling Technology) at 1:1-3,000, at 4° C. overnight in blocking buffer. HRP-conjugated goat anti-mouse (115-035-003, Jackson ImmunoResearch) or goat anti-rabbit (111-035-144, Jackson ImmunoResearch Laboratories) were used at 1:10-20,000. Pierce ECL Western Blotting Substrate (32109, ThermoScientfic) were used for ECL immunoblotting. Membranes were scanned using a Bio-Rad ChemiDoc XRS system. Experiments were repeated for more than three times. Cell passaging numbers were within the range of 12-17 which had no influence on the phenotype.

Quantification of Western Blotting Data

All experiments were performed in a blinded format. The intensities of protein bands were measured by ImageJ (ver. 1.48V, NIH). The intensity of each band was normalized to that of the loading control GAPDH from the same blot, and expressed as a fraction of that of "Healthy-1 with DMSO treatment" from the same experiment; this control was included in every independent experiment. The ratio of Miro1 was calculated by dividing the mean of Miro1 intensities treated with CCCP by the mean of Miro1 with DMSO of the same subject, and imported into the heat map. Student T Test was performed for comparing normalized Miro1 band intensities within the same subject ("with DMSO" vs "with CCCP"). The number of subjects with a P value>0.05 together with subjects that showed significant Miro1 upregulation after CCCP, or the number of subjects with P<0.05 for Miro1 reduction after CCCP was counted, respectively, and used in Fisher Exact Test in FIG. 2C. n=3-55 independent experiments.

Multivariance regression or Anova was used to determine the interactions among multiple variables for affecting Miro1 ratio and P values were calculated by linear fit in FIGS. 3, 4. During the analysis, Hoehn and Yahr Scale and Mini-Mental Status Examination were detected to show an interaction. Partial regression plots were subsequently generated to help decipher the relationship between an individual variable and the response variable in a multivariable regression problem. Seven partial regression plots, one for each individual variable in the regression problem (Hoehn and Yahr Scale, Mini-Mental Status Examination, onset age), their interaction terms, and the intercept were generated. Out of all the partial regression plots for interaction terms, the plot of Hoehn and Yahr Scale and Mini-Mental Status Examination with linear fit showed significance (P=0.012). This plot and additional representative partial regression plots were shown in FIG. 5.

Enzyme-Linked Immunosorbent Assay

All experiments were performed as blinded tests. 40 mM CCCP in DMSO or the same volume of DMSO alone was applied to iPSCs for 6 h, and then cells were lysed in NP40 Cell lysis buffer (FNN0021, ThermoFisher Scientific) with protease inhibitor cocktail (539134, Calbiochem). Cell debris was removed by centrifugation at 17,000 g for 10 min at 4° C. The Rhot1 ELISA kit (EKL54911, Biomatik) was used according to the manufacturer's instructions. The specificity and stability were validated by Biomatik. The dynamic detection range, sensitivity (lower limit of detection-LLOD), and precision (inter- and intraassay) were determined by both Biomatik and us (FIGS. 2E-2G), and the results were comparable. Briefly, 50 ml of cell lysate prepared from above, or serial dilutions of the standard (0-40 ng/ml) were added and incubated for 2 h at 37° C. Each well was then incubated with 100 ml of Detection Reagent A for 1 h at 37° C. Next, plates were washed, and each well was incubated with 100 ml of Detection Reagent B for 1 h at 37° C. Plates were washed again, and 90 ml of Substrate Solution was added to each well for 15-25 min at 37° C. The colorimetric reactions were stopped by 50 ml of Stop Solution and absorbance was read at 450 nm by a microplate reader (Infinite 200 Pro, Tecan). An experiment for generating the standard curve was included in each plate and the representative standard plot was shown in the figure. Each data point was from 3 to 4 independent experiments with 2 technical repeats each time. Student T Test was performed for comparing Miro1 signals within the same subject (DMSO vs CCCP). A loading control, GAPDH, was detected by Western blotting in each experiment and there was no significant difference in loading between "DMSO" and "CCCP" for each cell line.

Statistics

Throughout this Example, the distribution of data points was expressed as box-whisker or dot-plot, except otherwise stated. Statistical analyses were performed using Prism, Excel, or Python's statsmodels package. For all experiments, between 3 and 55 independent experiments were performed. The number of experimental replications (n) can be found in Figure Legends. No data was excluded. *P<0.05, P<0.01, and *P<0.001 for all figures.

Results

Methods used were described in Hsieh, C. H., Li, L., Vanhauwaert, R., Nguyen, K. T., Davis, M. D., Bu, G., et al. (2019). *Cell Metab.* 30, 1131-1140. iPSCs were cultured, and CCCP, a mitochondrial uncoupler, was applied to depolarize the mitochondrial membrane potential. In healthy controls at 6 h following CCCP treatment, Miro1 was significantly degraded as detected by Western blotting (FIGS. 2A, 2B); this time point was prior to the completion of mitophagy when multiple mitochondrial markers were degraded. This method was applied to a total of 87 iPSC lines obtained from the PPMI and NINDS human and cell repository. This cohort included 9 wild-type controls (8 healthy subjects and 1 corrected wild-type), 30 PD patients bearing mutations in SNCA, LRRK2, or GBA without the presence of signs for other neurological disorders, 42 asymptomatic genetic carriers (named "Risk"), and 6 individuals exhibiting prodromal symptoms such as hyposmia or RBD but without PD diagnosis (named "Risk-Hyposmia" and "Risk-RBD," respectively. 57 individuals have a positive family history. The experiments were performed in a blinded manner. Cell passaging numbers were within the range of 12-17 which had no influence on the phenotype. Notably, a unifying impairment in degrading Miro1 at 6 h after CCCP treatment was evident in 25 PD (83.3%) and 36 Risk (genetic carriers) lines (85.7%; FIG. 2).

Figure 2A:
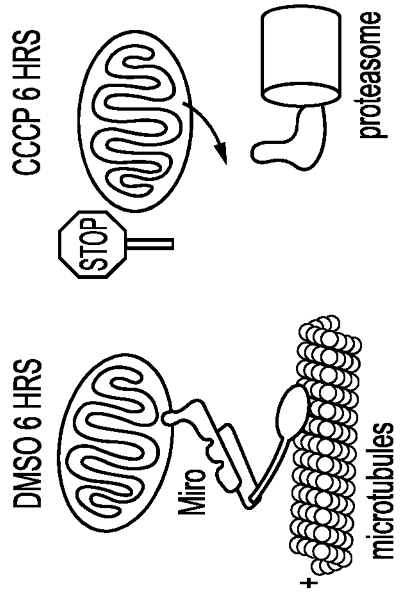
FIG. 2 shows the Miro1 Response to carbonyl cyanide 3-chlorophenylhydrazone (CCCP) in induced pluripotent stem cells (iPSCs). (A) Schematic representation of the readout. (B) Examples of the readout using Healthy-2, PD-29, and Risk-39. Cell lysates were blotted as indicated. (C) Summary of the Western blotting results. Normalized Miro1 intensities of "with DMSO" and "with CCCP" within the same subject were compared by Student T Test, and the number of subjects with $P>0.05$ together with subjects that showed significant Miro1 upregulation after CCCP, or the number of subjects with $P<0.05$ for Miro1 reduction after CCCP, was indicated in the column of "No. (Miro1 DMSO vs CCCP $P>0.05$ or $<0.05$)." Fisher Exact Test was used to determine the P value of a specific group in comparison with "Healthy." (D) The heatmap showed the relative ratio of mean normalized Miro1 intensities ("with CCCP" divided by "with DMSO") of the same subject measured by Western blotting. n=3-55. (E-G) Validation of ELISA for Miro1. (E) A representative standard curve is shown. LLOD=0.112 ng/ml. Dynamic range=0.625-40 ng/ml. (F) Inter-plate variability was demonstrated by measuring the same sample (Healthy-1) in 4 different plates. (G) Intra-plate variability was shown by measuring the same sample (Healthy-1) 4 times in the same plate. (H) The heatmap shows the relative ratio of mean Miro1 values ("with CCCP" divided by "with DMSO") of the same subject measured by ELISA. n=3-4. $^{*}P<0.05$; $^{}P<0.01$; and $^{*}P<0.001$.
Figure 2B:
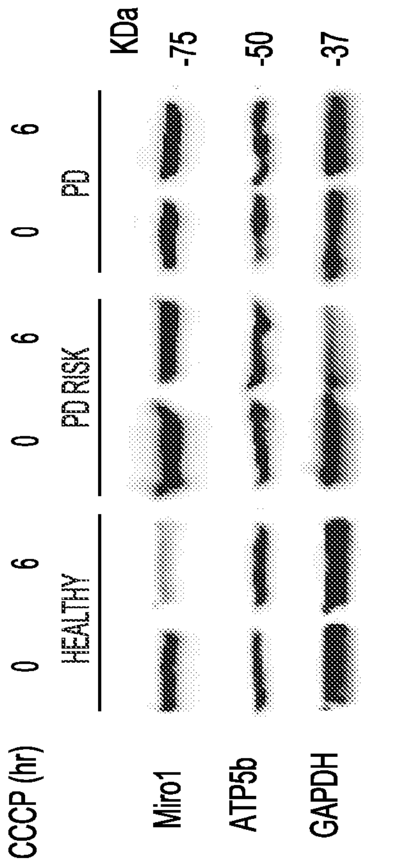
Figure 2D:
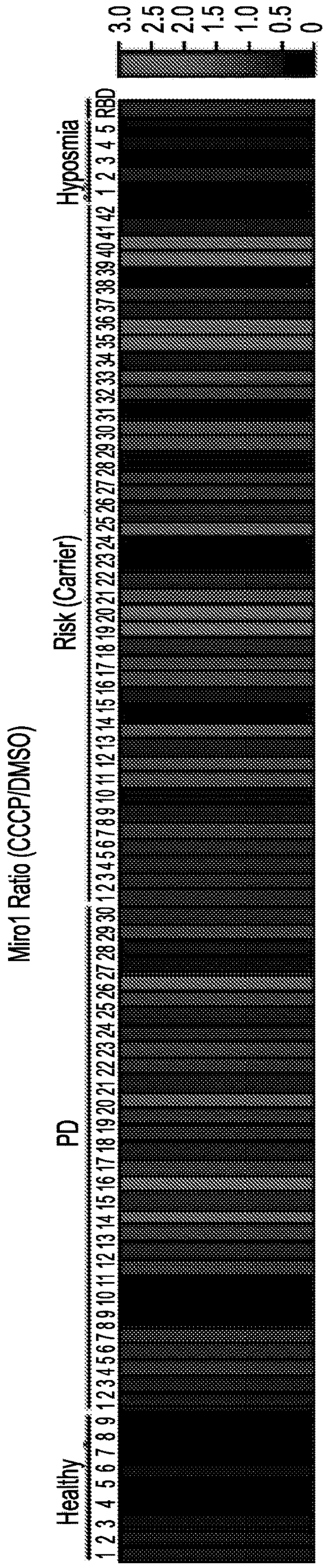

By contrast, Miro1 was efficiently removed following depolarization in every single control subject (0%; FIG. 2C). This phenotype was clearly demonstrated when the Miro1 ratio of each individual (Miro1 intensities "with CCCP" divided by "with DMSO") was imported into a heat map. The majority of the PD and at-risk subjects showed high Miro1 ratios whereas all healthy subjects displayed low Miro1 ratios (FIG. 2D). The frequency of the Miro1 phenotype in iPSCs was significantly higher in patients and non-manifesting carriers than healthy subjects (FIG. 2C). Individuals who were positive for both LRRK2 mutations and hyposmia had a significantly higher rate of the Miro1 phenotype (FIG. 2C).

Figure 2E:
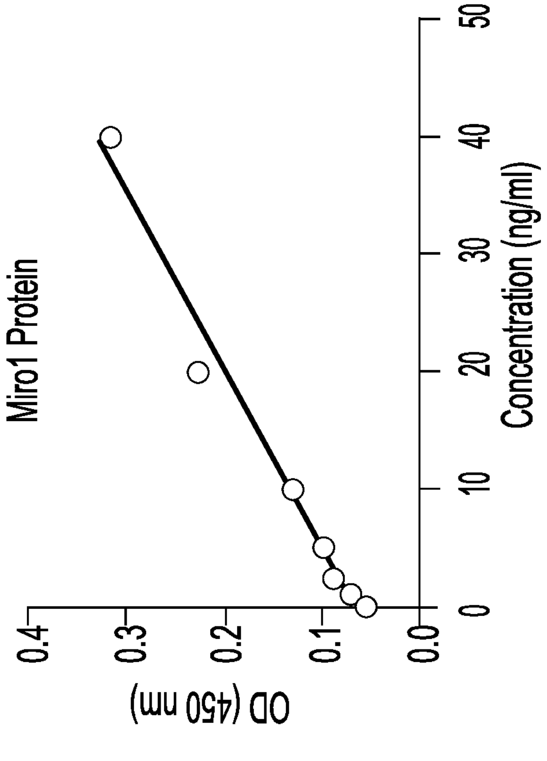
Figure 2F:
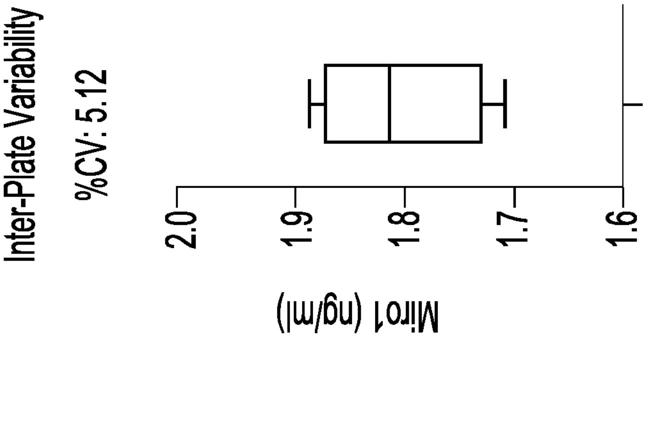
Figure 2G:
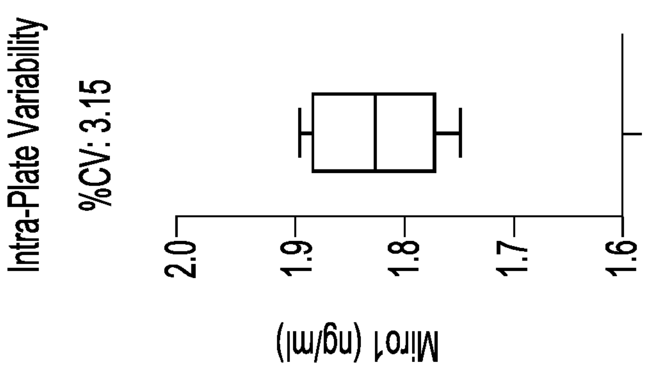
Figure 2H:
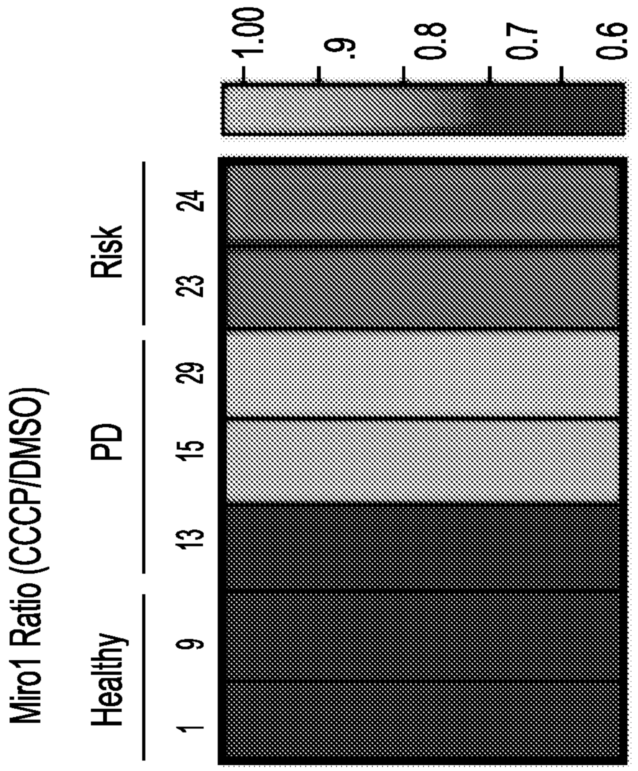
Figure 3B:
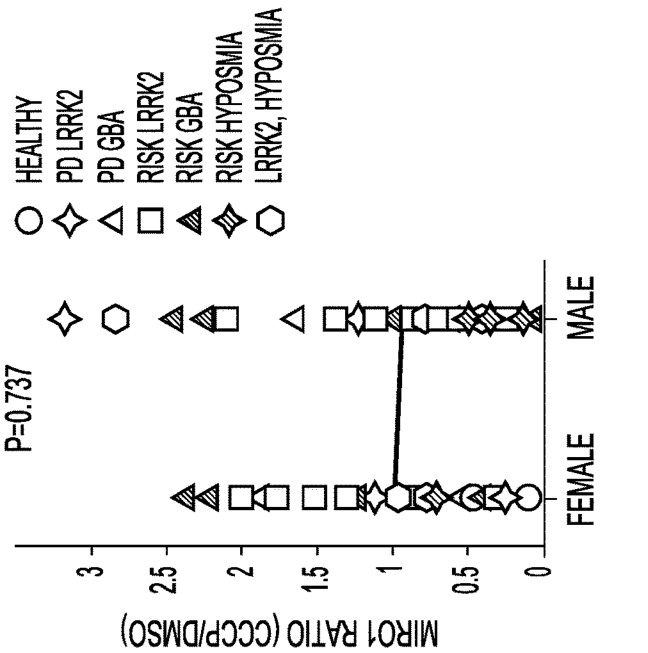
FIG. 3 shows Correlation Analysis of Miro1 Ratio in iPSCs. (A) One-Way Anova was used to determine the significant difference among all groups. (B) Two-Way Anova was used to determine the interaction between sex and genetic background with Miro1 ratio as the response variable. (C, D) Multivariable regression was used to determine the interaction between age and genetic background (C), or age and sex (D), with Miro1 ratio as the response variable. All P values were calculated by linear fit.
Figure 3A:
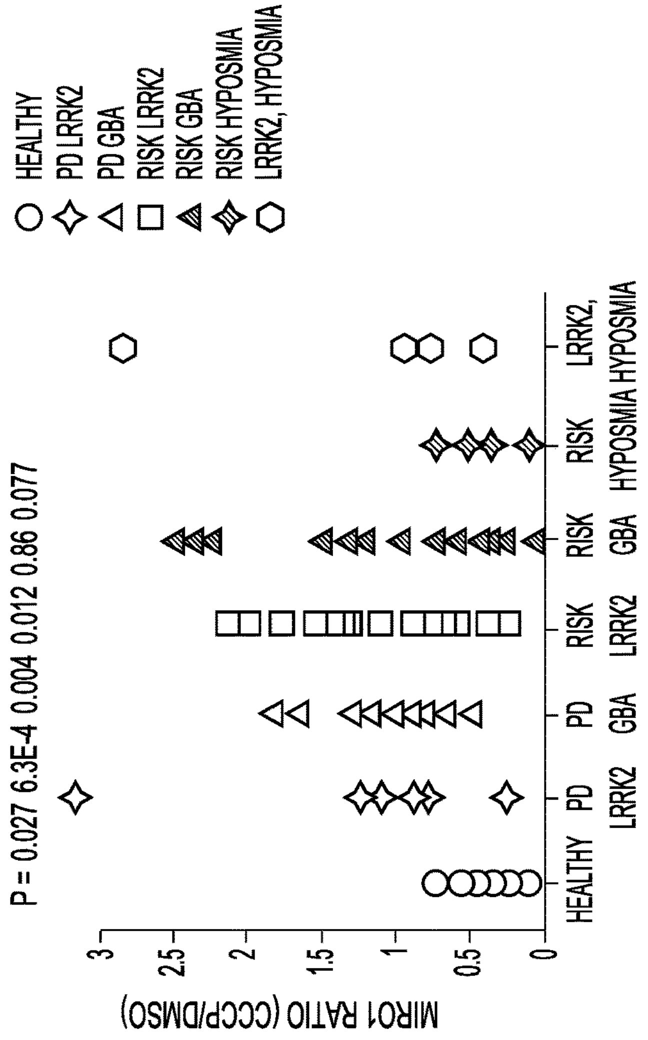
Figure 3D:
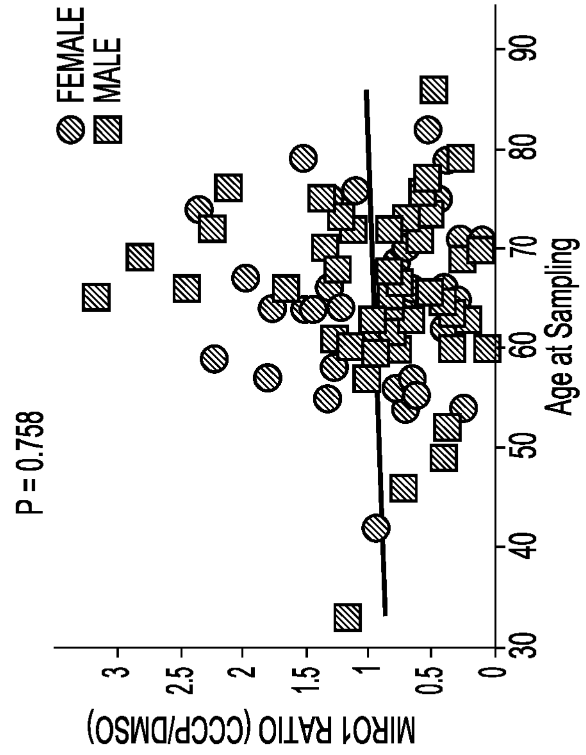
Figure 3C:
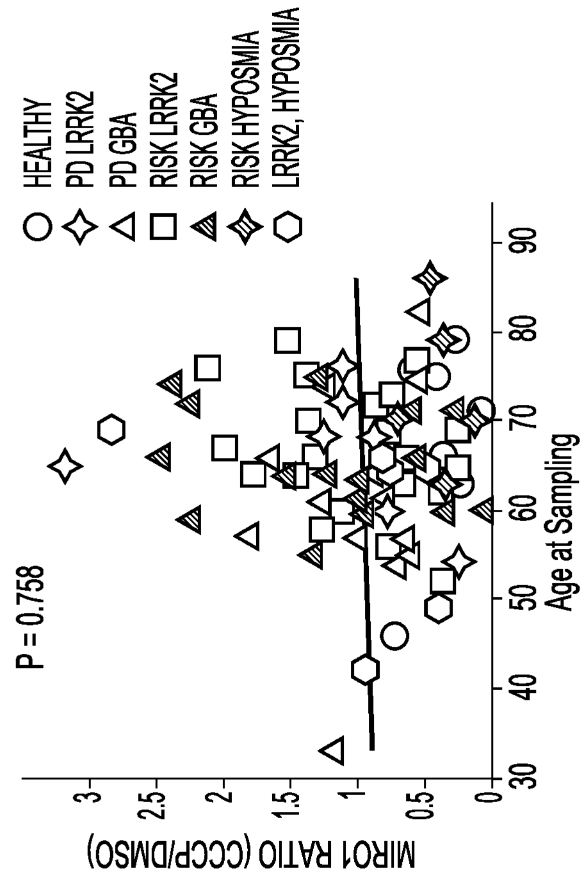

The results from Western blotting were also analyzed with an alternative method: Enzyme-Linked Immunosorbent Assay (ELISA; FIGS. 2E-G). Seven cell lines used in FIG. 2D were examined. For each individual line, the ELISA result of the Miro1 response to mitochondrial depolarization was consistent with that from Western blotting (FIGS. 2D, 2H), demonstrating the robustness of both methods for detecting Miro1 in iPSCs. The two methods to measure Miro1 in patients' cells may be useful for clinical practice. Miro1 ratio (Miro1 intensities "with CCCP" divided by "with DMSO") was also significantly correlated with PD and genetic risk (FIG. 3A), but not with age (at sampling) or sex (FIGS. 3B-3D). There were no interactions among age, sex, and genetic background for affecting Miro1 ratio (FIGS. 3B-3D). Taken together, these observations showed that the failure to remove Miro1 following mitochondrial depolarization was a common cellular defect in this cohort of at-risk individuals.

Figure 4A:
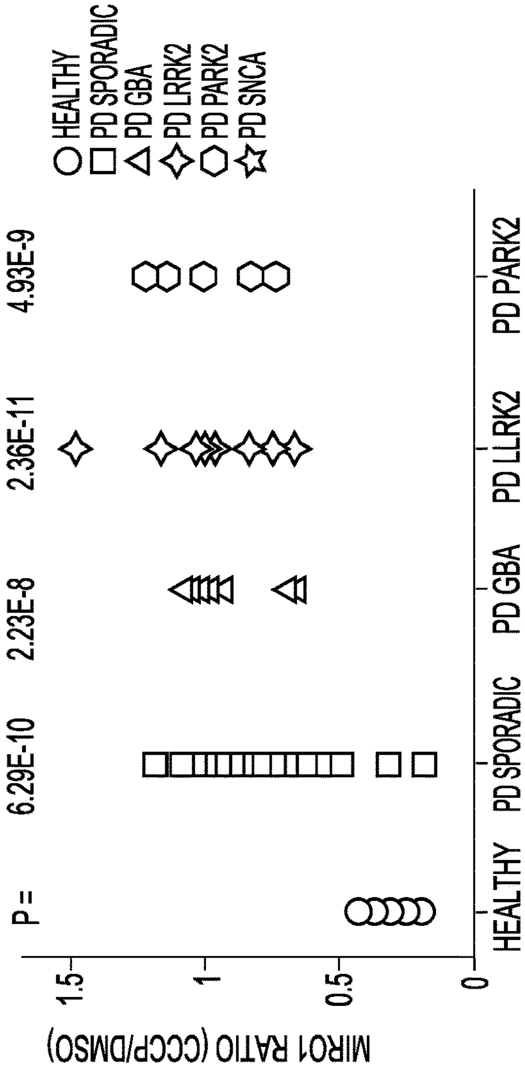
FIG. 4 shows Correlation Analysis of Miro1 Ratio in Fibroblasts. (A) One-Way Anova was used. (B) Two-Way Anova was used to determine the interaction between sex and genetic background with Miro1 ratio as the response variable. (C, D) Multivariable regression was used to determine the interaction between age and genetic background (C), or age and sex (D), with Miro1 ratio as the response variable. All P values were calculated by linear fit.
Figure 4B:
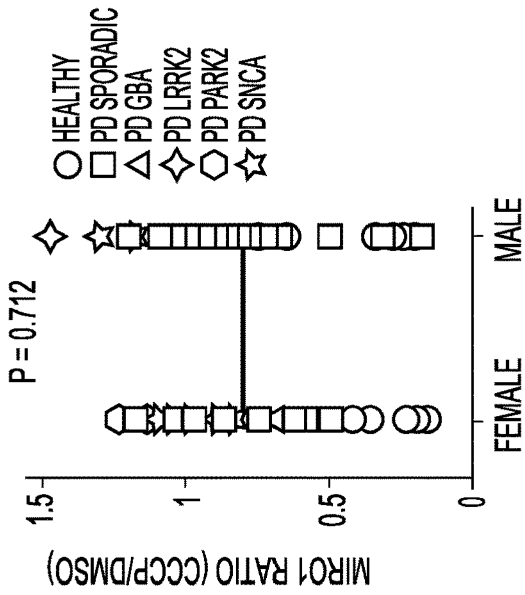
Figure 4C:
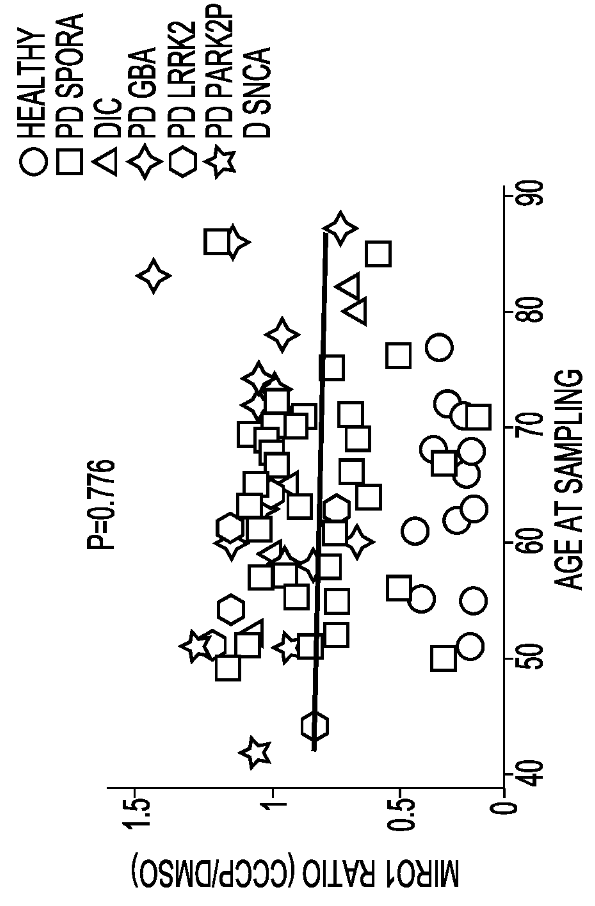
Figure 4D:
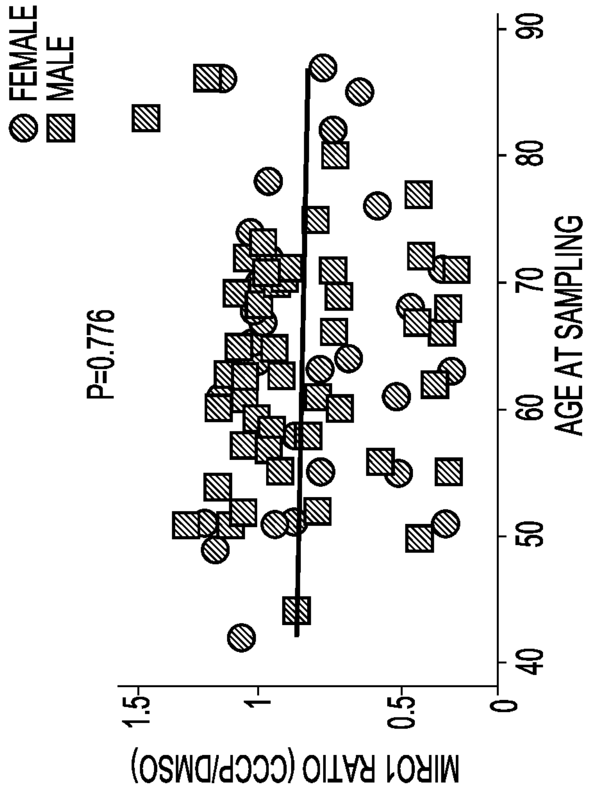
Figure 5B:
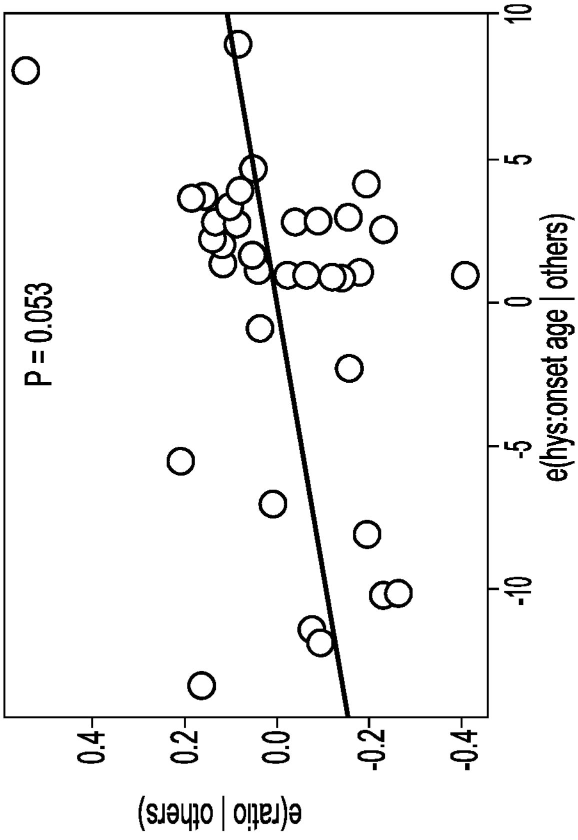
FIG. 5 shows Interactions among Demographic and Clinical Variables. (A) A representative partial regression plot shows the influence of a single variable, Mini-Mental Status Examination (MMSE), on Miro1 ratio. (B-D) Representative partial regression plots shows the interactions of two variables for influencing Miro1 ratio. (B) Hoehn and Yahr Scale (hys) and onset age. (C) MMSE and hys. (D) Onset age and MMSE.
Figure 5A:
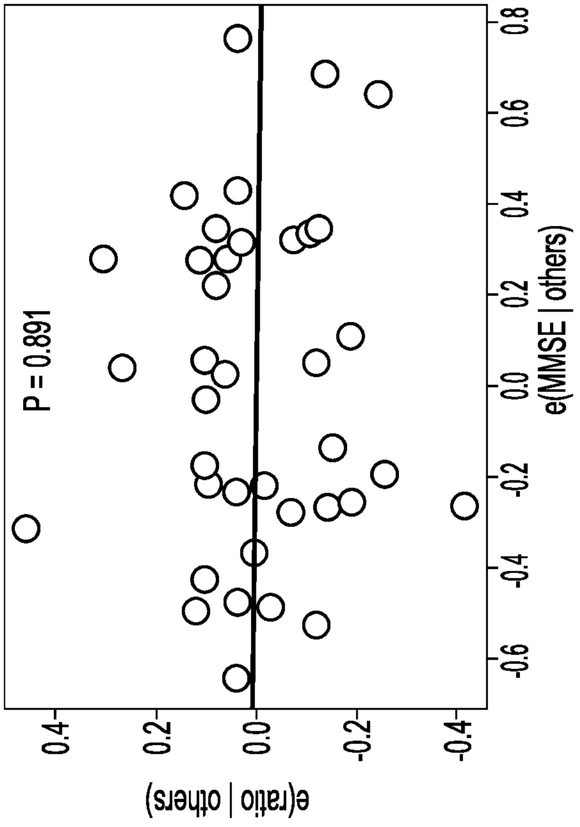
Figure 5D:
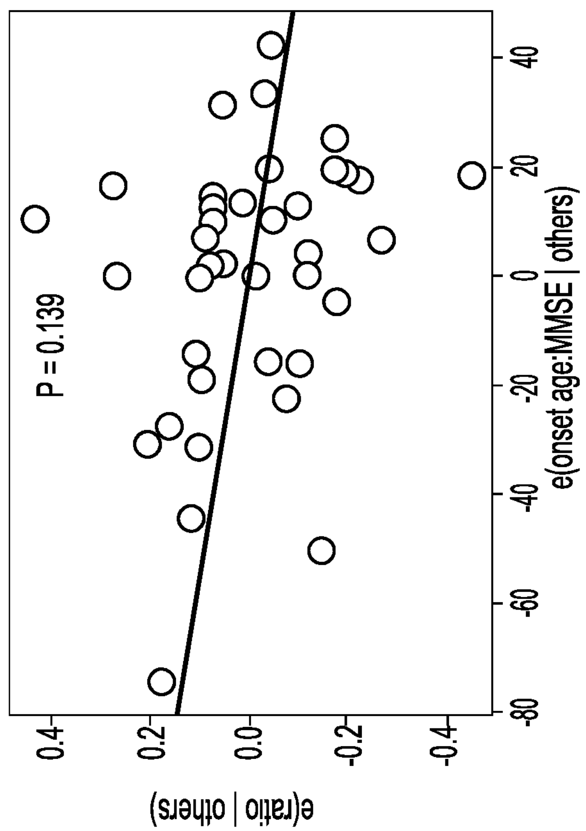
Figure 5C:
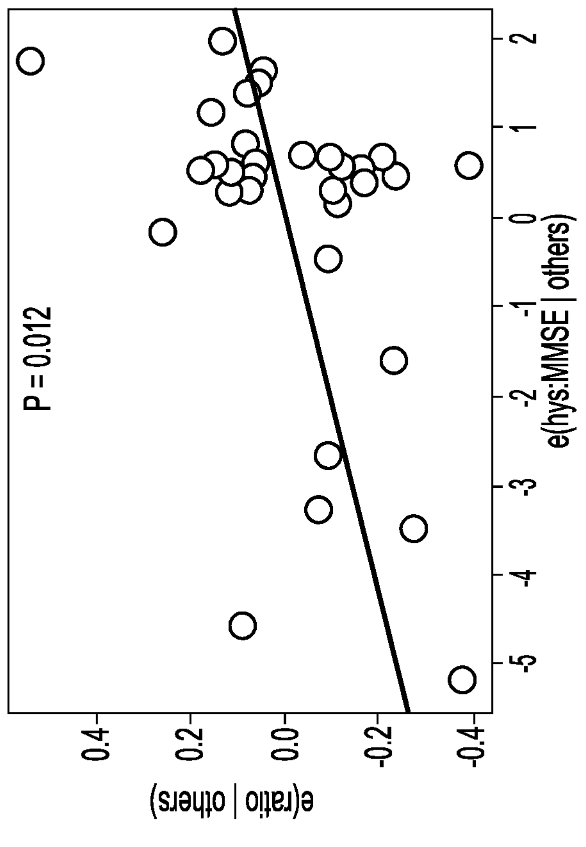

Crosssectional analyses of the overall outcome were performed. The frequency of the Miro1 defect in total PD patients was compared between this cohort using iPSCs and the previous cohort using fibroblasts (Hsieh, C. H., Li, L., Vanhauwaert, R., Nguyen, K. T., Davis, M. D., Bu, G., et al. (2019). *Cell Metab.* 30, 1131-1140), and found that it was largely consistent (83.3% in iPSCs, 94% in fibroblasts). The frequency in specific subgroups were then examined (sample size>5; FIGS. 3A, 4A). The rate of the Miro1 defect was slightly lower in PD patients bearing mutations in LRRK2 or GBA in this cohort using iPSCs than that in the previous cohort using fibroblasts (iPSCs: 83.3 and 93.3%; fibroblasts: 100 and 100%, for LRRK2 and GBA, respectively). The occurrence of the Miro1 phenotype in iPSCs from PD patients and asymptomatic genetic carriers harboring mutations in the same gene was compared. Notably, nonmanifesting genetic carriers bearing mutations in LRRK2 or GBA showed a similar rate of the Miro1 defect as symptomatic patients carrying mutations in the same gene (carriers: 86.4 and 83.3%; PD: 83.3 and 93.3%, for LRRK2 and GBA, respectively). Lastly, whether there were interactions among genetic background, demographics, and clinical manifestations of PD patients for influencing the Miro1 phenotype using the Western blotting data from fibroblasts were examined, given the large sample size of this PD cohort (12 healthy subjects and 71 PD patients). Although each individual variable alone including age, sex, Unified PD Rating Scale, Hoehn and Yahr Scale, and Mini-Mental Status Examination did not affect Miro1 ratio, there was a significant interaction between Hoehn and Yahr Scale and Mini-Mental Status Examination (FIGS. 4B-4D, 5), suggesting that Miro1 ratio might respond to PD progression combined with cognitive impairment.

Example 65. Rescue of Miro1 Deficit in Cells from Frontotemporal Dementia Subject The compound of Example 15 rescued Miro1 deficit in P301L tau donor at risk for developing frontotemporal dementia (FTD). Method: A fibroblast was obtained from a non-symptomatic at risk carrier of the pathogenic P301L mutation in the MAPT/Tau gene, a highly penetrant risk factor for frontotemporal dementia (FTD). NINDS line ID: ND32956, collected from a Caucasian male at age 47. Fibroblasts were seeded into 96-well assay plates. After 24 hours, cells were pre-treated with either vehicle (DMSO) or a dose-response of Example 15 compound. After 6 hrs of pre-treatment, cells were challenged with the mitochondrial stressor FCCP for 14 hours. After 14 hours of challenge, cells were fixed in paraformaldehyde and a standard immunocytochemistry protocol was followed to stain for Miro1 using a specific antibody. Images were acquired on the Yokogawa CQ1 confocal high-content imaging platform and the signal from the Miro1 antibody was quantified. Average Miro1 signal intensity was quantified from ~400 cells/condition.

Similar to the method illustrated in Example 64, a Miro1 ratio could be calculated based on the Miro1 level after treatment of fibroblasts with FCCP compared with a control Miro1 level measured from fibroblasts that were not treated. A Miro1 ratio of about 1 was measured in the P301L tau donor fibroblasts, demonstrating a lack of Miro1 reduction observed in the fibroblasts in response to FCCP. In contrast, a Miro1 ratio of about 0.3 was measured in the healthy donor fibroblasts, demonstrating a Miro1 reduction in the healthy fibroblasts in response to FCCP.

With respect to the Miro1 ratio, the P301L tau donor fibroblasts was converted to healthy donor phenotype in a dose-dependent manner by treating with Example 15. The compound of Example 15 completely rescued Miro1 reduction deficit in P301L tau donor fibroblasts in response to FCCP, with an $IC_{50}$=584 nM. These results suggest that compounds of the disclosure, such as Example 15, could be used to treat asymptomatic Miro1-related disorders, such as FTD.

Example 66. In Vitro Stability of Calcium Channel Antagonists

In vitro liver microsome stability of calcium channel antagonists of the disclosure were determined. Such methods are known in the art. See, Knights, K M et al. Current Protocols in Pharmacology 2016, 74: 7.8.1-7.8.24; Hill, JR. Current Protocols in Pharmacology 2004, 7: 7.8.

Example 67. In Vivo Pharmacokinetics of Calcium Channel Antagonists

Rat Experiments

Fasted male Sprague-Dawley rats between 6 to 8 weeks of age were dosed with calcium channel antagonists of the present disclosure to evaluate in vivo pharmacokinetics. Each compound was formulated in 5% DMAC+5% Solutol HS15+90% Saline to yield a solution for dosing. The rats were dosed intravenously (IV) at 1 mg/kg (1 mL/kg) via foot dorsal vein (N=3) or orally (PO) at 10 mg/kg (10 mL/kg) via oral gavage (N=3).

Blood collection: The animals were restrained manually, and approximately 200 μL blood/time point was collected into pre-cooled EDTA-K2 tubes via jugular vein and put on wet ice. The blood sample was centrifuged at 4° C. (2000 g, 5 min) to obtain plasma within 15 min after sample collection. The plasma samples were stored at approximately −70° C. until analysis.

In an illustrative example, the average concentration of the compound of Example 15 found in rat blood after IV or PO dosing was as shown in the table below.

TABLE 7

24-Hour Time Course of Example 15 in Male Sprague-Dawley Rats

| Sampling time (hr) | Mean (ng/mL) Example 15 after 1 mg/kg IV dose | Mean (ng/mL) Example 15 after 10 mg/kg PO dose |
|---|---|---|
| 0.25 | 890 | 4107 |
| 0.5 | 764 | 4510 |
| 1 | 621 | 4710 |
| 2 | 423 | 5443 |
| 4 | 193 | 4067 |
| 8 | 26.3 | 1239 |
| 12 | 4.42 | 329 |
| 24 | BQL | 2.49 |

(BQL = below quantitation level)

Example 15 compound exhibited higher AUC and $C_{max}$, with about two-fold higher half-life ($t_{1/2}$), compared to Example 16 of U.S. Pat. No. 7,875,636.

Dogs

In vivo experiments were performed in dogs to evaluate certain calcium channel antagonists of the present disclosure. For instance, Example 15 was evaluated in adult male non-naïve beagle dogs (N=6), 8-10 kg, at 1 mg/kg IV and 3 mg/kg PO. The dogs were given free access to food and water for the IV group, were fasted overnight and fed 4 hr post-dosing for the PO group. The IV group was administered Example 15 via cephalic vein injection. The PO group was administered 3 mg/kg Example 15 by oral gavage.

Dosing formulations were prepared at 1 mg/mL in 5% dimethylacetamide, 5% Solutol HS 15, 90% saline prior to use.

Blood collection: The animals were restrained manually, and approximately 0.5 mL blood/time point was collected via cephalic vein into pre-cold EDTA-$K_2$ tubes. Blood samples were chilled on wet ice until centrifuged at 4° C. to obtain plasma within 15 minutes of sample collection. Acceptable $C_{max}$ (>1 g/L) and oral bioavailability (F>50%) was observed for Example 15.

Example 68. Brain Penetration of Calcium Channel Antagonists

Male C57BL/6 mice at 6-8 weeks were dosed once with Example 15 in two experiments (N=3 per timepoint) at 1 mg/kg IV or 10 mg/kg PO, and then compound concentration was measured at various times up to 24 hours. Dosing solutions were prepared of Example 15 in 0.2 mg/mL (IV) or 1 mg/mL (PO) in 5% dimethylacetamide, 5% Solutol HS 15, 90% saline solution prior to use. Compound was administered either IV by tail vein injection or PO by oral gavage.

Blood collection: The animal was restrained manually at the designated time points, approximately 110 µL of blood sample was collected via facial vein into $K_2$EDTA tubes. Blood sample was put on ice and centrifuged at 2000 g for 5 mins to obtain plasma sample within 15 minutes.

Brain collection: After the blood collection, the animals were euthanized via $CO_2$. The whole brain was collected, rinsed with cold saline, dried on filtrate paper, weighed, and snap frozen by placing into dry-ice.

The brain penetrance of Example 15 was calculated using mouse plasma/brain PK and relative mouse plasma and brain homogenate binding. Example 15 exhibited measurable brain penetration in both IV and PO experiments. For instance, at 4 hours post-dose: Example 15 brain concentration>100 ng/mL (IV); Example 15 brain concentration>1000 ng/mL (PO).

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula (II):

(II)

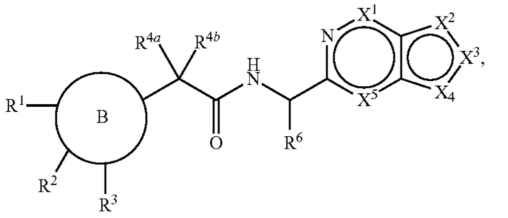

or a pharmaceutically acceptable salt thereof, wherein ring B is $C_6$-$C_{10}$ aryl or 5- to 10-membered heteroaryl;

$R^1$, $R^2$, and $R^3$ are each independently H, halogen, CN, $OR^{11}$, $NR^{12a}R^{12b}$, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, phenyl, 5- to 6-membered heteroaryl, $C_3$-$C_7$ cycloalkyl, $-(CH_2)_n-(C_3$-$C_7$ cycloalkyl), 4- to 7-membered heterocyclyl, or $-(CH_2)_n$-(4- to 7-membered heterocyclyl), wherein the phenyl, heteroaryl, cycloalkyl or heterocyclyl is optionally substituted by 1, 2, or 3 halogen, CN, $OR^{11}$, $NR^{12a}R^{12b}$, $C_1$-$C_6$ alkyl, $C_1$-$C_6$ alkoxy, $C_1$-$C_6$ alkylamino, or $C_1$-$C_6$ haloalkyl;

$R^{4a}$ and $R^{4b}$ are each independently H or $C_1$-$C_6$ alkyl, or $R^{4a}$ and $R^{4b}$ and the carbon atom to which they are attached form a $C_3$-$C_5$ cycloalkyl;

$R^6$ is H, $C_1$-$C_6$ alkyl, or $C_1$-$C_6$ haloalkyl;

$X^1$ is $CR^8$;

$X^2$ and $X^3$ are each independently N or $NR^9$;

$X^4$ is N, $NR^9$, or $CR^9$;

$X^5$ is $CR^8$;

$R^8$ is H, halogen, CN, $OR^{11}$, $C_1$-$C_6$ alkyl, $C_2$-$C_6$ alkoxyalkyl, or $C_1$-$C_6$ haloalkyl;

each $R^9$ is independently H, $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl;

each $R^{11}$, $R^{12a}$, and $R^{12b}$ is independently $C_1$-$C_6$ alkyl, $C_2$-$C_6$ alkoxyalkyl, $C_1$-$C_6$ haloalkyl, $C_2$-$C_6$ alkenyl, $C_2$-$C_6$ alkynyl, $C_3$-$C_7$ cycloalkyl, or 4- to 7-membered heterocyclyl, wherein the cycloalkyl or heterocyclyl is optionally substituted by 1, 2, or 3 halogen or CN; and n is 1, 2, or 3.

2. The compound or a pharmaceutically acceptable salt thereof of claim 1, wherein $R^8$ is H.

3. The compound of claim 1 or a pharmaceutically acceptable salt thereof having the structure of Formula (III):

(III)

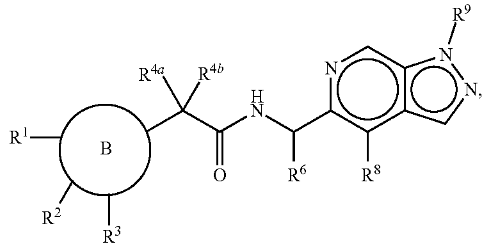

or a pharmaceutically acceptable salt thereof.

4. The compound or a pharmaceutically acceptable salt thereof of claim 1, wherein $R^1$, $R^2$, and $R^3$ are each independently H, halogen, CN, OH, $NH_2$, $C_1$-$C_6$ alkyl, $C_1$-$C_6$ alkoxy, $C_1$-$C_6$ alkylamino, $C_2$-$C_6$ alkoxyalkyl, $C_1$-$C_6$ haloalkyl, or $C_3$-$C_7$ cycloalkyl, wherein the cycloalkyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl.

5. The compound or a pharmaceutically acceptable salt thereof of claim 1, wherein $R^1$ and $R^2$ are each independently H, halogen, $C_1$-$C_6$ alkyl, $C_1$-$C_6$ alkoxy, $C_2$-$C_6$ alkoxyalkyl, $C_1$-$C_6$ haloalkyl, or $C_3$-$C_7$ cycloalkyl, wherein the cycloalkyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl.

6. The compound or a pharmaceutically acceptable salt thereof of claim 1, wherein $R^1$ and $R^2$ are each independently H, halogen, $C_1$-$C_3$ alkyl, $C_1$-$C_3$ alkoxy, $C_2$-$C_3$ alkoxyalkyl, $C_1$-$C_3$ haloalkyl, or $C_3$-$C_5$ cycloalkyl, wherein the cycloalkyl is optionally substituted by 1, 2, or 3 halogen, CN, $C_1$-$C_3$ alkyl, $C_1$-$C_3$ alkoxy, $C_1$-$C_3$ alkylamino, or $C_1$-$C_3$ haloalkyl.

7. The compound or a pharmaceutically acceptable salt thereof of claim 1, wherein $R^{4a}$ and $R^{4b}$ are each independently H or $CH_3$.

8. The compound or a pharmaceutically acceptable salt thereof of claim 1, wherein $R^6$ is $CH_3$.

9. The compound or a pharmaceutically acceptable salt thereof of claim 1 having the structure of Formula (IV):

(IV)

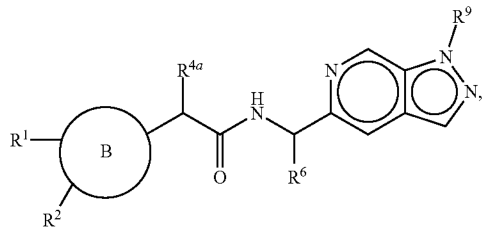

or a pharmaceutically acceptable salt thereof.

10. The compound or a pharmaceutically acceptable salt thereof of claim 1, wherein $R^9$ is $C_1$-$C_6$ alkyl, $C_2$-$C_6$ alkoxyalkyl, $C_1$-$C_6$ haloalkyl, $C_3$-$C_7$ cycloalkyl, or 4- to 7-membered heterocyclyl, wherein the cycloalkyl or heterocyclyl is optionally substituted by 1, 2, or 3 halogen, CN, OH, $NH_2$, $C_1$-$C_6$ alkyl, $C_1$-$C_6$ alkoxy, $C_1$-$C_6$ alkylamino, or $C_1$-$C_6$ haloalkyl.

11. The compound or a pharmaceutically acceptable salt thereof of claim 1 having the structure of Formula (V):

(V)

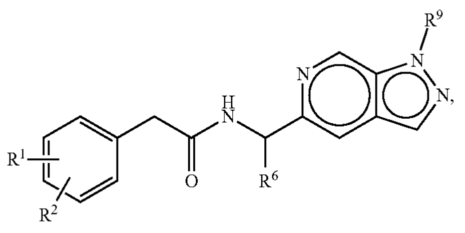

or a pharmaceutically acceptable salt thereof.

12. The compound or a pharmaceutically acceptable salt thereof of claim 1, wherein the compound has the structure:

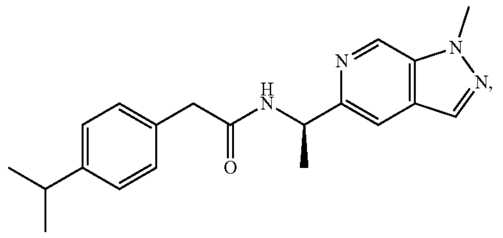

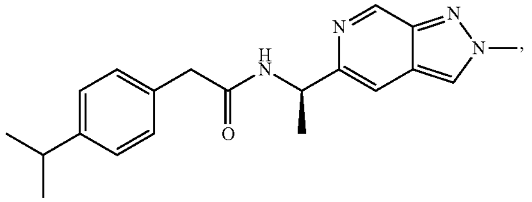

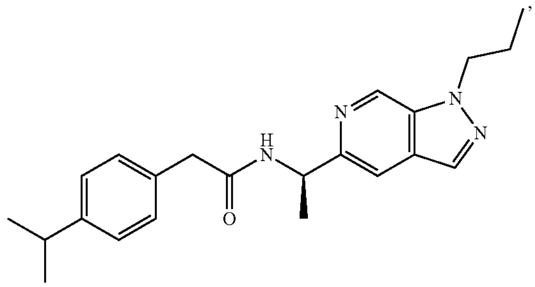

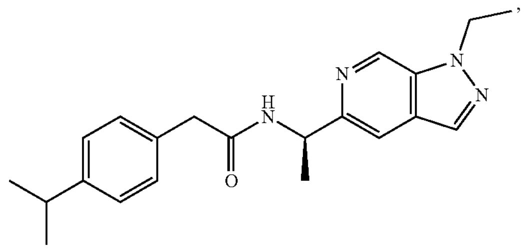

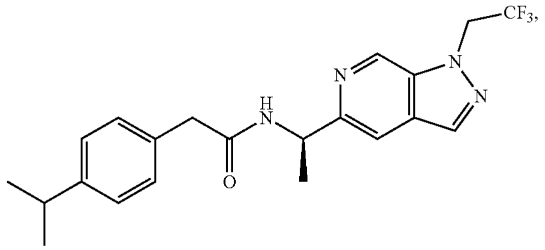

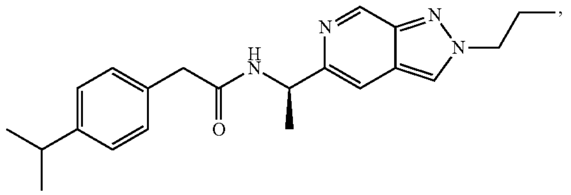

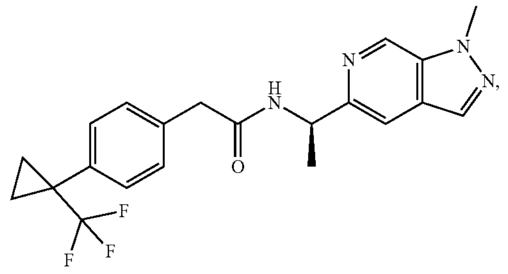

-continued
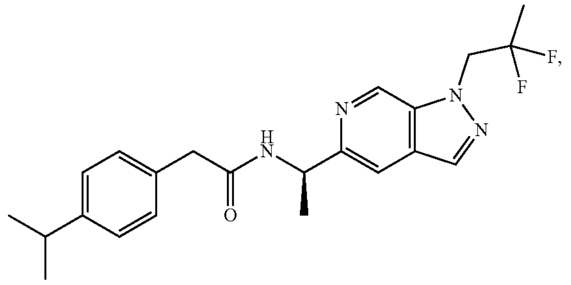
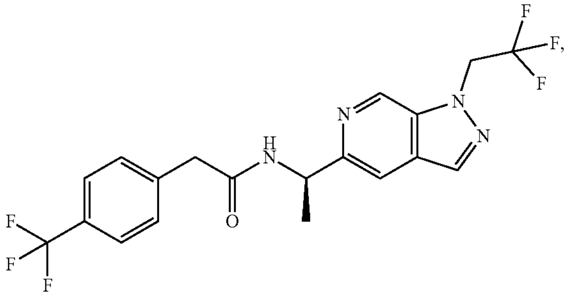
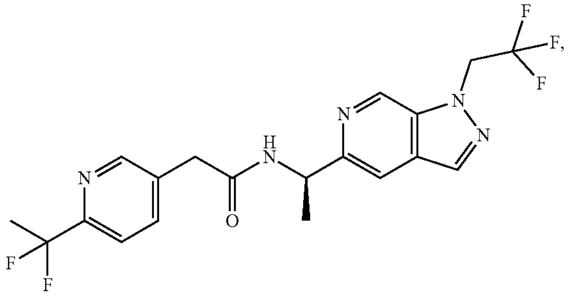
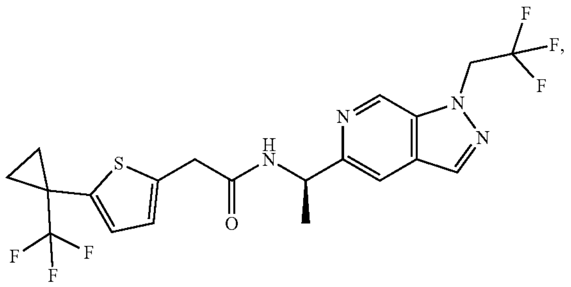
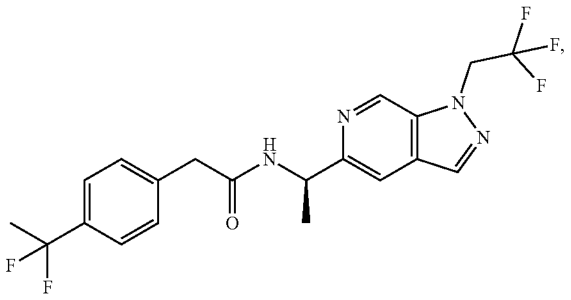
-continued
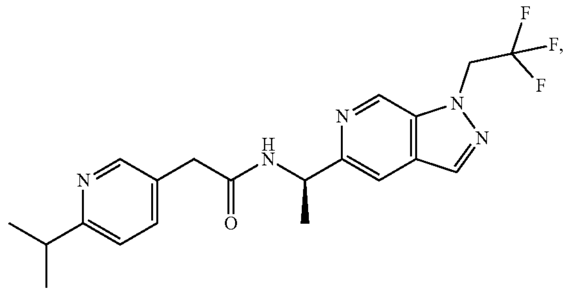
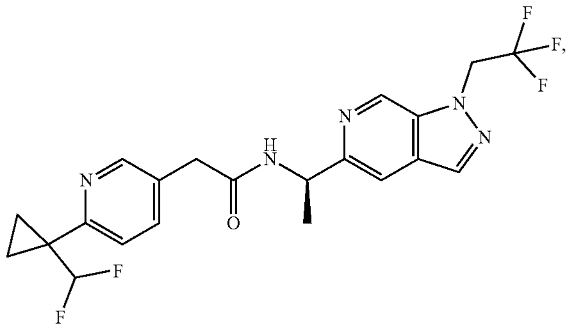
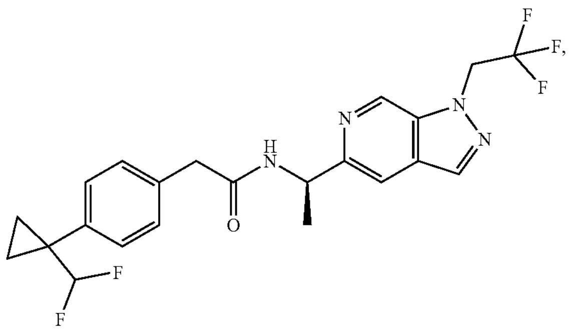
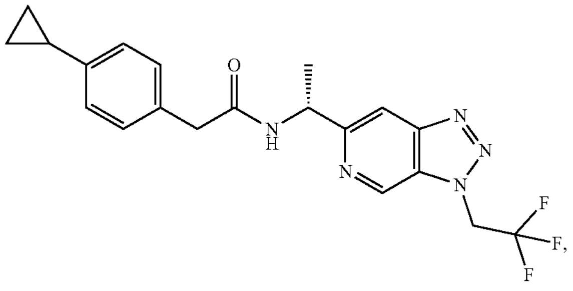
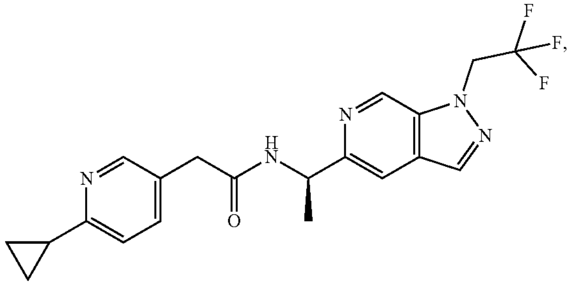

-continued
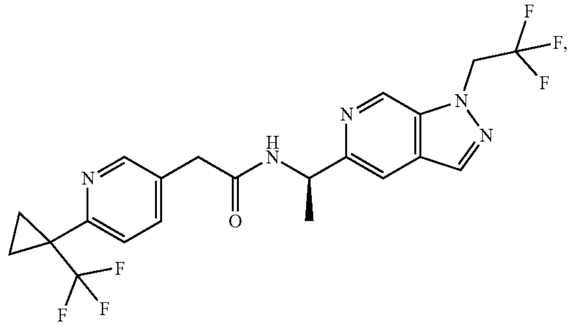
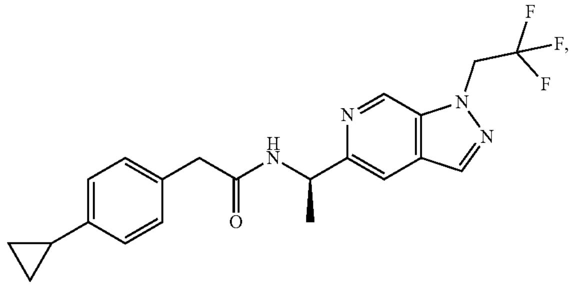
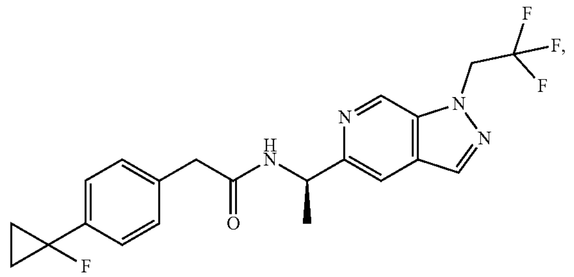
Diastereomer A
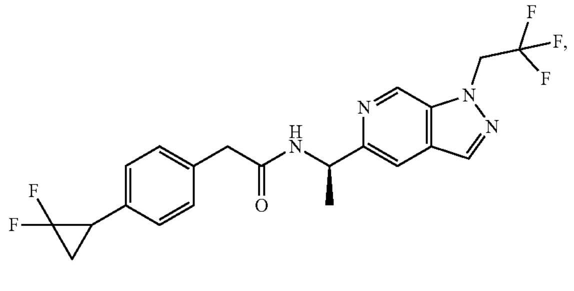
Diastereomer B
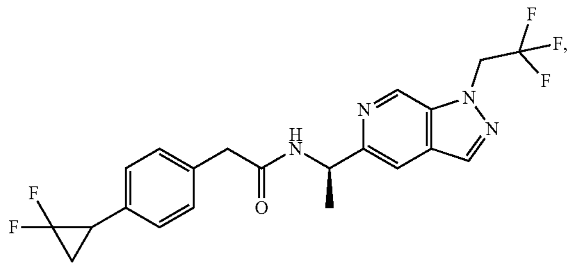
-continued
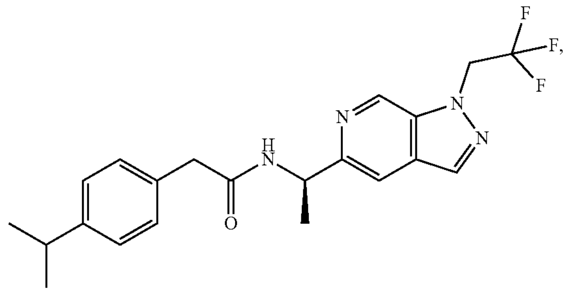
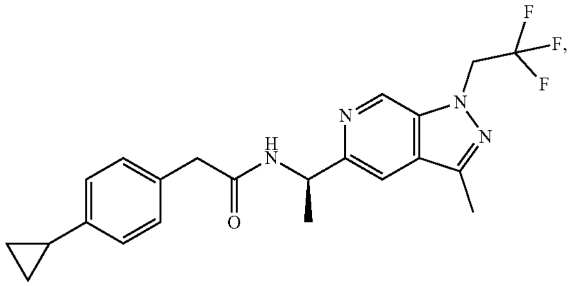
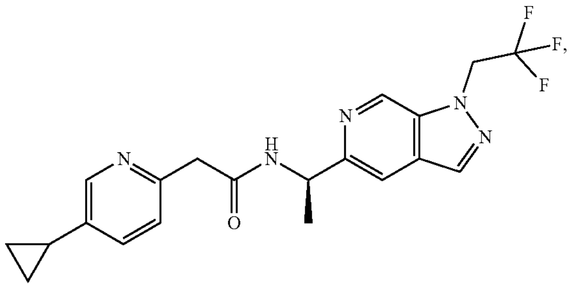
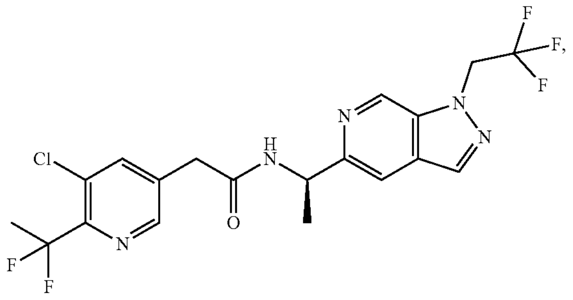
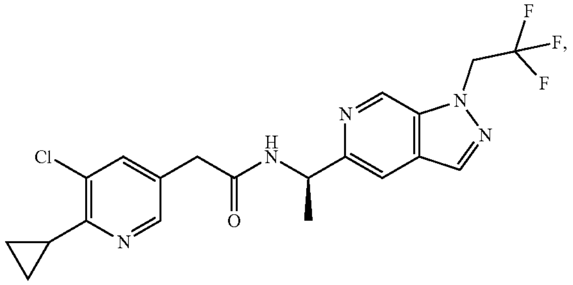

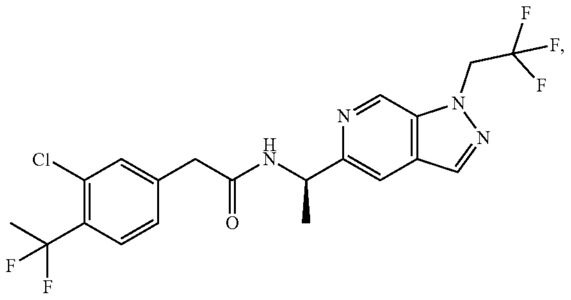
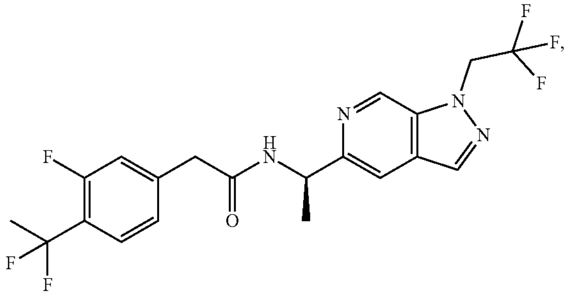
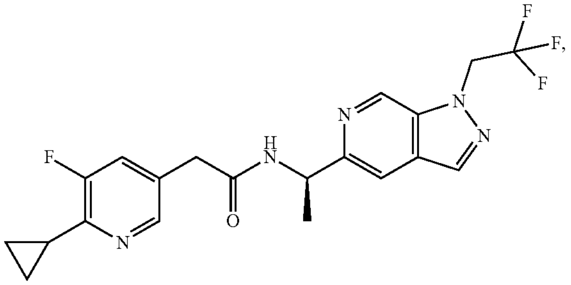
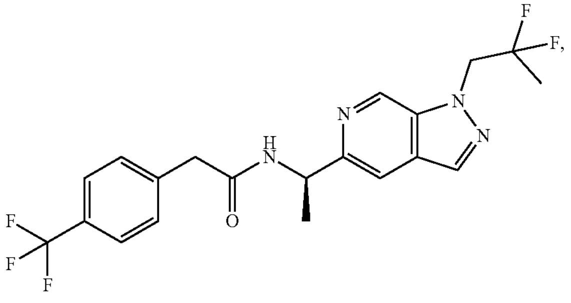
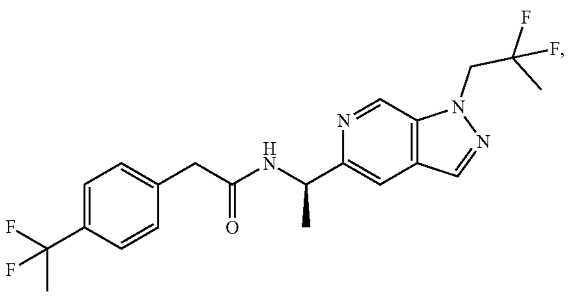
-continued
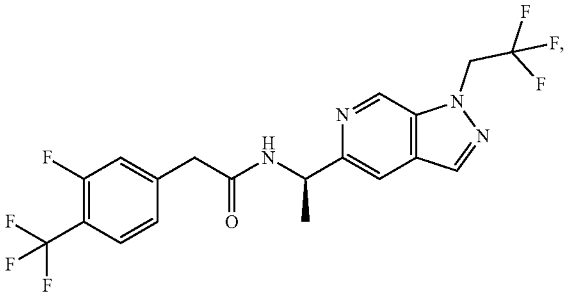
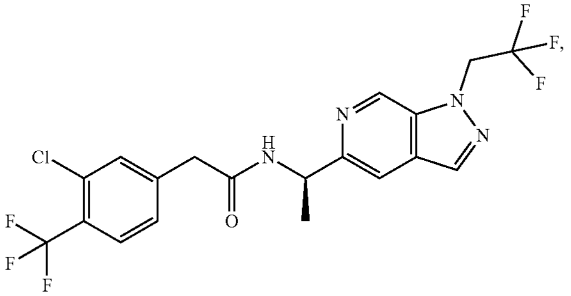
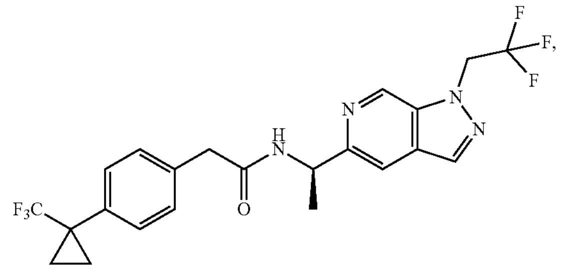
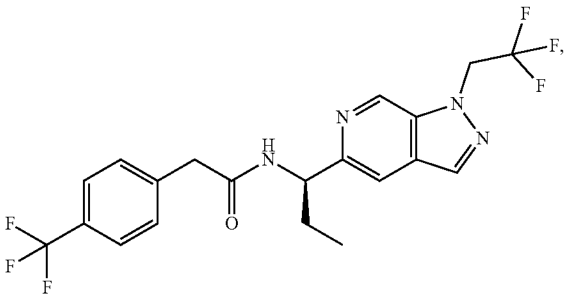
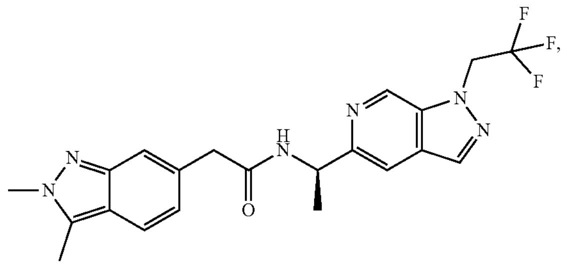
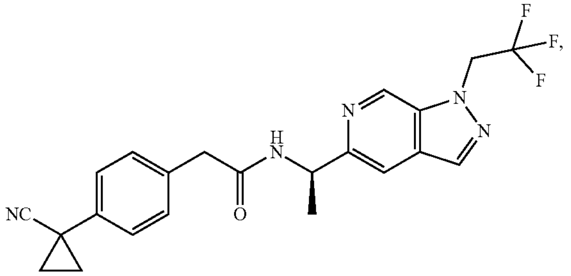

-continued

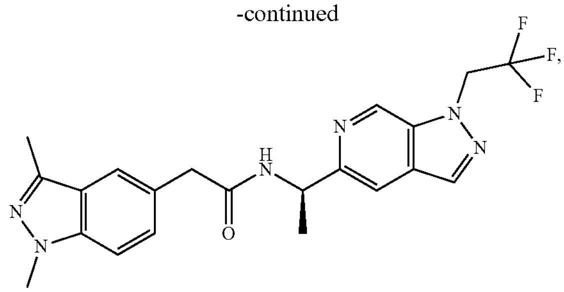

,

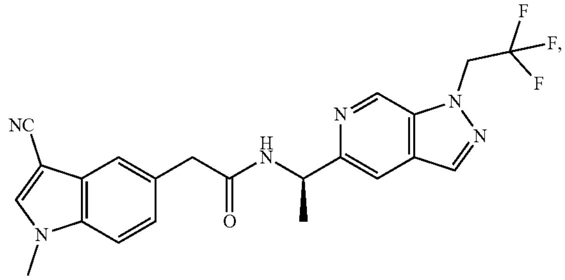

,

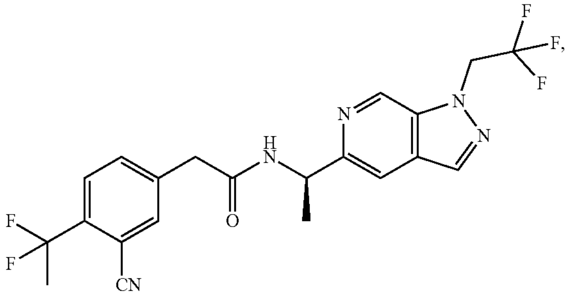

,

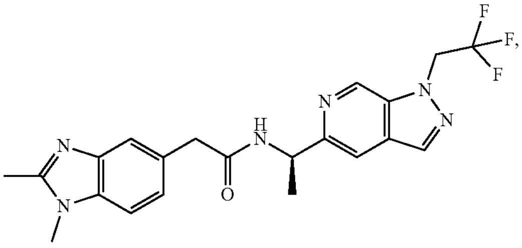

or

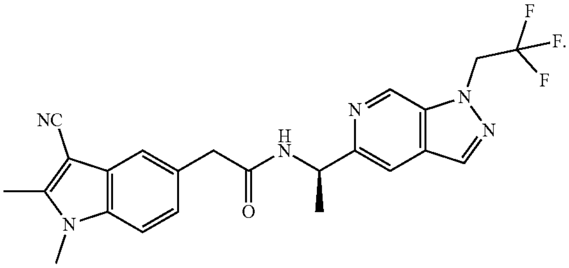

.

13. A pharmaceutical composition comprising a compound of claim 1, or a pharmaceutically acceptable salt thereof, and a pharmaceutically acceptable carrier.

14. The compound or pharmaceutically acceptable salt thereof of claim 1, wherein $R^1$ and $R^2$ is each independently H, halogen, $C_1$-$C_3$ alkyl, $C_1$-$C_3$ alkoxy, $C_2$-$C_3$ alkoxyalkyl, $C_1$-$C_3$ haloalkyl, or $C_3$-$C_5$ cycloalkyl, wherein the cycloalkyl is optionally substituted by 1, 2, or 3 halogen, CN, $C_1$-$C_3$ alkyl, $C_1$-$C_3$ alkoxy, $C_1$-$C_3$ alkylamino, or $C_1$-$C_3$ haloalkyl.

15. The compound or pharmaceutically acceptable salt thereof of claim 1, wherein $R^9$ is $C_1$-$C_3$ alkyl, $C_2$-$C_3$ alkoxyalkyl, $C_1$-$C_3$ haloalkyl, $C_3$-$C_7$ cycloalkyl, or 4- to 7-membered heterocyclyl, wherein the cycloalkyl or heterocyclyl is substituted by 0, 1, 2, or 3 F, Cl, CN, OH, $NH_2$, $C_1$-$C_3$ alkyl, $C_1$-$C_3$ alkoxy, $C_1$-$C_3$ alkylamino, or $C_1$-$C_3$ haloalkyl.

16. The compound or pharmaceutically acceptable salt thereof of claim 9, wherein $R^1$ and $R^2$ is each independently H, halogen, $C_1$-$C_3$ alkyl, $C_1$-$C_3$ alkoxy, $C_2$-$C_3$ alkoxyalkyl, $C_1$-$C_3$ haloalkyl, or $C_3$-$C_5$ cycloalkyl, wherein the cycloalkyl is optionally substituted by 1, 2, or 3 halogen, CN, $C_1$-$C_3$ alkyl, $C_1$-$C_3$ alkoxy, $C_1$-$C_3$ alkylamino, or $C_1$-$C_3$ haloalkyl.

17. The compound or pharmaceutically acceptable salt thereof of claim 9, wherein $R^9$ is $C_1$-$C_3$ alkyl, $C_2$-$C_3$ alkoxyalkyl, $C_1$-$C_3$ haloalkyl, $C_3$-$C_7$ cycloalkyl, or 4- to 7-membered heterocyclyl, wherein the cycloalkyl or heterocyclyl is substituted by 0, 1, 2, or 3 F, Cl, CN, OH, $NH_2$, $C_1$-$C_3$ alkyl, $C_1$-$C_3$ alkoxy, $C_1$-$C_3$ alkylamino, or $C_1$-$C_3$ haloalkyl.

18. The compound or pharmaceutically acceptable salt thereof of claim 11, wherein $R^1$ and $R^2$ is each independently H, halogen, $C_1$-$C_3$ alkyl, $C_1$-$C_3$ alkoxy, $C_2$-$C_3$ alkoxyalkyl, $C_1$-$C_3$ haloalkyl, or $C_3$-$C_5$ cycloalkyl, wherein the cycloalkyl is optionally substituted by 1, 2, or 3 halogen, CN, $C_1$-$C_3$ alkyl, $C_1$-$C_3$ alkoxy, $C_1$-$C_3$ alkylamino, or $C_1$-$C_3$ haloalkyl.

19. The compound or pharmaceutically acceptable salt thereof of claim 11, wherein $R^9$ is $C_1$-$C_3$ alkyl, $C_2$-$C_3$ alkoxyalkyl, $C_1$-$C_3$ haloalkyl, $C_3$-$C_7$ cycloalkyl, or 4- to 7-membered heterocyclyl, wherein the cycloalkyl or heterocyclyl is substituted by 0, 1, 2, or 3 F, Cl, CN, OH, $NH_2$, $C_1$-$C_3$ alkyl, $C_1$-$C_3$ alkoxy, $C_1$-$C_3$ alkylamino, or $C_1$-$C_3$ haloalkyl.

* * * * *